(12) United States Patent
Midwood et al.

(10) Patent No.: US 10,533,047 B2
(45) Date of Patent: *Jan. 14, 2020

(54) ANTI-TENASCIN C ANTIBODIES AND USES THEREOF

(71) Applicant: NASCIENT LIMITED, London (GB)

(72) Inventors: Kim Suzanne Midwood, Buckinghamshire (GB); Philip Antony Bland-Ward, London (GB); Nigel Burns, London (GB); Patrick John Hextall, Cambridge (GB); Susan Rebecca Aungier, Oxford (GB)

(73) Assignee: NASCIENT LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/104,610

(22) Filed: Aug. 17, 2018

(65) Prior Publication Data

US 2019/0055306 A1 Feb. 21, 2019

Related U.S. Application Data

(63) Continuation of application No. 15/501,979, filed as application No. PCT/GB2015/052298 on Aug. 7, 2015, now Pat. No. 10,093,723.

(30) Foreign Application Priority Data

Aug. 7, 2014 (GB) .................................. 1414021.4

(51) Int. Cl.
| | |
|---|---|
| C07K 16/42 | (2006.01) |
| C07K 16/46 | (2006.01) |
| C07K 16/00 | (2006.01) |
| A61K 39/395 | (2006.01) |
| C07K 16/18 | (2006.01) |
| G01N 33/68 | (2006.01) |
| C07K 14/78 | (2006.01) |
| A61K 39/00 | (2006.01) |

(52) U.S. Cl.
CPC .......... *C07K 16/18* (2013.01); *A61K 39/3955* (2013.01); *C07K 14/78* (2013.01); *G01N 33/6893* (2013.01); *A61K 2039/505* (2013.01); *C07K 2317/33* (2013.01); *C07K 2317/55* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,124,260 A | 9/2000 | Sharifi et al. | |
| 10,093,723 B2 * | 10/2018 | Midwood | A61K 39/3955 |

FOREIGN PATENT DOCUMENTS

| | | |
|---|---|---|
| WO | 2010103289 A1 | 9/2010 |
| WO | 2016020702 A1 | 2/2016 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91 (Year: 1996).*
Vajdos et al. Comprehensive functional maps of the antigen-binding site of an anti-ErbB2 antibody obtained with shotgun scanning mutagenesis. J. Mol. Biol. Jul. 5, 2002 320(2):415-28. (Year: 2002).*
"Anti-Tenascin C antibody [DB7] ab86182", Jul. 18, 2012 (Jul. 18, 2012), XP055232075, Retrieved from the Internet: URL:http://www.abcam.com/Tenascin-C-antibody-DB7-ab86182.pdf [retrieved on Nov. 27, 2015].
International Search Report and Written Opinion for PCT International Application No. PCT/GB2015/052298 dated Dec. 17, 2015.
Clark, et al., Tenascin supports lymphocyte rolling, J Cell Biol. 137(3), May 1997, 755-765.
Herold-Mende, et al., Clinical impact and functional aspects of tenascin-C expression during glioma progression, Int J Cancer. 98(3) ,2002 ,362-369.
Midwood, et al., Tenascin-C is an endogenous activator of Toll-like receptor 4 that is essential for maintaining inflammation in arthritic joint disease, Nat Med. 15(7) ,Jul. 2009 ,774-780.
Midwood, et al., The role of tenascin-C in tissue injury and tumorigenesis, J Cell Commun Signal. 3(3-4) ,Dec. 2009 ,287-310.
Reardon, et al., Antitenascin-C monoclonal antibody radioimmunotherapy for malignant glioma patients, Expert Rev Anticancer Ther. 7(5) ,2007 ,675-687.
Szalai, et al., Fibrillin-2, tenascin-C, matrilin-2, and matrilin-4 are strongly expressed in the epithelium of human granular and lattice type I corneal dystrophies, Mol Vis. 18, Jul. 2012 ,1927-1936.

* cited by examiner

*Primary Examiner* — Maher M Haddad
(74) *Attorney, Agent, or Firm* — Debora Plehn-Dujowich; Eckert Seamans Cherin & Mellott, LLC

(57) ABSTRACT

There is provided antibodies or antigen-binding fragments, derivatives or variants thereof which are capable of binding to the FBG domain of tenascin-C. There are also provided uses of such antibodies or antigen-binding fragments, derivatives or variants thereof, as well as methods of identifying such antibodies.

3 Claims, 36 Drawing Sheets

Figure 3:
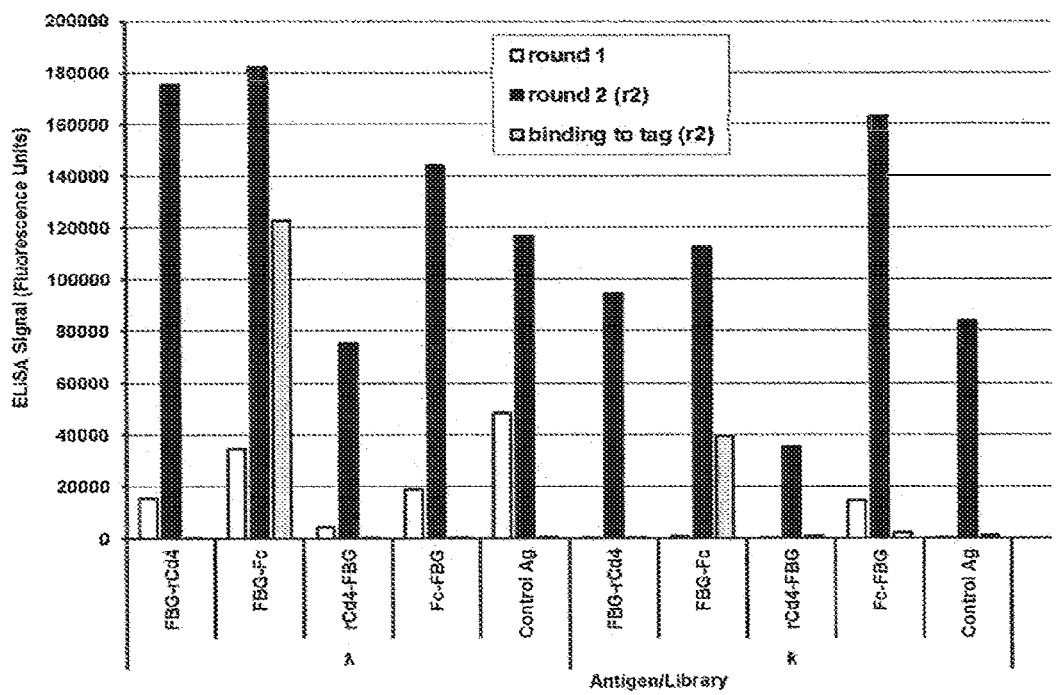

Specification includes a Sequence Listing.

TA domain

```
 23 gvlkkvir hkrqsgvnat lpeen   45
```

EGFL domain

```
 146                                           cclqp atgrldtrpf csgrgnfste gcgcvcepgw
 181 kgpncsepec pgnchlrgrc idgqcicddg ftgedcsqla cpsdcndqgk cvngvcicfe
 241 gyagadcsre icpvpcseeh gtcvdglcvc hdgfagddcn kplclnncyn rgrcvenecv
 301 cdegftgedc selicpndcf drgrcingtc yceeqftged cgkptcphac htqgrceegq
 361 cvcdegfagl dcsekrcpad chnrgrcvdg rcecddgftg adcgelkcpn gcsghgrcvn
 421 gqcvcdegyt gedcsqlrcp ndchsrgrcv egkcvceqgf kgydcsdmsc pndchqhgrc
 481 vngmcvcddg ytgedcrdrq cprdcsnrgl cvdgqcvced gftgpdcael scpndchgqg
 541 rcvngqcvch egfmgkdcke qrcpsdchgq grcvdgqcic hegftgldcg qhscpsdcnn
 601 lgqcvsgrci cnegysgedc s         621
```

FNIII domain

```
 622                              evsppkdlv vtevteetvn lawdnemrvt eylvvytpth
 661 egglemqfrv pgdqtstiiq elepgveyfi rvfailenkk sipvsarvat ylpapeglkf
 721 ksiketsvev ewdpldiafe tweiifrnmn kedegeitks lrrpetsyrq tglapgqeye
 781 islhivknnt rgpglkrvtt trldapsqie vkdvtdttal itwfkplaei dgieltygik
 841 dvpgdrttid ltedenqysi gnlkpdteye vslisrrgdm ssnpaketft tgldaprnlr
 901 rvsqtdnsit lewrngkaai dsyrikyapi sggdhaevdv pksqqattkt tltglrpgte
 961 ygigvsavke dkesnpatin aateldtpkd lqvsetaets ltllwktpla kfdryrlnys
1021 lptgqwvgvq lprnttsyvl rglepgqeyn vlltaekgrh kskparvkas teqapelenl
1081 tvtevgwdgl rlnwtaadqa yehfiiqvqe ankveaarnl tvpgslravd ipglkaatpy
1141 tvsiygviqg yrtpvlsaea stgetpnlge vvvaevgwda lklnwtapeg ayeyffiqvq
1201 eadtveaaqn ltvpgglrst dlpglkaath ytitirgvtq dfsttplsve vlteevpdmg
1261 nltvtevswd alrlnwttpd gtydqftiqv qeadqveeah nltvpgslrs meipglragt
1321 pytvtlhgev rghstrplav evvtedlpql gdlavsevgw dglrlnwtaa dnayehfviq
1381 vqevnkveaa qnltlpgslr avdipgleaa tpyrvsiygv irgyrtpvls aeastakepe
1441 ignlnvsdit pesfnlswma tdgifetfti eiidsnrlle tveynisqae rtahisglpp
1501 stdfivylsg lapsirtkti satattealp llenltisdi npygftvswm asenafdsfl
1561 vtvvdsgkll dpqeftlsgt qrklelrgli tgigyevmvs gftqghqtkp lraeivteae
1621 pevdnllvsd atpdgfrlsw tadegvfdnf vlkirdtkkq sepleitlla pertrdltgl
1681 reateyeiel ygiskgrrsq tvsaiattam gspkevifsd itensatvsw raptaqvesf
1741 rityvpitgg tpsmvtvdgt ktqtrlvkli pgveylvsii amkgfeesep vsgsfttald
1801 gpsglvtani tdsealarwq paiatvdsyv isytgekvpe itrtvsgntv eyaltdlepa
1861 teytlrifae kgpqksstit akfttdldsp rdltatevqs etalltwrpp rasvtgyllv
1921 yesvdgtvke vivgpdttsy sladlspsth ytakiqalng plrsnmiqti ftt   1973
```

FBG domain

```
1974                                                            iglypf
1981 pkdcsqamln gdttsglyti ylngdkaqal evfcdmtsdg ggwivflrrk ngrenfyqnw
2041 kayaagfgdr reefwlgldn lnkitaqgqy elrvdlrdhg etafavydkf svgdaktryk
2101 lkvegysgta gdsmayhngr sfstfdkdtd saitncalsy kgafwyrnch rvnlmgrygd
2161 nnhsqgvnwf hwkghehsiq faemklrpsn frnlegrrkr a   2201
```

FIGURE 1

```
   1 attacagagg aaggagctcg ctatataagc cagccaaagt tggctgcacc ggccacagcc
  61 tgcctactgt caccogcctc tcccgcgcgc agatacacgc ccccgcctcc gtgggcacaa
 121 aggcagcgct gctggggaac tcgggggaac gcgcacgtgg gaaccgccgc agctccacac
 181 tccaggtact tcttccaagg acctaggtct ctcgcccatc ggaagaaaa taattctttc
 241 aagaagatca gggacaactg atttgaagtc tactctgtgc ttctaaatcc ccaattctgc
 301 tgaaagtgag ataccctaga gccctagagc cccagcagca cccagccaaa cccacctcca
 361 ccatgggggc catgactcag ctgttggcag gtgtcttcct tgctttcctt gccctgcta
 421 ccgaaggtgg ggtcctcaag aaagtcatcc ggcacaagcg acagagtggg gtgaacgcca
 481 ccctgccaga agagaaccag ccagtggtgt taaccacgt ttacaacatc aagctgccag
 541 tgggatccca gtgttcggtg gatctggagt cagccagtgg ggagaaagac ctggcaccgc
 601 cttcagagcc cagcgaaagc tttcaggagc acacagtgga tggggaaaac cagattgtct
 661 tcacacatcg catcaacatc ccccgccggg cctgtggctg tgccgcagcc cctgatgtta
 721 aggagctgct gagcagactg gaggagctgg agaacctggt gtcttcctg agggagcaat
 781 gtactgcagg agcaggctgc tgtctccagc ctgccacagg ccgcttggac accaggccct
 841 tctgtagcgg tcggggcaac ttcagcactg aaggatgtgg ctgtgtctgc gaacctggct
 901 ggaaaggccc caactgctct gagcccgaat gtccaggcaa ctgtcacctt cgaggccggt
 961 gcattgatgg gcagtgcatc tgtgacgacg gcttcacggg cgaggactgc agccagctgg
1021 cttgccccag cgactgcaat gaccagggca agtgcgtaaa tggagtctgc atctgtttcg
1081 aaggctacgc cggggctgac tgcagccgtg aaatctgccc agtgcctgc agtgaggagc
1141 acggcacatg tgtagatggc ttgtgtgtgt gccacgatgg ctttgcaggc gatgactgca
1201 acaagcctct gtgtctcaac aattgctaca accgtggacg atgcgtggag aatgagtgcg
1261 tgtgtgatga gggtttcacg ggcgaagact gcagtgagct catctgcccc aatgactgct
1321 tcgaccgggg ccgctgcatc aatggcacct gctactgcga agaaggcttc acaggtgaag
1381 actgcgggaa acccacctgc ccacatgcct gccacaccca gggccggtgt gaggagggcc
1441 agtgtgtatg tgatgagggc tttgccggtg tggactgcag cgagaagagg tgtcctgctg
1501 actgtcacaa tcgtggccgc tgtgtagacg ggcggtgtga gtgtgatgat ggtttcactg
1561 gagctgactg tggggagctc aagtgtccca atggctgcag tggccatggc cgctgtgtca
1621 atgggcagtg tgtgtgtgat gagggctata ctggggagga ctgcagccag ctacggtgcc
1681 ccaatgactg tcacagtcgg ggccgctgtg tcgagggcaa atgtgtatgt gagcaaggct
1741 tcaagggcta tgactgcagt gacatgagct gccctaatga ctgtcaccag cacggccgct
1801 gtgtgaatgg catgtgtgtt tgtgatgacg gctacacagg ggaagactgc cgggatcgcc
1861 aatgccccag ggactgcagc aacagggcc tctgtgtgga cggacagtgc gtctgtgagg
1921 acggcttcac cggccctgac tgtgcagaac tctcctgtcc aaatgactgc catggccagg
1981 gtcgctgtgt gaatgggcag tgcgtgtgcc atgaaggatt tatgggcaaa gactgcaagg
2041 agcaaagatg tcccagtgac tgtcatggcc agggccgctg cgtggacggc cagtgcatct
2101 gccacgaggg cttcacaggc ctggactgtg ccagcactc ctgcccagt gactgcaaca
2161 acttaggaca atgcgtctcg ggccgctgca tctgcaacga gggctacagc ggagaagact
2221 gctcagaggt gtctcctccc aaagacctcg ttgtgacaga agtgacggaa gagacggtca
2281 acctggcctg ggacaatgag atgcgggtca cagagtacct tgtcgtgtac acgcccacc
2341 acgagggtgg tctggaaatg cagttccgtg tgcctgggga ccagacgtcc accatcatcc
2401 aggagctgga gcctggtgtg gagtacttta tccgtgtatt tgccatcctg gagaacaaga
2461 agagcattcc tgtcagcgcc agggtggcca cgtacttacc tgcacctgaa ggcctgaaat
2521 tcaagtccat caaggagaca tctgtggaag tggagtggga tcctctagac attgcttttg
2581 aaacctggga gatcatcttc cggaatatga taaagaaga tgaggagag atcaccaaaa
2641 gcctgaggag gccagagacc tcttaccggc aaactggtct agctcctggg caagagtatg
2701 agatatctct gcacatagtg aaaaacaata cccgggccc tggcctgaag agggtgacca
2761 ccacacgctt ggatgccccc agccagatcg aggtgaaaga tgtcacagac accactgcct
2821 tgatcacctg gttcaagccc ctgctgaga tcgatggcat tgagctgacc tacggcatca
2881 aagacgtgcc aggagaccgt accaccatcg atctcacaga ggacgagaac cagtactcca
2941 tcgggaacct gaagcctgac actgagtacg aggtgtccct catctcccgc agaggtgaca
3001 tgtcaagcaa cccagccaaa gagaccttca acaggcct cgatgctccc aggaatcttc
```

FIGURE 2

```
3061 gacgtgtttc ccagacagat aacagcatca ccctggaatg gaggaatggc aaggcagcta
3121 ttgacagtta cagaattaag tatgccccca tctctggagg ggaccacgct gaggttgatg
3181 ttccaaagag ccaacaagcc acaaccaaaa ccacactcac aggtctgagg ccgggaactg
3241 aatatgggat tggagtttct gctgtgaagg aagacaagga gagcaatcca gcgaccatca
3301 acgcagccac agagttggac acgccaagg accttcaggt ttctgaaact gcagagacca
3361 gcctgaccct gctctggaag acaccgttgg ccaaatttga ccgctaccgc ctcaattaca
3421 gtctccccac aggccagtgg gtgggagtgc agcttccaag aaacaccact tcctatgtcc
3481 tgagaggcct ggaaccagga caggagtaca atgtcctcct gacagccgag aaaggcagac
3541 acaagagcaa gcccgcacgt gtgaaggcat ccactgaaca agccctgag ctggaaaacc
3601 tcaccgtgac tgaggttggc tgggatggcc tcagactcaa ctggaccgca gctgaccagg
3661 cctatgagca ctttatcatt caggtgcagg aggccaacaa ggtggaggca gctcggaacc 3721 tcaccgtgcc tggcagcctt cgggctgtgg acataccggg cctcaaggct gctacgcctt
3781 atacagtctc catctatggg gtgatccagg gctatagaac accagtgctc tctgctgagg
3841 cctccacagg ggaaactccc aatttgggag aggtcgtggt ggccgaggtg ggctgggatg
3901 ccctcaaact caactggact gctccagaag gggcctatga gtacttttc attcaggtgc
3961 aggaggctga cacagtagag gcagcccaga acctcaccgt cccaggagga ctgaggtcca
4021 cagacctgcc tgggctcaaa gcagccactc attataccat caccatccgc ggggtcactc
4081 aggacttcag cacaaccct ctctctgttg aagtcttgac agaggaggtt ccagatatgg
4141 gaaacctcac agtgaccgag gttagctggg atgctctcag actgaactgg accacgccag
4201 atggaaccta tgaccagttt actattcagg tccaggaggc tgaccaggtg gaagaggctc
4261 acaatctcac ggttcctggc agcctgcgtt ccatggaaat cccaggcctc agggctggca
4321 ctccttacac agtcaccctg cacggcgagg tcagggccaa cagcactcga ccccttgctg
4381 tagaggtcgt cacagaggat ctcccacagc tgggagattt agccgtgtct gaggttggct
4441 gggatggcct cagactcaac tggaccgcag ctgacaatgc ctatgagcac tttgtcattc
4501 aggtgcagga ggtcaacaaa gtggaggcag cccagaacct cacgttgcct ggcagcctca
4561 gggctgtgga catcccgggc ctcgaggctg ccacgcctta tagtctcc atctatgggg
4621 tgatccgggg ctatagaaca ccagtactct ctgctgaggc ctccacagcc aaagaacctg
4681 aaattggaaa cttaaatgtt tctgacataa ctcccgagag cttcaatctc tcctggatgg
4741 ctaccgatgg gatcttcgag acctttacca ttgaaattat tgattccaat aggttgctgg
4801 agactgtgga atataatatc tctggtgctg aacgaactgc ccatatctca gggctacccc
4861 ctagtactga ttttattgtc tacctctctg gacttgctcc cagcatccgg accaaaacca
4921 tcagtgccac agccacgaca gaggccctgc cccttctgga aaacctaacc atttccgaca
4981 ttaatcccta cgggttcaca gtttcctgga tggcatcgga gaatgccttt gacagctttc
5041 tagtaacggt ggtggattct gggaagctgc tggaccccca ggaattcaca ctttcaggaa
5101 cccagaggaa gctggagctt agaggcctca taactggcat tggctatgag gttatggtct
5161 ctggcttcac ccaagggcat caaaccaagc ccttgagggc tgagattgtt acagaagccg
5221 aaccggaagt tgacaacctt ctggtttcag atgccacccc agacggtttc cgtctgtcct
5281 ggacagctga tgaaggggtc ttcgacaatt ttgttctcaa aatcagagat accaaaaagc
5341 agtctgagcc actggaaata accctacttg ccccgaacg taccagggac ataacaggtc
5401 tcagagaggc tactgaatac gaaattgaac tctatggaat aagcaaagga aggcgatccc
5461 agacagtcag tgctatagca acaacagcca tgggctcccc aaaggaagtc attttctcag
5521 acatcactga aaattcggct actgtcagct ggaggcacc cacagcccaa gtggagagct
5581 tccggattac ctatgtgccc attacaggag gtacaccctc catggtaact gtggacggaa
5641 ccaagactca gaccaggctg gtgaaactca tacctggcgt ggagtacctt gtcagcatca
5701 tcgccatgaa gggctttgag gaaagtgaac ctgtctcagg gtcattcacc acagctctgg
5761 atggcccatc tggcctggtg acagccaaca tcactgactc agaagccttg gccaggtggc
5821 agccagccat tgccactgtg gacagttatg tcatctccta cacaggcgag aaagtgccag
5881 aaattacacg cacggtgtcc gggaacacag tggagtatgc tctgaccgac ctcgagcctg
5941 ccacggaata cacactgaga atcttgcag agaaagggcc ccagaagagc tcaaccatca
```

*Figure 2 (Continued)*

```
6001 ctgccaagtt cacaacagac ctcgattctc caagagactt gactgctact gaggttcagt
6061 cggaaactgc cctccttacc tggcgacccc cccgggcatc agtcaccggt tacctgctgg
6121 tctatgaatc agtggatggc acagtcaagg aagtcattgt gggtccagat accacctcct
6181 acagcctggc agacctgagc ccatccaccc actacacagc caagatccag gcactcaatg
6241 ggccctgag gagcaatatg atccagacca tcttcaccac aattggactc ctgtacccct
6301 tccccaagga ctgctcccaa gcaatgctga atggagacac gacctctggc ctctacacca
6361 tttatctgaa tggtgataag gctgaggcgc tggaagtctt ctgtgacatg acctctgatg
6421 gggtggatg gattgtgttc ctgagacgca aaacggacg cgagaacttc taccaaaact
6481 ggaaggcata tgctgctgga tttggggacc gcagagaaga attctggctt gggctggaca
6541 acctgaacaa aatcacagcc caggggcagt acgagctccg ggtggacctg cgggaccatg
6601 gggagacagc ctttgctgtc tatgacaagt tcagcgtggg agatgccaag actcgctaca
6661 agctgaaggt ggaggggtac agtgggacag caggtgactc catggcctac cacaatggca
6721 gatccttctc caccttgac aaggacacag attcagccat caccaactgt gctctgtcct
6781 acaaagggc tttctggtac aggaactgtc accgtgtcaa cctgatgggg agatatgggg
6841 acaataacca cagtcagggc gttaactggt ccactggaa gggccacgaa cactcaatcc
6901 agtttgctga gatgaagctg agaccaagca acttcagaaa tcttgaaggc aggcgcaaac
6961 gggcataaat tccagggacc actgggtgag agaggaataa ggcccagagc gaggaaagga
7021 ttttaccaaa gcatcaatac aaccagccca accatcggtc cacacctggg catttggtga
7081 gagtcaaagc tgaccatgga tccctggggc caacggcaac agcatggcc tcacctcctc
7141 tgtgatttct tctttgcac caaagacatc agtctccaac atgtttctgt ttgttgttt
7201 gattcagcaa aaatctccca gtgacaacat cgcaatagtt ttttacttct cttaggtggc
7261 tctgggaatg ggagaggggt aggatgtaca ggggtagttt gttttagaac cagccgtatt
7321 ttacatgaag ctgtataatt aattgtcatt attttgtta gcaaagatta aatgtgtcat
7381 tggaagccat ccctttttt acatttcata caacagaaac cagaaagca atactgtttc
7441 catttaagg atatgattaa tattattaat ataataatga tgatgatgat gatgaaaact
7501 aaggattttt caagagatct ttctttccaa aacatttctg gacagtacct gattgtattt
7561 ttttttaaa taaaagcaca agtactttg agtttgttaa aaaaaaaaa aaaaa
```

*FIGURE 2 (Continued)*

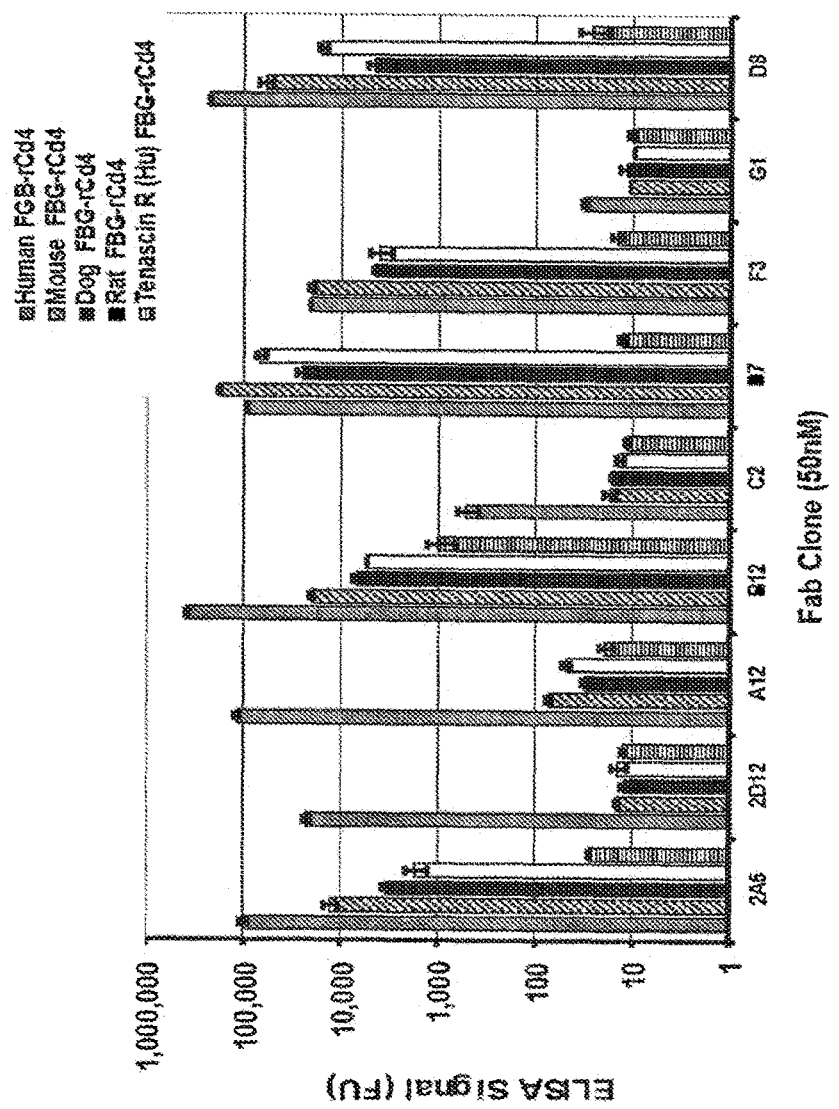

Figure 6C:
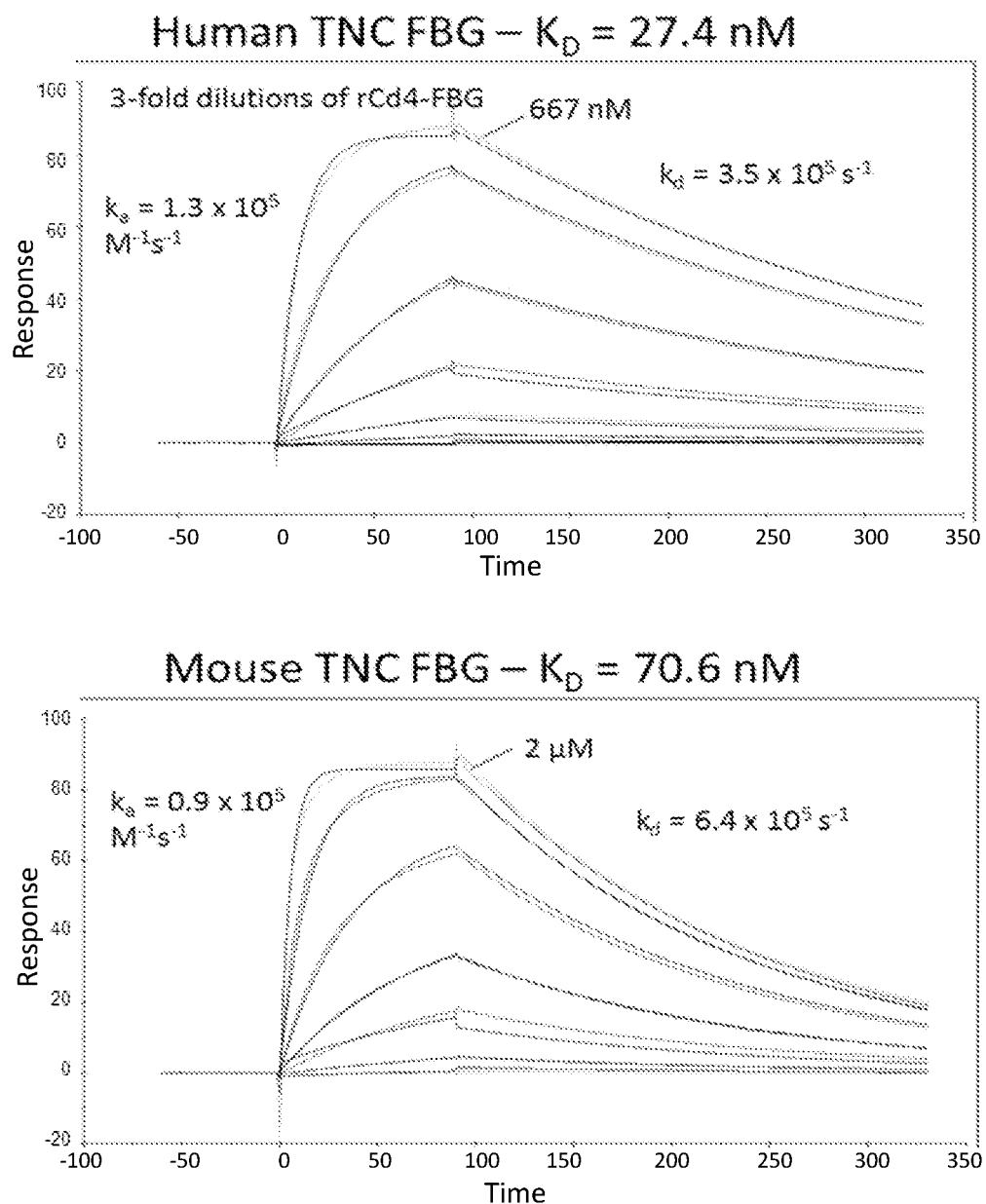

Fab B12 – SPR Results
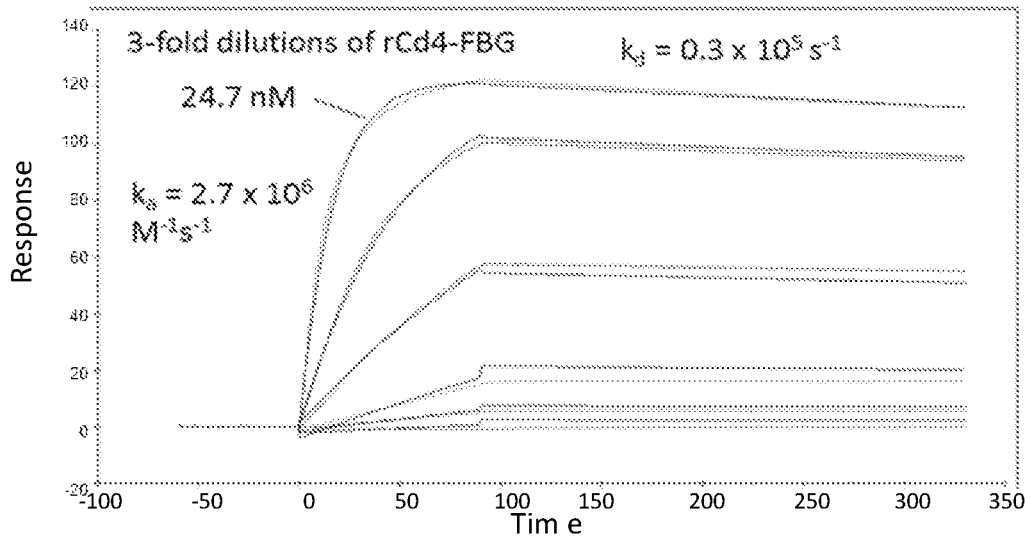
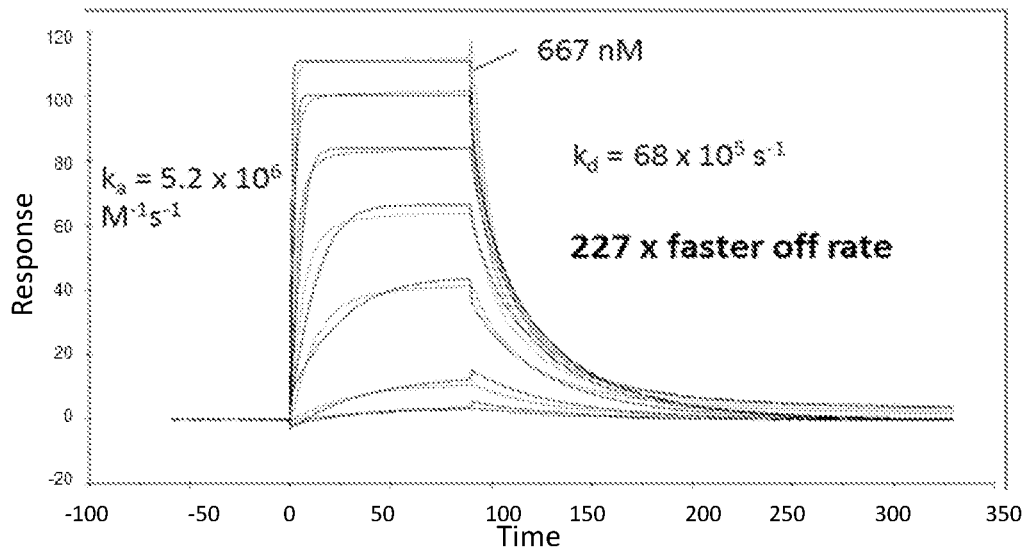
Assay format = Fab capture (23 nM) on anti-$C_L\kappa$ / anti-$C_L\lambda$ CM5 sensor chip followed by rCd4-FBG injection. Regeneration with 10 mM Glycine, pH2
*Figure 6A*

Fab B12 – SPR Results
Rat TNR FBG – $K_D = 7.9$ nM
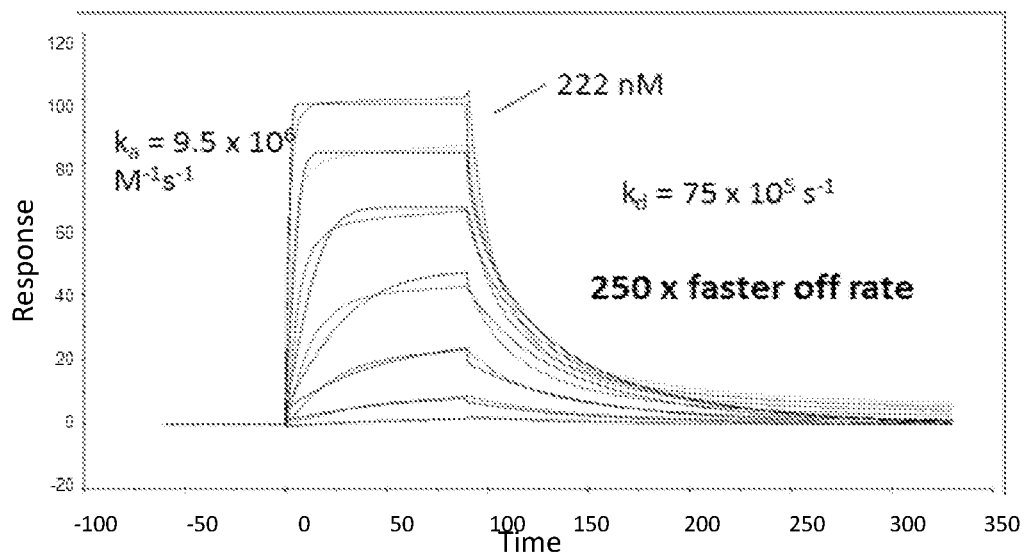
Human TNR FBG – $K_D = 33.9$ nM
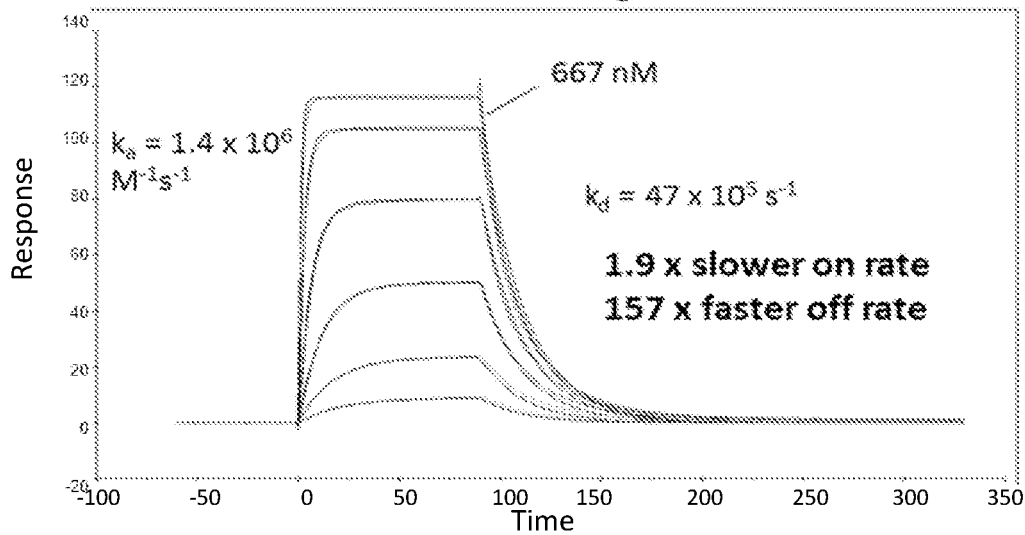
Assay format = Fab capture (23 nM) on anti-$C_L\kappa$ / anti-$C_L\lambda$ CM5 sensor chip followed by rCd4-FBG injection. Regeneration with 10 mM Glycine, pH2
*Figure 6A (Continued)*

Fab 2A5 – SPR Results
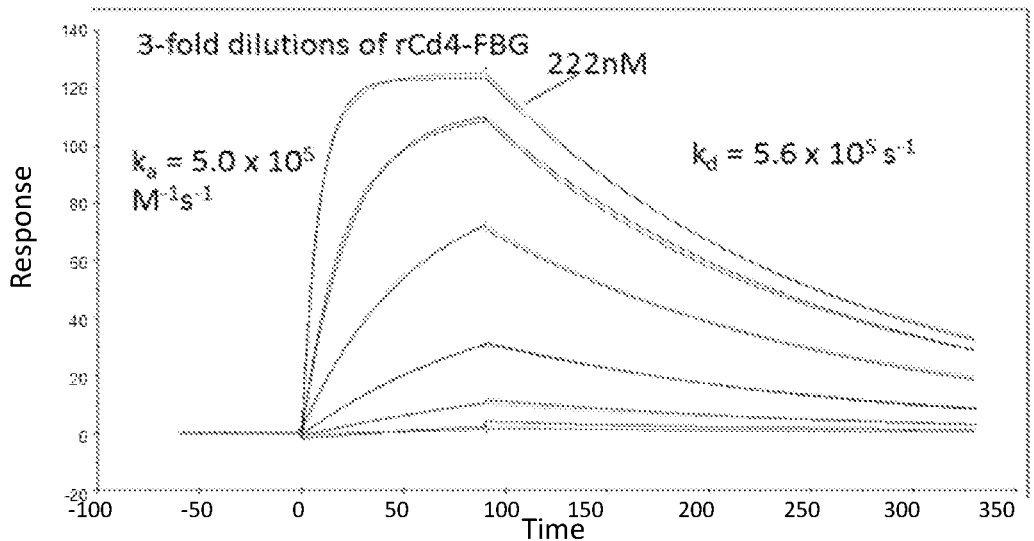
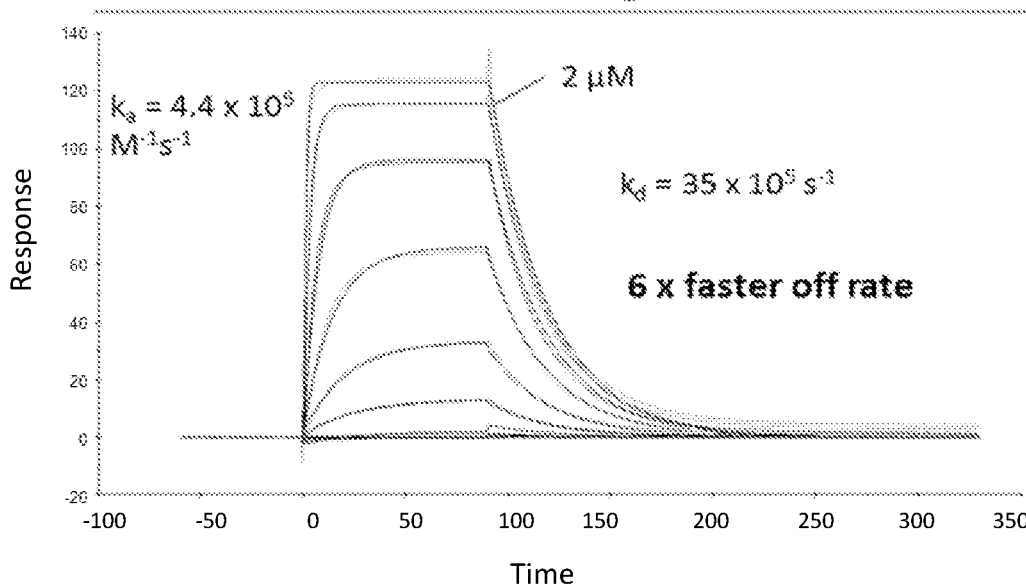
Assay format = Fab capture (23 nM) on anti-$C_L\kappa$ / anti-$C_L\lambda$ CM5 sensor chip followed by rCd4-FBG injection. Regeneration with 10 mM Glycine, pH2
*Figure 6B*

Fab 2A5 – SPR Results
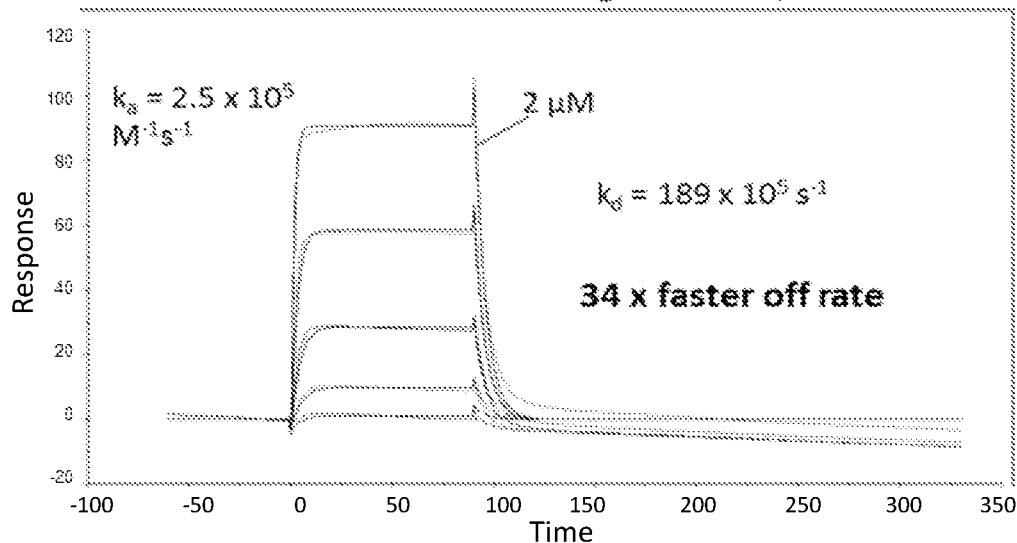
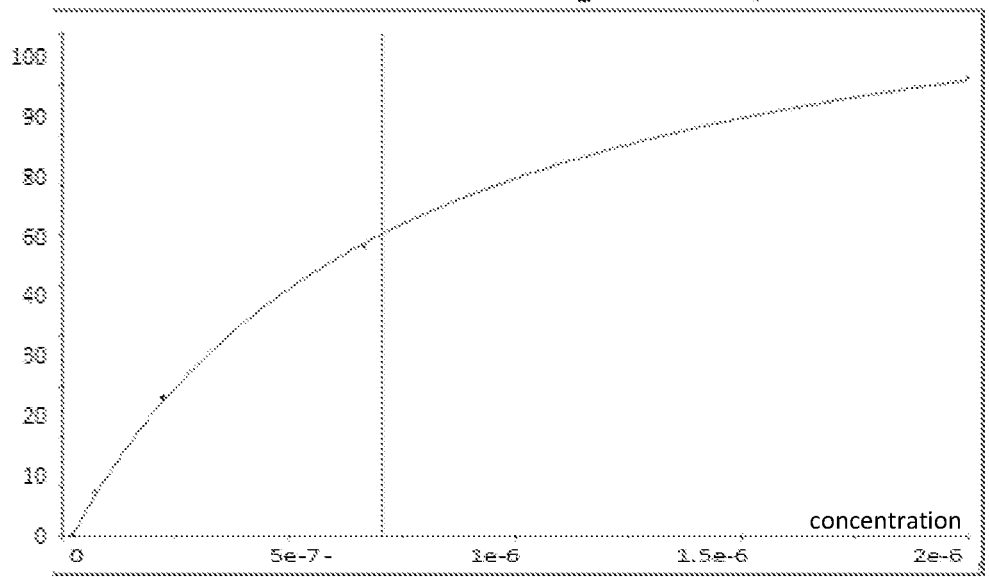
Assay format = Fab capture (23 nM) on anti-$C_L\kappa$ / anti-$C_L\lambda$ CM5 sensor chip followed by rCd4-FBG injection. Regeneration with 10 mM Glycine, pH2
*Figure 6B (Continued)*

Fab F3 – SPR Results
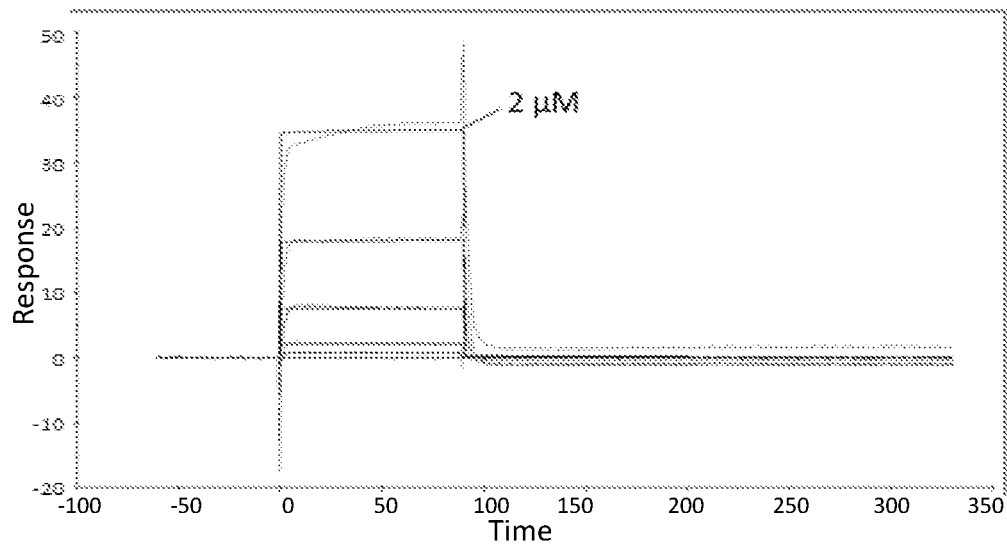
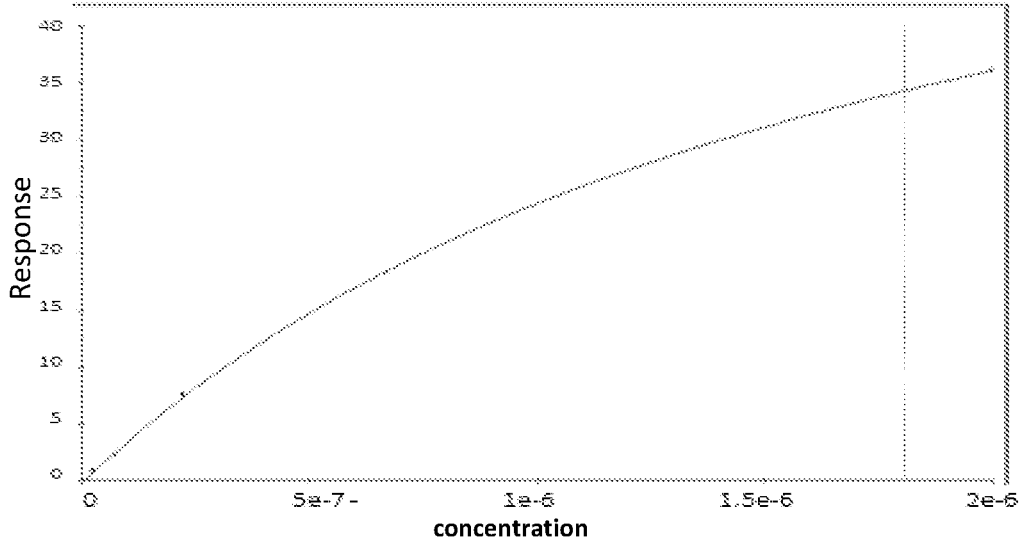
Assay format = Fab capture (23 nM) on anti-$C_L\kappa$ / anti-$C_L\lambda$ CM5 sensor chip followed by rCd4-FBG injection. Regeneration with 10 mM Glycine, pH2
*Figure 6C (Continued)*

Fab D8 – SPR Results
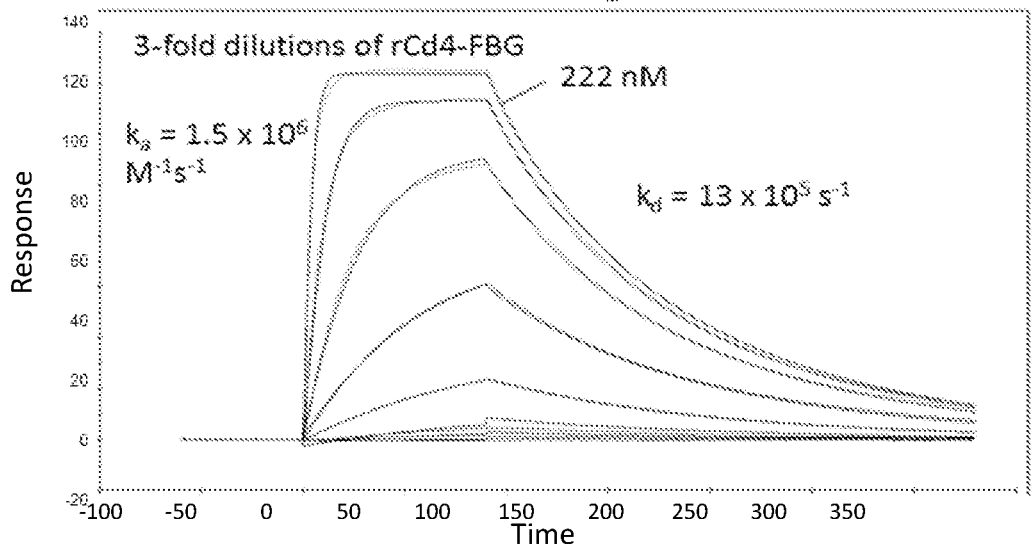
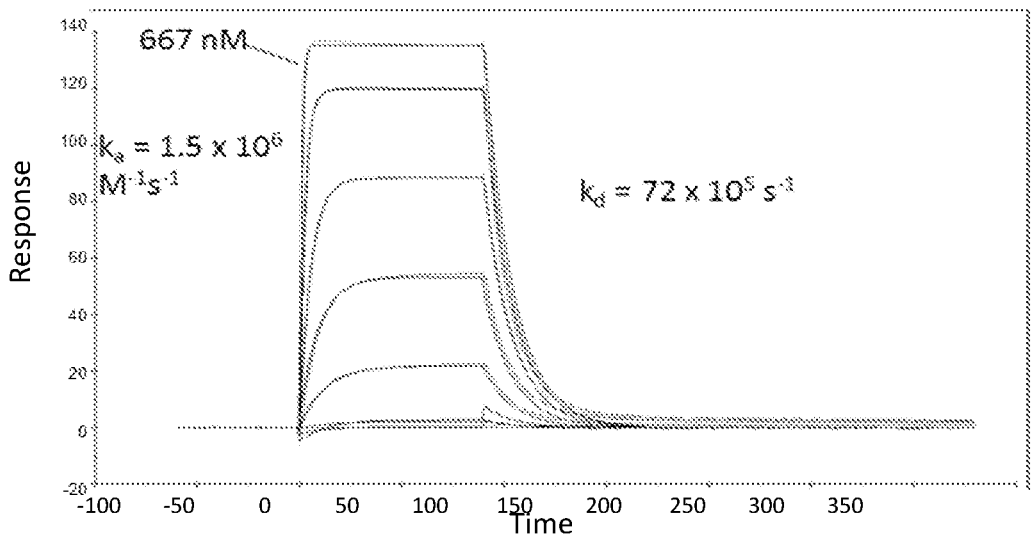
Assay format = Fab capture (23 nM) on anti-$C_L\kappa$ / anti-$C_L\lambda$ CM5 sensor chip followed by rCd4-FBG injection. Regeneration with 10 mM Glycine, pH2
*Figure 6D*

Fab D8 – SPR Results
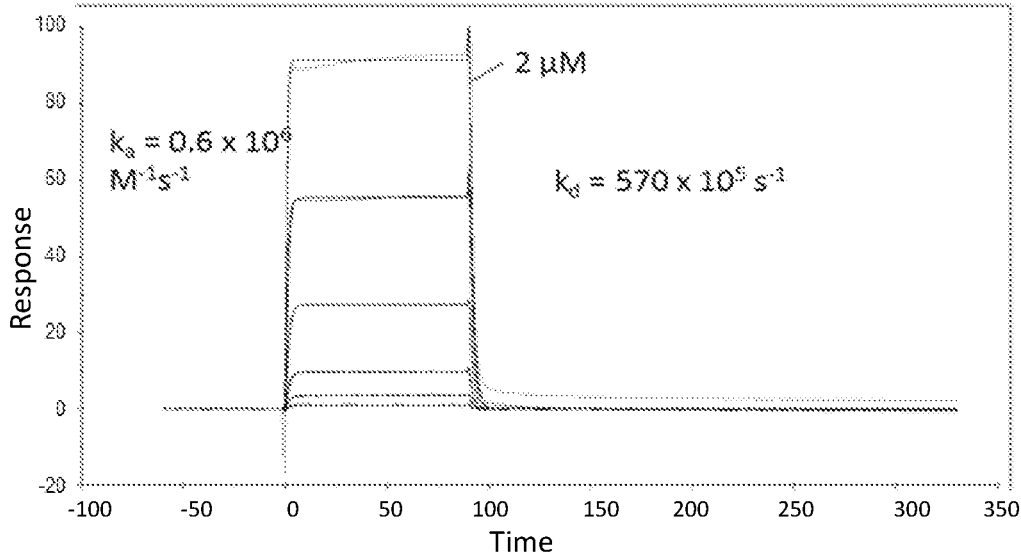
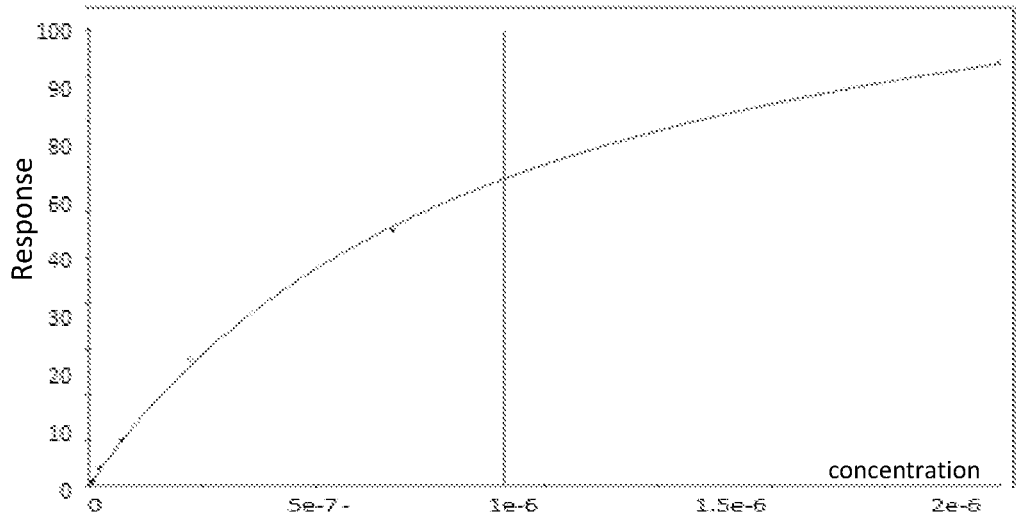
Assay format = Fab capture (23 nM) on anti-$C_L\kappa$ / anti-$C_L\lambda$ CM5 sensor chip followed by rCd4-FBG injection. Regeneration with 10 mM Glycine, pH2
*Figure 6D (Continued)*

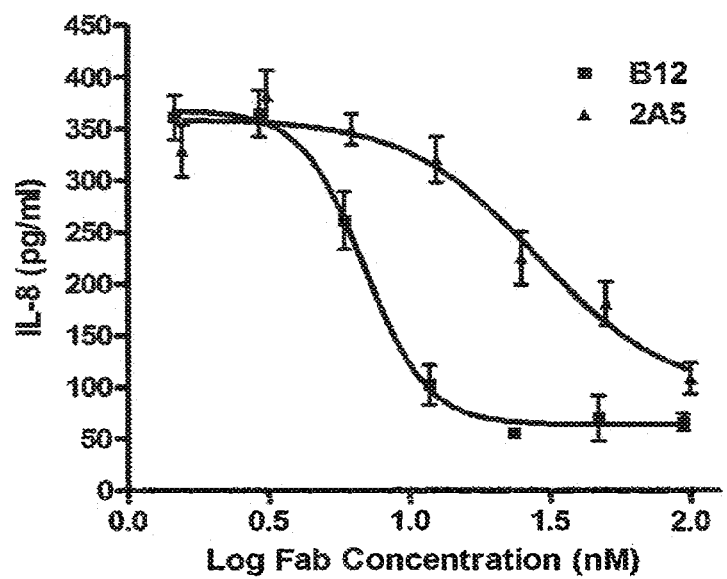
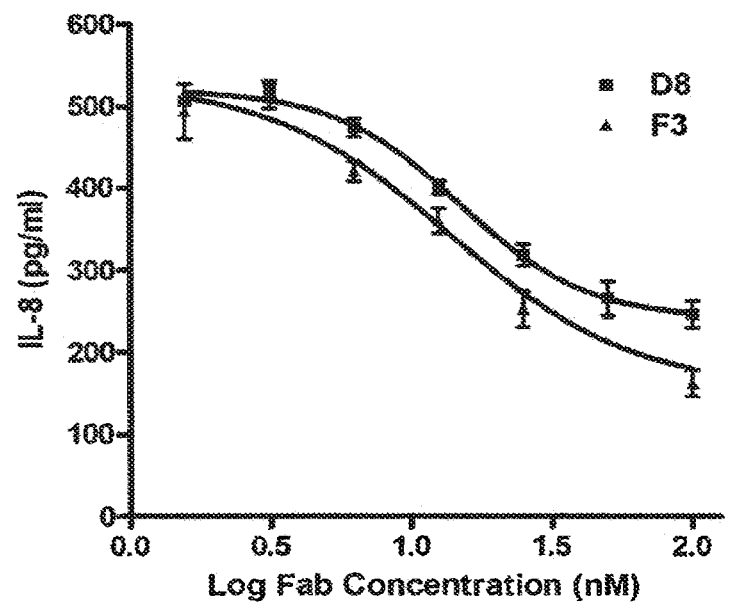
FIGURE 8

Oligonucleotides for VH and VL CDR3 mutagenesis

| | | |
|---|---|---|
| F3 VH 3.1 | AGCATTAGTCAGTCAGCAGAAAAGNNSNNSNNSNNSNNSNNSNNSNNTCGCACAGTAATACACAGCCGTGTC | SEQ ID NO: 97 |
| F3 VH 3.2 | CTGGCCCCAGATATCAAAAGCATTNNSNNSNNSNNSNNSNNSNNTTGGTCATATAGCCTTCTCGCACAG | SEQ ID NO: 98 |
| F3 VH 3.3 | GGTGACCAGGGTTCCTGGCCCCAGNNSNNSNNSNNSNNSNNSNNCTCAGCAGTAGTAAATAGTTGGTCATAGCC | SEQ ID NO: 99 |
| F3 VL 3.1 | GGTCCTTCGCGGCCGAACACCCAATTSNNSNNSNNSNNSNNACAGTAGTAGTCAGCCTCGTCTC | SEQ ID NO: 100 |
| F3 VL 3.2 | GGTGACTTGGTCCTTCGCGGCCGAASNNSNNSNNSNNSNNSNNATAAGACTGCACAGTAGTCAGC | SEQ ID NO: 101 |
| B12 VH 3.1 | CTTGGCCCCAGATATCAAAAGTATCSNNSNNSNNSNNSNNSNNTTTGCACAGTAATACAAGGCCGTGTC | SEQ ID NO: 102 |
| B12 VH 3.2 | CATTGTCCCTTGGCCCCAGATATCSNNSNNSNNSNNSNNCGAGATATCTTTGCACAGTAATAC | SEQ ID NO: 103 |
| B12 VH 3.3 | GGTGACCATTGTCCCTTGGCCCCASNNSNNSNNSNNSNNSNNACTGCCGAGATATCTTTGCACAG | SEQ ID NO: 104 |
| B12 VL 3.1 | GGTCCCTTGGCCGAACGTCTTGGTCCCCGAASNNSNNSNNSNNSNNAACAGTAGTAAGTAAGTTC | SEQ ID NO: 105 |
| B12 VL 3.2 | GATATCCACTTTGGTCCTGGGCCCTTGGCCCCAGTAGGTCAAGSCNNSNNSNNSNNTGTTGACACAGTAATACACGGCCGGT | SEQ ID NO: 106 |
| 2A5 VH 3.1 | GGCGGTTCCCTGGGCCCAGTAGGTSNNSNNSNNSNNSNNSNNTGGGCTGTTGCACAGTAATACAC | SEQ ID NO: 107 |
| 2A5 VH 3.2 | CAGGGTTCCCTGGGCCCAGTAGGTSNNSNNSNNSNNSNNSNNSNNACTCTTCTGGGCTGTTGCACAGTA | SEQ ID NO: 108 |
| 2A5 VH 3.3 | GGTGACCAGGGTTCCCTGGGCCCASNNSNNSNNSNNSNNSNNSNNACTCTTCTGGGCTGTTGCACAGTA | SEQ ID NO: 109 |
| 2A5 VL 3.1 | GGTCCCTTGGCCGAACGTCCACGGSSNNSNNSNNSNNSNNACAGTAGTAAGTTGACAGTAAGTTC | SEQ ID NO: 110 |
| 2A5 VL 3.2 | CCTCCACCTGGTCCCTTGGCCGAASNNSNNSNNSNNSNNSNNACTCTGTTGACAGTAAGTTGC | SEQ ID NO: 111 |

FIGURE 9B

FIGURE 13A
FIGURE 13C
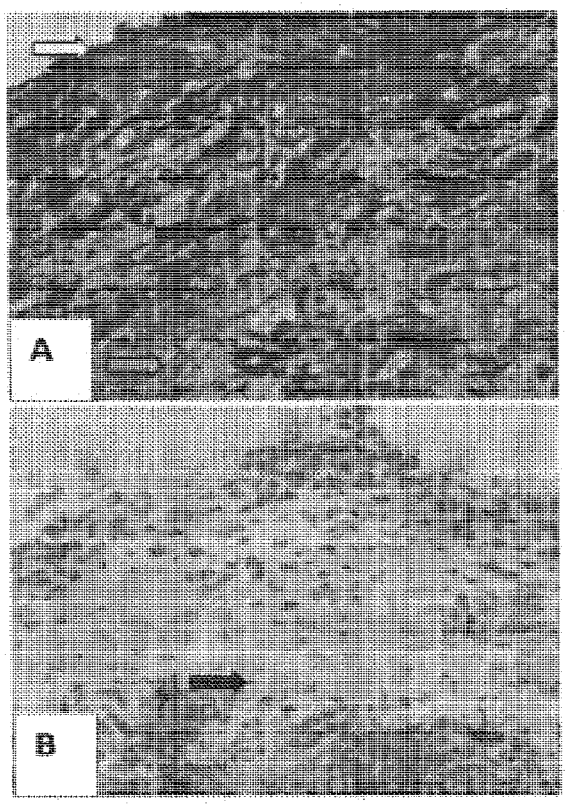
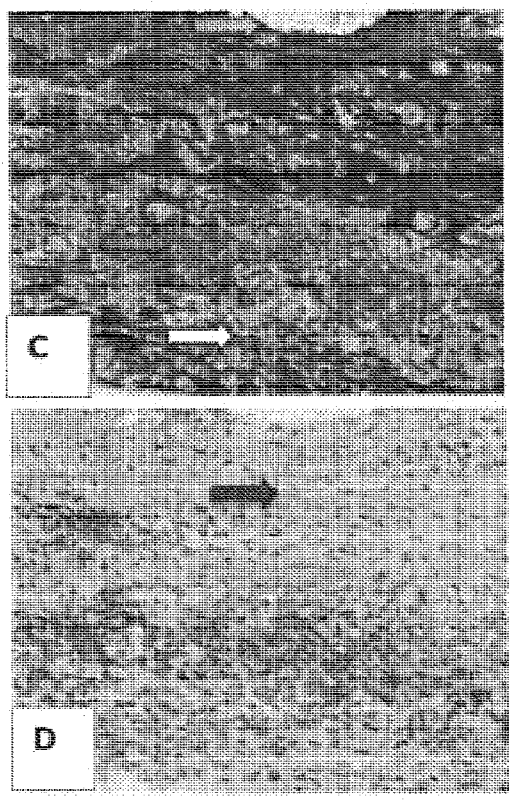
FIGURE 13B
FIGURE 13D

B12  IgG4 control

| Construct | N-term | Species | Primer name (F) | Primer sequence (F) | Primer name (R) | Primer sequence (R) |
|---|---|---|---|---|---|---|
| FBG-X | minus | human | 2561 | GGTACCTCGCGAATGCATCTAG | 2562 | CATGCAGGCCTCTGCAGTCG |
| FBG-X | plus | human | 2565 | TTTTTTCCATGGCCCAGATTGGACTCCTGTACCCCTT CCCAAAGATTGCTCTCAGGC | 2562 | CATGCAGGCCTCTGCAGTCG |
| FBG-X | minus | mouse | 2561 | GGTACCTCGCGAATGCATCTAG | 2562 | CATGCAGGCCTCTGCAGTCG |
| FBG-X | plus | mouse | 2566 | TTTTTCCATGGCCCAGATTGGACTCCTGTACCCCTT CCCTCGCGACTGCTCACAG | 2562 | CATGCAGGCCTCTGCAGTCG |
| X-FBG | minus | human | 2567C | TTTTTGGATCCATCATCATCATCATCATCACTTCCCA AAGATTGCTCTCAGGC | 2570 | TTTTTAAGCTTTTATTACGCCCGT TTACGCCGACCCTC |
| X-FBG | plus | human | 2567 | TTTTTGGATCCATCATCATCATCATCATCACATGGAC TCCTGTACCCCTTCCCAAAGATTGCTCTCAGGC | 2570 | TTTTTAAGCTTTTATTACGCCCGT TTACGCCGACCCTC |
| X-FBG | minus | mouse | 2568C | TTTTTGGATCCATCATCATCATCATCATCACTTCCCTG GCGAGTGCTCACAG | 2571 | TTTTTAAGCTTTTATTACGCCCGT TTCCGCCGACCTTC |
| X-FBG | plus | mouse | 2568 | TTTTTGGATCCATCATCATCATCATCATCACATGGAC TCCTGTACCCCTTCCCTCGCGACTGCTCACAG | 2571 | TTTTTAAGCTTTTATTACGCCCGT TTCCGCCGACCTTC |
| BamHI-His6-HindIII | N/A | N/A | 2574 | TTTTTGGATCCATCATCATCATCATCATCACTAATAAAA G | 2575 | TTTTTAAGCTTTTATTAGTGATGG TGATGATGGG |
| His-FBG | plus | human | 2580 | TTTTTCTCGAGCATCATCATCATCATCATCACATTGGAC TCC | 2570 | TTTTTAAGCTTTTATTACGCCCGT TTACGCCGACCCTC |
| His-FBG | plus | mouse | 2580 | TTTTTCTCGAGCATCATCATCATCATCATCACATTGGAC TCC | 2571 | TTTTTAAGCTTTTATTACGCCCGT TTCCGCCGACCTTC |

FIGURE 23

SEQUENCE LISTING

```
<160> NUMBER OF SEQ ID NOS: 170

<210> SEQ ID NO 1
<211> LENGTH: 5
<212> TYPE: PRT
<213> ORGANISM: Artificial Sequence
<220> FEATURE:
<223> OTHER INFORMATION: Antibody 2A5 VH CDR1

<400> SEQUENCE: 1
```

Glu Leu Ser Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Antibody 2A5 VH CDR2

<400> SEQUENCE: 2

Gly Phe Asp Pro Glu Asp Gly Glu Thr Ile Tyr Ala Gln Lys Phe Gln
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: Antibody 2A5 VH CDR3

<400> SEQUENCE: 3

Ala Gln Lys Glu Thr Tyr Ala Leu Thr Tyr
1               5                   10

<210> SEQ ID NO 4
<211> LENGTH: 119
<212> TYPE: PRT
<213> ORGANISM: Artificial Sequence
<220> FEATURE:
<223> OTHER INFORMATION: Antibody 2A5 VH amino acid sequence

<400> SEQUENCE: 4

Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Lys Glu Thr Tyr Ala Leu Thr Tyr Trp Gly Gln Gly
            100                 105                 110

Thr Leu Val Thr Val Ser Ser
        115

<210> SEQ ID NO 5
<211> LENGTH: 11
<212> TYPE: PRT
<213> ORGANISM: Artificial Sequence
<220> FEATURE:
<223> OTHER INFORMATION: Antibody 2A5 VL CDR1

<400> SEQUENCE: 5

Arg Ala Ser Gln Tyr Ile Gln Gly Phe Leu Asn
1               5                   10

-continued

```
<210> SEQ ID NO 6
<211> LENGTH: 7
<212> TYPE: PRT
<213> ORGANISM: Artificial Sequence
<220> FEATURE:
<223> OTHER INFORMATION: Antibody 2A5 VL CDR2

<400> SEQUENCE: 6

Ala Ala Ser Thr Leu Gln Asp
1               5

<210> SEQ ID NO 7
<211> LENGTH: 9
<212> TYPE: PRT
<213> ORGANISM: Artificial Sequence
<220> FEATURE:
<223> OTHER INFORMATION: Antibody 2A5 VL CDR3

<400> SEQUENCE: 7

Gln Gln Ser Tyr Ser Thr Pro Trp Thr
1               5

<210> SEQ ID NO 8
<211> LENGTH: 108
<212> TYPE: PRT
<213> ORGANISM: Artificial Sequence
<220> FEATURE:
<223> OTHER INFORMATION: Antibody 2A5 VL amino acid sequence

<400> SEQUENCE: 8

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys Arg
            100                 105

<210> SEQ ID NO 9
<211> LENGTH: 5
<212> TYPE: PRT
<213> ORGANISM: Artificial Sequence
<220> FEATURE:
<223> OTHER INFORMATION: Antibody B12 VH CDR1

<400> SEQUENCE: 9

Asp Tyr Ala Met His
1               5

<210> SEQ ID NO 10
<211> LENGTH: 17
<212> TYPE: PRT
<213> ORGANISM: Artificial Sequence
<220> FEATURE:
<223> OTHER INFORMATION: Antibody B12 VH CDR2

<400> SEQUENCE: 10
```

```
Gly Ile Ser Gly Ser Gly Gly Ser Thr Tyr Tyr Ala Asp Ser Val Lys
1               5                   10                  15

Gly

<210> SEQ ID NO 11
<211> LENGTH: 11
<212> TYPE: PRT
<213> ORGANISM: Artificial Sequence
<220> FEATURE:
<223> OTHER INFORMATION: Antibody B12 VH CDR3

<400> SEQUENCE: 11

Asp Ile Ser Ala Val Pro Asp Thr Phe Asp Ile
1               5                   10

<210> SEQ ID NO 12
<211> LENGTH: 120
<212> TYPE: PRT
<213> ORGANISM: Artificial Sequence
<220> FEATURE:
<223> OTHER INFORMATION: Antibody B12 VH amino acid sequence

<400> SEQUENCE: 12

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ala Val Pro Asp Thr Phe Asp Ile Trp Gly Gln
            100                 105                 110

Gly Thr Met Val Thr Val Ser Ser
        115                 120

<210> SEQ ID NO 13
<211> LENGTH: 7
<212> TYPE: PRT
<213> ORGANISM: Artificial Sequence
<220> FEATURE:
<223> OTHER INFORMATION: Antibody B12 VL CDR2

<400> SEQUENCE: 13

Asp Ala Ser Asn Leu Glu Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Antibody B12 VL CDR3

<400> SEQUENCE: 14

Gln Gln Ser Tyr Ser Thr Pro Gln Thr
1               5
```

```
<210> SEQ ID NO 15
<211> LENGTH: 108
<212> TYPE: PRT
<213> ORGANISM: Artificial Sequence
<220> FEATURE:
<223> OTHER INFORMATION: Antibody B12 VL amino acid sequence

<400> SEQUENCE: 15

Asp Ile Gln Met Thr Gln Ser Pro Ala Ser Leu Pro Thr Pro Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys Arg
            100                 105

<210> SEQ ID NO 16
<211> LENGTH: 5
<212> TYPE: PRT
<213> ORGANISM: Artificial Sequence
<220> FEATURE:
<223> OTHER INFORMATION: Antibody D8 VH CDR1

<400> SEQUENCE: 16

Ser Tyr Gly Ile Ser
1               5

<210> SEQ ID NO 17
<211> LENGTH: 17
<212> TYPE: PRT
<213> ORGANISM: Artificial Sequence
<220> FEATURE:
<223> OTHER INFORMATION: Antibody D8 VH CDR2

<400> SEQUENCE: 17

Trp Ile Ser Ala Tyr Asn Gly Asn Thr Asn Tyr Ala Gln Lys Leu Gln
1               5                   10                  15

Gly

<210> SEQ ID NO 18
<211> LENGTH: 8
<212> TYPE: PRT
<213> ORGANISM: Artificial Sequence
<220> FEATURE:
<223> OTHER INFORMATION: Antibody D8 VH CDR3

<400> SEQUENCE: 18

Asn Gln Asp Ser Ser Ser Asp Tyr
1               5

<210> SEQ ID NO 19
<211> LENGTH: 117
<212> TYPE: PRT
<213> ORGANISM: Artificial Sequence
<220> FEATURE:
<223> OTHER INFORMATION: Antibody D8 VH amino acid sequence
```

<400> SEQUENCE: 19

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gln Asp Ser Ser Ser Asp Tyr Trp Gly Gln Gly Thr Leu
            100                 105                 110

Val Thr Val Ser Ser
        115

<210> SEQ ID NO 20
<211> LENGTH: 9
<212> TYPE: PRT
<213> ORGANISM: Artificial Sequence
<220> FEATURE:
<223> OTHER INFORMATION: Antibody D8 VL CDR3

<400> SEQUENCE: 20

Gln Gln Ser Tyr Ser Thr Leu Gln Thr
1               5

<210> SEQ ID NO 21
<211> LENGTH: 108
<212> TYPE: PRT
<213> ORGANISM: Artificial Sequence
<220> FEATURE:
<223> OTHER INFORMATION: Antibody D8 VL amino acid sequence

<400> SEQUENCE: 21

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Gln
                85                  90                  95

Thr Phe Gly Gln Gly Thr Lys Val Asp Ile Lys Arg
            100                 105

<210> SEQ ID NO 22
<211> LENGTH: 5
<212> TYPE: PRT
<213> ORGANISM: Artificial Sequence
<220> FEATURE:
<223> OTHER INFORMATION: Antibody F3 VH CDR1

<400> SEQUENCE: 22

Ser Tyr Gly Met His
1               5

<210> SEQ ID NO 23
<211> LENGTH: 17
<212> TYPE: PRT
<213> ORGANISM: Artificial Sequence
<220> FEATURE:
<223> OTHER INFORMATION: Antibody F3 VH CDR2

<400> SEQUENCE: 23

Val Ile Ser Tyr Asp Gly Ser Asn Lys Tyr Tyr Ala Asp Ser Val Lys
1               5                   10                  15

Gly

<210> SEQ ID NO 24
<211> LENGTH: 16
<212> TYPE: PRT
<213> ORGANISM: Artificial Sequence
<220> FEATURE:
<223> OTHER INFORMATION: Antibody F3 VH CDR3

<400> SEQUENCE: 24

Glu Gly Tyr Asp Gln Leu Phe Ser Ala Glu Ser Asn Ala Phe Asp Ile
1               5                   10                  15

<210> SEQ ID NO 25
<211> LENGTH: 125
<212> TYPE: PRT
<213> ORGANISM: Artificial Sequence
<220> FEATURE:
<223> OTHER INFORMATION: Antibody F3 VH amino acid sequence

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Gly Asn Ser Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Arg Glu Gly Tyr Asp Gln Leu Phe Ser Ala Glu Ser Asn Ala Phe
            100                 105                 110

Asp Ile Trp Gly Gln Gly Thr Leu Val Thr Val Ser Ser
        115                 120                 125

<210> SEQ ID NO 26
<211> LENGTH: 13
<212> TYPE: PRT
<213> ORGANISM: Artificial Sequence
<220> FEATURE:
<223> OTHER INFORMATION: Antibody F3 VL CDR1

<400> SEQUENCE: 26

Thr Arg Ser Ser Gly Ser Ile Ala Ser Tyr Phe Val Gln
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Antibody F3 VL CDR2

<400> SEQUENCE: 27

Glu Asp Asn Gln Arg Pro Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Antibody F3 VL CDR3

<400> SEQUENCE: 28

Gln Ser Tyr Asp Ser Ser Asn Trp Val
1               5

<210> SEQ ID NO 29
<211> LENGTH: 113
<212> TYPE: PRT
<213> ORGANISM: Artificial Sequence
<220> FEATURE:
<223> OTHER INFORMATION: Antibody F3 VL amino acid sequence

<400> SEQUENCE: 29

Asn Phe Met Leu Ala Gln Pro His Ser Val Ser Glu Ser Pro Gly Lys
1               5                   10                  15

Thr Val Thr Ile Ser Cys Thr Arg Ser Ser Gly Ser Ile Ala Ser Tyr
            20                  25                  30

Phe Val Gln Trp Phe Gln Gln Arg Pro Gly Ser Ala Pro Thr Ala Val
        35                  40                  45

Ile Tyr Glu Asp Asn Gln Arg Pro Ser Gly Val Pro Asp Arg Phe Ser
    50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Trp Val Phe Gly Gly Gly Thr Lys Val Thr Val Leu Gly Gln
            100                 105                 110

Pro

<210> SEQ ID NO 30
<211> LENGTH: 11
<212> TYPE: PRT
<213> ORGANISM: Artificial Sequence
<220> FEATURE:
<223> OTHER INFORMATION: Antibody 165_13_B1 (derived from B12) VH CDR3

<400> SEQUENCE: 30

Val Met Ser Ser Met Glu Asp Ala Phe Asp Ile
1               5                   10

<210> SEQ ID NO 31
<211> LENGTH: 120
<212> TYPE: PRT
<213> ORGANISM: Artificial Sequence
<220> FEATURE:
<223> OTHER INFORMATION: Antibody 165_13_B1 (derived from B12) VH amino -continued acid sequence

<400> SEQUENCE: 31

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Val Met Ser Ser Met Glu Asp Ala Phe Asp Ile Trp Gly Gln
            100                 105                 110

Gly Thr Met Val Thr Val Ser Ser
        115                 120

<210> SEQ ID NO 32
<211> LENGTH: 11
<212> TYPE: PRT
<213> ORGANISM: Artificial Sequence
<220> FEATURE:
<223> OTHER INFORMATION: Antibody 165_13_B6 (derived from B12) VH CDR3

<400> SEQUENCE: 32

Gly Gln Lys Gly Glu Gly Asp Thr Phe Asp Ile
1               5                   10

<210> SEQ ID NO 33
<211> LENGTH: 120
<212> TYPE: PRT
<213> ORGANISM: Artificial Sequence
<220> FEATURE:
<223> OTHER INFORMATION: Antibody 165_13_B6 (derived from B12) VH amino
      acid sequence

<400> SEQUENCE: 33

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Gln Lys Gly Glu Gly Asp Thr Phe Asp Ile Trp Gly Gln
            100                 105                 110

Gly Thr Met Val Thr Val Ser Ser
        115                 120

<210> SEQ ID NO 34
<211> LENGTH: 11

```
<212> TYPE: PRT
<213> ORGANISM: Artificial Sequence
<220> FEATURE:
<223> OTHER INFORMATION: Antibody 165_13_D1 (derived from B12) VH CDR3

<400> SEQUENCE: 34

Gly Thr Arg Gly Glu Gly Asp Thr Phe Asp Ile
1               5                   10

<210> SEQ ID NO 35
<211> LENGTH: 120
<212> TYPE: PRT
<213> ORGANISM: Artificial Sequence
<220> FEATURE:
<223> OTHER INFORMATION: Antibody 165_13_D1 (derived from B12) VH amino
      acid sequence

<400> SEQUENCE: 35

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Gly Thr Arg Gly Glu Gly Asp Thr Phe Asp Ile Trp Gly Gln
            100                 105                 110

Gly Thr Met Val Thr Val Ser Ser
        115                 120

<210> SEQ ID NO 36
<211> LENGTH: 11
<212> TYPE: PRT
<213> ORGANISM: Artificial Sequence
<220> FEATURE:
<223> OTHER INFORMATION: Antibody 165_13_C3 (derived from B12) VH CDR3

<400> SEQUENCE: 36

Ser Tyr Gln Ser Asp Glu Asp Ala Phe Asp Ile
1               5                   10

<210> SEQ ID NO 37
<211> LENGTH: 120
<212> TYPE: PRT
<213> ORGANISM: Artificial Sequence
<220> FEATURE:
<223> OTHER INFORMATION: Antibody 165_13_C3 (derived from B12) VH amino
      acid sequence

<400> SEQUENCE: 37

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
```

```
                    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                     85                  90                  95

Ala Lys Ser Tyr Gln Ser Asp Glu Asp Ala Phe Asp Ile Trp Gly Gln
            100                 105                 110

Gly Thr Met Val Thr Val Ser Ser
        115                 120

<210> SEQ ID NO 38
<211> LENGTH: 11
<212> TYPE: PRT
<213> ORGANISM: Artificial Sequence
<220> FEATURE:
<223> OTHER INFORMATION: Antibody 165_13_D4 (derived from B12) VH CDR3

<400> SEQUENCE: 38

Gly Thr Val Gly Glu Gly Asp Thr Phe Asp Ile
1               5                   10

<210> SEQ ID NO 39
<211> LENGTH: 120
<212> TYPE: PRT
<213> ORGANISM: Artificial Sequence
<220> FEATURE:
<223> OTHER INFORMATION: Antibody 165_13_D4 (derived from B12) VH amino
      acid sequence

<400> SEQUENCE: 39

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                     85                  90                  95

Ala Lys Gly Thr Val Gly Glu Gly Asp Thr Phe Asp Ile Trp Gly Gln
            100                 105                 110

Gly Thr Met Val Thr Val Ser Ser
        115                 120

<210> SEQ ID NO 40
<211> LENGTH: 11
<212> TYPE: PRT
<213> ORGANISM: Artificial Sequence
<220> FEATURE:
<223> OTHER INFORMATION: Antibody 165_13_A4 (derived from B12) VH CDR3

<400> SEQUENCE: 40

Asp Lys Tyr Pro Val Leu Asp Thr Phe Asp Ile
1               5                   10

<210> SEQ ID NO 41
<211> LENGTH: 120
<212> TYPE: PRT
```

<213> ORGANISM: Artificial Sequence
<220> FEATURE:
<223> OTHER INFORMATION: Antibody 165_13_A4 (derived from B12) VH amino
      acid sequence

<400> SEQUENCE: 41

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Gly Ser Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Lys Tyr Pro Val Leu Asp Thr Phe Asp Ile Trp Gly Gln
            100                 105                 110

Gly Thr Met Val Thr Val Ser Ser
            115                 120

<210> SEQ ID NO 42
<211> LENGTH: 11
<212> TYPE: PRT
<213> ORGANISM: Artificial Sequence
<220> FEATURE:
<223> OTHER INFORMATION: Antibody 165_13_B3 (derived from B12) VH CDR3

<400> SEQUENCE: 42

Ala Leu Ala Arg Gly His Asp Thr Phe Asp Ile
1               5                   10

<210> SEQ ID NO 43
<211> LENGTH: 120
<212> TYPE: PRT
<213> ORGANISM: Artificial Sequence
<220> FEATURE:
<223> OTHER INFORMATION: Antibody 165_13_B3 (derived from B12) VH amino
      acid sequence

<400> SEQUENCE: 43

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ala Leu Ala Arg Gly His Asp Thr Phe Asp Ile Trp Gly Gln
            100                 105                 110

Gly Thr Met Val Thr Val Ser Ser
            115                 120

<210> SEQ ID NO 44
<211> LENGTH: 11
<212> TYPE: PRT
<213> ORGANISM: Artificial Sequence
<220> FEATURE:
<223> OTHER INFORMATION: Antibody 165_13_E1 (derived from B12) VH CDR3

<400> SEQUENCE: 44

Asp Ile Ser Ala Val Met Asp Val Pro Gln Thr
1               5                   10

<210> SEQ ID NO 45
<211> LENGTH: 120
<212> TYPE: PRT
<213> ORGANISM: Artificial Sequence
<220> FEATURE:
<223> OTHER INFORMATION: Antibody 165_13_E1 (derived from B12) VH amino
      acid sequence

<400> SEQUENCE: 45

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ala Val Met Asp Val Pro Gln Thr Trp Gly Gln
            100                 105                 110

Gly Thr Met Val Thr Val Ser Ser
        115                 120

<210> SEQ ID NO 46
<211> LENGTH: 11
<212> TYPE: PRT
<213> ORGANISM: Artificial Sequence
<220> FEATURE:
<223> OTHER INFORMATION: Antibody 180_11_F5 (derived from B12) VH CDR3

<400> SEQUENCE: 46

Val Met Arg Thr Gly Leu Asp Thr Phe Asp Ile
1               5                   10

<210> SEQ ID NO 47
<211> LENGTH: 120
<212> TYPE: PRT
<213> ORGANISM: Artificial Sequence
<220> FEATURE:
<223> OTHER INFORMATION: Antibody 180_11_F5 (derived from B12) VH amino
      acid sequence

<400> SEQUENCE: 47

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val

```
                35                  40                  45
Ser Gly Ile Ser Gly Ser Gly Gly Ser Thr Tyr Tyr Ala Asp Ser Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr Tyr Cys
                85                  90                  95
Ala Lys Val Met Arg Thr Gly Leu Asp Thr Phe Asp Ile Trp Gly Gln
            100                 105                 110
Gly Thr Met Val Thr Val Ser Ser
            115                 120
```

<210> SEQ ID NO 48
<211> LENGTH: 10
<212> TYPE: PRT
<213> ORGANISM: Artificial Sequence
<220> FEATURE:
<223> OTHER INFORMATION: Antibody 160_01_E3 (derived from 2A5) VH CDR3

<400> SEQUENCE: 48

```
Gln Arg Tyr Val Trp Glu Ala Leu Thr Tyr
 1               5                  10
```

<210> SEQ ID NO 49
<211> LENGTH: 119
<212> TYPE: PRT
<213> ORGANISM: Artificial Sequence
<220> FEATURE:
<223> OTHER INFORMATION: Antibody 160_01_E3 (derived from 2A5) VH amino
      acid sequence

<400> SEQUENCE: 49

```
Glu Val Arg Leu Val Gln Ser Gly Ala Glu Val Lys Lys Pro Gly Ala
 1               5                  10                  15
Ser Val Lys Val Ser Cys Lys Val Ser Gly Tyr Thr Leu Thr Glu Leu
            20                  25                  30
Ser Met His Trp Val Arg Gln Ala Pro Gly Lys Gly Leu Glu Trp Met
        35                  40                  45
Gly Gly Phe Asp Pro Glu Asp Gly Glu Thr Ile Tyr Ala Gln Lys Phe
    50                  55                  60
Gln Gly Arg Val Thr Met Thr Glu Asp Thr Ser Thr Asp Thr Ala Tyr
 65                  70                  75                  80
Met Glu Leu Ser Ser Leu Arg Ser Glu Asp Thr Ala Val Tyr Tyr Cys
                85                  90                  95
Ala Thr Gln Arg Tyr Val Trp Glu Ala Leu Thr Tyr Trp Gly Gln Gly
            100                 105                 110
Thr Leu Val Thr Val Ser Ser
            115
```

<210> SEQ ID NO 50
<211> LENGTH: 10
<212> TYPE: PRT
<213> ORGANISM: Artificial Sequence
<220> FEATURE:
<223> OTHER INFORMATION: Antibody 160_01_D6 (derived from 2A5) VH CDR3

<400> SEQUENCE: 50

```
Ala Gln Ala Asp Pro His Leu Phe Thr Tyr
 1               5                  10
```

```
<210> SEQ ID NO 51
<211> LENGTH: 119
<212> TYPE: PRT
<213> ORGANISM: Artificial Sequence
<220> FEATURE:
<223> OTHER INFORMATION: Antibody 160_01_D6 (derived from 2A5) VH amino
      acid sequence

<400> SEQUENCE: 51

Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Ala Asp Pro His Leu Phe Tyr Trp Gly Gln Gly
            100                 105                 110

Thr Leu Val Thr Val Ser Ser
        115

<210> SEQ ID NO 52
<211> LENGTH: 10
<212> TYPE: PRT
<213> ORGANISM: Artificial Sequence
<220> FEATURE:
<223> OTHER INFORMATION: Antibody 160_01_H4 (derived from 2A5) VH CDR3

<400> SEQUENCE: 52

Gly Arg Phe Val Trp Glu Ala Leu Thr Tyr
1               5                   10

<210> SEQ ID NO 53
<211> LENGTH: 119
<212> TYPE: PRT
<213> ORGANISM: Artificial Sequence
<220> FEATURE:
<223> OTHER INFORMATION: Antibody 160_01_H4 (derived from 2A5) VH amino
      acid sequence

<400> SEQUENCE: 53

Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Arg Phe Val Trp Glu Ala Leu Thr Tyr Trp Gly Gln Gly
            100                 105                 110
```

Thr Leu Val Thr Val Ser Ser
        115

<210> SEQ ID NO 54
<211> LENGTH: 10
<212> TYPE: PRT
<213> ORGANISM: Artificial Sequence
<220> FEATURE:
<223> OTHER INFORMATION: Antibody 160_01_A4 (derived from 2A5) VH CDR3

<400> SEQUENCE: 54

Ala Gln Lys Glu Thr Leu Gly Asn Ala Ile
1               5                   10

<210> SEQ ID NO 55
<211> LENGTH: 119
<212> TYPE: PRT
<213> ORGANISM: Artificial Sequence
<220> FEATURE:
<223> OTHER INFORMATION: Antibody 160_01_A4 (derived from 2A5) VH amino
      acid sequence

<400> SEQUENCE: 55

Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Lys Glu Thr Leu Gly Asn Ala Ile Trp Gly Gln Gly
            100                 105                 110

Thr Leu Val Thr Val Ser Ser
        115

<210> SEQ ID NO 56
<211> LENGTH: 10
<212> TYPE: PRT
<213> ORGANISM: Artificial Sequence
<220> FEATURE:
<223> OTHER INFORMATION: Antibody 160_01_F1 (derived from 2A5) VH CDR3

<400> SEQUENCE: 56

Ala Gln Ser Pro Trp Ser Gly Met Thr Tyr
1               5                   10

<210> SEQ ID NO 57
<211> LENGTH: 119
<212> TYPE: PRT
<213> ORGANISM: Artificial Sequence
<220> FEATURE:
<223> OTHER INFORMATION: Antibody 160_01_F1 (derived from 2A5) VH amino
      acid sequence

<400> SEQUENCE: 57

Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu

```
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Ser Pro Trp Ser Gly Met Thr Tyr Trp Gly Gln Gly
            100                 105                 110

Thr Leu Val Thr Val Ser Ser
            115

<210> SEQ ID NO 58
<211> LENGTH: 10
<212> TYPE: PRT
<213> ORGANISM: Artificial Sequence
<220> FEATURE:
<223> OTHER INFORMATION: Antibody 160_01_G2 (derived from 2A5) VH CDR3

<400> SEQUENCE: 58

Tyr Thr Leu Asp Asn Met Ala Leu Thr Tyr
1               5                   10

<210> SEQ ID NO 59
<211> LENGTH: 119
<212> TYPE: PRT
<213> ORGANISM: Artificial Sequence
<220> FEATURE:
<223> OTHER INFORMATION: Antibody 160_01_G2 (derived from 2A5) VH amino
      acid sequence

<400> SEQUENCE: 59

Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Tyr Thr Leu Asp Asn Met Ala Leu Thr Tyr Trp Gly Gln Gly
            100                 105                 110

Thr Leu Val Thr Val Ser Ser
            115

<210> SEQ ID NO 60
<211> LENGTH: 10
<212> TYPE: PRT
<213> ORGANISM: Artificial Sequence
<220> FEATURE:
<223> OTHER INFORMATION: Antibody 161_01_F6, also known as 160_01_F6
      (derived from 2A5) VH CDR3

<400> SEQUENCE: 60
```

```
Ala Gln Lys Glu Asn Ile Ala Asn Arg His
1               5                   10
```

<210> SEQ ID NO 61
<211> LENGTH: 119
<212> TYPE: PRT
<213> ORGANISM: Artificial Sequence
<220> FEATURE:
<223> OTHER INFORMATION: Antibody 161_01_F6, also known as 160_01_F6
      (derived from 2A5) VH amino acid sequence

<400> SEQUENCE: 61

```
Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Lys Glu Asn Ile Ala Asn Arg His Trp Gly Gln Gly
            100                 105                 110

Thr Leu Val Thr Val Ser Ser
        115
```

<210> SEQ ID NO 62
<211> LENGTH: 10
<212> TYPE: PRT
<213> ORGANISM: Artificial Sequence
<220> FEATURE:
<223> OTHER INFORMATION: Antibody 161_01_A12 (derived from 2A5) VH CDR3

<400> SEQUENCE: 62

```
Ala Gln Pro Thr Ala Leu Ala Asn Thr Tyr
1               5                   10
```

<210> SEQ ID NO 63
<211> LENGTH: 119
<212> TYPE: PRT
<213> ORGANISM: Artificial Sequence
<220> FEATURE:
<223> OTHER INFORMATION: Antibody 161_01_A12 (derived from 2A5) VH amino
      acid sequence

<400> SEQUENCE: 63

```
Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95
```

```
Ala Thr Ala Gln Pro Thr Ala Leu Ala Asn Thr Tyr Trp Gly Gln Gly
            100                 105                 110

Thr Leu Val Thr Val Ser Ser
        115

<210> SEQ ID NO 64
<211> LENGTH: 10
<212> TYPE: PRT
<213> ORGANISM: Artificial Sequence
<220> FEATURE:
<223> OTHER INFORMATION: Antibody 161_01_C09 (derived from 2A5) VH CDR3

<400> SEQUENCE: 64

Ala Gln Leu Pro Tyr Leu Ala Gln Thr Tyr
1               5                   10

<210> SEQ ID NO 65
<211> LENGTH: 119
<212> TYPE: PRT
<213> ORGANISM: Artificial Sequence
<220> FEATURE:
<223> OTHER INFORMATION: Antibody 161_01_C09 (derived from 2A5) VH amino
      acid sequence

<400> SEQUENCE: 65

Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Leu Pro Tyr Leu Ala Gln Thr Tyr Trp Gly Gln Gly
            100                 105                 110

Thr Leu Val Thr Val Ser Ser
        115

<210> SEQ ID NO 66
<211> LENGTH: 10
<212> TYPE: PRT
<213> ORGANISM: Artificial Sequence
<220> FEATURE:
<223> OTHER INFORMATION: Antibody 161_01_H10 (derived from 2A5) VH CDR3

<400> SEQUENCE: 66

Ala Gln Pro Val Trp Ala Pro Gly Thr Tyr
1               5                   10

<210> SEQ ID NO 67
<211> LENGTH: 119
<212> TYPE: PRT
<213> ORGANISM: Artificial Sequence
<220> FEATURE:
<223> OTHER INFORMATION: Antibody 161_01_H10 (derived from 2A5) VH amino
      acid sequence

<400> SEQUENCE: 67
```

```
Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Pro Val Trp Ala Pro Gly Tyr Trp Gly Gln Gly
                100                 105                 110

Thr Leu Val Thr Val Ser Ser
        115
```

<210> SEQ ID NO 68
<211> LENGTH: 10
<212> TYPE: PRT
<213> ORGANISM: Artificial Sequence
<220> FEATURE:
<223> OTHER INFORMATION: Antibody 161_01_C11 (derived from 2A5) VH CDR3

<400> SEQUENCE: 68

```
Ala Gln Lys Glu Trp Leu Pro Asp Val Thr
1               5                   10
```

<210> SEQ ID NO 69
<211> LENGTH: 119
<212> TYPE: PRT
<213> ORGANISM: Artificial Sequence
<220> FEATURE:
<223> OTHER INFORMATION: Antibody 161_01_C11 (derived from 2A5) VH amino
      acid sequence

<400> SEQUENCE: 69

```
Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Lys Glu Trp Leu Pro Asp Val Thr Trp Gly Gln Gly
                100                 105                 110

Thr Leu Val Thr Val Ser Ser
        115
```

<210> SEQ ID NO 70
<211> LENGTH: 10
<212> TYPE: PRT
<213> ORGANISM: Artificial Sequence
<220> FEATURE:
<223> OTHER INFORMATION: Antibody 162_02_D3 (derived from 2A5) VH CDR3

<400> SEQUENCE: 70

Ala Gln Ile His Pro Leu Gly Leu Thr Tyr
1               5                   10

<210> SEQ ID NO 71
<211> LENGTH: 119
<212> TYPE: PRT
<213> ORGANISM: Artificial Sequence
<220> FEATURE:
<223> OTHER INFORMATION: Antibody 162_02_D3 (derived from 2A5) VH amino
      acid sequence

<400> SEQUENCE: 71

Glu Val Arg Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
                20                  25                  30

Ser Met His Trp Val Arg Gln Ala Pro Gly Lys Gly Leu Glu Trp Met
            35                  40                  45

Gly Gly Phe Asp Pro Glu Asp Gly Glu Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Ile His Pro Leu Gly Leu Thr Tyr Trp Gly Gln Gly
            100                 105                 110

Thr Leu Val Thr Val Ser Ser
        115

<210> SEQ ID NO 72
<211> LENGTH: 9
<212> TYPE: PRT
<213> ORGANISM: Artificial Sequence
<220> FEATURE:
<223> OTHER INFORMATION: Antibody 162_02_C6 (derived from 2A5) VL CDR3

<400> SEQUENCE: 72

Gln Asn Gln Tyr Ala Gly Pro Trp Thr
1               5

<210> SEQ ID NO 73
<211> LENGTH: 108
<212> TYPE: PRT
<213> ORGANISM: Artificial Sequence
<220> FEATURE:
<223> OTHER INFORMATION: Antibody 162_02_C6 (derived from 2A5) VL amino
      acid sequence

<400> SEQUENCE: 73

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
                20                  25                  30

Leu Asn Trp Tyr Gln Gln Lys Pro Gly Lys Ala Pro Arg Leu Leu Ile
            35                  40                  45

Tyr Ala Ala Ser Thr Leu Gln Asp Gly Val Pro Ser Arg Phe Ser Gly
        50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Asn Gln Tyr Ala Gly Pro Trp
            85                  90                  95

Thr Phe Gly Gln Gly Thr Lys Val Glu Ile Lys Arg
            100                 105

<210> SEQ ID NO 74
<211> LENGTH: 9
<212> TYPE: PRT
<213> ORGANISM: Artificial Sequence
<220> FEATURE:
<223> OTHER INFORMATION: Antibody 162_02_H5 (derived from 2A5) VL CDR3

<400> SEQUENCE: 74

Gln Asn Gln Tyr Thr Gly Pro Trp Thr
1               5

<210> SEQ ID NO 75
<211> LENGTH: 108
<212> TYPE: PRT
<213> ORGANISM: Artificial Sequence
<220> FEATURE:
<223> OTHER INFORMATION: Antibody 162_02_H5 (derived from 2A5) VL amino
      acid sequence

<400> SEQUENCE: 75

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
            35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Asn Gln Tyr Thr Gly Pro Trp
            85                  90                  95

Thr Phe Gly Gln Gly Thr Lys Val Glu Ile Lys Arg
            100                 105

<210> SEQ ID NO 76
<211> LENGTH: 9
<212> TYPE: PRT
<213> ORGANISM: Artificial Sequence
<220> FEATURE:
<223> OTHER INFORMATION: Antibody 162_02_F3 (derived from 2A5) VL CDR3

<400> SEQUENCE: 76

Gln Asn Gln Tyr Arg Gly Pro Trp Thr
1               5

<210> SEQ ID NO 77
<211> LENGTH: 108
<212> TYPE: PRT
<213> ORGANISM: Artificial Sequence
<220> FEATURE:
<223> OTHER INFORMATION: Antibody 162_02_F3 (derived from 2A5) VL amino
      acid sequence

<400> SEQUENCE: 77

Asp Ile Gln Met Thr Gln Ser Pro Ala Ser Leu Pro Thr Ser Val Gly
1               5                   10                  15

```
Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
 50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Asn Tyr Arg Gly Pro Trp
                85                  90                  95

Thr Phe Gly Gln Gly Thr Lys Val Glu Ile Lys Arg
            100                 105

<210> SEQ ID NO 78
<211> LENGTH: 9
<212> TYPE: PRT
<213> ORGANISM: Artificial Sequence
<220> FEATURE:
<223> OTHER INFORMATION: Antibody 162_02_C1 (derived from 2A5) VL CDR3

<400> SEQUENCE: 78

Leu His His Tyr Arg Ala Pro Trp Thr
1               5

<210> SEQ ID NO 79
<211> LENGTH: 108
<212> TYPE: PRT
<213> ORGANISM: Artificial Sequence
<220> FEATURE:
<223> OTHER INFORMATION: Antibody 162_02_C1 (derived from 2A5) VL amino
      acid sequence

<400> SEQUENCE: 79

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
 50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu His His Tyr Arg Ala Pro Trp
                85                  90                  95

Thr Phe Gly Gln Gly Thr Lys Val Glu Ile Lys Arg
            100                 105

<210> SEQ ID NO 80
<211> LENGTH: 9
<212> TYPE: PRT
<213> ORGANISM: Artificial Sequence
<220> FEATURE:
<223> OTHER INFORMATION: Antibody 162_02_C2 (derived from 2A5) VL CDR3

<400> SEQUENCE: 80

Met His His Tyr Arg Ala Pro Trp Thr
1               5

<210> SEQ ID NO 81
<211> LENGTH: 108
```

```
<212> TYPE: PRT
<213> ORGANISM: Artificial Sequence
<220> FEATURE:
<223> OTHER INFORMATION: Antibody 162_02_C2 (derived from 2A5) VL amino
      acid sequence

<400> SEQUENCE: 81

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Met His His Tyr Arg Ala Pro Trp
                85                  90                  95

Thr Phe Gly Gln Gly Thr Lys Val Glu Ile Lys Arg
            100                 105

<210> SEQ ID NO 82
<211> LENGTH: 9
<212> TYPE: PRT
<213> ORGANISM: Artificial Sequence
<220> FEATURE:
<223> OTHER INFORMATION: Antibody 162_02_F4 (derived from 2A5) VL CDR3

<400> SEQUENCE: 82

Met His His Tyr Arg Ser Pro Trp Thr
1               5

<210> SEQ ID NO 83
<211> LENGTH: 108
<212> TYPE: PRT
<213> ORGANISM: Artificial Sequence
<220> FEATURE:
<223> OTHER INFORMATION: Antibody 162_02_F4 (derived from 2A5) VL amino
      acid sequence

<400> SEQUENCE: 83

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Met His His Tyr Arg Ser Pro Trp
                85                  90                  95

Thr Phe Gly Gln Gly Thr Lys Val Glu Ile Lys Arg
            100                 105

<210> SEQ ID NO 84
<211> LENGTH: 9
<212> TYPE: PRT
<213> ORGANISM: Artificial Sequence
```

```
<220> FEATURE:
<223> OTHER INFORMATION: Antibody 162_02_C3 (derived from 2A5) VL CDR3

<400> SEQUENCE: 84

Met Gln His Tyr Asp Gly Pro Trp Thr
1               5

<210> SEQ ID NO 85
<211> LENGTH: 108
<212> TYPE: PRT
<213> ORGANISM: Artificial Sequence
<220> FEATURE:
<223> OTHER INFORMATION: Antibody 162_02_C3 (derived from 2A5) VL amino
      acid sequence

<400> SEQUENCE: 85

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
                20                  25                  30

Leu Asn Trp Tyr Gln Gln Lys Pro Gly Lys Ala Pro Arg Leu Leu Ile
            35                  40                  45

Tyr Ala Ala Ser Thr Leu Gln Asp Gly Val Pro Ser Arg Phe Ser Gly
        50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Met Gln His Tyr Asp Gly Pro Trp
                85                  90                  95

Thr Phe Gly Gln Gly Thr Lys Val Glu Ile Lys Arg
            100                 105

<210> SEQ ID NO 86
<211> LENGTH: 10
<212> TYPE: PRT
<213> ORGANISM: Artificial Sequence
<220> FEATURE:
<223> OTHER INFORMATION: Antibody 162_02_E11 (derived from 2A5) VL CDR3

<400> SEQUENCE: 86

Leu His His Tyr Arg Ser Pro Thr Trp Thr
1               5                   10

<210> SEQ ID NO 87
<211> LENGTH: 109
<212> TYPE: PRT
<213> ORGANISM: Artificial Sequence
<220> FEATURE:
<223> OTHER INFORMATION: Antibody 162_02_E11 (derived from 2A5) VL amino
      acid sequence

<400> SEQUENCE: 87

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
                20                  25                  30

Leu Asn Trp Tyr Gln Gln Lys Pro Gly Lys Ala Pro Arg Leu Leu Ile
            35                  40                  45

Tyr Ala Ala Ser Thr Leu Gln Asp Gly Val Pro Ser Arg Phe Ser Gly
        50                  55                  60

Ser Gly Tyr Gly Thr Asp Phe Thr Leu Thr Ile Ser Ser Leu Gln Pro
65                  70                  75                  80
```

Glu Asp Phe Ala Thr Tyr Tyr Cys Leu His His Tyr Arg Ser Pro Thr
            85                  90                  95

Trp Thr Phe Gly Gln Gly Thr Lys Val Glu Ile Lys Arg
            100                 105

<210> SEQ ID NO 88
<211> LENGTH: 9
<212> TYPE: PRT
<213> ORGANISM: Artificial Sequence
<220> FEATURE:
<223> OTHER INFORMATION: Antibody 163_02_A12 (derived from 2A5) VL CDR3

<400> SEQUENCE: 88

Leu His His Tyr Arg Glu Pro Trp Thr
1               5

<210> SEQ ID NO 89
<211> LENGTH: 108
<212> TYPE: PRT
<213> ORGANISM: Artificial Sequence
<220> FEATURE:
<223> OTHER INFORMATION: Antibody 163_02_A12 (derived from 2A5) VL amino
      acid sequence

<400> SEQUENCE: 89

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu His His Tyr Arg Glu Pro Trp
            85                  90                  95

Thr Phe Gly Gln Gly Thr Lys Val Glu Ile Lys Arg
            100                 105

<210> SEQ ID NO 90
<211> LENGTH: 9
<212> TYPE: PRT
<213> ORGANISM: Artificial Sequence
<220> FEATURE:
<223> OTHER INFORMATION: Antibody 163_02_D11 (derived from 2A5) VL CDR3

<400> SEQUENCE: 90

Leu His His Tyr Lys Ser Pro Trp Thr
1               5

<210> SEQ ID NO 91
<211> LENGTH: 108
<212> TYPE: PRT
<213> ORGANISM: Artificial Sequence
<220> FEATURE:
<223> OTHER INFORMATION: Antibody 163_02_D11 (derived from 2A5) VL amino
      acid sequence

<400> SEQUENCE: 91

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe

```
                20              25              30
Leu Asn Trp Tyr Gln Gln Lys Pro Gly Lys Ala Pro Arg Leu Leu Ile
            35              40              45

Tyr Ala Ala Ser Thr Leu Gln Asp Gly Val Pro Ser Arg Phe Ser Gly
        50              55              60

Ser Gly Tyr Gly Thr Asp Phe Thr Leu Thr Ile Ser Ser Leu Gln Pro
65              70              75              80

Glu Asp Phe Ala Thr Tyr Tyr Cys Leu His His Tyr Lys Ser Pro Trp
                85              90              95

Thr Phe Gly Gln Gly Thr Lys Val Glu Ile Lys Arg
            100             105

<210> SEQ ID NO 92
<211> LENGTH: 228
<212> TYPE: PRT
<213> ORGANISM: Artificial Sequence
<220> FEATURE:
<223> OTHER INFORMATION: Amino acid sequence of human tenascin-C FBG
      domain

<400> SEQUENCE: 92

Ile Gly Leu Leu Tyr Pro Phe Pro Lys Asp Cys Ser Gln Ala Met Leu
1               5               10              15

Asn Gly Asp Thr Thr Ser Gly Leu Tyr Thr Ile Tyr Leu Asn Gly Asp
            20              25              30

Lys Ala Glu Ala Leu Glu Val Phe Cys Asp Met Thr Ser Asp Gly Gly
        35              40              45

Gly Trp Ile Val Phe Leu Arg Arg Lys Asn Gly Arg Glu Asn Phe Tyr
    50              55              60

Gln Asn Trp Lys Ala Tyr Ala Ala Gly Phe Gly Asp Arg Arg Glu Glu
65              70              75              80

Phe Trp Leu Gly Leu Asp Asn Leu Asn Lys Ile Thr Ala Gln Gly Gln
                85              90              95

Tyr Glu Leu Arg Val Asp Leu Arg Asp His Gly Glu Thr Ala Phe Ala
            100             105             110

Val Tyr Asp Lys Phe Ser Val Gly Asp Ala Lys Thr Arg Tyr Lys Leu
        115             120             125

Lys Val Glu Gly Tyr Ser Gly Thr Ala Gly Asp Ser Met Ala Tyr His
    130             135             140

Asn Gly Arg Ser Phe Ser Thr Phe Asp Lys Asp Thr Asp Ser Ala Ile
145             150             155             160

Thr Asn Cys Ala Leu Ser Tyr Lys Gly Ala Phe Trp Tyr Arg Asn Cys
                165             170             175

His Arg Val Asn Leu Met Gly Arg Tyr Gly Asp Asn Asn His Ser Gln
            180             185             190

Gly Val Asn Trp Phe His Trp Lys Gly His Glu His Ser Ile Gln Phe
        195             200             205

Ala Glu Met Lys Leu Arg Pro Ser Asn Phe Arg Asn Leu Glu Gly Arg
    210             215             220

Arg Lys Arg Ala
225

<210> SEQ ID NO 93
<211> LENGTH: 228
<212> TYPE: PRT
<213> ORGANISM: Artificial Sequence
<220> FEATURE:
```

<223> OTHER INFORMATION: Amino acid sequence of mouse tenascin-C FBG
       domain

<400> SEQUENCE: 93

Ile Gly Leu Leu Tyr Pro Phe Pro Arg Asp Cys Ser Gln Ala Met Leu
1               5                   10                  15

Asn Gly Asp Thr Thr Ser Gly Leu Tyr Thr Ile Tyr Ile Asn Gly Asp
            20                  25                  30

Lys Thr Gln Ala Leu Glu Val Tyr Cys Asp Met Thr Ser Asp Gly Gly
        35                  40                  45

Gly Trp Ile Val Phe Leu Arg Arg Lys Asn Gly Arg Glu Asp Phe Tyr
    50                  55                  60

Arg Asn Trp Lys Ala Tyr Ala Ala Gly Phe Gly Asp Arg Arg Glu Glu
65                  70                  75                  80

Phe Trp Leu Gly Leu Asp Asn Leu Ser Lys Ile Thr Ala Gln Gly Gln
                85                  90                  95

Tyr Glu Leu Arg Val Asp Leu Gln Asp His Gly Glu Ser Ala Tyr Ala
            100                 105                 110

Val Tyr Asp Arg Phe Ser Val Gly Asp Ala Lys Ser Arg Tyr Lys Leu
        115                 120                 125

Lys Val Glu Gly Tyr Ser Gly Thr Ala Gly Asp Ser Met Asn Tyr His
    130                 135                 140

Asn Gly Arg Ser Phe Ser Thr Tyr Asp Lys Asp Thr Asp Ser Ala Ile
145                 150                 155                 160

Thr Asn Cys Ala Leu Ser Tyr Lys Gly Ala Phe Trp Tyr Lys Asn Cys
                165                 170                 175

His Arg Val Asn Leu Met Gly Arg Tyr Gly Asp Asn Asn His Ser Gln
            180                 185                 190

Gly Val Asn Trp Phe His Trp Lys Gly His Glu Tyr Ser Ile Gln Phe
        195                 200                 205

Ala Glu Met Lys Leu Arg Pro Ser Asn Phe Arg Asn Leu Glu Gly Arg
    210                 215                 220

Arg Lys Arg Ala
225

<210> SEQ ID NO 94
<211> LENGTH: 228
<212> TYPE: PRT
<213> ORGANISM: Artificial Sequence
<220> FEATURE:
<223> OTHER INFORMATION: Amino acid sequence of rat tenascin-C FBG
       domain

<400> SEQUENCE: 94

Ile Gly Leu Leu Tyr Pro Phe Pro Arg Asp Cys Ser Gln Ala Met Leu
1               5                   10                  15

Asn Gly Asp Thr Thr Ser Gly Leu Tyr Thr Ile Tyr Ile Asn Gly Asp
            20                  25                  30

Lys Thr Gln Ala Leu Glu Val Tyr Cys Asp Met Thr Ser Asp Gly Gly
        35                  40                  45

Gly Trp Ile Val Phe Leu Arg Arg Lys Asn Gly Arg Glu Asp Phe Tyr
    50                  55                  60

Arg Asn Trp Lys Ala Tyr Ala Thr Gly Phe Gly Asp Arg Arg Glu Glu
65                  70                  75                  80

Phe Trp Leu Gly Leu Asp Asn Leu Ser Lys Ile Thr Ala Gln Gly Gln
                85                  90                  95

```
Tyr Glu Leu Arg Val Asp Leu Gln Asp His Gly Glu Ser Ala Tyr Ala
            100                 105                 110

Val Tyr Asp Arg Phe Ser Val Gly Asp Ala Lys Ser Arg Tyr Lys Leu
            115                 120                 125

Lys Val Glu Gly Tyr Ser Gly Thr Ala Gly Asp Ser Met Asn Tyr His
            130                 135                 140

Asn Gly Arg Ser Phe Ser Thr Tyr Asp Lys Asp Thr Asp Ser Ala Ile
145                 150                 155                 160

Thr Asn Cys Ala Leu Ser Tyr Lys Gly Ala Phe Trp Tyr Lys Asn Cys
                165                 170                 175

His Arg Val Asn Leu Met Gly Arg Tyr Gly Asp Asn Asn His Ser Gln
            180                 185                 190

Gly Val Asn Trp Phe His Trp Lys Gly His Glu Tyr Ser Ile Gln Phe
            195                 200                 205

Ala Glu Met Lys Leu Arg Pro Ser Asn Phe Arg Asn Leu Glu Gly Arg
210                 215                 220

Arg Lys Arg Ala
225

<210> SEQ ID NO 95
<211> LENGTH: 228
<212> TYPE: PRT
<213> ORGANISM: Artificial Sequence
<220> FEATURE:
<223> OTHER INFORMATION: Amino acid sequence of dog tenascin-C FBG
      domain

<400> SEQUENCE: 95

Ile Gly Leu Leu Tyr Pro Phe Pro Arg Asp Cys Ser Gln Ala Met Leu
1               5                   10                  15

Asn Gly Asp Thr Thr Ser Gly Leu Tyr Thr Ile Tyr Leu Asn Gly Asp
            20                  25                  30

Lys Ala Gln Ala Leu Glu Val Tyr Cys Asp Met Thr Ser Asp Gly Gly
            35                  40                  45

Gly Trp Ile Val Phe Leu Arg Arg Lys Asn Gly Arg Glu Asp Phe Tyr
        50                  55                  60

Arg Asn Trp Lys Ala Tyr Ala Ala Gly Phe Gly Asp Arg Arg Glu Glu
65                  70                  75                  80

Phe Trp Leu Gly Leu Asp Asn Leu His Lys Ile Thr Ala Gln Gly Gln
                85                  90                  95

Tyr Glu Leu Arg Val Asp Leu Arg Asp His Gly Lys Thr Ala Tyr Ala
            100                 105                 110

Val Tyr Asp Arg Phe Ser Val Gly Asp Ala Lys Thr Arg Tyr Lys Leu
            115                 120                 125

Lys Val Glu Gly Tyr Ser Gly Thr Ala Gly Asp Ser Met Ala Tyr His
            130                 135                 140

Asn Gly Arg Ser Phe Ser Thr Phe Asp Lys Asp Thr Asp Ser Ala Ile
145                 150                 155                 160

Thr Asn Cys Ala Leu Ser Tyr Lys Gly Ala Phe Trp Tyr Lys Asn Cys
                165                 170                 175

His Arg Val Asn Leu Met Gly Arg Tyr Gly Asp Asn Asn His Ser Gln
            180                 185                 190

Gly Val Asn Trp Phe His Trp Lys Gly His Glu Tyr Ser Ile Gln Phe
            195                 200                 205

Ala Glu Met Lys Leu Arg Pro Ser Asn Phe Arg Asn Leu Glu Gly Arg
210                 215                 220
```

Arg Lys Arg Ala
225

<210> SEQ ID NO 96
<211> LENGTH: 227
<212> TYPE: PRT
<213> ORGANISM: Artificial Sequence
<220> FEATURE:
<223> OTHER INFORMATION: Amino acid sequence of human tenascin-R FBG
      domain

<400> SEQUENCE: 96

Phe Pro His Pro Gln Asp Cys Ala Gln His Leu Met Asn Gly Asp Thr
1               5                   10                  15

Leu Ser Gly Val Tyr Pro Ile Phe Leu Asn Gly Glu Leu Ser Gln Lys
            20                  25                  30

Leu Gln Val Tyr Cys Asp Met Thr Thr Asp Gly Gly Gly Trp Ile Val
        35                  40                  45

Phe Gln Arg Arg Gln Asn Gly Gln Thr Asp Phe Phe Arg Lys Trp Ala
    50                  55                  60

Asp Tyr Arg Val Gly Phe Gly Asn Val Glu Asp Glu Phe Trp Leu Gly
65                  70                  75                  80

Leu Asp Asn Ile His Arg Ile Thr Ser Gln Gly Arg Tyr Glu Leu Arg
                85                  90                  95

Val Asp Met Arg Asp Gly Gln Glu Ala Ala Phe Ala Ser Tyr Asp Arg
            100                 105                 110

Phe Ser Val Glu Asp Ser Arg Asn Leu Tyr Lys Leu Arg Ile Gly Ser
        115                 120                 125

Tyr Asn Gly Thr Ala Gly Asp Ser Leu Ser Tyr His Gln Gly Arg Pro
    130                 135                 140

Phe Ser Thr Glu Asp Arg Asp Asn Asp Val Ala Val Thr Asn Cys Ala
145                 150                 155                 160

Met Ser Tyr Lys Gly Ala Trp Trp Tyr Lys Asn Cys His Arg Thr Asn
                165                 170                 175

Leu Asn Gly Lys Tyr Gly Glu Ser Arg His Ser Gln Gly Ile Asn Trp
            180                 185                 190

Tyr His Trp Lys Gly His Glu Phe Ser Ile Pro Phe Val Glu Met Lys
        195                 200                 205

Met Arg Pro Tyr Asn His Arg Leu Met Ala Gly Arg Lys Arg Gln Ser
    210                 215                 220

Leu Gln Phe
225

<210> SEQ ID NO 97
<211> LENGTH: 66
<212> TYPE: DNA
<213> ORGANISM: Artificial Sequence
<220> FEATURE:
<223> OTHER INFORMATION: unassigned DNA F3 VH 3.1 primer
<220> FEATURE:
<221> NAME/KEY: source
<222> LOCATION: (1)..(66)
<223> OTHER INFORMATION: /mol_type="unassigned DNA" /note="F3 VH 3.1
      primer" /organism="Artificial Sequence"
<220> FEATURE:
<221> NAME/KEY: misc_feature
<222> LOCATION: (23)..(24)
<223> OTHER INFORMATION: /note="wherein 'n' is A, T, G, or C"
<220> FEATURE:
<221> NAME/KEY: misc_feature
<222> LOCATION: (26)..(27)

```
<223> OTHER INFORMATION: /note="wherein 'n' is A, T, G, or C"
<220> FEATURE:
<221> NAME/KEY: misc_feature
<222> LOCATION: (29)..(30)
<223> OTHER INFORMATION: /note="wherein 'n' is A, T, G, or C"
<220> FEATURE:
<221> NAME/KEY: misc_feature
<222> LOCATION: (32)..(33)
<223> OTHER INFORMATION: /note="wherein 'n' is A, T, G, or C"
<220> FEATURE:
<221> NAME/KEY: misc_feature
<222> LOCATION: (35)..(36)
<223> OTHER INFORMATION: /note="wherein 'n' is A, T, G, or C"
<220> FEATURE:
<221> NAME/KEY: misc_feature
<222> LOCATION: (38)..(39)
<223> OTHER INFORMATION: /note="wherein 'n' is A, T, G, or C"

<400> SEQUENCE: 97
agcattactc tcagcagaaa asnnsnnsnn snnsnnsnnt ctcgcacagt aatacacagc      60
cgtgtc                                                                66

<210> SEQ ID NO 98
<211> LENGTH: 67
<212> TYPE: DNA
<213> ORGANISM: Artificial Sequence
<220> FEATURE:
<223> OTHER INFORMATION: unassigned DNA F3 VH 3.2 primer
<220> FEATURE:
<221> NAME/KEY: source
<222> LOCATION: (1)..(67)
<223> OTHER INFORMATION: /mol_type="unassigned DNA" /note="F3 VH 3.2
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G, or C"
<220> FEATURE:
<221> NAME/KEY: misc_feature
<222> LOCATION: (29)..(30)
<223> OTHER INFORMATION: /note="wherein 'n' is A, T, G, or C"
<220> FEATURE:
<221> NAME/KEY: misc_feature
<222> LOCATION: (32)..(33)
<223> OTHER INFORMATION: /note="wherein 'n' is A, T, G, or C"
<220> FEATURE:
<221> NAME/KEY: misc_feature
<222> LOCATION: (35)..(36)
<223> OTHER INFORMATION: /note="wherein 'n' is A, T, G, or C"
<220> FEATURE:
<221> NAME/KEY: misc_feature
<222> LOCATION: (38)..(39)
<223> OTHER INFORMATION: /note="wherein 'n' is A, T, G, or C"
<220> FEATURE:
<221> NAME/KEY: misc_feature
<222> LOCATION: (41)..(42)
<223> OTHER INFORMATION: /note="wherein 'n' is A, T, G, or C"

<400> SEQUENCE: 98
ctggccccag atatcaaaag cattsnnsnn snnsnnsnns nnttggtcat agccttctct      60
cgcacag                                                               67

<210> SEQ ID NO 99
<211> LENGTH: 69
<212> TYPE: DNA
<213> ORGANISM: Artificial Sequence
<220> FEATURE:
<223> OTHER INFORMATION: unassigned DNA F3 VH 3.3 primer
<220> FEATURE:
<221> NAME/KEY: source
<222> LOCATION: (1)..(69)
<223> OTHER INFORMATION: /mol_type="unassigned DNA" /note="F3 VH 3.3
      primer" /organism="Artificial Sequence"
```

```
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 99
ggtgaccagg gttccctggc cccasnnsnn snnsnnsnns nnctcagcag aaaatagttg     60
gtcatagcc                                                            69

<210> SEQ ID NO 100
<211> LENGTH: 66
<212> TYPE: DNA
<213> ORGANISM: Artificial Sequence
<220> FEATURE:
<223> OTHER INFORMATION: unassigned DNA F3 VL 3.1 primer
<220> FEATURE:
<221> NAME/KEY: source
<222> LOCATION: (1)..(66)
<223> OTHER INFORMATION: /mol_type="unassigned DNA" /note="F3 VL 3.1
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 100
ggtccctccg ccgaacaccc aattsnnsnn snnsnnsnns nnacagtagt agtcagcctc     60
gtcctc                                                               66

<210> SEQ ID NO 101
<211> LENGTH: 66
<212> TYPE: DNA
<213> ORGANISM: Artificial Sequence
```

```
<220> FEATURE:
<223> OTHER INFORMATION: unassigned DNA F3 VL 3.2 primer
<220> FEATURE:
<221> NAME/KEY: source
<222> LOCATION: (1)..(66)
<223> OTHER INFORMATION: /mol_type="unassigned DNA" /note="F3 VL 3.2
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 101
ggtgaccttg gtccctccgc cgaasnnsnn snnsnnsnns nnataagact gacagtagta      60
gtcagc                                                                66

<210> SEQ ID NO 102
<211> LENGTH: 70
<212> TYPE: DNA
<213> ORGANISM: Artificial Sequence
<220> FEATURE:
<223> OTHER INFORMATION: unassigned DNA B12 VH 3.1 primer
<220> FEATURE:
<221> NAME/KEY: source
<222> LOCATION: (1)..(70)
<223> OTHER INFORMATION: /mol_type="unassigned DNA" /note="B12 VH 3
      primer" /organism="Artificial Sequence"
<220> FEATURE:
<221> NAME/KEY: misc_feature
<222> LOCATION: (27)..(28)
<223> OTHER INFORMATION: /note="wherein 'n' is A, T, G or C"
<220> FEATURE:
<221> NAME/KEY: misc_feature
<222> LOCATION: (30)..(31)
<223> OTHER INFORMATION: /note="wherein 'n' is A, T, G or C"
<220> FEATURE:
<221> NAME/KEY: misc_feature
<222> LOCATION: (33)..(34)
<223> OTHER INFORMATION: /note="wherein 'n' is A, T, G or C"
<220> FEATURE:
<221> NAME/KEY: misc_feature
<222> LOCATION: (36)..(37)
<223> OTHER INFORMATION: /note="wherein 'n' is A, T, G or C"
<220> FEATURE:
<221> NAME/KEY: misc_feature
<222> LOCATION: (39)..(40)
<223> OTHER INFORMATION: /note="wherein 'n' is A, T, G or C"
<220> FEATURE:
<221> NAME/KEY: misc_feature
<222> LOCATION: (42)..(43)
<223> OTHER INFORMATION: /note="wherein 'n' is A, T, G or C"

<400> SEQUENCE: 102
cttggcccca gatatcaaaa gtatcsnnsn nsnnsnnsnn snntttttgca cagtaataca     60
```
aggccgtgtc                                                              70

<210> SEQ ID NO 103
<211> LENGTH: 67
<212> TYPE: DNA
<213> ORGANISM: Artificial Sequence
<220> FEATURE:
<223> OTHER INFORMATION: B12 VH 3.2
<220> FEATURE:
<221> NAME/KEY: source
<222> LOCATION: (1)..(67)
<223> OTHER INFORMATION: /mol_type="unassigned DNA" /note="B12 VH 3.2
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 103
cattgtccct tggccccaga tatcsnnsnn snnsnnsnns nncgagatat cttttgcaca     60
gtaatac                                                               67

<210> SEQ ID NO 104
<211> LENGTH: 67
<212> TYPE: DNA
<213> ORGANISM: Artificial Sequence
<220> FEATURE:
<223> OTHER INFORMATION: unassigned DNA B12 VH 3.3 primer
<220> FEATURE:
<221> NAME/KEY: source
<222> LOCATION: (1)..(67)
<223> OTHER INFORMATION: /mol_type="unassigned DNA" /note="B12 VH 3.3
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 104
ggtgaccatt gtcccttggc cccasnnsnn snnsnnsnns nngactgccg agatatcttt    60
tgcacag    67

<210> SEQ ID NO 105
<211> LENGTH: 66
<212> TYPE: DNA
<213> ORGANISM: Artificial Sequence
<220> FEATURE:
<223> OTHER INFORMATION: unassigned DNA B12 VL 3.1 primer
<220> FEATURE:
<221> NAME/KEY: source
<222> LOCATION: (1)..(66)
<223> OTHER INFORMATION: /mol_type="unassigned DNA" /note="B12 VL3.1
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 105
ggtcccttgg ccgaacgtct gaggsnnsnn snnsnnsnns nnacagtagt aagttgcaaa    60
atcttc    66

<210> SEQ ID NO 106
<211> LENGTH: 69
<212> TYPE: DNA
<213> ORGANISM: Artificial Sequence
<220> FEATURE:
<223> OTHER INFORMATION: unassigned DNA B12 VL 3.2 primer
<220> FEATURE:
<221> NAME/KEY: source
<222> LOCATION: (1)..(69)
<223> OTHER INFORMATION: /mol_type="unassigned DNA" /note="B12 VL 3.2
      primer" /organism="Artificial Sequence"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)

<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"
<220> FEATURE:
<221> NAME/KEY: misc_feature
<222> LOCATION: (44)..(45)
<223> OTHER INFORMATION: /note="wherein 'n' is A, T, G or C"

<400> SEQUENCE: 106
gatatccact ttggtccctt ggccgaasnn snnsnnsnns nnsnnactct gttgacagta    60
gtaagttgc                                                           69

<210> SEQ ID NO 107
<211> LENGTH: 69
<212> TYPE: DNA
<213> ORGANISM: Artificial Sequence
<220> FEATURE:
<223> OTHER INFORMATION: unassigned DNA 2A5 VH 3.1 primer
<220> FEATURE:
<221> NAME/KEY: source
<222> LOCATION: (1)..(69)
<223> OTHER INFORMATION: /mol_type="unassigned DNA" /note="2A5 VH 3.1
      primer" /organism="Artificial Sequence"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"
<220> FEATURE:
<221> NAME/KEY: misc_feature
<222> LOCATION: (44)..(45)
<223> OTHER INFORMATION: /note="wherein 'n' is A, T, G or C"

<400> SEQUENCE: 107
ggttccctgg ccccagtagg tcaaggcsnn snnsnnsnns nnsnntgttg cacagtaata    60
cacggccgt                                                           69

<210> SEQ ID NO 108
<211> LENGTH: 66
<212> TYPE: DNA
<213> ORGANISM: Artificial Sequence
<220> FEATURE:
<223> OTHER INFORMATION: unassigned DNA 2A5 VH 3.2 primer
<220> FEATURE:
<221> NAME/KEY: source
<222> LOCATION: (1)..(66)
<223> OTHER INFORMATION: /mol_type="unassigned DNA" /note="2A5 VH 3.2
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"

```
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 108
cagggttccc tggccccagt aggtsnnsnn snnsnnsnns nnctgggctg ttgcacagta      60
atacac                                                                66

<210> SEQ ID NO 109
<211> LENGTH: 66
<212> TYPE: DNA
<213> ORGANISM: Artificial Sequence
<220> FEATURE:
<223> OTHER INFORMATION: unassigned DNA 2A5 VH 3.3 primer
<220> FEATURE:
<221> NAME/KEY: source
<222> LOCATION: (1)..(66)
<223> OTHER INFORMATION: /mol_type="unassigned DNA" /note="2A5 VH 3.3
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 109
ggtgaccagg gttccctggc cccasnnsnn snnsnnsnns nnctctttct gggctgttgc      60
acagta                                                                66

<210> SEQ ID NO 110
<211> LENGTH: 66
<212> TYPE: DNA
<213> ORGANISM: Artificial Sequence
<220> FEATURE:
<223> OTHER INFORMATION: unassigned DNA 2A5 VL 3.1 primer
<220> FEATURE:
<221> NAME/KEY: source
<222> LOCATION: (1)..(66)
<223> OTHER INFORMATION: /mol_type="unassigned DNA" /note="2A5 VL 3.1
      primer" /organism="Artificial Sequence"
<220> FEATURE:
```

<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 110
ggtcccttgg ccgaacgtcc acggsnnsnn snnsnnsnns nnacagtagt aagttgcaaa    60
atcttc                                                              66

<210> SEQ ID NO 111
<211> LENGTH: 66
<212> TYPE: DNA
<213> ORGANISM: Artificial Sequence
<220> FEATURE:
<223> OTHER INFORMATION: unassigned DNA 2A5 VL 3.2 unassigned DNA
<220> FEATURE:
<221> NAME/KEY: source
<222> LOCATION: (1)..(66)
<223> OTHER INFORMATION: /mol_type="unassigned DNA" /note="2A5 VL 3.2
      primer" /organism="Artificial Sequence"
<220> FEATURE:
<221> NAME/KEY: misc_feature
<222> LOCATION: (26)..(27)
<223> OTHER INFORMATION: /note="wherein 'n' is A, T, G or C"
<220> FEATURE:
<221> NAME/KEY: misc_feature
<222> LOCATION: (29)..(30)
<223> OTHER INFORMATION: /note="wherein 'n' is A, T, G or C"
<220> FEATURE:
<221> NAME/KEY: misc_feature
<222> LOCATION: (32)..(33)
<223> OTHER INFORMATION: /note="wherein 'n' is A, T, G or C"
<220> FEATURE:
<221> NAME/KEY: misc_feature
<222> LOCATION: (35)..(36)
<223> OTHER INFORMATION: /note="wherein 'n' is A, T, G or C"
<220> FEATURE:
<221> NAME/KEY: misc_feature
<222> LOCATION: (38)..(39)
<223> OTHER INFORMATION: /note="wherein 'n' is A, T, G or C"
<220> FEATURE:
<221> NAME/KEY: misc_feature
<222> LOCATION: (41)..(42)
<223> OTHER INFORMATION: /note="wherein 'n' is A, T, G or C"

<400> SEQUENCE: 111
ctccaccttg gtcccttggc cgaasnnsnn snnsnnsnns nnactctgtt gacagtagta    60
agttgc                                                              66

<210> SEQ ID NO 112
<211> LENGTH: 119
<212> TYPE: PRT
<213> ORGANISM: Artificial Sequence
<220> FEATURE:

<223> OTHER INFORMATION: Antibody 2A5 Framework Germlined: VH amino acid
      sequence

<400> SEQUENCE: 112

Gln Val Gln Leu Val Gln Ser Gly Ala Glu Val Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ala Gln Lys Glu Thr Tyr Ala Leu Thr Tyr Trp Gly Gln Gly
            100                 105                 110

Thr Leu Val Thr Val Ser Ser
            115

<210> SEQ ID NO 113
<211> LENGTH: 108
<212> TYPE: PRT
<213> ORGANISM: Artificial Sequence
<220> FEATURE:
<223> OTHER INFORMATION: Antibody 2A5 Framework Germlined: VL amino acid
      sequence

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys Arg
            100                 105

<210> SEQ ID NO 114
<211> LENGTH: 7
<212> TYPE: PRT
<213> ORGANISM: Artificial Sequence
<220> FEATURE:
<223> OTHER INFORMATION: Antibody 2A5 CDRs changed as a result of the
      germlined sequence VL CDR2

<400> SEQUENCE: 114

Ala Ala Ser Ser Leu Gln Ser
1               5

<210> SEQ ID NO 115
<211> LENGTH: 120
<212> TYPE: PRT

```
<213> ORGANISM: Artificial Sequence
<220> FEATURE:
<223> OTHER INFORMATION: Antibody B12 Framework Germlined: VH amino acid
      sequence

<400> SEQUENCE: 115

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Tyr Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Ser Ala Val Pro Asp Thr Phe Asp Ile Trp Gly Gln
            100                 105                 110

Gly Thr Met Val Thr Val Ser Ser
        115                 120

<210> SEQ ID NO 116
<211> LENGTH: 17
<212> TYPE: PRT
<213> ORGANISM: Artificial Sequence
<220> FEATURE:
<223> OTHER INFORMATION: Antibody B12 CDRs changed as a result of the
      germlined sequence VH CDR2

<400> SEQUENCE: 116

Gly Ile Ser Gly Ser Gly Gly Ser Thr Tyr Tyr Ala Asp Ser Val Lys
1               5                   10                  15

Tyr

<210> SEQ ID NO 117
<211> LENGTH: 108
<212> TYPE: PRT
<213> ORGANISM: Artificial Sequence
<220> FEATURE:
<223> OTHER INFORMATION: Antibody B12 Framework Germlined: VL amino acid
      sequence

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys Arg
            100                 105
```

<210> SEQ ID NO 118
<211> LENGTH: 7
<212> TYPE: PRT
<213> ORGANISM: Artificial Sequence
<220> FEATURE:
<223> OTHER INFORMATION: Antibody B12 CDRs changed as a result of the germlined sequence VL CDR2

<400> SEQUENCE: 118

Asp Ala Ser Ser Leu Gln Ser
1               5

<210> SEQ ID NO 119
<211> LENGTH: 117
<212> TYPE: PRT
<213> ORGANISM: Artificial Sequence
<220> FEATURE:
<223> OTHER INFORMATION: Antibody D8 Framework Germlined: VH amino acid sequence

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gln Asp Ser Ser Ser Asp Tyr Trp Gly Gln Gly Thr Leu
                100                 105                 110

Val Thr Val Ser Ser
        115

<210> SEQ ID NO 120
<211> LENGTH: 108
<212> TYPE: PRT
<213> ORGANISM: Artificial Sequence
<220> FEATURE:
<223> OTHER INFORMATION: Antibody D8 Framework Germlined: VL amino acid sequence

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
                20                  25                  30

Leu Asn Trp Tyr Gln Gln Lys Pro Gly Lys Ala Pro Lys Leu Leu Ile
            35                  40                  45

Tyr Asp Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Gln
                85                  90                  95

Thr Phe Gly Gln Gly Thr Lys Val Glu Ile Lys Arg

<210> SEQ ID NO 121
<211> LENGTH: 7
<212> TYPE: PRT
<213> ORGANISM: Artificial Sequence
<220> FEATURE:
<223> OTHER INFORMATION: Antibody D8 CDRs changed as a result of the
      germlined sequence VL CDR2

<400> SEQUENCE: 121

Asp Ala Ser Ser Leu Gln Ser
1               5

<210> SEQ ID NO 122
<211> LENGTH: 125
<212> TYPE: PRT
<213> ORGANISM: Artificial Sequence
<220> FEATURE:
<223> OTHER INFORMATION: Antibody F3 Framework germlined: VH amino acid
      sequence

<400> SEQUENCE: 122

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Asp Gln Leu Phe Ser Ala Glu Ser Asn Ala Phe
            100                 105                 110

Asp Ile Trp Gly Gln Gly Thr Leu Val Thr Val Ser Ser
        115                 120                 125

<210> SEQ ID NO 123
<211> LENGTH: 113
<212> TYPE: PRT
<213> ORGANISM: Artificial Sequence
<220> FEATURE:
<223> OTHER INFORMATION: Antibody F3 Framework germlined: VL amino acid
      sequence

<400> SEQUENCE: 123

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Tyr
                20                  25                  30

Phe Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Trp Val Phe Gly Gly Gly Thr Lys Leu Thr Val Leu Gly Gln
            100                 105                 110

Pro

<210> SEQ ID NO 124
<211> LENGTH: 107
<212> TYPE: PRT
<213> ORGANISM: Artificial Sequence
<220> FEATURE:
<223> OTHER INFORMATION: Antibody 2A5 VL amino acid sequence

<400> SEQUENCE: 124

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 125
<211> LENGTH: 107
<212> TYPE: PRT
<213> ORGANISM: Artificial Sequence
<220> FEATURE:
<223> OTHER INFORMATION: Antibody B12 VL amino acid sequence

<400> SEQUENCE: 125

Asp Ile Gln Met Thr Gln Ser Pro Ala Ser Leu Pro Thr Pro Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys
            100                 105

<210> SEQ ID NO 126
<211> LENGTH: 107
<212> TYPE: PRT
<213> ORGANISM: Artificial Sequence
<220> FEATURE:
<223> OTHER INFORMATION: Antibody D8 VL amino acid sequence

<400> SEQUENCE: 126

Asp Ile Gln Met Thr Gln Ser Pro Ala Ser Leu Pro Thr Ser Val Gly

```
                1               5                  10                  15
Asp Arg Val Thr Ile Thr Cys Arg Ala Ser Gln Tyr Ile Gln Gly Phe
                    20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Gln
                    85                  90                  95

Thr Phe Gly Gln Gly Thr Lys Val Asp Ile Lys
                100                 105

<210> SEQ ID NO 127
<211> LENGTH: 110
<212> TYPE: PRT
<213> ORGANISM: Artificial Sequence
<220> FEATURE:
<223> OTHER INFORMATION: Antibody F3 VL amino acid sequence

<400> SEQUENCE: 127

Asn Phe Met Leu Ala Gln Pro His Ser Val Ser Glu Ser Pro Gly Lys
1               5                   10                  15

Thr Val Thr Ile Ser Cys Thr Arg Ser Ser Gly Ser Ile Ala Ser Tyr
                    20                  25                  30

Phe Val Gln Trp Phe Gln Gln Arg Pro Gly Ser Ala Pro Thr Ala Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                    85                  90                  95

Ser Asn Trp Val Phe Gly Gly Gly Thr Lys Val Thr Val Leu
                100                 105                 110

<210> SEQ ID NO 128
<211> LENGTH: 107
<212> TYPE: PRT
<213> ORGANISM: Artificial Sequence
<220> FEATURE:
<223> OTHER INFORMATION: Antibody 162_02_C6 (derived from 2A5) VL amino
      acid sequence

<400> SEQUENCE: 128

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
                    20                  25                  30

Leu Asn Trp Tyr Gln Gln Lys Pro Gly Lys Ala Pro Arg Leu Leu Ile
            35                  40                  45

Tyr Ala Ala Ser Thr Leu Gln Asp Gly Val Pro Ser Arg Phe Ser Gly
        50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Asn Gln Tyr Ala Gly Pro Trp
                    85                  90                  95
```

```
Thr Phe Gly Gln Gly Thr Lys Val Glu Ile Lys
            100                 105
```

<210> SEQ ID NO 129
<211> LENGTH: 107
<212> TYPE: PRT
<213> ORGANISM: Artificial Sequence
<220> FEATURE:
<223> OTHER INFORMATION: Antibody 162_02_H5 (derived from 2A5) VL amino
      acid sequence

<400> SEQUENCE: 129

```
Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Asn Gln Tyr Thr Gly Pro Trp
                85                  90                  95

Thr Phe Gly Gln Gly Thr Lys Val Glu Ile Lys
            100                 105
```

<210> SEQ ID NO 130
<211> LENGTH: 107
<212> TYPE: PRT
<213> ORGANISM: Artificial Sequence
<220> FEATURE:
<223> OTHER INFORMATION: Antibody 162_02_F3 (derived from 2A5) VL amino
      acid sequence

<400> SEQUENCE: 130

```
Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Asn Gly Tyr Arg Gly Pro Trp
                85                  90                  95

Thr Phe Gly Gln Gly Thr Lys Val Glu Ile Lys
            100                 105
```

<210> SEQ ID NO 131
<211> LENGTH: 107
<212> TYPE: PRT
<213> ORGANISM: Artificial Sequence
<220> FEATURE:
<223> OTHER INFORMATION: Antibody 162_02_C1 (derived from 2A5) VL amino
      acid sequence

<400> SEQUENCE: 131

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu His His Tyr Arg Ala Pro Trp
                85                  90                  95

Thr Phe Gly Gln Gly Thr Lys Val Glu Ile Lys
            100                 105

<210> SEQ ID NO 132
<211> LENGTH: 107
<212> TYPE: PRT
<213> ORGANISM: Artificial Sequence
<220> FEATURE:
<223> OTHER INFORMATION: Antibody 162_02_C2 (derived from 2A5) VL amino
      acid sequence

<400> SEQUENCE: 132

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Met His His Tyr Arg Ala Pro Trp
                85                  90                  95

Thr Phe Gly Gln Gly Thr Lys Val Glu Ile Lys
            100                 105

<210> SEQ ID NO 133
<211> LENGTH: 107
<212> TYPE: PRT
<213> ORGANISM: Artificial Sequence
<220> FEATURE:
<223> OTHER INFORMATION: Antibody 162_02_F4 (derived from 2A5) VL amino
      acid sequence

<400> SEQUENCE: 133

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Met His His Tyr Arg Ser Pro Trp
                85                  90                  95

Thr Phe Gly Gln Gly Thr Lys Val Glu Ile Lys
            100                 105

<210> SEQ ID NO 134
<211> LENGTH: 107
<212> TYPE: PRT
<213> ORGANISM: Artificial Sequence
<220> FEATURE:
<223> OTHER INFORMATION: Antibody 162_02_C3 (derived from 2A5) VL amino
      acid sequence

<400> SEQUENCE: 134

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
                20                  25                  30

Leu Asn Trp Tyr Gln Gln Lys Pro Gly Lys Ala Pro Arg Leu Leu Ile
            35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Met Gln His Tyr Asp Gly Pro Trp
                85                  90                  95

Thr Phe Gly Gln Gly Thr Lys Val Glu Ile Lys
            100                 105

<210> SEQ ID NO 135
<211> LENGTH: 9
<212> TYPE: PRT
<213> ORGANISM: Artificial Sequence
<220> FEATURE:
<223> OTHER INFORMATION: Antibody 162_02_E11 (derived from 2A5) VL CDR3

<400> SEQUENCE: 135

Leu His His Tyr Arg Ser Pro Trp Thr
1               5

<210> SEQ ID NO 136
<211> LENGTH: 107
<212> TYPE: PRT
<213> ORGANISM: Artificial Sequence
<220> FEATURE:
<223> OTHER INFORMATION: Antibody 162_02_E11 (derived from 2A5) VL amino
      acid sequence

<400> SEQUENCE: 136

Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
                20                  25                  30

Leu Asn Trp Tyr Gln Gln Lys Pro Gly Lys Ala Pro Arg Leu Leu Ile
            35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu His His Tyr Arg Ser Pro Trp
                85                  90                  95

```
Thr Phe Gly Gln Gly Thr Lys Val Glu Ile Lys
            100                 105
```

<210> SEQ ID NO 137
<211> LENGTH: 107
<212> TYPE: PRT
<213> ORGANISM: Artificial Sequence
<220> FEATURE:
<223> OTHER INFORMATION: Antibody 163_02_A12 (derived from 2A5) VL amino
      acid sequence

<400> SEQUENCE: 137

```
Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu His His Tyr Arg Glu Pro Trp
                85                  90                  95

Thr Phe Gly Gln Gly Thr Lys Val Glu Ile Lys
            100                 105
```

<210> SEQ ID NO 138
<211> LENGTH: 107
<212> TYPE: PRT
<213> ORGANISM: Artificial Sequence
<220> FEATURE:
<223> OTHER INFORMATION: Antibody 163_02_D11 (derived from 2A5) VL amino
      acid sequence

<400> SEQUENCE: 138

```
Asp Ile Gln Met Thr Gln Ser Pro Ala Ser Leu Pro Thr Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Arg Leu Leu Ile
        35                  40                  45

Tyr Ala Ala Ser Thr Leu Gln Asp Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu His His Tyr Lys Ser Pro Trp
                85                  90                  95

Thr Phe Gly Gln Gly Thr Lys Val Glu Ile Lys
            100                 105
```

<210> SEQ ID NO 139
<211> LENGTH: 107
<212> TYPE: PRT
<213> ORGANISM: Artificial Sequence
<220> FEATURE:
<223> OTHER INFORMATION: Antibody 2A5 Framework Germlined: VL amino acid
      sequence

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 140
<211> LENGTH: 107
<212> TYPE: PRT
<213> ORGANISM: Artificial Sequence
<220> FEATURE:
<223> OTHER INFORMATION: Antibody B12 Framework Germlined: VL amino acid
      sequence

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Gln
                85                  90                  95

Thr Phe Gly Gln Gly Thr Lys Val Asp Ile Lys
            100                 105

<210> SEQ ID NO 141
<211> LENGTH: 107
<212> TYPE: PRT
<213> ORGANISM: Artificial Sequence
<220> FEATURE:
<223> OTHER INFORMATION: Antibody D8 Framework Germlined: VL amino acid
      sequence

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile Gln Gly Phe
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Ser Thr Leu Gln
                85                  90                  95

Thr Phe Gly Gln Gly Thr Lys Val Glu Ile Lys
            100                 105
```

<210> SEQ ID NO 142
<211> LENGTH: 110
<212> TYPE: PRT
<213> ORGANISM: Artificial Sequence
<220> FEATURE:
<223> OTHER INFORMATION: Antibody F3 Framework germlined: VL amino acid
      sequence

<400> SEQUENCE: 142

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Tyr
            20                  25                  30

Phe Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn Trp Val Phe Gly Gly Gly Thr Lys Leu Thr Val Leu
            100                 105                 110
```

<210> SEQ ID NO 143
<211> LENGTH: 446
<212> TYPE: PRT
<213> ORGANISM: Artificial Sequence
<220> FEATURE:
<223> OTHER INFORMATION: IgG4 165_13_C3 (constant region with hinge
      modification as described in Angal 1993)

<400> SEQUENCE: 143

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Gly Ser Gly Ser Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ser Tyr Gln Ser Asp Glu Asp Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
            245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
            325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
            405                 410                 415
Gln Glu Gly Asn Val Phe Ser Cys Ser Val Met His Glu Ala Leu His
        420                 425                 430
Asn His Tyr Thr Gln Lys Ser Leu Ser Leu Ser Leu Gly Lys
        435                 440                 445

<210> SEQ ID NO 144
<211> LENGTH: 23
<212> TYPE: PRT
<213> ORGANISM: Artificial Sequence
<220> FEATURE:
<223> OTHER INFORMATION: Human Tenascin-C TA domain

<400> SEQUENCE: 144

Gly Val Leu Lys Lys Val Ile Arg His Lys Arg Gln Ser Gly Val Asn
1               5                   10                  15
Ala Thr Leu Pro Glu Glu Asn
            20

<210> SEQ ID NO 145
<211> LENGTH: 476
<212> TYPE: PRT
<213> ORGANISM: Artificial Sequence
<220> FEATURE:
<223> OTHER INFORMATION: Human Tenascin-C EGFL domain

<400> SEQUENCE: 145
```

```
Cys Cys Leu Gln Pro Ala Thr Gly Arg Leu Asp Thr Arg Pro Phe Cys
1               5                   10                  15

Ser Gly Arg Gly Asn Phe Ser Thr Glu Gly Cys Gly Cys Val Cys Glu
            20                  25                  30

Pro Gly Trp Lys Gly Pro Asn Cys Ser Glu Pro Glu Cys Pro Gly Asn
            35                  40                  45

Cys His Leu Arg Gly Arg Cys Ile Asp Gly Gln Cys Ile Cys Asp Asp
        50                  55                  60

Gly Phe Thr Gly Glu Asp Cys Ser Gln Leu Ala Cys Pro Ser Asp Cys
65                  70                  75                  80

Asn Asp Gln Gly Lys Cys Val Asn Gly Val Cys Ile Cys Phe Glu Gly
                85                  90                  95

Tyr Ala Gly Ala Asp Cys Ser Arg Glu Ile Cys Pro Val Pro Cys Ser
            100                 105                 110

Glu Glu His Gly Thr Cys Val Asp Gly Leu Cys Val Cys His Asp Gly
        115                 120                 125

Phe Ala Gly Asp Asp Cys Asn Lys Pro Leu Cys Leu Asn Asn Cys Tyr
130                 135                 140

Asn Arg Gly Arg Cys Val Glu Asn Glu Cys Val Cys Asp Glu Gly Phe
145                 150                 155                 160

Thr Gly Glu Asp Cys Ser Glu Leu Ile Cys Pro Asn Asp Cys Phe Asp
            165                 170                 175

Arg Gly Arg Cys Ile Asn Gly Thr Cys Tyr Cys Glu Glu Gly Phe Thr
        180                 185                 190

Gly Glu Asp Cys Gly Lys Pro Thr Cys Pro His Ala Cys His Thr Gln
            195                 200                 205

Gly Arg Cys Glu Glu Gly Gln Cys Val Cys Asp Glu Gly Phe Ala Gly
        210                 215                 220

Leu Asp Cys Ser Glu Lys Arg Cys Pro Ala Asp Cys His Asn Arg Gly
225                 230                 235                 240

Arg Cys Val Asp Gly Arg Cys Glu Cys Asp Asp Gly Phe Thr Gly Ala
            245                 250                 255

Asp Cys Gly Glu Leu Lys Cys Pro Asn Gly Cys Ser Gly His Gly Arg
        260                 265                 270

Cys Val Asn Gly Gln Cys Val Cys Asp Glu Gly Tyr Thr Gly Glu Asp
        275                 280                 285

Cys Ser Gln Leu Arg Cys Pro Asn Asp Cys His Ser Arg Gly Arg Cys
        290                 295                 300

Val Glu Gly Lys Cys Val Cys Glu Gln Gly Phe Lys Gly Tyr Asp Cys
305                 310                 315                 320

Ser Asp Met Ser Cys Pro Asn Asp Cys His Gln His Gly Arg Cys Val
            325                 330                 335

Asn Gly Met Cys Val Cys Asp Asp Gly Tyr Thr Gly Glu Asp Cys Arg
        340                 345                 350

Asp Arg Gln Cys Pro Arg Asp Cys Ser Asn Arg Gly Leu Cys Val Asp
            355                 360                 365

Gly Gln Cys Val Cys Glu Asp Gly Phe Thr Gly Pro Asp Cys Ala Glu
        370                 375                 380

Leu Ser Cys Pro Asn Asp Cys His Gly Gln Gly Arg Cys Val Asn Gly
385                 390                 395                 400

Gln Cys Val Cys His Glu Gly Phe Met Gly Lys Asp Cys Lys Glu Gln
            405                 410                 415
```

-continued

```
Arg Cys Pro Ser Asp Cys His Gly Gln Gly Arg Cys Val Asp Gly Gln
            420                 425                 430

Cys Ile Cys His Glu Gly Phe Thr Gly Leu Asp Cys Gly Gln His Ser
            435                 440                 445

Cys Pro Ser Asp Cys Asn Asn Leu Gly Gln Cys Val Ser Gly Arg Cys
            450                 455                 460

Ile Cys Asn Glu Gly Tyr Ser Gly Glu Asp Cys Ser
465                 470                 475

<210> SEQ ID NO 146
<211> LENGTH: 1352
<212> TYPE: PRT
<213> ORGANISM: Artificial Sequence
<220> FEATURE:
<223> OTHER INFORMATION: Human Tenascin-C FNIII domain

<400> SEQUENCE: 146

Glu Val Ser Pro Pro Lys Asp Leu Val Val Thr Glu Val Thr Glu Glu
1               5                   10                  15

Thr Val Asn Leu Ala Trp Asp Asn Glu Met Arg Val Thr Glu Tyr Leu
            20                  25                  30

Val Val Tyr Thr Pro Thr His Glu Gly Gly Leu Glu Met Gln Phe Arg
            35                  40                  45

Val Pro Gly Asp Gln Thr Ser Thr Ile Ile Gln Glu Leu Glu Pro Gly
50                  55                  60

Val Glu Tyr Phe Ile Arg Val Phe Ala Ile Leu Glu Asn Lys Lys Ser
65                  70                  75                  80

Ile Pro Val Ser Ala Arg Val Ala Thr Tyr Leu Pro Ala Pro Glu Gly
                85                  90                  95

Leu Lys Phe Lys Ser Ile Lys Glu Thr Ser Val Glu Val Glu Trp Asp
                100                 105                 110

Pro Leu Asp Ile Ala Phe Glu Thr Trp Glu Ile Ile Phe Arg Asn Met
            115                 120                 125

Asn Lys Glu Asp Glu Gly Glu Ile Thr Lys Ser Leu Arg Arg Pro Glu
    130                 135                 140

Thr Ser Tyr Arg Gln Thr Gly Leu Ala Pro Gly Gln Glu Tyr Glu Ile
145                 150                 155                 160

Ser Leu His Ile Val Lys Asn Asn Thr Arg Gly Pro Gly Leu Lys Arg
                165                 170                 175

Val Thr Thr Thr Arg Leu Asp Ala Pro Ser Gln Ile Glu Val Lys Asp
            180                 185                 190

Val Thr Asp Thr Thr Ala Leu Ile Thr Trp Phe Lys Pro Leu Ala Glu
            195                 200                 205

Ile Asp Gly Ile Glu Leu Thr Tyr Gly Ile Lys Asp Val Pro Gly Asp
    210                 215                 220

Arg Thr Thr Ile Asp Leu Thr Glu Asp Glu Asn Gln Tyr Ser Ile Gly
225                 230                 235                 240

Asn Leu Lys Pro Asp Thr Glu Tyr Glu Val Ser Leu Ile Ser Arg Arg
                245                 250                 255

Gly Asp Met Ser Ser Asn Pro Ala Lys Glu Thr Phe Thr Thr Gly Leu
            260                 265                 270

Asp Ala Pro Arg Asn Leu Arg Arg Val Ser Gln Thr Asp Asn Ser Ile
            275                 280                 285

Thr Leu Glu Trp Arg Asn Gly Lys Ala Ala Ile Asp Ser Tyr Arg Ile
    290                 295                 300
```

```
Lys Tyr Ala Pro Ile Ser Gly Gly Asp His Ala Glu Val Asp Val Pro
305                 310                 315                 320
Lys Ser Gln Gln Ala Thr Thr Lys Thr Thr Leu Thr Gly Leu Arg Pro
            325                 330                 335
Gly Thr Glu Tyr Gly Ile Gly Val Ser Ala Val Lys Glu Asp Lys Glu
                340                 345                 350
Ser Asn Pro Ala Thr Ile Asn Ala Ala Thr Glu Leu Asp Thr Pro Lys
        355                 360                 365
Asp Leu Gln Val Ser Glu Thr Ala Glu Thr Ser Leu Thr Leu Leu Trp
    370                 375                 380
Lys Thr Pro Leu Ala Lys Phe Asp Arg Tyr Arg Leu Asn Tyr Ser Leu
385                 390                 395                 400
Pro Thr Gly Gln Trp Val Gly Val Gln Leu Pro Arg Asn Thr Thr Ser
            405                 410                 415
Tyr Val Leu Arg Gly Leu Glu Pro Gly Gln Glu Tyr Asn Val Leu Leu
                420                 425                 430
Thr Ala Glu Lys Gly Arg His Lys Ser Lys Pro Ala Arg Val Lys Ala
        435                 440                 445
Ser Thr Glu Gln Ala Pro Glu Leu Glu Asn Leu Thr Val Thr Glu Val
    450                 455                 460
Gly Trp Asp Gly Leu Arg Leu Asn Trp Thr Ala Ala Asp Gln Ala Tyr
465                 470                 475                 480
Glu His Phe Ile Ile Gln Val Gln Glu Ala Asn Lys Val Glu Ala Ala
            485                 490                 495
Arg Asn Leu Thr Val Pro Gly Ser Leu Arg Ala Val Asp Ile Pro Gly
                500                 505                 510
Leu Lys Ala Ala Thr Pro Tyr Thr Val Ser Ile Tyr Gly Val Ile Gln
        515                 520                 525
Gly Tyr Arg Thr Pro Val Leu Ser Ala Glu Ala Ser Thr Gly Glu Thr
    530                 535                 540
Pro Asn Leu Gly Glu Val Val Val Ala Glu Val Gly Trp Asp Ala Leu
545                 550                 555                 560
Lys Leu Asn Trp Thr Ala Pro Glu Gly Ala Tyr Glu Tyr Phe Phe Ile
            565                 570                 575
Gln Val Gln Glu Ala Asp Thr Val Glu Ala Ala Gln Asn Leu Thr Val
                580                 585                 590
Pro Gly Gly Leu Arg Ser Thr Asp Leu Pro Gly Leu Lys Ala Ala Thr
        595                 600                 605
His Tyr Thr Ile Thr Ile Arg Gly Val Thr Gln Asp Phe Ser Thr Thr
    610                 615                 620
Pro Leu Ser Val Glu Val Leu Thr Glu Glu Val Pro Asp Met Gly Asn
625                 630                 635                 640
Leu Thr Val Thr Glu Val Ser Trp Asp Ala Leu Arg Leu Asn Trp Thr
            645                 650                 655
Thr Pro Asp Gly Thr Tyr Asp Gln Phe Thr Ile Gln Val Gln Glu Ala
                660                 665                 670
Asp Gln Val Glu Glu Ala His Asn Leu Thr Val Pro Gly Ser Leu Arg
        675                 680                 685
Ser Met Glu Ile Pro Gly Leu Arg Ala Gly Thr Pro Tyr Thr Val Thr
    690                 695                 700
Leu His Gly Glu Val Arg Gly His Ser Thr Arg Pro Leu Ala Val Glu
705                 710                 715                 720
Val Val Thr Glu Asp Leu Pro Gln Leu Gly Asp Leu Ala Val Ser Glu
```

```
                725                 730                 735
Val Gly Trp Asp Gly Leu Arg Leu Asn Trp Thr Ala Ala Asp Asn Ala
                740                 745                 750

Tyr Glu His Phe Val Ile Gln Val Gln Glu Val Asn Lys Val Glu Ala
                755                 760                 765

Ala Gln Asn Leu Thr Leu Pro Gly Ser Leu Arg Ala Val Asp Ile Pro
                770                 775                 780

Gly Leu Glu Ala Ala Thr Pro Tyr Arg Val Ser Ile Tyr Gly Val Ile
785                 790                 795                 800

Arg Gly Tyr Arg Thr Pro Val Leu Ser Ala Glu Ala Ser Thr Ala Lys
                805                 810                 815

Glu Pro Glu Ile Gly Asn Leu Asn Val Ser Asp Ile Thr Pro Glu Ser
                820                 825                 830

Phe Asn Leu Ser Trp Met Ala Thr Asp Gly Ile Phe Glu Thr Phe Thr
                835                 840                 845

Ile Glu Ile Ile Asp Ser Asn Arg Leu Leu Glu Thr Val Glu Tyr Asn
                850                 855                 860

Ile Ser Gly Ala Glu Arg Thr Ala His Ile Ser Gly Leu Pro Pro Ser
865                 870                 875                 880

Thr Asp Phe Ile Val Tyr Leu Ser Gly Leu Ala Pro Ser Ile Arg Thr
                885                 890                 895

Lys Thr Ile Ser Ala Thr Ala Thr Thr Glu Ala Leu Pro Leu Leu Glu
                900                 905                 910

Asn Leu Thr Ile Ser Asp Ile Asn Pro Tyr Gly Phe Thr Val Ser Trp
                915                 920                 925

Met Ala Ser Glu Asn Ala Phe Asp Ser Phe Leu Val Thr Val Val Asp
930                 935                 940

Ser Gly Lys Leu Leu Asp Pro Gln Glu Phe Thr Leu Ser Gly Thr Gln
945                 950                 955                 960

Arg Lys Leu Glu Leu Arg Gly Leu Ile Thr Gly Ile Gly Tyr Glu Val
                965                 970                 975

Met Val Ser Gly Phe Thr Gln Gly His Gln Thr Lys Pro Leu Arg Ala
                980                 985                 990

Glu Ile Val Thr Glu Ala Glu Pro Glu Val Asp Asn Leu Leu Val Ser
                995                1000                1005

Asp Ala Thr Pro Asp Gly Phe Arg Leu Ser Trp Thr Ala Asp Glu
                1010                1015                1020

Gly Val Phe Asp Asn Phe Val Leu Lys Ile Arg Asp Thr Lys Lys
                1025                1030                1035

Gln Ser Glu Pro Leu Glu Ile Thr Leu Leu Ala Pro Glu Arg Thr
                1040                1045                1050

Arg Asp Leu Thr Gly Leu Arg Glu Ala Thr Glu Tyr Glu Ile Glu
                1055                1060                1065

Leu Tyr Gly Ile Ser Lys Gly Arg Arg Ser Gln Thr Val Ser Ala
                1070                1075                1080

Ile Ala Thr Thr Ala Met Gly Ser Pro Lys Glu Val Ile Phe Ser
                1085                1090                1095

Asp Ile Thr Glu Asn Ser Ala Thr Val Ser Trp Arg Ala Pro Thr
                1100                1105                1110

Ala Gln Val Glu Ser Phe Arg Ile Thr Tyr Val Pro Ile Thr Gly
                1115                1120                1125

Gly Thr Pro Ser Met Val Thr Val Asp Gly Thr Lys Thr Gln Thr
                1130                1135                1140
```

```
Arg Leu Val Lys Leu Ile Pro Gly Val Glu Tyr Leu Val Ser Ile
    1145                1150                1155

Ile Ala Met Lys Gly Phe Glu Glu Ser Glu Pro Val Ser Gly Ser
    1160                1165                1170

Phe Thr Thr Ala Leu Asp Gly Pro Ser Gly Leu Val Thr Ala Asn
    1175                1180                1185

Ile Thr Asp Ser Glu Ala Leu Ala Arg Trp Gln Pro Ala Ile Ala
    1190                1195                1200

Thr Val Asp Ser Tyr Val Ile Ser Tyr Thr Gly Glu Lys Val Pro
    1205                1210                1215

Glu Ile Thr Arg Thr Val Ser Gly Asn Thr Val Glu Tyr Ala Leu
    1220                1225                1230

Thr Asp Leu Glu Pro Ala Thr Glu Tyr Thr Leu Arg Ile Phe Ala
    1235                1240                1245

Glu Lys Gly Pro Gln Lys Ser Ser Thr Ile Thr Ala Lys Phe Thr
    1250                1255                1260

Thr Asp Leu Asp Ser Pro Arg Asp Leu Thr Ala Thr Glu Val Gln
    1265                1270                1275

Ser Glu Thr Ala Leu Leu Thr Trp Arg Pro Pro Arg Ala Ser Val
    1280                1285                1290

Thr Gly Tyr Leu Leu Val Tyr Glu Ser Val Asp Gly Thr Val Lys
    1295                1300                1305

Glu Val Ile Val Gly Pro Asp Thr Thr Ser Tyr Ser Leu Ala Asp
    1310                1315                1320

Leu Ser Pro Ser Thr His Tyr Thr Ala Lys Ile Gln Ala Leu Asn
    1325                1330                1335

Gly Pro Leu Arg Ser Asn Met Ile Gln Thr Ile Phe Thr Thr
    1340                1345                1350
```

<210> SEQ ID NO 147
<211> LENGTH: 228
<212> TYPE: PRT
<213> ORGANISM: Artificial Sequence
<220> FEATURE:
<223> OTHER INFORMATION: Human Tenascin-C FBG domain

<400> SEQUENCE: 147

```
Ile Gly Leu Leu Tyr Pro Phe Pro Lys Asp Cys Ser Gln Ala Met Leu
1               5                   10                  15

Asn Gly Asp Thr Thr Ser Gly Leu Tyr Thr Ile Tyr Leu Asn Gly Asp
                20                  25                  30

Lys Ala Gln Ala Leu Glu Val Phe Cys Asp Met Thr Ser Asp Gly Gly
            35                  40                  45

Gly Trp Ile Val Phe Leu Arg Arg Lys Asn Gly Arg Glu Asn Phe Tyr
        50                  55                  60

Gln Asn Trp Lys Ala Tyr Ala Ala Gly Phe Gly Asp Arg Arg Glu Glu
65                  70                  75                  80

Phe Trp Leu Gly Leu Asp Asn Leu Asn Lys Ile Thr Ala Gln Gly Gln
                85                  90                  95

Tyr Glu Leu Arg Val Asp Leu Arg Asp His Gly Glu Thr Ala Phe Ala
            100                 105                 110

Val Tyr Asp Lys Phe Ser Val Gly Asp Ala Lys Thr Arg Tyr Lys Leu
        115                 120                 125

Lys Val Glu Gly Tyr Ser Gly Thr Ala Gly Asp Ser Met Ala Tyr His
    130                 135                 140
```

Asn Gly Arg Ser Phe Ser Thr Phe Asp Lys Asp Thr Asp Ser Ala Ile
145                 150                 155                 160

Thr Asn Cys Ala Leu Ser Tyr Lys Gly Ala Phe Trp Tyr Arg Asn Cys
            165                 170                 175

His Arg Val Asn Leu Met Gly Arg Tyr Gly Asp Asn Asn His Ser Gln
        180                 185                 190

Gly Val Asn Trp Phe His Trp Lys Gly His Glu His Ser Ile Gln Phe
    195                 200                 205

Ala Glu Met Lys Leu Arg Pro Ser Asn Phe Arg Asn Leu Glu Gly Arg
210                 215                 220

Arg Lys Arg Ala
225

<210> SEQ ID NO 148
<211> LENGTH: 7616
<212> TYPE: DNA
<213> ORGANISM: Artificial Sequence
<220> FEATURE:
<223> OTHER INFORMATION: unassigned DNA Human Tenascin-C nucleotide
      sequence

<400> SEQUENCE: 148
attacagagg aaggagctcg ctatataagc cagccaaagt tggctgcacc ggccacagcc        60
tgcctactgt cacccgcctc tcccgcgcgc agatacacgc cccgcctcc gtgggcacaa       120 aggcagcgct gctggggaac tcgggggaac gcgcacgtgg aaccgccgc agctccacac       180 tccaggtact tcttccaagg acctaggtct ctcgcccatc ggaaagaaaa taattctttc       240
aagaagatca gggacaactg atttgaagtc tactctgtgc ttctaaatcc ccaattctgc       300
tgaaagtgag ataccctaga gcccagagc cccagcagca cccagccaaa cccacctcca       360
ccatgggggc catgactcag ctgttggcag gtgtctttct tgctttcctt gccctcgcta       420
ccgaaggtgg ggtcctcaag aaagtcatcc ggcacaagcg acagagtggg gtgaacgcca       480
ccctgccaga agagaaccag ccagtggtgt taaccacgt ttacaacatc aagctgccag       540
tgggatccca gtgttcggtg gatctggagt cagccagtgg ggagaaagac ctggcaccgc       600
cttcagagcc cagcgaaagc tttcaggagc acacagtgga tggggaaaac cagattgtct       660
tcacacatcg catcaacatc ccccgccggg cctgtggctg tgccgcagcc cctgatgtta       720
aggagctgct gagcagactg gaggagctgg agaacctggt gtcttccctg agggagcaat       780
gtactgcagg agcaggctgc tgtctccagc ctgccacagg ccgcttggac accaggccct       840
tctgtagcgg tcggggcaac ttcagcactg aaggatgtgg ctgtgtctgc gaacctggct       900
ggaaaggccc caactgctct gagcccgaat gtccaggcaa ctgtcacctt cgaggccggt       960
gcattgatgg gcagtgcatc tgtgacgacg gcttcacggg cgaggactgc agccagctgg      1020
cttgccccag cgactgcaat gaccagggca gtgcgtaaa tggagtctgc atctgtttcg      1080
aaggctacgc cggggctgac tgcagccgtg aaatctgccc agtgccctgc agtgaggagc      1140
acggcacatg tgtagatggc ttgtgtgtgt gccacgatgg ctttgcaggc gatgactgca      1200
acaagcctct gtgtctcaac aattgctaca accgtggacg atgcgtggag atgagtgcg      1260 tgtgtgatga gggtttcacg ggcgaagact gcagtgagct catctgcccc aatgactgct      1320
tcgaccgggg ccgctgcatc aatggcacct gctactgcga agaaggcttc acaggtgaag      1380
actgcgggaa accacctgc ccacatgcct gccacaccca gggccggtgt gaggaggggc      1440
agtgtgtatg tgatgagggc tttgccggtg tggactgcag cgagaagagg tgtcctgctg      1500

```
actgtcacaa tcgtggccgc tgtgtagacg ggcggtgtga gtgtgatgat ggtttcactg    1560
gagctgactg tggggagctc aagtgtccca atggctgcag tggccatggc cgctgtgtca    1620
atgggcagtg tgtgtgtgat gagggctata ctggggagga ctgcagccag ctacggtgcc    1680
ccaatgactg tcacagtcgg ggccgctgtg tcgagggcaa atgtgtatgt gagcaaggct    1740
tcaagggcta tgactgcagt gacatgagct gccctaatga ctgtcaccag cacggccgct    1800
gtgtgaatgg catgtgtgtt tgtgatgacg gctacacagg ggaagactgc cgggatcgcc    1860
aatgccccag ggactgcagc aacaggggcc tctgtgtgga cggacagtgc gtctgtgagg    1920
acggcttcac cggccctgac tgtgcagaac tctcctgtcc aaatgactgc catggccagg    1980
gtcgctgtgt gaatgggcag tgcgtgtgcc atgaaggatt tatgggcaaa gactgcaagg    2040
agcaaagatg tcccagtgac tgtcatggcc agggccgctg cgtggacggc cagtgcatct    2100
gccacgaggg cttcacaggc ctggactgtg ccagcactc  ctgccccagt gactgcaaca    2160
acttaggaca atgcgtctcg ggccgctgca tctgcaacga gggctacagc ggagaagact    2220
gctcagaggt gtctcctccc aaagacctcg ttgtgacaga agtgacggaa gagacggtca    2280
acctggcctg ggacaatgag atgcgggtca cagagtacct tgtcgtgtac acgcccaccc    2340
acgagggtgg tctggaaatg cagttccgtg tgcctgggga ccagacgtcc accatcatcc    2400
aggagctgga gctggtgtg gagtacttta tccgtgtatt tgccatcctg agaacaaga     2460
agagcattcc tgtcagcgcc agggtggcca cgtacttacc tgcacctgaa ggcctgaaat    2520
tcaagtccat caaggagaca tctgtggaag tggagtggga tcctctagac attgctttg    2580
aaacctggga gatcatcttc cggaatatga ataaagaaga tgagggagag atcaccaaaa    2640
gcctgaggag gccagagacc tcttaccggc aaactggtct agctcctggg caagagtatg    2700
agatatctct gcacatagtg aaaacaata cccggggccc tggcctgaag agggtgacca    2760
ccacacgctt ggatgccccc agccagatcg aggtgaaaga tgtcacagac accactgcct    2820
tgatcacctg gttcaagccc ctggctgaga tcgatggcat tgagctgacc tacggcatca    2880
aagacgtgcc aggagaccgt accaccatcg atctcacaga ggacgagaac cagtactcca    2940
tcgggaacct gaagcctgac actgagtacg aggtgtccct catctcccgc agaggtgaca    3000
tgtcaagcaa cccagccaaa gagaccttca acaggcct cgatgctccc aggaatcttc     3060
gacgtgtttc ccagacagat aacagcatca ccctggaatg gaggaatggc aaggcagcta    3120
ttgacagtta cagaattaag tatgcccca tctctggagg ggaccacgct gaggttgatg    3180
ttccaaagag ccaacaagcc acaaccaaaa ccacactcac aggtctgagg ccgggaactg    3240
aatatgggat tggagtttct gctgtgaagg aagacaagga gagcaatcca gcgaccatca    3300
acgcagccac agagttggac acgcccaagg accttcaggt ttctgaaact gcagagacca    3360
gcctgaccct gctctggaag acaccgttgg ccaaatttga ccgctaccgc ctcaattaca    3420
gtctccccac aggccagtgg gtgggagtgc agcttccaag aaacaccact tcctatgtcc    3480
tgagaggcct ggaaccagga caggagtaca atgtcctcct gacagccgag aaaggcagac    3540
acaagagcaa gcccgcacgt gtgaaggcat ccactgaaca agcccctgag ctggaaaacc    3600
tcaccgtgac tgaggttggc tgggatggcc tcagactcaa ctggaccgca gctgaccagg    3660
cctatgagca ctttatcatt caggtgcagg aggccaacaa ggtggaggca gctcggaacc    3720
tcaccgtgcc tggcagcctt cgggctgtgg acataccggg cctcaaggct gctacgcctt    3780
atacagtctc catctatggg gtgatccagg gctatagaac accagtgctc tctgctgagg    3840
```

```
cctccacagg ggaaactccc aatttgggag aggtcgtggt ggccgaggtg ggctgggatg    3900
ccctcaaact caactggact gctccagaag gggcctatga gtacttttc attcaggtgc     3960 aggaggctga cacagtagag gcagcccaga acctcaccgt cccaggagga ctgaggtcca    4020
cagacctgcc tgggctcaaa gcagccactc attataccat caccatccgc ggggtcactc    4080
aggacttcag cacaacccct ctctctgttg aagtcttgac agaggaggtt ccagatatgg    4140
gaaacctcac agtgaccgag gttagctggg atgctctcag actgaactgg accacgccag    4200
atggaaccta tgaccagttt actattcagg tccaggaggc tgaccaggtg gaagaggctc    4260
acaatctcac ggttcctggc agcctgcgtt ccatggaaat cccaggcctc agggctggca    4320
ctccttacac agtcaccctg cacggcgagg tcaggggcca cagcactcga ccccttgctg    4380
tagaggtcgt cacagaggat ctcccacagc tgggagattt agccgtgtct gaggttggct    4440
gggatggcct cagactcaac tggaccgcag ctgacaatgc ctatgagcac tttgtcattc    4500
aggtgcagga ggtcaacaaa gtggaggcag cccagaacct cacgttgcct ggcagcctca    4560
gggctgtgga catcccgggc ctcgaggctg ccacgcctta tagagtctcc atctatgggg    4620
tgatccgggg ctatagaaca ccagtactct ctgctgaggc ctccacagcc aaagaacctg    4680
aaattggaaa cttaaatgtt tctgacataa ctcccgagag cttcaatctc tcctggatgg    4740
ctaccgatgg gatcttcgag acctttacca ttgaaattat tgattccaat aggttgctgg    4800
agactgtgga atataaatatc tctggtgctg aacgaactgc ccatatctca gggctacccc    4860
ctagtactga ttttattgtc tacctctctg gacttgctcc cagcatccgg accaaaaacca    4920 tcagtgccac agccacgaca gaggccctgc cccttctgga aaacctaacc atttccgaca    4980
ttaatcccta cgggttcaca gtttcctgga tggcatcgga gaatgccttt gacagctttc    5040
tagtaacggt ggtggattct gggaagctgc tggaccccca ggaattcaca ctttcaggaa    5100
cccagaggaa gctggagctt agaggcctca taactggcat tggctatgag gttatggtct    5160
ctggcttcac ccaagggcat caaaccaagc ccttgagggc tgagattgtt acagaagccg    5220
aaccggaagt tgacaacctt ctggtttcag atgccacccc agacggtttc cgtctgtcct    5280
ggacagctga tgaaggggtc ttcgacaatt ttgttctcaa aatcagagat accaaaaagc    5340
agtctgagcc actggaaata accctacttg cccccgaacg taccagggac ataacaggtc    5400
tcagagaggc tactgaatac gaaattgaac tctatggaat aagcaaagga aggcgatccc    5460
agacagtcag tgctatagca acaacagcca tgggctcccc aaaggaagtc atttctcag     5520 acatcactga aaattcggct actgtcagct ggagggcacc cacagcccaa gtggagagct    5580
tccggattac ctatgtgccc attacaggag gtacaccctc catggtaact gtggacggaa    5640
ccaagactca gaccaggctg gtgaaactca tacctggcgt ggagtacctt gtcagcatca    5700
tcgccatgaa gggctttgag gaaagtgaac ctgtctcagg gtcattcacc acagctctgg    5760
atggcccatc tggcctggtg acagccaaca tcactgactc agaagccttg gccaggtggc    5820
agccagccat tgccactgtg acagttatg tcatctccta cacaggcgag aaagtgccag    5880
aaattacacg cacggtgtcc gggaacacag tggagtatgc tctgaccgac ctcgagcctg    5940
ccacggaata cacactgaga atcttttcag agaaagggcc ccagaagagc tcaaccatca    6000
ctgccaagtt cacaacagac ctcgattctc caagagactt gactgctact gaggttcagt    6060
cggaaactgc cctccttacc tggcgacccc ccgggcatc agtcaccggt tacctgctgg     6120
tctatgaatc agtggatggc acagtcaagg aagtcattgt gggtccagat accacctcct    6180
acagcctggc agacctgagc ccatccaccc actacacagc caagatccag gcactcaatg    6240
```

```
ggcccctgag gagcaatatg atccagacca tcttcaccac aattggactc ctgtacccct    6300
tccccaagga ctgctcccaa gcaatgctga atggagacac gacctctggc ctctacacca    6360
tttatctgaa tggtgataag gctgaggcgc tggaagtctt ctgtgacatg acctctgatg    6420
ggggtggatg gattgtgttc ctgagacgca aaaacggacg cgagaacttc taccaaaact    6480
ggaaggcata tgctgctgga tttggggacc gcagagaaga attctggctt gggctggaca    6540
acctgaacaa aatcacagcc caggggcagt acgagctccg ggtggacctg cgggaccatg    6600
gggagacagc ctttgctgtc tatgacaagt tcagcgtggg agatgccaag actcgctaca    6660
agctgaaggt ggaggggtac agtgggacag caggtgactc catggcctac cacaatggca    6720
gatccttctc cacctttgac aaggacacag attcagccat caccaactgt gctctgtcct    6780 acaaagggc tttctggtac aggaactgtc accgtgtcaa cctgatgggg agatatgggg    6840
acaataacca cagtcagggc gttaactggt ccactggaa gggccacgaa cactcaatcc    6900
agtttgctga tgaagctg agaccaagca acttcagaaa tcttgaaggc aggcgcaaac    6960
gggcataaat tccagggacc actgggtgag agaggaataa ggcccagagc gaggaaagga    7020
ttttaccaaa gcatcaatac aaccagccca accatcggtc cacacctggg catttggtga    7080
gagtcaaagc tgaccatgga tccctggggc caacggcaac agcatgggcc tcacctcctc    7140
tgtgatttct ttcttttgcac caaagacatc agtctccaac atgttctgt tttgttgttt    7200 gattcagcaa aaatctccca gtgacaacat cgcaatagtt ttttacttct cttaggtggc    7260
tctgggaatg ggagaggggt aggatgtaca ggggtagttt gttttagaac cagccgtatt    7320
ttacatgaag ctgtataatt aattgtcatt attttttgtta gcaaagatta aatgtgtcat    7380
tggaagccat cccttttttt acatttcata caacagaaac cagaaaagca atactgtttc    7440
cattttaagg atatgattaa tattattaat ataataatga tgatgatgat gatgaaaact    7500
aaggattttt caagagatct ttcttttccaa aacatttctg gacagtacct gattgtattt    7560
tttttttaaa taaaagcaca agtactttg agtttgttaa aaaaaaaaaa aaaaaa    7616
```

<210> SEQ ID NO 149
<211> LENGTH: 22
<212> TYPE: DNA
<213> ORGANISM: Artificial Sequence
<220> FEATURE:
<223> OTHER INFORMATION: unassigned DNA Human FBG-X forward primer minus

<400> SEQUENCE: 149
ggtacctcgc gaatgcatct ag                                              22

<210> SEQ ID NO 150
<211> LENGTH: 58
<212> TYPE: DNA
<213> ORGANISM: Artificial Sequence
<220> FEATURE:
<223> OTHER INFORMATION: unassigned DNA Human FBG-X forward primer plus

<400> SEQUENCE: 150 tttttccat ggcccagatt ggactcctgt accccttccc caaagattgc tctcaggc       58

<210> SEQ ID NO 151
<211> LENGTH: 22
<212> TYPE: DNA
<213> ORGANISM: Artificial Sequence
<220> FEATURE:
<223> OTHER INFORMATION: unassigned DNA Mouse FBG-X forward primer minus

```
<400> SEQUENCE: 151
ggtacctcgc gaatgcatct ag                                          22

<210> SEQ ID NO 152
<211> LENGTH: 56
<212> TYPE: DNA
<213> ORGANISM: Artificial Sequence
<220> FEATURE:
<223> OTHER INFORMATION: unassigned DNA Mouse FBG-X forward primer plus

<400> SEQUENCE: 152 tttttccat ggcccagatt ggactcctgt acccctccc tcgcgactgc tcacag      56

<210> SEQ ID NO 153
<211> LENGTH: 53
<212> TYPE: DNA
<213> ORGANISM: Artificial Sequence
<220> FEATURE:
<223> OTHER INFORMATION: unassigned DNA Human X-FBG forward primer minus

<400> SEQUENCE: 153 tttttggat cccatcatca tcaccatcac ttccccaaag attgctctca ggc        53

<210> SEQ ID NO 154
<211> LENGTH: 71
<212> TYPE: DNA
<213> ORGANISM: Artificial Sequence
<220> FEATURE:
<223> OTHER INFORMATION: unassigned DNA Human X-FBG forward primer plus

<400> SEQUENCE: 154 tttttggat cccatcatca tcaccatcac attggactcc tgtaccccctt ccccaaagat 60 tgctctcagg c                                                      71

<210> SEQ ID NO 155
<211> LENGTH: 51
<212> TYPE: DNA
<213> ORGANISM: Artificial Sequence
<220> FEATURE:
<223> OTHER INFORMATION: unassigned DNA Mouse X-FBG forward primer minus

<400> SEQUENCE: 155 tttttggat cccatcatca tcaccatcac ttccctcgcg actgctcaca g           51

<210> SEQ ID NO 156
<211> LENGTH: 69
<212> TYPE: DNA
<213> ORGANISM: Artificial Sequence
<220> FEATURE:
<223> OTHER INFORMATION: unassigned DNA Mouse X-FBG forward primer plus

<400> SEQUENCE: 156 tttttggat cccatcatca tcaccatcac attggactcc tgtacccctt ccctcgcgac  60
tgctcacag                                                         69

<210> SEQ ID NO 157
<211> LENGTH: 39
<212> TYPE: DNA
<213> ORGANISM: Artificial Sequence
<220> FEATURE:
<223> OTHER INFORMATION: unassigned DNA BamHI-His6-HindIII forward
      primer

<400> SEQUENCE: 157
```

```
tttttttggat cccatcatca tcaccatcac taataaaag                    39

<210> SEQ ID NO 158
<211> LENGTH: 40
<212> TYPE: DNA
<213> ORGANISM: Artificial Sequence
<220> FEATURE:
<223> OTHER INFORMATION: unassigned DNA Human His-FBG forward primer
      plus

<400> SEQUENCE: 158 tttttttctcg agcatcatca tcaccatcac attggactcc                   40

<210> SEQ ID NO 159
<211> LENGTH: 40
<212> TYPE: DNA
<213> ORGANISM: Artificial Sequence
<220> FEATURE:
<223> OTHER INFORMATION: unassigned DNA Mouse His-FBG forward primer
      plus

<400> SEQUENCE: 159 tttttttctcg agcatcatca tcaccatcac attggactcc                   40

<210> SEQ ID NO 160
<211> LENGTH: 20
<212> TYPE: DNA
<213> ORGANISM: Artificial Sequence
<220> FEATURE:
<223> OTHER INFORMATION: unassigned DNA Human FBG-X reverse primer minus

<400> SEQUENCE: 160
catgcaggcc tctgcagtcg                                          20

<210> SEQ ID NO 161
<211> LENGTH: 20
<212> TYPE: DNA
<213> ORGANISM: Artificial Sequence
<220> FEATURE:
<223> OTHER INFORMATION: unassigned DNA Human FBG-X reverse primer plus

<400> SEQUENCE: 161
catgcaggcc tctgcagtcg                                          20

<210> SEQ ID NO 162
<211> LENGTH: 20
<212> TYPE: DNA
<213> ORGANISM: Artificial Sequence
<220> FEATURE:
<223> OTHER INFORMATION: unassigned DNA Mouse FBG-X reverse primer minus

<400> SEQUENCE: 162
catgcaggcc tctgcagtcg                                          20

<210> SEQ ID NO 163
<211> LENGTH: 20
<212> TYPE: DNA
<213> ORGANISM: Artificial Sequence
<220> FEATURE:
<223> OTHER INFORMATION: unassigned DNA Mouse FBG-X reverse primer plus

<400> SEQUENCE: 163
catgcaggcc tctgcagtcg                                          20

<210> SEQ ID NO 164
<211> LENGTH: 39
```

```
<212> TYPE: DNA
<213> ORGANISM: Artificial Sequence
<220> FEATURE:
<223> OTHER INFORMATION: unassigned DNA Human X-FBG reverse primer minus

<400> SEQUENCE: 164 tttttttaagc ttttattacg cccgtttacg ccgaccctc                                      39

<210> SEQ ID NO 165
<211> LENGTH: 39
<212> TYPE: DNA
<213> ORGANISM: Artificial Sequence
<220> FEATURE:
<223> OTHER INFORMATION: unassigned DNA Human X-FBG reverse primer plus

<400> SEQUENCE: 165 tttttttaagc ttttattacg cccgtttacg ccgaccctc                                      39

<210> SEQ ID NO 166
<211> LENGTH: 39
<212> TYPE: DNA
<213> ORGANISM: Artificial Sequence
<220> FEATURE:
<223> OTHER INFORMATION: unassigned DNA Mouse X-FBG reverse primer minus

<400> SEQUENCE: 166 tttttttaagc ttttattacg cccgtttccg ccgaccttc                                      39

<210> SEQ ID NO 167
<211> LENGTH: 39
<212> TYPE: DNA
<213> ORGANISM: Artificial Sequence
<220> FEATURE:
<223> OTHER INFORMATION: unassigned DNA Mouse X-FBG reverse primer plus

<400> SEQUENCE: 167 tttttttaagc ttttattacg cccgtttccg ccgaccttc                                      39

<210> SEQ ID NO 168
<211> LENGTH: 38
<212> TYPE: DNA
<213> ORGANISM: Artificial Sequence
<220> FEATURE:
<223> OTHER INFORMATION: unassigned DNA BamHI-His6-HindIII reverse
      primer

<400> SEQUENCE: 168 tttttttaagc ttttattagt gatggtgatg atgatggg                                       38

<210> SEQ ID NO 169
<211> LENGTH: 39
<212> TYPE: DNA
<213> ORGANISM: Artificial Sequence
<220> FEATURE:
<223> OTHER INFORMATION: unassigned DNA Human His-FBG reverse primer
      plus

<400> SEQUENCE: 169 tttttttaagc ttttattacg cccgtttacg ccgaccctc                                      39

<210> SEQ ID NO 170
<211> LENGTH: 39
<212> TYPE: DNA
```

```
<213> ORGANISM: Artificial Sequence
<220> FEATURE:
<223> OTHER INFORMATION: unassigned DNA Mouse His-FBG reverse primer
      plus

<400> SEQUENCE: 170 tttttttaagc ttttattacg cccgtttccg ccgaccttc                                 39
```

ANTI-TENASCIN C ANTIBODIES AND USES THEREOF

CROSS REFERENCE TO RELATED APPLICATIONS

The present application is a continuation of, and claims priority to, U.S. patent application Ser. No. 15/501,979 filed Feb. 6, 2017, now U.S. Pat. No. 10,093,723, which was filed under 35 U.S.C. § 371 as the U.S. national phase of International Application No. PCT/GB2015/052298, filed Aug. 7, 2015, which designated the U.S. and claims the benefit of priority to GB 1414021.4, filed Aug. 7, 2014, each of which is hereby incorporated herein in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Oct. 4, 2018, is named 370908-3005US2_SequenceListing_New.txt and is 144 kilobytes in size.

The present invention relates to antibodies for binding the fibrinogen-like globe (FBG) domain of tenascin-C and their use in the diagnosis, determination of prognosis and/or treatment of disorders associated with chronic inflammation, as well as methods of identifying such antibodies.

Inflammation is the complex biological response of tissues to harmful stimuli, such as pathogens, tissue damage, or irritants. It is a protective attempt by the tissue to remove the injurious stimuli as well as initiate the healing process for the tissue. Abnormalities associated with inflammation comprise a large, unrelated group of disorders which underlie a variety of human diseases (inflammatory disorders). Examples of diseases with an inflammatory aspect include (but are not limited to) asthma, autoimmune disease, glomerulonephritis, allergy (hypersensitivities), cancer, inflammatory bowel diseases, reperfusion injury, rheumatoid arthritis and transplant rejection.

In particular, chronic inflammation is a debilitating and serious condition associated with many of the above diseases and is characterised by persistent inflammation at a site of infection or injury, or persistent inflammation of an unknown origin, or in relation to altered immune responses such as in autoimmune disease.

Rheumatoid arthritis (RA) is a typical example of, though by no means the only, a chronic inflammatory condition. RA is characterised by synovial inflammation and destruction of joint cartilage and bone mediated by persistent synthesis of pro-inflammatory cytokines and matrix metalloproteinases (MMPs). Biological compounds that suppress the synthesis of inflammatory cytokines such as TNFα and IL-6 are successful at treating RA in the short-term. However, repeated treatments are required, which renders this an expensive therapeutic approach, and does not provide long-term remission. Furthermore, total systemic suppression of cytokine function is not without inherent problems such as increased infectious risk. Thus, despite advances in care, there remains an unmet need for an economical mode of treatment of chronic inflammatory conditions that is efficacious over the long term (Smolen (2006) and Williams (2007)).

The mechanisms that underpin disease chronicity remain unclear and the factor(s) that drive the prolonged expression of inflammatory and destructive mediators are currently unknown.

Toll-like receptors (TLRs) play a key role in driving the production of inflammatory mediators in RA and blockade of TLR function may be of significant clinical benefit (reviewed in Brentano (2005) and O'Neill (2002)). This receptor family forms an integral part of the immune system. TLRs mediate host defense against infection and injury by recognising both pathogen-associated molecular patterns (PAMPs) and damage-associated molecular patterns (DAMPs) (Matzinger (2002)). DAMPs are endogenous pro-inflammatory molecules generated upon tissue injury and include intracellular molecules released from damaged or necrotic cells, fragments of extracellular matrix (ECM) molecules or ECM molecules up regulated upon injury (reviewed in Bianchi (2007) and Gordon (2002)).

Upon activation, TLRs promote both innate and adaptive immune responses including stimulation of expression of pro-inflammatory cytokines and MMPs (Medzhitov (2002)). TLRs are expressed at high levels in synovial tissue from RA patients (Radstake (2004), Roelofs (2005), Sacre (2007), and (Sacre, manuscript submitted 2008) and mice with targeted deletions or loss of function mutations in TLR4 are protected from experimental arthritis (Choe (2003) and Lee (2005). Furthermore, inhibitors of TLR4 can reduce destructive arthritis in mice (Abdollahi-Roodsaz (2007)) and a putative TLR4 inhibitor improved symptoms in 15 out of 23 patients with moderate to severe RA in a preliminary phase I trial (Vanags (2006). However, it is unclear which TLR ligand(s) are involved in disease pathogenesis.

Tenascin-C (TNC) is an ECM glycoprotein that is associated with tissue injury and wound repair. Tenascin-C is expressed specifically during active tissue remodelling during embryogenesis, being first observed during gastrulation and somite formation. In later stages of development expression is restricted to sites of branching morphogenesis of mammary gland and the lung, in the developing skeleton, cardiovascular system and in connective tissues at sites of epithelial to mesenchymal transformation. Expression is down-regulated once these processes cease and before embryogenesis is complete (Jones (2000)).

Tenascin-C is not normally expressed in healthy adult tissue but, in adults, is specifically and transiently up-regulated during acute inflammation and persistently expressed in chronic inflammation (reviewed in Chiquet-Ehrismann (2003)). Immunohistochemical studies show that little tenascin-C is expressed in normal human joints but levels are greatly increased in RA synovia, in areas of inflammation and fibrosis, specifically below the synovial lining, in the invading pannus and around blood vessels (Cutolo (1992), MacCachren (1992) and Salter (1993)). There is also a significant increase in tenascin-C levels in synovial fluid from RA patients (Chevalier (1994) and Hasegawa (2007)) and in RA cartilage (Salter (1993) and Chevalier (1994)).

Tenascin-C is a large hexameric protein of 1.5 million Da. Each chain comprises different domains, including an assembly domain (TA), EGF-like repeats (EGF-L), fibronectin type III-like repeats (TNIII) and a fibrinogen-like globe (FBG) (reviewed in Orend (2005)). The sequences of tenascin-C and its domains are shown in FIG. 1.

The inventors have shown previously that tenascin-C is a pro-inflammatory stimulus and that it is required for destructive joint inflammation observed in arthritis and is involved in the prolonging of the inflammatory response characterising the chronic inflammatory condition. In particular, tenascin-C has been shown to be an endogenous activator of TLR4 and it has been demonstrated that this molecule is required for destructive joint inflammation (WO 2010/103289).

In WO 2010/103289, a role for tenascin-C in mediating an immune response in the joint was demonstrated by induction of joint inflammation upon intra-articular injection of the FBG domain of tenascin-C in mice in vivo. Moreover, acute joint inflammation induced by zymosan was not as prolonged in tenascin-C deficient mice. Both the wild type and tenascin-C null mice responded to acute inflammation induction by zymosan equally, demonstrating that tenascin-C does not appear to be involved in the initiation of inflammation. However, the less persistent synovitis exhibited by tenascin-C null mice indicates a role in the maintenance of joint inflammation. The importance of tenascin-C in prolonging joint inflammation was underscored by the observation that targeted deletion of tenascin-C protected mice from sustained erosive joint inflammation during arthritis induced by immunization with mBSA.

Tenascin-C was shown to be capable of activating cells in the joint and the primary active domain of tenascin-C has been mapped to the fibrinogen-like globe (FBG), a 227 amino acid (26.9 kDa) globular domain at the C terminal of the molecule (Siri (1991)).

Addition of FBG to synovial membrane cultures from RA patients enhanced the spontaneous release of pro-inflammatory cytokines. It also stimulated synthesis of TNF-α, IL-6 and IL-8 in primary human macrophages and IL-6 in RA synovial fibroblasts via activation of TLR4 and MyD88 dependent signalling pathways.

It has been shown that, as in the case of LPS, TLR4 expression is necessary for induction of cytokine synthesis by FBG. However, unlike LPS, neither CD14 nor MD-2 appears to be required for TLR-4 activation. CD14 is dispensable for activation of TLR4 by other ligands. It is not required for TLR4 to respond to lipid A in a MyD88 dependent manner (Jiang (2005)), fibronectin EDA (extra domain A) can activate mast cells even in the absence of CD14 (Gondokaryono (2007)) and hyaluronic acid activation of human monocytic THP-1 cells requires a complex of TLR4, CD44 and MD-2, but not CD14 (Taylor (2007)).

Formation of distinct receptor complexes by each TLR4 ligand may facilitate recruitment of different intracellular adapter/signalling molecules. This may account for the differential cellular responses we observe with FBG and LPS. Similarly, hyaluronic acid activation of the TLR4 and CD44 complex induces a pattern of gene expression in mouse alveolar macrophage cell lines that is different to LPS (Taylor (2007)).

The tightly regulated pattern of expression of tenascin-C makes it an attractive target for treating chronic inflammation. It is predominantly absent from healthy adults, however expression is specifically induced upon tissue injury. During acute inflammation tenascin-C is transiently expressed: induction often precedes inflammation and both mRNA and protein are absent from the tissue by the time inflammation is resolved (reviewed in Chiquet-Ehrismann (2003)).

Persistent expression of tenascin-C has now been shown to be associated with chronic inflammation. In addition to RA, increased tenascin-C levels are observed in other autoimmune diseases including multiple sclerosis (Gutowski (1999)) and Sjogrens disease (Amin (2001)), and in non-healing wounds and diabetic and venous ulcers (Loots (1998)). De novo synthesis of tenascin-C correlates well with the intensity of inflammation in diseases of the oral mucosa and plasma levels of tenascin-C are a reliable indicator for the activity of inflammatory bowel diseases before and after medication or surgery (reviewed in Chiquet-Ehrismann (2003)).

WO 2010/103289 describes the use of agents for modulation of a chronic inflammatory response wherein the agent modulates the biological activity of tenascin-C and their use in treating conditions associated with chronic inflammation. However, there remains an ongoing need for new and improved treatments for such conditions.

Clark et al. (1997) (52) describes investigations into tenascin and describes an antibody specific for the FBG domain. That antibody is of mouse origin, and therefore is not suitable as a therapeutic. Furthermore, that antibody is described only as having the property of interfering with "lymphocyte rolling", which is believed to be a measure of cell migration, and not cell activation and production of inflammatory cytokines. The cellular counter receptor involved in the cell rolling activity described by Clark was not identified. Participation in the process of cell rolling or migration is not believed to be a significant property of TLR4, nor was TLR4 included by Clark in a list of potential candidate counter receptors involved in rolling behaviour. Additionally, not all antibodies which bind FBG are able to inhibit the production of inflammatory cytokines. The novel set of improved properties of the antibody sequences described herein was neither taught nor suggested by Clark, nor were they tested for. Thus, there is nothing to indicate that the antibody described in Clark binds to the same region of FBG as the antibodies described herein, it appears not to be related to TLR4 activity since TLR4 is not commonly considered (including by Clark by its omission from their list of potential candidates) to be involved in lymphocyte rolling activity, the function studied by Clark et al is unrelated to the key anti-inflammatory property of the novel antibodies described herein.

Therefore, there remains a need to produce new and improved antibodies specific for the FBG domain of tenascin-C, particularly those which have the properties required to make them useful as therapeutics.

The inventors have designed antibodies and fragments thereof with properties that are suitable for use in therapy, in particular human antibodies, with very high affinity to the fibrinogen-like globe (FBG) domain of tenascin-C, and which neutralise the biological activity of FBG. These high affinity antibodies are useful in a variety of therapeutic methods, such as those which use anti-FBG antibody molecules in the diagnosis or treatment of tenascin-C related disorders, particularly those associated with chronic inflammation, including rheumatoid arthritis (RA). The antibodies are also useful in related diagnostic and prognostic methods.

In a first aspect of the invention there is provided an antibody or antigen-binding fragment, derivative or variant thereof which is capable of binding to the FBG domain of tenascin-C, wherein the antibody or antigen-binding fragment, derivative or variant thereof comprises: one or more sequences selected from SEQ ID NOs: 9-15, 5, 125, 36, 37, 30-35, 38-47, 115-118 and 140; and/or one or more sequences selected from SEQ ID NOs: 1-8, 124, 48-91, 128-138, 112-114 and 139; and/or one or more sequences selected from SEQ ID NOs: 5, 13, 16-21, 126, 119-121 and 141; and/or one or more sequences selected from SEQ ID NOs: 22-29, 127, 122-123 and 142.

The sequence ID numbers (SEQ ID NOs) refer to those designating the particular antibody and antibody related sequences listed in Examples 9 and 11. Where not explicitly stated, reference to "antibodies" includes antigen-binding fragments, derivatives or variants thereof.

In one embodiment the antibody or antigen-binding fragment, derivative or variant thereof according to the present disclosure comprises a heavy chain variable region and/or a light chain variable region which is human or humanised.

In one embodiment the antibody or antigen-binding fragment, derivative or variant thereof according to the present disclosure is human or humanised, including fully human.

In one embodiment the antibody or antigen-binding fragment, derivative or variant thereof according to the present disclosure neutralises, reduces or blocks activation of TLR4.

In one embodiment the antibody or antigen-binding fragment, derivative or variant thereof according to the present disclosure comprises heavy chain variable region and/or a light chain variable region which is human or humanised (including a fully human antibody or binding fragment), which inhibits release for a cytokine such as IL-8 in an assay described herein.

In one embodiment the antibody or antigen-binding fragment, derivative or variant thereof according to the present disclosure is specific to the FBG domain of tenascin C. That is to say it does not cross-react with other members of the tenascin-C family.

In one embodiment the antibody or antigen-binding fragment, derivative or variant thereof according to the present disclosure is cross-reactive with the FBG domain of at least murine and/or rattus tenascin C, in particular cross-reactive with the FBG domain of primitive tenascin-C. This is particularly important for a potential therapeutic as it allows, safety and efficacy studies to be performed in vivo before administration to humans.

In one embodiment there is provided an antibody or antigen-binding fragment, derivative or variant thereof according to the present disclosure which comprises 6 CDRs, namely 3 heavy chain CDRs and 3 light chains CDRs, for example disclosed in an antibody herein and further comprising a human framework.

In one embodiment the antibody or antigen-binding fragment, derivative or variant thereof is provided with an affinity for the FBG domain of human tenascin C of at least 100 nM or higher, for example 50 nM or higher, such as 1 nM or higher affinity. The higher the affinity the lower the numerical value.

In one embodiment the present disclosure extends to an "antibody" explicitly disclosed in the sequence listing provided in Examples 9 or 11.

In one embodiment there is provided an antibody, for example a human or humanised antibody, which cross-blocks an antibody disclosed herein or competively binds the same epitope as an antibody disclosed herein.

In one embodiment the antibody of the present disclosure is provided in a full length antibody format, for example a format with no-effector function such as an IgG4 format.

In one embodiment the antibody or antigen-binding fragment, derivative or variant thereof is for use in therapy, in particular use in the treatment of an autoimmune disease or inflammation, in particular a condition describe herein.

The antibody or antigen-binding fragment, derivative or variant thereof of the first aspect of the invention may therefore be an antigen-binding fragment. The antigen-binding "fragment" may be selected from the group consisting of Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]).

The terms antibody "derivative" and "variant" refer to any modified antibody molecule (including homologues) that is capable of binding to an antigen in an immunoassay format that is known to those skilled in the art, such as a fragment of an antibody (e.g. Fab or Fv fragment), or a modified antibody molecule that is modified by the addition of one or more amino acids or other molecules to facilitate coupling the antibodies to another peptide or polypeptide, to a large carrier protein or to a solid support (e.g. the amino acids tyrosine, lysine, glutamic acid, aspartic acid, cysteine and derivatives thereof, NH2-acetyl groups or COOH-terminal amido groups, amongst others).

The variant may include a variation of the amino acid sequence of the antibody. For example, the amino acid sequence of the variant might be 50%, 55%, 60%, 65%, 70%, 75%, 80%, 85%, 90%, 95%, 96%, 97%, 98% or 99% identical to the specified antibody at the amino acid sequence level.

The variant may also include sequence changes in order to utilise the most common natural human germline antibody frameworks and CDR diversity. This may be done by tailor-engineering of key residues with amino acids commonly found in natural human antibodies. This approach minimizes the likelihood of anti-antibody reactions in humans, since germline antibody framework sequences are highly tolerated between individuals. This technique is known as "germlining" and the resultant sequences are termed "germlined sequences". Sequences may be fully or partially germlined. Examples of germlined sequences of the antibodies of the invention are described in Example 11.

The antibody of the invention may bind to the FBG domain that binds TLR4, blocking TLR4 activation directly, for example by physically occluding the binding site with TLR4. Whilst not wishing to be bound by theory the present inventors have evidence to suggest the TLR4 binds an FBG domain of tenascin C directly. This has not been previously established even though tenascin C was known to be capable of enhancing the activity of TLR4.

Alternatively the antibody may bind to a part of the FBG domain that does not bind TLR4, but this may still prevent TLR4 activation (allosteric effect); the antibody may bind to an FBG domain that interacts with another receptor blocking its activity, this may or may not have an impact on TLR4 activity; and/or the antibody may bind to the FBG domain which does not bind to any other receptor but still prevents the activation of this receptor (allosteric effect).

In one embodiment the disclosure relates to an antibody or antigen-binding fragment, derivative or variant thereof that binds the FBG domain but does not inhibit activation of TLR4 and/or release of cytokines, in particular those described herein, such as IL-8.

The advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from E. coli, thus allowing the facile production of large amounts of the said fragments.

Also included within the scope of the invention are modified versions of antibodies and antigen-binding fragments thereof, e.g. modified by the covalent attachment of polyethylene glycol or other suitable polymer. Conjugates of antibodies and antigen-binding fragments thereof are also included, e.g. antibody-drug conjugates.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Biol.* 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, humanised antibodies are preferably used. Humanised forms of non-human (e.g. murine) antibodies are genetically engineered chimeric antibodies or antibody fragments having preferably minimalportions derived from non-human antibodies. Humanised antibodies include antibodies in which complementary determining regions of a human antibody (recipient antibody) are replaced by residues from a complementary determining region of a non-human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567) by substituting human complementarity determining regions with corresponding rodent complementarity determining regions. Accordingly, such humanised antibodies are chimeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

The CDRs of the antibodies explicitly disclosed herein are of human origin. This is advantageous because they are generally less immunogenic than antibodies of non-human origin.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

In one embodiment there is provided an antibody or antigen-binding fragment comprising the CDRs, such as 6 CDRs or variable regions from an antibody disclosed herein. The antibody or antigen-binding fragment may be chimeric. Chimeric antibodies comprise fragments, for example frameworks and/or constant regions from a non-human species, for example mouse, rat, monkey etc. This may be used to prepare a parallel reagent, for example for use in the in vivo safety and/or efficacy studies.

Once suitable antibodies are obtained, they may be tested for activity, for example by ELISA.

In one embodiment of the first aspect of the invention the antibody or antigen-binding fragment, derivative or variant thereof comprises: one or more CDR sequences selected from SEQ ID NOs: 9-11, 5, 13-14, 36, 30, 32, 34, 38, 40, 42, 44, 46, 116 and 118; and/or one or more CDR sequences selected from SEQ ID NOs: 1-3, 5-7, 48, 50, 52, 54, 56, 58, 60, 62, 64, 66, 68, 70, 72, 74, 76, 78, 80, 82, 84, 86, 135, 88, 90 and 114; and/or one or more CDR sequences selected from SEQ ID NOs 16-18, 5, 13, 20 and 121; and/or one or more CDR sequences selected from SEQ ID NOs 22-24 and 26-28.

By "CDR" we refer to a complementarity determining region as found in an intact immunoglobulin variable heavy (VH) or variable light (VL) chain. Three complementarity determining regions (CDRs) are present on the variable domains of both the heavy and light chains of complete immunoglobulins. The CDRs are numbered as CDR1, CDR2 and CDR3 on both the heavy and light chains. For example, the VH chain comprises a CDR1, CDR2 and CDR3 and the VL chain also comprises a CDR1, CDR2 and CDR3.

The assignment of amino acids to each CDR region described herein is in accordance with the definitions according to Kabat E A et al. 1991, In "Sequences of Proteins of Immunological Interest" Fifth Edition, NIH Publication No. 91-3242, pp xv-xvii.

Accordingly, six CDR sequences are most preferably included in the antibody or antigen-binding fragment, derivative or variant thereof. However, fewer CDR sequences, including as few as one, may be included, for example in a single chain antibody fragment.

In a further embodiment the antibody or antigen-binding fragment, derivative or variant thereof comprises: one or more CDR3 sequences selected from SEQ ID NOs: 11, 14, 36, 30, 32, 34, 38, 40, 42, 44 and 46; and/or one or more CDR3 sequences selected from SEQ ID NOs: 3, 7, 48, 50, 52, 54, 56, 58, 60, 62, 64, 66, 68, 70, 72, 74, 76, 78, 80, 82, 84, 86, 135, 88 and 90; and/or one or more CDR3 sequences selected from SEQ ID NOs 18 and 20; and/or one or more CDR3 sequences selected from SEQ ID NOs 24 and 28.

As described above, "CDR3" refers to the third CDR present on either the full length variable heavy (VH) or full length variable light (VL) antibody chain.

In one embodiment, the antibody or antigen-binding fragment, derivative or variant thereof comprises: one or more CDR3 sequences selected from SEQ ID NOs: 11, 36, 30 and 34; and/or one or more CDR3 sequences selected from SEQ ID NOs: 3, 54, 66 and 70; and/or one or more CDR3 sequences selected from SEQ ID NOs: 7, 76, 88 and 90.

In a particular embodiment, the antibody or antigen-binding fragment, derivative or variant thereof comprises: a VH CDR3 sequence selected from SEQ ID NOs: 3, 48, 50, 52, 54, 56, 58, 60, 62, 64, 66, 68 and 70; a VH CDR3 sequence selected from SEQ ID NOs: 3, 54, 66 and 70; or a VH CDR3 sequence selected from SEQ ID NOs: 3 and 54.

In another particular embodiment, the antibody or antigen-binding fragment, derivative or variant thereof comprises: a VL CDR3 sequence selected from SEQ ID NOs: 7, 72, 74, 76, 78, 80, 82, 84, 86, 135, 88 and 90; a VL CDR3 sequence selected from SEQ ID NOs: 7, 76, 88 and 90; or a VL CDR3 sequence of SEQ ID NO 7.

In a further embodiment, the antibody or antigen-binding fragment, derivative or variant thereof comprises a VH sequence comprising the sequence of SEQ ID NO: 4 or 112, and wherein the VH sequence comprises a CDR3 sequence which is replaced with: a VH CDR3 sequence selected from SEQ ID NOs: 48, 50, 52, 54, 56, 58, 60, 62, 64, 66, 68 and 70; a VH CDR3 sequence selected from SEQ ID NOs: 54, 66 and 70; or a VH CDR3 sequence of SEQ ID NO: 54.

By "replaced" it is meant that the CDR3 sequence of the VH sequence is deleted and an alternative CDR3 sequence (as specified) is included in its place.

In this specific context, by "replaced" it is meant that the CDR3 sequence of the VH sequence SEQ ID NO: 4 or 112 is deleted from the sequence and an alternative CDR3 sequence (as specified) is included in its place. In other words, SEQ ID NO: 3 (which is the CDR3 sequence of SEQ ID NO: 4 and 112) is replaced with an alternative CDR3 sequence (as specified).

Optionally, the antibody or antigen-binding fragment, derivative or variant thereof comprises a VL sequence comprising the sequence of SEQ ID NO: 8, 124, 113 or 139 and wherein the VL sequence comprises a CDR3 sequence which is replaced with: a VL CDR3 sequence selected from SEQ ID NOs: 72, 74, 76, 78, 80, 82, 84, 86, 135, 88 and 90; or a VL CDR3 sequence selected from SEQ ID NOs: 76, 88 and 90.

By "replaced" in this specific context it is meant that the CDR3 sequence of the VL sequence SEQ ID NO: 8, 124, 113 or 139 is deleted from the sequence and an alternative CDR3 sequence (as specified) is included in its place. In other words, SEQ ID NO: 7 (which is the CDR3 sequence of SEQ ID NO: 8, 124, 113 and 139) is replaced with an alternative CDR3 sequence (as specified).

In a further embodiment, the antibody or antigen-binding fragment, derivative or variant thereof comprises: a VH CDR3 sequence selected from SEQ ID NOs: 11, 30, 32, 34, 36, 38, 40, 42, 44 and 46; a VH CDR3 sequence from SEQ ID NOs: 11, 30, 34 and 36; or a VH CDR3 sequence selected from SEQ ID NOs 11, 30 and 36.

In one embodiment, the antibody or antigen-binding fragment, derivative or variant thereof comprises a VL sequence comprising the sequence of SEQ ID NO: 15, 125, 117 or 140.

In another embodiment, the antibody or antigen-binding fragment, derivative or variant thereof comprises a VH sequence comprising the sequence of SEQ ID NO: 12 or SEQ ID NO: 115, and wherein the VH sequence comprises a CDR3 sequence which is replaced with: a VH CDR3 sequence selected from SEQ ID NOs: 30, 32, 34, 36, 38, 40, 42, 44 and 46; a VH CDR3 sequence selected from SEQ ID NOs: 30, 34 and 36; or a VH CDR3 sequence selected from SEQ ID NOs 30 and 36.

By "replaced" in this specific context it is meant that the CDR3 sequence of the VH sequence SEQ ID NO: 12 or 115 is deleted from the sequence and an alternative CDR3 sequence (as specified) is included in its place. In other words, SEQ ID NO: 11 (which is the CDR3 sequence of SEQ ID NO: 12 and 115) is replaced with an alternative CDR3 sequence (as specified).

In a particular embodiment, the antibody or antigen-binding fragment, derivative or variant thereof comprises: a VL CDR3 sequence of SEQ ID NO: 14 and a VH CDR3 sequence selected from SEQ ID NOs: 11 and 30-46; or comprises a VL CDR3 sequence of SEQ ID NO: 7 and a VH CDR3 sequence selected from SEQ ID NOs: 3 and 48-70; or comprises a VH CDR3 sequence of SEQ ID NO: 3 and a VL CDR3 sequence selected from SEQ ID NOs: 7 and 72, 74, 76, 78, 80, 82, 84, 86, 135, 88 and 90; or comprises a VH CDR3 sequence of SEQ ID NO: 18 and a VL CDR3 sequence of SEQ ID NO: 20; or comprises a VH CDR3 sequence of SEQ ID NO: 24 and a VL CDR3 sequence of SEQ ID NO: 28.

Preferably, the antibody or antigen-binding fragment, derivative or variant thereof comprises:

at least one CDR sequence selected from SEQ ID NOs: 1-3, and 5-7; or at least one CDR sequence selected from SEQ ID NOs: 1, 2, 48 and 5-7; or at least one CDR sequence selected from SEQ ID NOs: 1, 2, 50 and 5-7; or at least one CDR sequence selected from SEQ ID NOs: 1, 2, 52 and 5-7; or at least one CDR sequence selected from SEQ ID NOs: 1, 2, 54 and 5-7; or at least one CDR sequence selected from SEQ ID NOs: 1, 2, 56 and 5-7; or at least one CDR sequence selected from SEQ ID NOs: 1, 2, 58 and 5-7; or at least one CDR sequence selected from SEQ ID NOs: 1, 2, 60 and 5-7; or at least one CDR sequence selected from SEQ ID NOs: 1, 2, 62 and 5-7; or at least one CDR sequence selected from SEQ ID NOs: 1, 2, 64 and 5-7; or at least one CDR sequence selected from SEQ ID NOs: 1, 2, 66 and 5-7; or at least one CDR sequence selected from SEQ ID NOs: 1, 2, 68 and 5-7; or at least one CDR sequence selected from SEQ ID NOs: 1, 2, 70 and 5-7; or at least one CDR sequence selected from SEQ ID NOs: 1-3, 5, 6 and 72; or at least one CDR sequence selected from SEQ ID NOs: 1-3, 5-6 and 74; or at least one CDR sequence selected from SEQ ID NOs: 1-3, 5, 6 and 76; or at least one CDR sequence selected from SEQ ID NOs: 1-3, 5, 6 and 78; or at least one CDR sequence selected from SEQ ID NOs: 1-3, 5, 6 and 80; or at least one CDR sequence selected from SEQ ID NOs: 1-3, 5, 6 and 82; or at least one CDR sequence selected from SEQ ID NOs: 1-3, 5, 6 and 84; or at least one CDR sequence selected from SEQ ID NOs: 1-3, 5, 6 and 86; or at least one CDR sequence selected from SEQ ID NOs: 1-3, 5, 6 and 135; or at least one CDR sequence selected from SEQ ID NOs: 1-3, 5, 6 and 88; or at least one CDR sequence selected from SEQ ID NOs: 1-3, 5, 6 and 90; or at least one CDR selected from SEQ ID NOs: 1-3, 5, 7 and 114; or at least one CDR sequence selected from SEQ ID NOs: 9-11 and 5, 13 and 14; or at least one CDR sequence selected from SEQ ID NOs: 9, 10, 30, 5, 13 and 14; or at least one CDR sequence selected from SEQ ID NOs: 9, 10, 32, 5, 13 and 14; or at least one CDR sequence selected from SEQ ID NOs: 9, 10, 34, 5, 13 and 14; or at least one CDR sequence selected from SEQ ID NOs: 9, 10, 36, 5, 13 and 14; or at least one CDR sequence selected from SEQ ID NOs: 9, 10, 38, 5, 13 and 14; or at least one CDR sequence selected from SEQ ID NOs: 9, 10, 40, 5, 13 and 14; or at least one CDR sequence selected from SEQ ID NOs: 9, 10, 42, 5, 13 and 14; or at least one CDR sequence selected from SEQ ID NOs: 9, 10, 44, 5, 13 and 14; or at least one CDR sequence selected from SEQ ID NOs: 9, 10, 46, 5, 13 and 14; or at least one CDR selected from SEQ ID NOs: 9, 11, 116, 5, 14 and 118; or at least one CDR sequence selected from SEQ ID NOs: 16-18 and 5, 13 and 20; or at least one CDR sequence selected from SEQ ID NOs: 16-18 and 5, 121 and 20; or at least one CDR sequence selected from SEQ ID NOs: 22-24 and 26-28.

Each of these groups of sequences correspond to the sequences of the VH CDR1, CDR2, CDR3 and VL CDR1, CDR2, CDR3 regions.

The antibody or antigen-binding fragment, derivative or variant thereof may comprise at least one of the CDR sequences selected from one of the groups listed above. Preferably, the antibody or antigen-binding fragment, derivative or variant thereof comprises at least one, two, three, four, five or six CDR sequences selected from one of the groups listed above. More preferably, the antibody or antigen-binding fragment, derivative or variant thereof comprises at least three or at least six CDR sequences selected from one of the groups listed above. Most preferably, the antibody or antigen-binding fragment, derivative or variant thereof comprises at least six CDR sequences selected from one of the groups listed above.

Optionally, the antibody or antigen-binding fragment, derivative or variant thereof comprises: at least one VH CDR sequence selected from SEQ ID NOs: 1-3; or at least one VH CDR sequence selected from SEQ ID NOs: 1, 2 and 48; or at least one VH CDR sequence selected from SEQ ID NOs: 1, 2 and 50; or at least one VH CDR sequence selected from SEQ ID NOs: 1, 2 and 52; or at least one VH CDR sequence selected from SEQ ID NOs: 1, 2 and 54; or at least one VH CDR sequence selected from SEQ ID NOs: 1, 2 and 56; or at least one VH CDR sequence selected from SEQ ID NOs: 1, 2 and 58; or at least one VH CDR sequence selected from SEQ ID NOs: 1, 2 and 60; or at least one VH CDR sequence selected from SEQ ID NOs: 1, 2 and 62; or at least one VH CDR sequence selected from SEQ ID NOs: 1, 2 and 64; or at least one VH CDR sequence selected from SEQ ID NOs: 1, 2 and 66; or at least one VH CDR sequence selected from SEQ ID NOs: 1, 2 and 68; or at least one VH CDR sequence selected from SEQ ID NOs: 1, 2 and 70; or at least one VH CDR sequence selected from SEQ ID NOs: 9-11; or at least one VH CDR sequence selected from SEQ ID NOs: 9, 10 and 30; or at least one VH CDR sequence selected from SEQ ID NOs: 9, 10 and 32; or at least one VH CDR sequence selected from SEQ ID NOs: 9, 10 and 34; or at least one VH CDR sequence selected from SEQ ID NOs: 9, 10 and 36; or at least one VH CDR sequence selected from SEQ ID NOs: 9, 10 and 38; or at least one VH CDR sequence selected from SEQ ID NOs: 9, 10 and 40; or at least one VH CDR sequence selected from SEQ ID NOs: 9, 10 and 42; or at least one VH CDR sequence selected from SEQ ID NOs: 9, 10 and 44; or at least one VH CDR sequence selected from SEQ ID NOs: 9, 10 and 46; or at least one VH CDR sequence selected from SEQ ID NOs: 9, 116 and 11; or at least one VH CDR sequence selected from SEQ ID NOs: 9, 116 and 30; or at least one VH CDR sequence selected from SEQ ID NOs: 9, 116 and 32; or at least one VH CDR sequence selected from SEQ ID NOs: 9, 116 and 34; or at least one VH CDR sequence selected from SEQ ID NOs: 9, 116 and 36; or at least one VH CDR sequence selected from SEQ ID NOs: 9, 116 and 38; or at least one VH CDR sequence selected from SEQ ID NOs: 9, 116 and 40; or at least one VH CDR sequence selected from SEQ ID NOs: 9, 116 and 42; or at least one VH CDR sequence selected from SEQ ID NOs: 9, 116 and 44; or at least one VH CDR sequence selected from SEQ ID NOs: 9, 116 and 46; or at least one VH CDR sequence selected from SEQ ID NOs: 16-18; or at least one VH CDR sequence selected from SEQ ID NOs: 22-24.

Each of these groups of sequences correspond to the sequences of the VH CDR1, CDR2 and CDR3 regions.

The antibody or antigen-binding fragment, derivative or variant thereof may comprises at least one of the VH CDR sequences selected from one of the groups listed above. Preferably, the antibody or antigen-binding fragment, derivative or variant thereof comprises at least one, two or three VH CDR sequences selected from one of the groups listed above. Most preferably, the antibody or antigen-binding fragment, derivative or variant thereof comprises at least three VH CDR sequences selected from one of the groups listed above.

Optionally, the antibody or antigen-binding fragment, derivative or variant thereof comprises: at least one VL CDR sequence selected from SEQ ID NOs: 5-7; or at least one VL CDR sequence selected from SEQ ID NOs: 5, 6 and 72; or at least one VL CDR sequence selected from SEQ ID NOs: 5-6 and 74; or at least one VL CDR sequence selected from SEQ ID NOs: 5, 6 and 76; or at least one VL CDR sequence selected from SEQ ID NOs: 5, 6 and 78; or at least one VL CDR sequence selected from SEQ ID NOs: 5, 6 and 80; or at least one VL CDR sequence selected from SEQ ID NOs: 5, 6 and 82; or at least one VL CDR sequence selected from SEQ ID NOs: 5, 6 and 84; or at least one VL CDR sequence selected from SEQ ID NOs: 5, 6 and 86; or at least one VL CDR sequence selected from SEQ ID NOs: 5, 6 and 135; or at least one VL CDR sequence selected from SEQ ID NOs: 5, 6 and 88; or at least one VL CDR sequence selected from SEQ ID NOs: 5, 6 and 90; or at least one VL CDR sequence selected from SEQ ID NOs: 5, 114 and 7; or at least one VL CDR sequence selected from SEQ ID NOs: 5, 114 and 72; or at least one VL CDR sequence selected from SEQ ID NOs: 5, 114 and 74; or at least one VL CDR sequence selected from SEQ ID NOs: 5, 114 and 76; or at least one VL CDR sequence selected from SEQ ID NOs: 5, 114 and 78; or at least one VL CDR sequence selected from SEQ ID NOs: 5, 114 and 80; or at least one VL CDR sequence selected from SEQ ID NOs: 5, 114 and 82; or at least one VL CDR sequence selected from SEQ ID NOs: 5, 114 and 84; or at least one VL CDR sequence selected from SEQ ID NOs: 5, 114 and 86; or at least one VL CDR sequence selected from SEQ ID NOs: 5, 114 and 88; or at least one VL CDR sequence selected from SEQ ID NOs: 5, 114 and 90; or at least one VL CDR sequence selected from SEQ ID NOs: 5, 13 and 14; or at least one VL CDR sequence selected from SEQ ID NOs: 5, 118 and 14; or at least one VL CDR sequence selected from SEQ ID NOs: 5, 13 and 20; or at least one VL CDR sequence selected from SEQ ID NOs: 5, 121 and 20; or at least one VL CDR sequence selected from SEQ ID NOs: 26-28.

Each of these groups of sequences correspond to the sequences of the VL CDR1, CDR2 and CDR3 regions.

The antibody or antigen-binding fragment, derivative or variant thereof may comprises at least one of the VL CDR sequences selected from one of the groups listed above. Preferably, the antibody or antigen-binding fragment, derivative or variant thereof comprises at least one, two or three VL CDR sequences selected from one of the groups listed above. Most preferably, the antibody or antigen-binding fragment, derivative or variant thereof comprises at least three VL CDR sequences selected from one of the groups listed above.

In a particular embodiment, the antibody or antigen-binding fragment, derivative or variant thereof comprises: a VH CDR3 sequence selected from SEQ ID NOs: 3 and 54; or a VH CDR3 sequence selected from SEQ ID NOs: 11, 30 and 36.

In another embodiment, the antibody or antigen-binding fragment, derivative or variant thereof comprises VH and/or VL sequences comprising: one or more sequences selected from SEQ ID NOs 12, 15, 125, 37, 31, 33, 35, 39, 41, 43, 45, 47, 115, 117 and 140; and/or one or more sequences selected from SEQ ID NOs: 4, 8, 124, 49, 51, 53, 55, 57, 59, 61, 63, 65, 67, 69, 71, 73, 128, 75, 129, 77, 130, 79, 131, 81, 132, 83, 133, 85, 134, 87, 136, 89, 137, 91, 138, 112, 113 and 139; and/or one or more sequences selected from SEQ ID NOs 19, 21, 126, 119, 120 and 141; and/or one or more sequences selected from SEQ ID NOs 25, 29, 127, 122, 123 and 142.

Optionally, the VH sequence of the antibody or antigen-binding fragment, derivative or variant thereof is selected from SEQ ID NOs 12, 37, 31, 33, 35, 39, 41, 43, 45, 47 and 115; and/or selected from SEQ ID NOs: 4, 49, 51, 53, 55, 57, 59, 61, 63, 65, 67, 69, 71 and 112; and/or selected from SEQ ID NOs: 19 and 119; and/or selected from: SEQ ID NOs 25 and 122.

Optionally, the VL sequence of the antibody or antigen-binding fragment, derivative or variant thereof is selected from SEQ ID NOs: 15, 125, 117 and 140; and/or is selected from SEQ ID NOs: 8, 124, 73, 128, 75, 129, 77, 130, 79, 131, 81, 132, 83, 133, 85, 134, 87, 136, 89, 137, 91, 138, 113 and 139; and/or is selected from SEQ ID NOs: 21, 126, 120 and 141; and/or is selected from SEQ ID NOs: 29, 127, 123 and 142.

In a particular embodiment, the antibody or antigen-binding fragment, derivative or variant thereof comprises both a VH and a VL sequence comprising the sequences of a VH and VL sequence pair selected from the sequence pairs: SEQ ID NOs 12, and 15 or 125; SEQ ID NOs 115, and 15 or 125; SEQ ID NOs 12, and 117 or 140; SEQ ID NOs 37, and 15 or 125; SEQ ID NOs 37, and 117 or 140; SEQ ID NOs 31, and 15 or 125; SEQ ID NOs 33, and 15 or 125; SEQ ID NOs 35, and 15 or 125; SEQ ID NOs 39, and 15 or 125; SEQ ID NOs 41, and 15 or 125; SEQ ID NOs 43, and 15 or 125; SEQ ID NOs 45, and 15 or 125; SEQ ID NOs 47, and 15 or 125; SEQ ID NOs 31, and 117 or 140; SEQ ID NOs 33, and 117 or 140; SEQ ID NOs 35, and 117 or 140; SEQ ID NOs 39, and 117 or 140; SEQ ID NOs 41, and 117 or 140; SEQ ID NOs 43, and 117 or 140; SEQ ID NOs 45, and 117 or 140; SEQ ID NOs 47, and 117 or 140; and SEQ ID NOs 115, and 117 or 140; or selected from the sequence pairs: SEQ ID NOs 4, and 8 or 124; SEQ ID NOs 49, and 8 or 124; SEQ ID NOs 51, and 8 or 124; SEQ ID NOs 53, and 8 or 124; SEQ ID NOs 55, and 8 or 124; SEQ ID NOs 57, and 8 or 124; SEQ ID NOs 59, and 8 or 124; SEQ ID NOs 61, and 8 or 124; SEQ ID NOs 63, and 8 or 124; SEQ ID NOs 65, and 8 or 124; SEQ ID NOs 67, and 8 or 124; SEQ ID NOs 69, and 8 or 124; SEQ ID NOs 71, and 8 or 124; SEQ ID NOs 112, and 8 or 124; SEQ ID NOs 4, and 113 or 139; SEQ ID NOs 49, and 113 or 139; SEQ ID NOs 51, and 113 or 139; SEQ ID NOs 53, and 113 or 139; SEQ ID NOs 55, and 113 or 139; SEQ ID NOs 57, and 113 or 139; SEQ ID NOs 59, and 113 or 139; SEQ ID NOs 61, and 113 or 139; SEQ ID NOs 63, and 113 or 139; SEQ ID NOs 65, and 113 or 139; SEQ ID NOs 67, and 113 or 139; SEQ ID NOs 69, and 113 or 139; SEQ ID NOs 71, and 113 or 139; SEQ ID NOs 4, and 73 or 128; SEQ ID NOs 4, and 75 or 129; SEQ ID NOs 4, and 77 or 130; SEQ ID NOs 4, and 79 or 131; SEQ ID NOs 4, and 81 or 132; SEQ ID NOs 4, and 83 or 133; SEQ ID NOs 4, and 85 or 134; SEQ ID NOs 4, and 87 or 136; SEQ ID NOs 4, and 89 or 137; SEQ ID NOs 4, and 91 or 138; SEQ ID NOs 112, and 73 or 128; SEQ ID NOs 112, and 75 or 129; SEQ ID NOs 112, and 77 or 130; SEQ ID NOs 112, and 79 or 131; SEQ ID NOs 112, and 81 or 132; SEQ ID NOs 112, and 83 or 133; SEQ ID NOs 112, and 85 or 134; SEQ ID NOs 112, and 87 or 136; SEQ ID NOs 112, and 89 or 137; SEQ ID NOs 112, and 91 or 138; and SEQ ID NOs 112, and 113 or 139; or selected from the sequence pairs: SEQ ID NOs 19, and 21 or 126; SEQ ID NOs 19, and 120 or 141; SEQ ID NOs 119, and 21 or 126; and SEQ ID NOs 119, and 120 or 141; or selected from the sequence pairs: SEQ ID NOs 25, and 29 or 127; SEQ ID NOs 25, and 123 or 142; SEQ ID NOs 122, and 29 or 127; and SEQ ID NOs 122, and 123 or 142.

In other words, the VH and VL sequences of the antibody or antigen-binding fragment, derivative or variant thereof comprise the VH and VL sequences of the specified sequence pairs, i.e. each pair will be made uo of the specified VH sequence and one of the two specified VL sequences.

In a preferred embodiment the antibody or antigen-binding fragment, derivative or variant thereof comprises a VH sequence comprising a sequence selected from SEQ ID NOs: 4, 49, 51, 53, 55, 57, 59, 61, 63, 65, 67, 69, 71 and 112.

In another preferred embodiment the antibody or antigen-binding fragment, derivative or variant thereof comprises a VL sequence comprising a sequence selected from SEQ ID NOs: 8, 124, 73, 128, 75, 129, 77, 130, 79, 131, 81, 132, 83, 133, 85, 134, 87, 136, 89, 137, 91, 138, 113 and 139.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 or 48 or 50 or 52 or 54 or 56 or 58 or 60 or 62 or 64 or 66 or 68 or 70 for CDRH3, SEQ ID NO: 5 for CDRL1, SEQ ID NO: 6 for CDRL2, and SEQ ID NO: 7 or 72 or 74 or 76 or 78 or 80 or 82 or 84 or 86 or 88 or 90 or 135 for CDRL3. Using this nomenclature, by "CDRH1" we mean the VH chain CDR1, for example.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 48 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 50 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 52 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 54 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 56 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 58 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 60 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 62 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 64 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 66 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 68 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 70 for CDRH3, SEQ ID NO: 5 for CDRL1, SEQ ID NO: 6 for CDRL2, and SEQ ID NO: 7 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 72 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 74 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 76 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 78 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 80 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 82 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 84 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 86 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 88 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 90 for CDRL3.

In one embodiment there is provided an antibody or antigen-binding fragment, derivative or variant thereof for example with human variable regions comprising SEQ ID NO: 1 for CDRH1, SEQ ID NO: 2 for CDRH2, SEQ ID NO: 3 for CDRH3, SEQ ID NO: 5 for CDRL1, SEQ ID NO: 6 for CDRL2, and SEQ ID NO: 135 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 11 or 30 or 32 or 34 or 38 or 40 or 42 or 44 or 46 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 11 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 30 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 11 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 32 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 34 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 38 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 40 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 42 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 44 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 9 for CDRH1, SEQ ID NO: 10 for CDRH2, SEQ ID NO: 46 for CDRH3, SEQ ID NO: 5 for CDRL1, SEQ ID NO: 13 for CDRL2, and SEQ ID NO: 14 for CDRL3.

In one embodiment there is provided an antibody or antigen-binding fragment, derivative or variant thereof for example with human variable regions comprising SEQ ID NO: 16 for CDRH1, SEQ ID NO: 17 for CDRH2, SEQ ID NO: 18 for CDRH3, SEQ ID NO: 5 for CDRL1, SEQ ID NO: 13 for CDRL2, and SEQ ID NO: 20 for CDRL3.

In one embodiment there is provided an antibody or antigen-binding fragment, derivative or variant thereof for example with human variable regions comprising SEQ ID NO: 22 for CDRH1, SEQ ID NO: 23 for CDRH2, SEQ ID NO: 24 for CDRH3, SEQ ID NO: 26 for CDRL1, SEQ ID NO: 27 for CDRL2, and SEQ ID NO: 28 for CDRL3.

In a further preferred embodiment the antibody or antigen-binding fragment, derivative or variant thereof comprises a VH sequence comprising the sequence of SEQ ID NO: 4 or 112.

In another preferred embodiment the antibody or antigen-binding fragment, derivative or variant thereof comprises a VH sequence comprising the sequence of SEQ ID NO: 55.

In a further preferred embodiment the antibody or antigen-binding fragment, derivative or variant thereof comprises a VH sequence comprising a sequence selected from SEQ ID NOs: 12, 31, 33, 35, 37, 39, 41, 43, 45, 47 and 115.

In another preferred embodiment the antibody or antigen-binding fragment, derivative or variant thereof comprises a VH sequence comprising the sequence of SEQ ID NO: 12 or 115.

In another preferred embodiment the antibody or antigen-binding fragment, derivative or variant thereof comprises a VH sequence comprising the sequence of SEQ ID NO: 31.

In another preferred embodiment the antibody or antigen-binding fragment, derivative or variant thereof comprises a VH sequence comprising the sequence of SEQ ID NO: 37.

Optionally the antibody or antigen-binding fragment, derivative or variant thereof additionally comprises a VL sequence comprising the sequence of SEQ ID NO: 8, 124, 113 or 139.

Optionally the antibody or antigen-binding fragment, derivative or variant thereof additionally comprises a VH sequence comprising the sequence of SEQ ID NO: 4 or 112.

Optionally the antibody or antigen-binding fragment, derivative or variant thereof additionally comprises a VL sequence comprising the sequence of SEQ ID NO: 15, 125, 117 or 140.

In a preferred embodiment, the antibody or antigen-binding fragment, derivative or variant thereof comprises: a VH sequence comprising the sequence of SEQ ID NO: 37; and a VL sequence comprising the sequence of SEQ ID NO: 15.

In a preferred embodiment, the antibody or antigen-binding fragment, derivative or variant thereof comprises: a VH sequence comprising the sequence of SEQ ID NO: 37; and a VL sequence comprising the sequence of SEQ ID NO: 125.

In a preferred embodiment, the antibody or antigen-binding fragment, derivative or to variant thereof comprises: a VH sequence comprising the sequence of SEQ ID NO: 31; and a VL sequence comprising the sequence of SEQ ID NO: 15.

In a preferred embodiment, the antibody or antigen-binding fragment, derivative or variant thereof comprises: a VH sequence comprising the sequence of SEQ ID NO: 31; and a VL sequence comprising the sequence of SEQ ID NO: 125.

In a preferred embodiment, the antibody or antigen-binding fragment, derivative or variant thereof comprises: a VH sequence comprising the sequence of SEQ ID NO: 55; and a VL sequence comprising the sequence of SEQ ID NO: 8.

In a preferred embodiment, the antibody or antigen-binding fragment, derivative or variant thereof comprises: a VH sequence comprising the sequence of SEQ ID NO: 55; and a VL sequence comprising the sequence of SEQ ID NO: 124.

In a preferred embodiment, the antibody or antigen-binding fragment, derivative or variant thereof comprises: a VH sequence comprising the sequence of SEQ ID NO: 4: and a VL sequence comprising the sequence of SEQ ID NO: 8.

In a preferred embodiment, the antibody or antigen-binding fragment, derivative or variant thereof comprises: a VH sequence comprising the sequence of SEQ ID NO: 4: and a VL sequence comprising the sequence of SEQ ID NO: 124.

In a preferred embodiment, the antibody or antigen-binding fragment, derivative or variant thereof comprises: a VH sequence comprising the sequence of SEQ ID NO: 12; and a VL sequence comprising the sequence of SEQ ID NO: 15.

In a preferred embodiment, the antibody or antigen-binding fragment, derivative or variant thereof comprises: a VH sequence comprising the sequence of SEQ ID NO: 12; and a VL sequence comprising the sequence of SEQ ID NO: 125.

In a preferred embodiment, the antibody or antigen-binding fragment, derivative or variant thereof comprises: a VH sequence comprising the sequence of SEQ ID NO: 19: and a VL sequence comprising the sequence of SEQ ID NO: 21.

In a preferred embodiment, the antibody or antigen-binding fragment, derivative or to variant thereof comprises: a VH sequence comprising the sequence of SEQ ID NO: 19: and a VL sequence comprising the sequence of SEQ ID NO: 126.

In a preferred embodiment, the antibody or antigen-binding fragment, derivative or variant thereof comprises: a VH sequence comprising the sequence of SEQ ID NO: 25; and a VL sequence comprising the sequence of SEQ ID NO: 29.

In a preferred embodiment, the antibody or antigen-binding fragment, derivative or variant thereof comprises: a VH sequence comprising the sequence of SEQ ID NO: 25; and a VL sequence comprising the sequence of SEQ ID NO: 127.

In another preferred embodiment, the antibody or antigen-binding fragment, derivative or variant thereof comprises: a VH CDR1 sequence corresponding to the sequence of SEQ ID NO: 9; a VH CDR2 sequence corresponding to the sequence of SEQ ID NO: 10 or SEQ ID NO: 116; a VL CDR1 sequence corresponding to the sequence of SEQ ID NO: 5; a VL CDR2 sequence corresponding to the sequence of SEQ ID NO: 13 or SEQ ID NO: 118; a VL CDR3 sequence corresponding to the sequence of SEQ ID NO: 14; and a VH CDR3 sequence corresponding to a sequence selected from SEQ ID NOs: 11, 36, 30, 32, 34, 38, 40, 42, 44 or 46. Preferably, the VH CDR3 sequence corresponds to the sequence of SEQ ID NO: 11 or SEQ ID NO: 36. Even more preferably, the VH CDR3 sequence corresponds to the sequence of SEQ ID NO: 36.

In another preferred embodiment, the antibody or antigen-binding fragment, derivative or variant thereof comprises: a VH CDR1 sequence corresponding to the sequence of SEQ ID NO: 1; a VH CDR2 sequence corresponding to the sequence of SEQ ID NO: 2; a VL CDR1 sequence corresponding to the sequence of SEQ ID NO: 5; a VL CDR2 sequence corresponding to the sequence of SEQ ID NO: 6 or SEQ ID NO: 114; a VL CDR3 sequence corresponding to the sequence of SEQ ID NO: 7; and a VH CDR3 sequence corresponding to a sequence selected from SEQ ID NOs: 3, 48, 50, 52, 54, 56, 58, 60, 62, 64, 66, 68 or 70. Preferably, the VH CDR3 sequence corresponds to the sequence of SEQ ID NO: 3 or SEQ ID NO: 54. Even more preferably, the VH CDR3 sequence corresponds to the sequence of SEQ ID NO: 54.

It will be clear to the skilled person that, where the terminal residue is an arginine (R) in the light chain variable region sequences disclosed herein, that is the first amino acid of the constant region. Thus in one embodiment there is provided a light chain variable region sequence wherein the terminal residue (when it is arginine (R) from the constant region) is absent.

The antibody or antigen-binding fragment, derivative or variant thereof of the first aspect of the invention may modulate the biological activity of tenascin-C by altering the transcription, translation and/or binding properties of tenascin-C.

Such antibodies may be identified using methods well known in the art, such as:

(a) by determining the effect of a test antibody on levels of expression of tenascin-C, for example by Southern blotting or related hybridisation techniques;

(b) by determining the effect of a test antibody on levels of tenascin-C protein, for example by immunoassays using anti-tenascin-C antibodies; and (c) by determining the effect of a test antibody on a functional marker or result of tenascin-C activity, for example via the methods of the examples.

The antibody or antigen-binding fragment, derivative or variant thereof of the first aspect of the invention may down-regulate the biological activity of tenascin-C.

The antibody or antigen-binding fragment, derivative or variant thereof of the first aspect of the invention may up-regulate the biological activity of tenascin-C. The desirability of up-regulating activity of immune and inflammatory molecules and cells is relevant to the production of therapies for compromised immune and inflammatory patients and in the development of vaccines. (see Harandi (2009)).

The antibody or antigen-binding fragment, derivative or variant thereof of the first aspect of the invention may be an inhibitor of transcription of tenascin-C.

The antibody or antigen-binding fragment, derivative or variant thereof of the first aspect of the invention may be an inhibitor of translation of tenascin-C.

The antibody or antigen-binding fragment, derivative or variant thereof of the first aspect of the invention may be an inhibitor of the binding properties of tenascin-C. For example, the antibody or antigen-binding fragment, derivative or variant thereof may alter the conformation of tenascin-C such that it is no longer able to bind to its receptor or receptors.

The antibody or antigen-binding fragment, derivative or variant thereof of the first aspect of the invention may be a competitive binding inhibitor of tenascin-C. It will be appreciated by persons skilled in the art that the antibody or antigen-binding fragment, derivative or variant thereof may also inhibit the biological activity of tenascin-C by blocking tenascin-C receptor function either directly (by acting as a tenascin-C receptor antagonist) or indirectly (by binding intermediary or assisting molecules).

The antibody or antigen-binding fragment, derivative or variant thereof of the first aspect of the invention may be an antagonist of the TLR-4 receptor. By an antagonist of TLR4 we include indirect antagonism. The antigen-binding fragment, derivative or variant thereof might prevent tenascin-C activation of TLR4 or also of any other receptor.

It will be appreciated by persons skilled in the art that inhibition of the biological activity of tenascin-C by an antibody or antigen-binding fragment, derivative or variant thereof of the invention may be in whole or in part. For example, the antibody or antigen-binding fragment, derivative or variant thereof may inhibit the biological activity of tenascin-C by at least 10%, preferably at least 20%, 30%, 40%, 50%, 60%, 70%, 80% or 90%, and most preferably by 100% compared to the biological activity of tenascin-C on inflammatory cells which have not been exposed to the antibody or antigen-binding fragment, derivative or variant thereof.

The antibody or antigen-binding fragment, derivative or variant thereof of the first aspect of the invention may be selected from polyclonal or monoclonal antibodies.

The antibody or antigen-binding fragment, derivative or variant thereof may bind substantially reversibly or substantially irreversibly to an active site of tenascin-C. In a further example, the antibody or antigen-binding fragment, derivative or variant thereof may bind to a portion of tenascin-C that is not the active site so as to interfere with the binding of the tenascin-C to a ligand or receptor. In a still further example, the antibody or antigen-binding fragment, derivative or variant thereof may bind to a portion of tenascin-C so as to decrease the proteins activity by an allosteric effect. This allosteric effect may be an allosteric effect that is involved in the natural regulation of the activity of tenascin-C, for example in the activation of the tenascin-C by an "upstream activator".

Methods for detecting interactions between a test antibody or antigen-binding fragment, derivative or variant thereof and tenascin-C are well known in the art.

For example ultrafiltration with ion spray mass spectroscopy/HPLC methods or other physical and analytical methods may be used. In addition, Fluorescence Energy Resonance Transfer (FRET) methods may be used, in which binding of two fluorescent labelled entities may be measured by measuring the interaction of the fluorescent labels when in close proximity to each other.

Alternative methods of detecting binding of a polypeptide to macromolecules, for example DNA, RNA, proteins and phospholipids, include a surface plasmon resonance assay, for example as described in Plant et al., 1995, *Analyt Biochem* 226(2), 342-348. Methods may make use of a polypeptide that is labelled, for example with a radioactive or fluorescent label.

A further method of identifying an antibody or antigen-binding fragment, derivative or variant thereof that is capable of binding to the polypeptide is one where the polypeptide is exposed to the antibody or antigen-binding fragment, derivative or variant thereof and any binding of the compound to the said polypeptide is detected and/or measured. The binding constant for the binding of the antibody or antigen-binding fragment, derivative or variant thereof to the polypeptide may be determined. Suitable methods for detecting and/or measuring (quantifying) the binding of an antibody or antigen-binding fragment, derivative or variant thereof to a polypeptide are well known to those skilled in the art and may be performed, for example, using a method capable of high throughput operation, for example a chip-based method. New technology, called VLSIPS™, has enabled the production of extremely small chips that contain hundreds of thousands or more of different molecular probes. These biological chips or arrays have probes arranged in arrays, each probe assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Another method of identifying antibody or antigen-binding fragment, derivative or variant thereof with binding affinity for tenascin-C is the yeast two-hybrid system, where the polypeptides of the invention can be used to "capture" proteins that bind tenascin-C. The yeast two-hybrid system is described in Fields & Song, *Nature* 340:245-246 (1989).

The antibody or antigen-binding fragment, derivative or variant thereof may be a high affinity molecule that mimics an antibody (a so-called 'affibody') (for example, see U.S. Pat. No. 5,831,012 and www.affibody.se). These ligands are small, simple proteins composed of a three-helix bundle based on the scaffold of one of the IgG-binding domains of Protein A (a surface protein from the bacterium *Staphylococcus aureus*). This scaffold has excellent features as an affinity ligand and can be designed to bind with high affinity to any given target protein.

The antibody or antigen-binding fragment, derivative or variant thereof of the first aspect of the invention may prevent tenascin-C activation of Toll-Like Receptor 4 (TLR4) or other receptors, co-receptors of Toll-Like Receptor 4, or co-receptors of those other receptors.

Co-receptors to primary receptors, such as TLR4, assist with binding of a signalling molecule to the primary receptor in order to facilitate ligand recognition and binding and initiate/maintain the biological process resulting from receptor binding.

The antibody or antigen-binding fragment, derivative or variant thereof of the first aspect of the invention may preferably have specificity for the FBG domain of tenascin-C.

In a second aspect of the invention there is provided a composition comprising an antibody or antigen-binding fragment, derivative or variant thereof as defined in the first aspects of the invention and a pharmaceutically acceptable carrier, excipient and/or diluent.

It will be appreciated by persons skilled in the art that such an effective amount of the antibody or antigen-binding fragment, derivative or variant thereof or formulation thereof may be delivered as a single bolus dose (i.e. acute administration) or, more preferably, as a series of doses over time (i.e. chronic administration).

The antibody or antigen-binding fragment, derivative or variant thereof of the invention can be formulated at various concentrations, depending on the efficacy/toxicity of the compound being used and the indication for which it is being used. Preferably, the formulation comprises the antibody or antigen-binding fragment, derivative or variant thereof of the invention at a concentration of between 0.1 µM and 1 mM, more preferably between 1 µM and 100 µM, between 5 µM and 50 µM, between 10 µM and 50 µM, between 20 µM and 40 µM and most preferably about 30 µM. Alternatively, between 60 µM and 70 µM, preferably about 67 µM. For in vitro applications, formulations may comprise a lower concentration of a compound of the invention, for example between 0.0025 µM and 1 µM.

It will be appreciated by persons skilled in the art that the antibody or antigen-binding fragment, derivative or variant thereof of the invention will generally be administered in admixture with a suitable pharmaceutical excipient diluent or carrier selected with regard to the intended route of administration and standard pharmaceutical practice (for example, see Remington: The Science and Practice of Pharmacy, 19$^{th}$ edition, 1995, Ed. Alfonso Gennaro, Mack Publishing Company, Pennsylvania, USA).

For example, the antibody or antigen-binding fragment, derivative or variant thereof of the invention can be administered orally, buccally or sublingually in the form of tablets, capsules, ovules, elixirs, solutions or suspensions, which may contain flavouring or colouring agents, for immediate-, delayed- or controlled-release applications. The antibody or antigen-binding fragment, derivative or variant thereof of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The antibody or antigen-binding fragment, derivative or variant thereof of the invention can also be administered parenterally, for example, intravenously, intra-articularly, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Example approaches:
1) Excipients such as buffers and detergents (usually Tween) that are added to inhibit aggregation in aqueous formulations.
2) Freeze drying with appropriate excipients to provide bulk, stability and cosmetic appeal to the cake
3) Formation of a glassy star using compounds such as trehalose.

For oral and parenteral administration, or other routes of administration, to human patients, the daily dosage level of the antibody or antigen-binding fragment, derivative or variant thereof of the invention will usually be from 1 to 1000 mg per adult (i.e. from about 0.015 to 15 mg/kg), administered in single or divided doses.

As an example, the dosage level may be from about 0.5 mg/kg to about 10 mg/kg, the administration regimen may be twice or three times weekly, the administration may be intravenous.

The antibody or antigen-binding fragment, derivative or variant thereof of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active antibody or antigen-binding fragment, derivative or variant thereof, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of an antibody or antigen-binding fragment, derivative or variant thereof of the invention for delivery to the patient. It will be appreciated that the overall daily dose with an aerosol will vary from patient to patient, and may be administered in a single dose or, more usually, in divided doses throughout the day.

Alternatively, the antibody or antigen-binding fragment, derivative or variant thereof of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For ophthalmic use, the antibody or antigen-binding fragment, derivative or variant thereof of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the antibody or antigen-binding fragment, derivative or variant thereof of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It may be preferable to use a sustained-release drug delivery system, such as a microspheres. These are designed specifically to reduce the frequency of injections. An example of such a system is Nutropin Depot which encapsulates recombinant human growth hormone (rhGH) in biodegradable microspheres that, once injected, release rhGH slowly over a sustained period.

Alternatively, the antibody or antigen-binding fragment, derivative or variant thereof of the present invention can be administered by a surgically implanted device that releases the drug directly to the required site.

Electroporation therapy (EPT) systems can also be employed for the administration of the antibody or antigen-binding fragment, derivative or variant thereof. A device which delivers a pulsed electric field to cells increases the permeability of the cell membranes to the drug, resulting in a significant enhancement of intracellular drug delivery.

The antibody or antigen-binding fragment, derivative or variant thereof can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of antibody or antigen-binding fragment, derivative or variant thereof delivery is the thermo-sensitive ReGel injectable. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Antibody or antigen-binding fragment, derivative or variant thereof pharmaceuticals can also be delivered orally. One such system employs a natural process for oral uptake of vitamin B12 in the body to co-deliver proteins and polypeptides. By riding the vitamin B12 uptake system, the protein or polypeptide can move through the intestinal wall. Complexes are produced between vitamin B12 analogues and the drug that retain both significant affinity for intrinsic factor (IF) in the vitamin B12 portion of the complex and significant bioactivity of the drug portion of the complex.

The composition of the second aspect of the invention may further comprise at least one other agent.

Such a further agent may be an anti-inflammatory agent which includes but is not limited to non-steroidal anti-inflammatory agent (NSAID), a disease modifying anti-rheumatic drug (DMARD), a statin (including HMG-CoA reductase inhibitors such as simvastatin), a biological agent (biologicals), a steroid, an immunosuppressive agent, a salicylate and/or a microbicidal agent. Non-steroidal anti-inflammatory agents include anti-metabolite agents (such as methotrexate) and anti-inflammatory gold agents (including gold sodium thiomalate, aurothiomalate or gold salts, such as auranofin). Biologicals include anti-TNF agents (including adalimumab, etanercept, infliximab, anti-IL-1 reagents, anti-IL-6 reagents, anti-B cell reagents (retoximab), anti-T cell reagents (anti-CD4 antibodies), anti-IL-15 reagents, anti-CLTA4 reagents, anti-RAGE reagents), antibodies, soluble receptors, receptor binding proteins, cytokine binding proteins, mutant proteins with altered or attenuated functions, RNAi, polynucleotide aptamers, antisense oligonucleotides or omega 3 fatty acids. Steroids (also known as corticosteroids) include cortisone, prednisolone or dexamethasone. Immunosuppressive agents include cyclosporin, FK506, rapamycin, mycophenolic acid. Salicylates include aspirin, sodium salicylate, choline salicylate and magnesium salicylate. Microbicidal agents include quinine and chloroquine. For example, the antibody or antigen-binding fragment, derivative or variant thereof may be administered in combination with one or more of an NSAID, DMARD, or immunosuppressant In a third aspect of the invention there is provided an antibody or antigen-binding fragment, derivative or variant thereof or composition as defined in the first and second aspects of the invention for use as a medicament.

In a fourth aspect of the invention there is provided an antibody or antigen-binding fragment, derivative or variant thereof or composition as defined in the first or second aspects of the invention for use in the treatment and/or diagnosis of a chronic inflammatory condition.

In a fifth aspect of the invention there is provided the use of an antibody or antigen-binding fragment, derivative or variant thereof or composition as defined in as defined in the first or second aspects of the invention in the manufacture of a medicament for the treatment and/or diagnosis of a chronic inflammatory condition.

In a sixth aspect of the invention there is provided a method of treating a chronic inflammatory condition comprising administering to a subject an effective amount of an antibody or antigen-binding fragment, derivative or variant thereof or composition as defined in the first or second aspects of the invention.

The antibody or antigen-binding fragment, derivative or variant thereof, composition, use or method as defined in the third, fourth, fifth or sixth aspects of the invention may relate to treatment of a chronic inflammatory condition wherein the condition is associated with any condition associated with inappropriate inflammation. Such conditions include, but are not limited to, rheumatoid arthritis (RA), autoimmune conditions, inflammatory bowel diseases, non-healing wounds, multiple sclerosis, cancer, atherosclerosis, sjogrens disease, diabetes, lupus erythematosus (including systemic lupus erythematosus), asthma, fibrotic diseases (including liver cirrhosis), pulmonary fibrosis, UV damage and psoriasis.

The antibody or antigen-binding fragment, derivative or variant thereof or composition as defined in the first or second aspects may be used, for example, for one or more of the following: to diagnose chronic inflammatory condition status in a subject; to assess the likelihood of a subject developing a chronic inflammatory condition; to determine the prognosis for a subject with a chronic inflammatory condition; to monitor disease progression of a chronic inflammatory condition; and/or to monitor effectiveness or response of a subject to a treatment for chronic inflammatory condition.

In a seventh aspect of the invention there is provided an antibody or antigen-binding fragment, derivative or variant thereof or composition as defined in the first or second aspects for use in the diagnosis of a chronic inflammatory condition and/or the determination of prognosis of a patient with a chronic inflammatory condition.

In an eighth aspect of the invention there is provided a method of diagnosing a chronic inflammatory condition and/or determination of the prognosis of a patient with a chronic inflammatory condition comprising detecting the presence or absence or amount of the FBG domain of tenascin-C using an antibody or antigen-binding fragment, derivative or variant thereof or composition as defined in the first or second aspects.

The prognosis determined may, for example, be a worsening of the chronic inflammatory condition. Alternatively, the prognosis may be a reduction (i.e. improvement) in the chronic inflammatory condition, or the prognosis may be that the chronic inflammatory condition stays the same (i.e. remains constant without worsening or improving).

In one embodiment the method of the eighth aspect is an in vitro method. In an alternative embodiment the method of the eighth aspect is an in vivo method.

An increase in the amount of the FBG domain of tenascin-C detected may be indicative of a chronic inflammatory condition determination and/or of prognosis of a patient with a chronic inflammatory condition. Alternatively, a decrease in the amount of the FBG domain of tenascin-C detected may be indicative of a chronic inflammatory condition determination and/or of prognosis of a patient with a chronic inflammatory condition.

Preferably the antibody or antigen-binding fragment, derivative or variant thereof or composition of the seventh aspect or the method of the eighth aspect allows the diagnosis of chronic inflammatory condition in a subject, or the determination of prognosis of a patient, from the analysis of the level or amount of the FBG domain of tenascin-C in a sample derived from the subject or patient.

In a preferred embodiment of all aspects, the chronic inflammatory condition is rheumatoid arthritis (RA) and/or erosive rheumatoid arthritis.

The level or amount of FBG domain of tenascin-C present in a sample derived from a subject may be determined by using the antibodies or antigen-binding fragments, derivatives or variants thereof of the invention in any suitable assay, which may comprise the use of one or more of: immunoassays; spectrometry; western blot; ELISA; immunoprecipitation; slot or dot blot assay; isoelectric focussing; SDS-PAGE; antibody microarray; immunohistological staining; radio immuno assay (RIA); fluoroimmunoassay; and/or an immunoassay using an avidin-biotin or streptoavidin-biotin system. These methods are well known in the art.

By "sample", we include samples of blood (e.g. serum or plasma), synovial fluid, cerebrospinal fluid (CSF), urine and/or joint tissue derived from the subject.

Preferably, the amount or level of FBG domain of tenascin-C detected is compared to a reference value in order to determine if the amount or level has increased, decreased or stayed the same compared to that reference value.

Preferably the reference value, to which the detected levels or amounts of the FBG domain of tenascin-C are compared, is the amount or level of FBG domain of tenascin-C detected in a sample derived from one or more subjects that do not have any detectable chronic inflammatory condition/disorder or any clinical symptoms of a chronic inflammatory condition/disorder (referred to herein as a "normal sample") and thus have so called "normal values" (also referred to as "normal levels" or "normal amounts") of the FBG domain of tenascin-C. The actual measured values of those normal levels will depend on the particular assay used to detect them. However, one example of a normal level/amount (i.e. a normal value) of the FBG domain of tenascin-C present in a sample would be 15-25 ng/ml, preferably 20-21 ng/ml, most preferably 20.7 ng/ml as has been previously described for tenascin-C levels in Table 2 of Page et al. (2012), where tenascin C expression in the serum of healthy individuals and patients with inflammatory conditions has been described.

Preferably an increase of about 50% or more in the level of FBG domain of tenascin-C measured in a sample, compared to the level in a normal sample (i.e. a normal value/level/amount of FBG domain of tenascin-C), is diagnostic of a chronic inflammatory condition or determines the prognosis of a patient with a chronic inflammatory condition.

However, in other embodiments, a 50%, 55%, 60%, 65%, 70%, 75%, 80%, 85%, 90%, 95% or 100% or more increase in the level of FBG domain of tenascin-C measured in a sample, compared to the level in a normal sample, is diagnostic of a chronic inflammatory condition or determines the prognosis of a patient with a chronic inflammatory condition.

For example, if the level of FBG domain of tenascin-C measured in a sample derived from a subject is 50% or more increased from the normal level of FBG domain of tenascin-C measured in a sample from a healthy subject (i.e. in just one particular example, if it is measured as 31 ng/ml or more), the subject is diagnosed as having a chronic inflammatory condition (e.g. RA) and/or the prognosis of that subject is determined. The prognosis determined may be a worsening of the chronic inflammatory condition. Alternatively, the prognosis may be a reduction (i.e. improvement) in the chronic inflammatory condition, or the prognosis may be that the chronic inflammatory condition stays the same (i.e. remains constant without worsening or improving).

In a particular embodiment of the antibody or antigen-binding fragment, derivative or variant thereof or method of the seventh and eighth aspects, an increase of at least 50% in the amount of FBG domain of tenascin-C detected compared to normal levels is indicative of a chronic inflammatory condition determination and/or prognosis of a patient with a chronic inflammatory condition.

In a ninth aspect of the invention there is provided an antibody or antigen-binding fragment, derivative or variant thereof or composition as defined in the first or second aspects for use in the determining the appropriate treatment for an individual, wherein the amount of the FBG domain of tenascin-C detected indicates the appropriate treatment for the individual.

In a tenth aspect of the invention there is provided a method of determining the appropriate treatment for an individual comprising detecting the presence or absence or amount of the FBG domain of tenascin-C using an antibody or antigen-binding fragment, derivative or variant thereof or composition as defined in the first or second aspects, wherein the amount of the FBG domain of tenascin-C detected indicates the appropriate treatment for the individual.

In one embodiment the method of the tenth aspect is an in vitro method. In an alternative embodiment the method of the tenth aspect is an in vivo method.

The appropriate treatment may comprise the administration of an effective amount of an agent or composition, the agent or composition may be one or more of: an antibody or antigen-binding fragment, derivative or variant thereof, or composition as defined in the first or second aspects; DMARDS (such as methotrexate); anti-TNF drug; an anti-IL17 therapy; a T-cell co-stimulation modulator (such as Orencia™—abatacept): an interleukin-6 (IL-6) inhibitor (such as Actemra™—tocilizumab); an anti-CD20 antibody (such as Rituxan™—rituxumab; a B cell activating factor (such as anti-BAFF); an inhibitor of janus kinase (JAK) (such as Tofacitinib™); an inhibitor of spleen tyrosine kinase (Syk) (such as Fostamatinib™); antiTNC antibodies or antibodies to citrullinated tenascin-C domains; and/or an agent that modulates the biological activity of citrullinated and/or non-citrullinated tenascin-C.

In a particular embodiment, the appropriate treatment targets the FBG domain of tenascin-C.

In another particular embodiment, the appropriate treatment is the administration of an effective amount of an antibody or antigen-binding fragment, derivative or variant thereof, or composition as defined in the first or second aspects.

Optionally, the individual defined in the ninth and tenth aspects has a chronic inflammatory condition. The individual may or may not have been diagnosed as such prior to the method being performed.

In certain embodiments, an increase in the amount of FBG domain of tenascin-C detected indicates the appropriate treatment. In alternative embodiments, a decrease in the amount of FBG domain of tenascin-C detected indicates the appropriate treatment.

In one embodiment an increase or decrease of about 50% or more in the level of FBG domain of tenascin-C measured in a sample, compared to the level in a normal sample (i.e. a normal level or amount of FBG domain of tenascin-C), determines the appropriate treatment of an individual. However, in other embodiments, a 50%, 55%, 60%, 65%, 70%, 75%, 80%, 85%, 90%, 95% or 100% or more increase or decrease in the level of FBG domain of tenascin-C measured in a sample, compared to the level in a normal sample, determines the appropriate treatment of an individual.

For example, if the level of FBG domain of tenascin-C measured in a sample derived from a subject is 50% or greater increased from the normal level of FBG domain of tenascin-C measured in a sample from a healthy subject (i.e. in just one particular example, if it is measured as 31 ng/ml or more), the appropriate treatment is determined. For example, it may then be determined to treat the subject by the administration of an effective amount of an agent or composition, the agent or composition may be one or more of: an antibody or antigen-binding fragment, derivative or variant thereof, or composition as defined in the first or second aspects; DMARDS (such as methotrexate); anti-TNF drug; an anti-IL17 therapy; a T-cell co-stimulation modulator (such as Orencia™—abatacept): an interleukin-6 (IL-6) inhibitor (such as Actemra™—tocilizumab); an anti-CD20 antibody (such as Rituxan™—rituxumab; a B cell activating factor (such as anti-BAFF); an inhibitor of janus kinase (JAK) (such as Tofacitinib™); an inhibitor of spleen tyrosine kinase (Syk) (such as Fostamatinib™); antiTNC antibodies or antibodies to citrullinated tenascin-C domains, and/or an agent that modulates the biological activity of citrullinated and/or non-citrullinated tenascin-C.

In one embodiment, an increase in FBG domain of tenascin-C detected indicates that an increased amount of the appropriate treatment is required. In an alternative embodiment, a decrease in FBG domain of tenascin-C detected indicates that an increased amount of the appropriate treatment is required.

Preferably an increase or decrease of 50% or more in the level of FBG domain of tenascin-C measured in a sample, compared to the level in a normal sample (i.e. a normal level or amount of FBG domain of tenascin-C), indicates that an increased or decreased amount of the appropriate treatment is required. However, in other embodiments, a 50%, 55%, 60%, 65%, 70%, 75%, 80%, 85%, 90%, 95% or 100% or more increase or decrease in the level of FBG domain of tenascin-C measured in a sample, compared to the level in a normal sample, indicates that an increased or decreased amount of the appropriate treatment is required. The increased or decreased amount of the appropriate treatment may be an increase or decrease in dose, frequency of dosing or duration of treatment.

In one embodiment of the antibody or antigen-binding fragment, derivative or variant thereof or composition or method of ninth and tenth aspects, an increase of at least 50% in the amount of FBG domain of tenascin-C detected compared to normal levels of FBG domain of tenascin-C determines the appropriate treatment and/or indicates that an increased amount of the appropriate treatment is required.

Conveniently, the method of diagnosis or method of determining the appropriate treatment of the eighth and/or tenth aspects comprises performing one or more of: immunoassays; spectrometry; western blot; ELISA; immunoprecipitation; slot or dot blot assay; isoelectric focussing; SDS-PAGE; antibody microarray; immunohistological staining; radio immuno assay (RIA); fluoroimmunoassay; and/or an immunoassay using an avidin-biotin or streptoavidin-biotin system.

The antibody or antigen-binding fragment, derivative or variant thereof, composition or to method as defined in the seventh, eighth, ninth or tenth aspects of the invention may relate to treatment of a chronic inflammatory condition wherein the condition is associated with any condition associated with inappropriate inflammation. Such conditions include, but are not limited to, rheumatoid arthritis (RA), autoimmune conditions, inflammatory bowel diseases, non-healing wounds, multiple sclerosis, cancer, atherosclerosis, sjogrens disease, diabetes, lupus erythrematosus (including systemic lupus erythrematosus), asthma, fibrotic diseases (including liver cirrhosis), pulmonary fibrosis, UV damage and psoriasis.

In an eleventh aspect of the invention there is provided a kit of parts comprising:
  (i) an antibody or antigen-binding fragment, derivative or variant thereof or composition as defined in the first or second aspects of the invention
  (ii) administration means
  (iii) instructions for their use
  The kit of the seventh aspect of the invention may further optionally comprise
  (iv) at least one other agent.

According to a further aspect of the invention there is provided a kit of parts for use in determining the chronic inflammatory condition status of a subject comprising:

(i) an antibody or antigen-binding fragment, derivative or variant thereof or composition as defined in the first or second aspects of the invention; and (ii) instructions for use By "chronic inflammatory condition status", we include the diagnosis of, determining the prognosis of and/or determining the appropriate treatment for a subject with or without a chronic inflammatory condition.

Further aspects of the invention relate to methods of identifying one or more therapeutic antibodies with specificity for FBG, such as the antibodies described in the earlier aspects (see the detailed antibody screening methodology described in the Examples).

A detailed specification for the final therapeutic molecule is important prior to initiating an antibody isolation project. For the antibodies isolated herein, the set specifications are provided in the table below:

ELISA screening incorporated testing of binding human, rat, mouse and dog TNC-FBG. Positive clones were also tested against human Tenascin R FBG. Those with the correct binding properties were subcloned into suitable antibody formats for testing in the potency screen (inhibition of the Fc-His-FBG induced alkaline phosphatase reporter in the THP-1 Blue™ assay was utilized for screening and then activity was confirmed by measuring the inhibition of Fc-His-FBG induced cytokine expression from THP-1 cells). Lead clones that passed the first milestone were taken into lead optimization where the phage display methods were tailored for provide antibodies that passed the $2^{nd}$ milestone. Of the 'parent' antibodies described herein that were taken into lead optimization (2A5, B12, F3 and D8) two (2A5 and B12) provided optimized clones that passed the pre-agreed specification.

TABLE A

Specifications for antibody selection.

| | First Milestones (Lead Isolation) | Second Milestones* (lead optimisation) |
|---|---|---|
| Panel | At least 2 antibody leads with unique CDR sequence combinations | 1 optimised preclinical development candidate and 1 backup with different CDR sequence |
| Format | Fab or whole antibody (human IgG2 or human IgG4) | Human IgG2 or IgG4 |
| Affinity Potency | Binding affinity of 1-10 nM, determined by Surface plasmon Resonance (SPR) Displays concentration-related inhibition of tenascin-C - evoked cytokine release with IC50 <100 nM in a cell-based assay | Either: Binding affinity of ≤320 pM, determined by SPR; or: IC50 1 nM (at least n = 3) or lower in assay of tenascin-C - evoked cytokine release in a cell-based assay |
| Cross Reactivity | In ELISA, binds to human, mouse, rat, dog FBG | Affinity to at least one rodent (e.g. rat) and one non-rodent (e.g. dog) tenascin-C isoform of ≤3 nM |
| Specificity | Evidence of non- binding to human tenascin-R, vs human tenascin-C positive control (provided antigen is available at the time of reaching other specifications), preferably in ELISA, or by SPR. | Concentration for half-maximal binding to human tenascin-R is at least 50-fold, preferably 100-fold, greater than equivalent binding signal to human tenascin-C, preferably in ELISA, or by SPR. |
| Solubility | Soluble to at least 1 mg/mL in PBS | IgG is soluble in PBS to at least 20 mg/mL without precipitation/ aggregation over 14 days |

*or if there is agreement that an acceptable profile is achieved before the "Second Milestones" criteria are met The key requirements were identification of antibodies with high affinity for Tenascin C FBG, able to block cell activation and production of inflammatory cytokines in response to Tenascin C FBG, and with sufficient cross reactivity to other species to allow relevant safety and efficacy studies to be conducted in those species (and hence no requirements for parallel reagents).

It was also deemed advantageous to have lead antibodies that had a lower affinity for other members of the Tenascin family and Tenascin R was therefore chosen for specificity testing based on this protein having a higher degree of homology (at the amino acid level) to Tenascin C than other closely related proteins. Cellular potency was defined as the half maximal concentration able to inhibit the Tenascin C FBG derived to cytokine release in a set of relevant cell based assays. Finally, the candidates needed to be stable in relevant antibody formats to provide some early indications that there were no critical issues in the manufacturability of the product.

The screening methods adopted were based on generating antibodies with the correct specification. Therefore initial Therefore, in a further aspect of the invention there is provided a method of identifying one or more therapeutic antibodies specific for the FBG domain of tenascin-C comprising selecting antibodies which have one or more of the properties listed in Table A. Preferably the antibodies exhibit all of the properties listed under "First Milestones", even more preferably the antibodies exhibit all of the properties in Table A.

In one embodiment, the method of identifying one or more therapeutic antibodies specific for the FBG domain of tenascin-C comprises selecting antibodies which have one or more of the following properties:

(a) the antibody is a Fab or whole antibody (preferably human IgG2 or human IgG4);

(b) the antibody has a binding affinity to human tenascin-C FBG of 1-10 nM, determined by Surface plasmon Resonance (SPR), and/or the antibody displays concentration-related inhibition of tenascin-C, preferably evoked cytokine release with IC50<100 nM in a cell-based assay, preferably using Fc-His-FBG; and (c) the antibody binds to human FBG and one or more of mouse, rat and dog FBG, preferably measured by ELISA, preferably the antibody binds to all of human, mouse, rat and dog FBG.

Preferably, the antibody also exhibits one or more of the following additional properties:
(d) the antibody does not bind to human tenascin-R, or exhibits reduced binding to human tenascin-R compared to human tenascin-C positive control; and
(e) The antibody is soluble to at least 1 mg/mL in PBS.

Preferably, the affinity potency determined by SPR is ≤320 pM and/or there is an IC50 of nM for evoked cytokine release in a cell based assay, preferably using Fc-His-FBG.

Preferably, the antibody has affinity to at least one rodent (e.g. rat) and one non-rodent (e.g. dog) tenascin-C isoform of ≤3 nM.

Preferably, concentration for half-maximal binding to human tenascin-R is at least 50-fold, preferably 100-fold, greater than equivalent binding signal to human tenascin-C, preferably measured by ELISA binding experiments, or by SPR. Preferably, the concentration for half-maximal binding to human tenascin-R is at least 50-fold greater than equivalent binding signal to human tenascin-C when measured by SPR. Preferably, the concentration for half-maximal binding to human tenascin-R is at least 100-fold greater than equivalent binding signal to human tenascin-C when measured by ELISA.

Preferably, the antibody is soluble in PBS to at least 20 mg/mL without precipitation/aggregation over 14 days.

In a further aspect of the invention there is provided a method of identifying one or more therapeutic antibodies specific for the FBG domain of tenascin-C comprising the following steps:
(i) Screening an antibody or antibody fragment library, e.g. a phage library, for antibodies or fragments which bind human tenascin-C FBG and one or more of rat, mouse and dog tenascin-C FBG, preferably by ELISA;
(ii) Testing positive antibodies or fragments identified in (i) for reduced binding to human tenascin-R FBG compared to human tenascin-C FBG, preferably by ELISA;
(iii) Subcloning antibodies or fragments identified with the desired properties from (i) and (ii) into suitable formats for potency screen (e.g. Fab, Fc-scFv, IgG2 or IgG4); and
(iv) Identifying antibodies or fragments from (iii) which exhibit inhibition of Fc-His-FBG activity.

Optionally, Surface plasmon Resonance (SPR) is used for step (i) and/or (ii).

Preferably step (iv) utilizes an Fc-His-FBG induced alkaline phosphatase reporter (e.g. in the THP-1 Blue™ assay); and/or measures the inhibition of Fc-His-FBG induced cytokine expression (e.g. from THP-1 cells).

In step (i), preferably the antibody or fragment binds to all of human, rat, mouse and dog tenascin-C FBG.

Optionally the method steps are performed in order, however they may alternatively be performed in any order.

In one embodiment, the therapeutic antibody or antibodies identified by performing the method of steps (i)-(iv) exhibits one or more of the properties (a)-(e) of the previous aspect.

Definitions

By "inflammation" we include the meaning of local accumulation of fluid, plasma proteins, and white blood cells that is initiated by tissue injury, infection or a local immune response.

By "acute inflammation" we include the meaning of the initial stages (initiation) of inflammation and the short-term transient inflammatory response immediately after injury, infection or local immune response. Typically, acute inflammation is rapidly resolved, lasting from a matter of minutes to no longer that a few days.

By "chronic inflammation" we include the meaning of persistent and/or non-resolved inflammation. It is often associated with inappropriate destruction of healthy tissue. This may be progressive and last over a period of weeks or longer. Chronic inflammation is typically associated with persistent infection or disease including, but not limited to, autoimmune conditions.

By "chronic joint inflammation" we include the meaning of persistent inflammation that is progressive and unremitting over a period of weeks to months, resulting in distortion of the affected joint and radiographic evidence of cartilage and bone destruction as observed in human disease (Kelly, Harris, Ruddy and Sledge, Textbook of Rheumatology 4th Edition).

In experimental murine models, chronic joint inflammation is characterised by inflammation that does not subside and causes inappropriate tissue destruction, even over a relatively short period of time. This is characterised (and can be identified) histologically by the prolonged presence of inflammatory cells in the synovium and joint space, chondrocyte death, and cartilage and bone erosion.

By "fragment" we mean at least four amino acids, for example at least 4, 5, 6, 7, 8, 9, 10, 11, 12, 13, 14, 15, 16, 17, 18, 19, 20, 25, 30, 35, 40, 45, 50 amino acids.

The percent sequence identity between two polypeptides may be determined using suitable computer programs, for example the GAP program of the University of Wisconsin Genetic Computing Group and it will be appreciated that percent identity is calculated in relation to polynucleotides whose sequences have been aligned optimally.

The alignment may alternatively be carried out using the Clustal W program (as described in Thompson et al., 1994, Nuc. Acid Res. 22:4673-4680).

The parameters used may be as follows:

Fast pairwise alignment parameters: K-tuple (word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

By "antibody" we include substantially intact antibody molecules, as well as chimeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to the FBG domain of tenascin-C.

The term "subject" or "individual" means all animals including humans. Examples of subjects include humans, cows, dogs, cats, goats, sheep, and pigs. The term "patient" means a subject or individual having a disorder in need of treatment.

As used herein, 'pharmaceutical formulation' means a therapeutically effective formulation according to the invention.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

Examples embodying an aspect of the invention will now be described with reference to the following figures:

FIG. 1. Amino acid sequence of human tenascin-C and its domains: TA domain (SEQ ID NO: 144), EGFL domain (SEQ ID NO: 145), FNIII domain (SEQ ID NO: 146), FBG domain (SEQ ID NO: 92).

FIG. 2. Nucleotide sequence of human tenascin-C(SEQ ID NO: 148).

FIG. 3. Polyclonal phage ELISA.

Polyclonal derived 2nd round output phage were incubated with wells coated with antigen or fusion partner (Fc or Cd4) and bound phage detected with anti-M13 mAb and Europium-labelled anti-mouse antibody. There is enrichment of antigen-specific binders between rounds 1 and 2 of selection and a greater proportion of huFBG binders compared to anti-Fc or -rCd4 phage in the round 2 output populations.

Figure 4A:
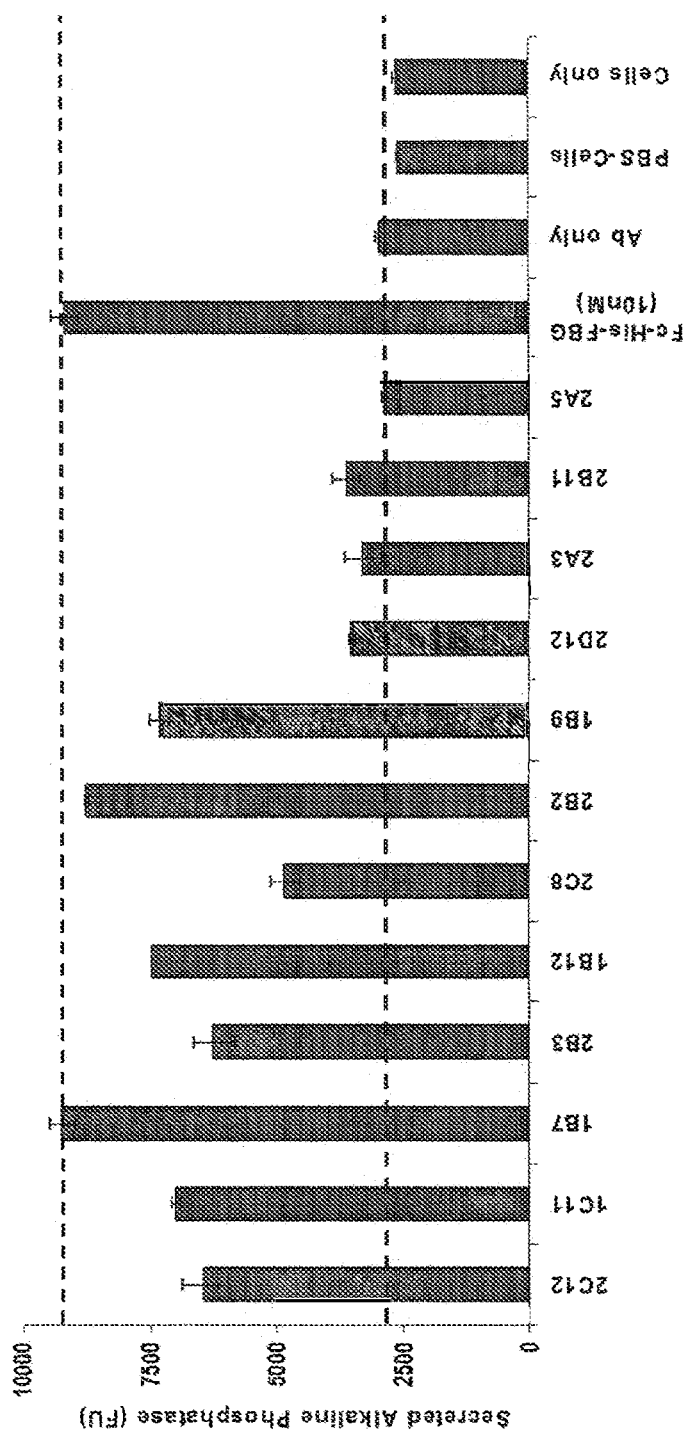
Figure 4B:
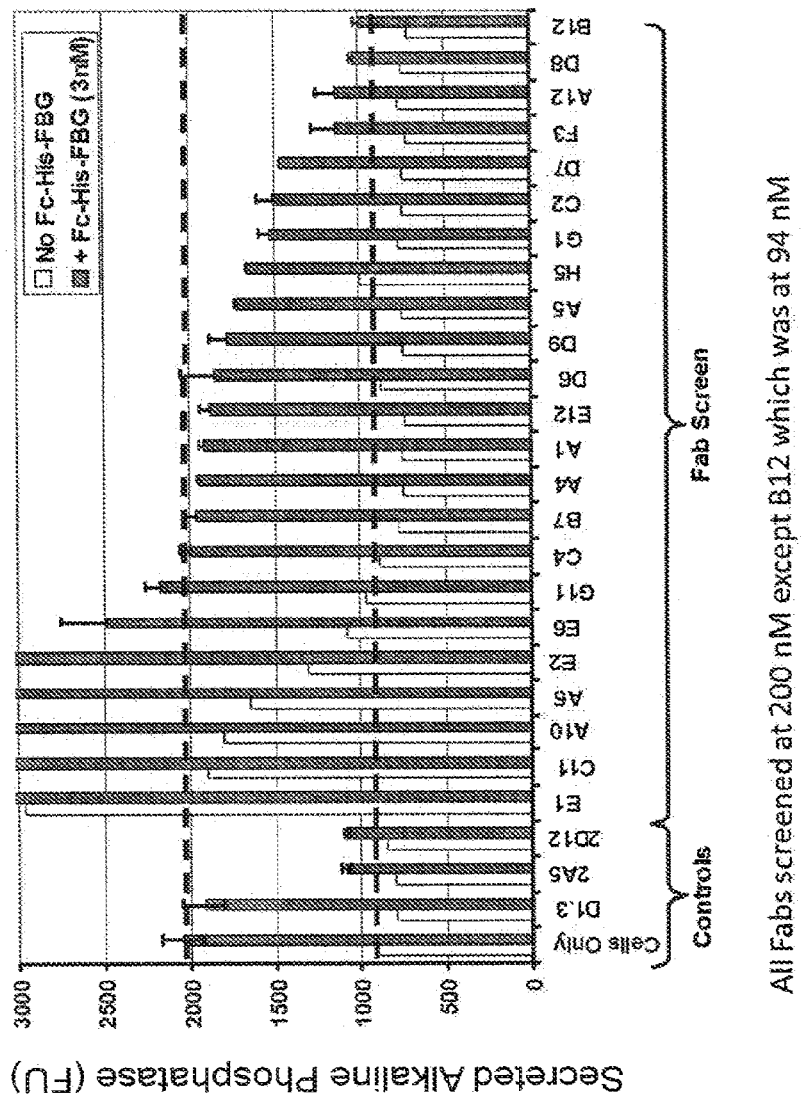

FIGS. 4A-4B. Screening of purified anti-FBG in the THP1-Blue assay of secreted alkaline phosphatase release, determined by fluorimetric assay.

Antibodies were tested at the highest concentration achievable. In a confirmatory assay of purified scFv-Fc clones, 2A3, 2A5, 2611 and 2D12 were identified as effective blockers of signalling evoked by 10 nM Fc-His-huFBG (FIG. 4A). Assay of purified anti-FBG FAbs highlighted a number of additional hits for further analysis including antibodies A12, B12, C2, D7, D8, F3 and G1. In this experiment cells were stimulated with 3 nM Fc-His-huFBG (FIG. 4B).

FIG. 5. Cross-reactivity ELISA results for purified Fab binding to immobilised TNC FBG-rCD4 proteins (human, mouse, rat and dog) and human TNR FBG-rCD4. Binding was detected using anti-kappa or anti-lambda mAb followed by Europium-conjugated anti-mouse mAb.

FIGS. 6A-6D illustrate BiAcore sensogram traces for determination of kinetics for binding of FBG proteins to anti-FBG Fabs B12 (FIG. 6A), 2A5 (FIG. 6B), F3 (FIG. 6C), and D8 (FIG. 6D) which were captured on a CM5 sensor chip.

Traces indicate binding of human, rat and mouse tenascin-C rCd4-FBG and human tenascin-R rCD4-FBG.

Figure 7:
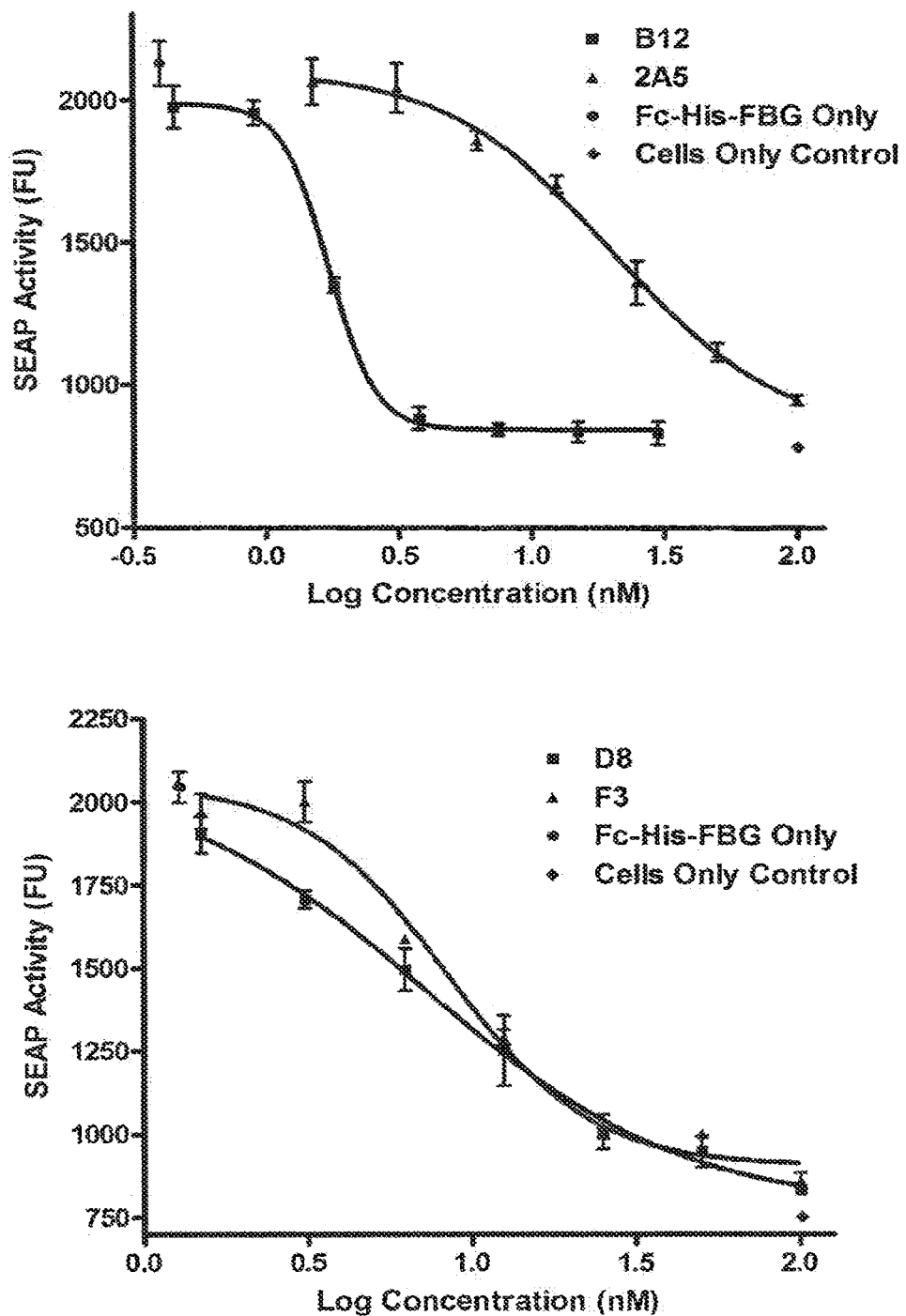

FIG. 7. Concentration-related inhibition of secreted alkaline phosphatase (SEAP) release by anti-FBG Fabs B12, 2A5, D8 and F3.

Purified antibodies were incubated with THP1-Blue cells in the presence of 3 nM human Fc-His-FBG for 18 h at 37° C. IC50 values for inhibition of Fc-His-FBG evoked SEAP were B12 (1.7 nM), 2A5 (20.6 nM), D8 (7.2 nM), F3 (8.4 nM).

FIG. 8. Concentration-related inhibition of IL-8 production by anti-FBG Fabs B12, 2A5, D8 and F3.

Purified antibodies were incubated with THP1-Blue cells in the presence of 3 nM human Fc-His-FBG for 18 h at 37° C. IC50 values for inhibition of Fc-His-FBG evoked IL-8 release were B12 (6.9 nM), 2A5 (28.5 nM), D8 (14.9 nM), F3 (13.8 nM).

Figure 9A:
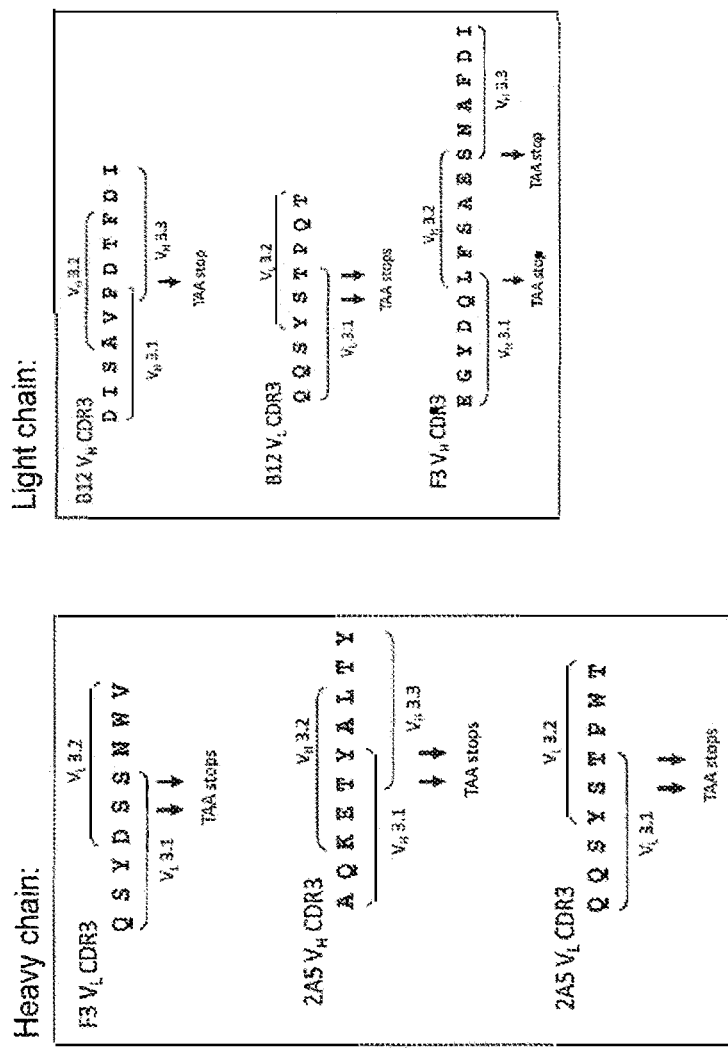

FIGS. 9A-9B. CDR3 randomisation strategy for anti-FBG lead antibodies. FIG. 9A: F3VLCDR3 (SEQ ID NO: 28), 2A5VHCDR3 (SEQ ID NO: 3), 2A5VLCDR3 (SEQ ID NO: 7), B12VHCDR3 (SEQ ID NO: 11), B12VLCDR3 (SEQ ID NO: 14), F3VHCDR3 (SEQ ID NO: 24) and oligonucleotides for VH and VL CDR3 mutagenesis (SEQ ID NOs: 97-111).

VH CDR3 randomisation was done in three overlapping blocks of 6 residues each (labelled VH 3.1, VH 3.2, and VH 3.3) and the VL CDR3s were randomised in blocks of two (labelled VL 3.1 and VL 3.2). Arrows indicate the positions of stop codons introduced into the template DNA to eliminate parental clones dominating the library. FIG. 9B: Oligonucleotides used for CDR3 library generation.

Figure 10:
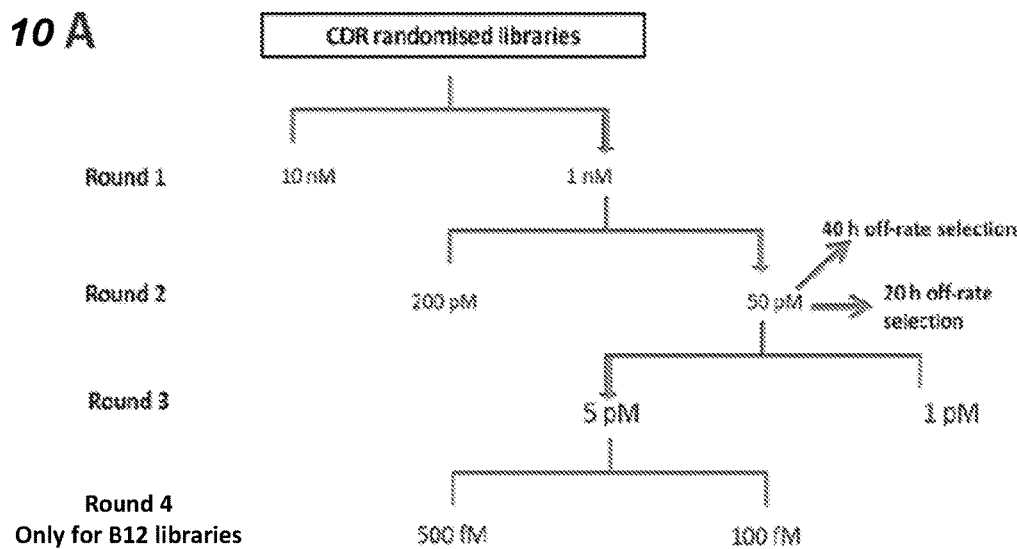
Figure 10:
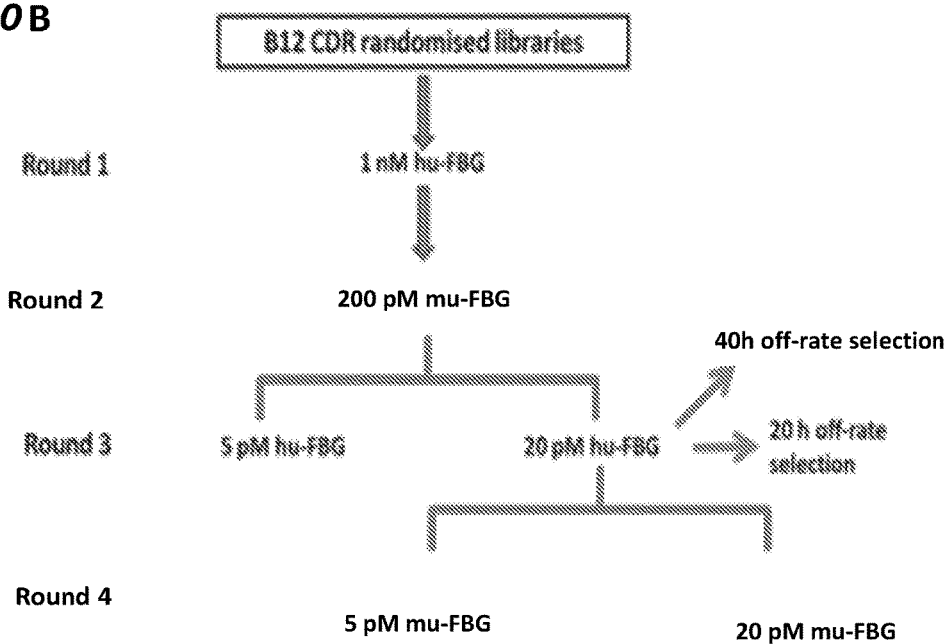

FIGS. 10A-10B. Selection strategy for CDR randomised antibody libraries. (FIG. 10A) Selections on human rCd4-His-FBG using CDR randomised libraries. (FIG. 10B) Hybrid selections on human and mouse FBG using B12 VH and VL CDR 3 randomised libraries.

Figure 11:
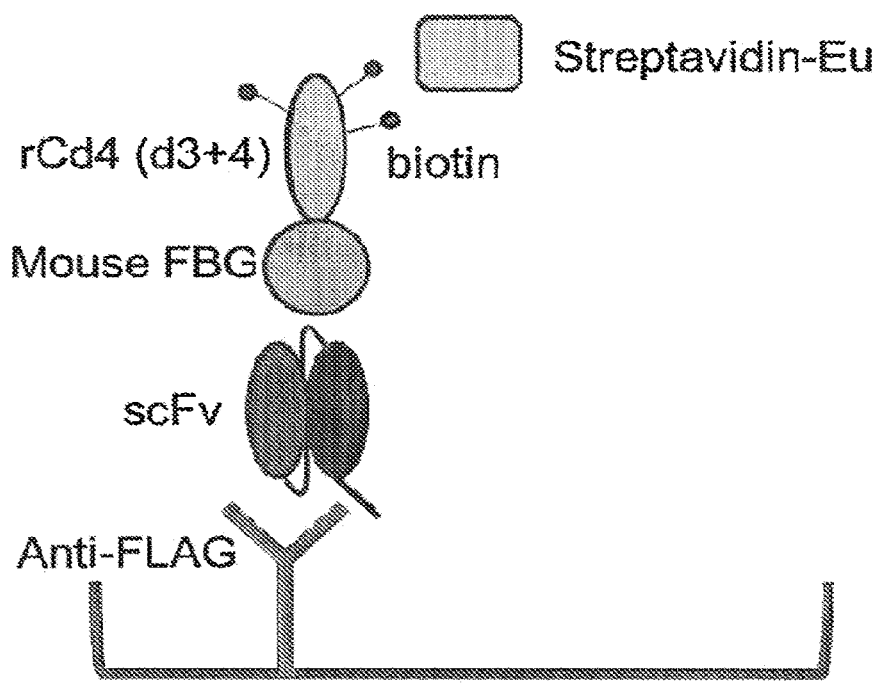

FIG. 11. Schematic diagram of the anti-FLAG capture ELISA format used to screen affinity-matured clones for improved binding to biotin-labelled mouse or human rCd4-FBG.

Figure 12A:
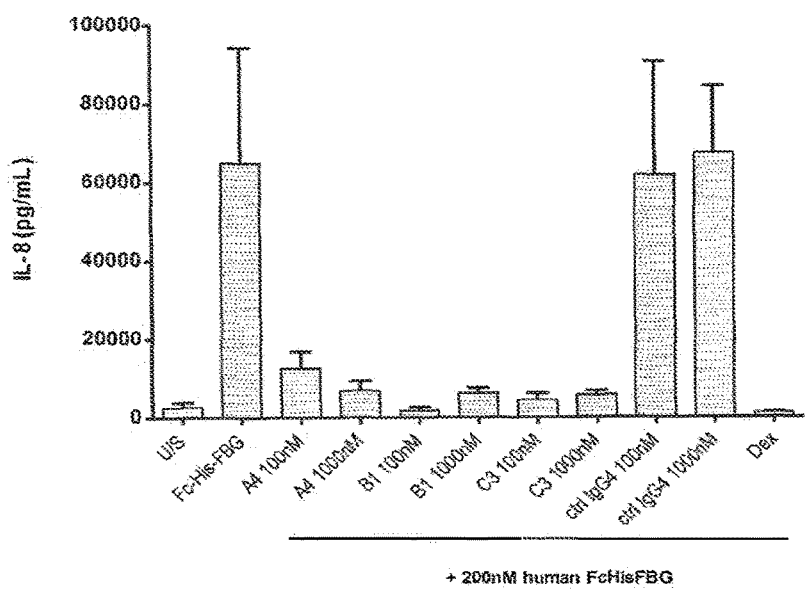
Figure 12B:
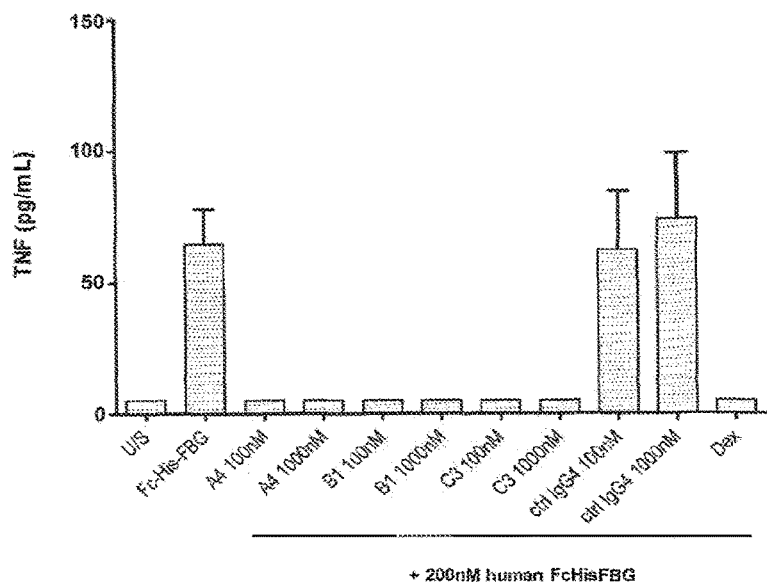

FIGS. 12A-12B. Inhibition of FBG-evoked cytokine release by the affinity-matured hIgG4 antibodies 165_13_131, 165_13_C3, and 160_01_A4.

Primary human PBMCs were incubated (37° C., 24 h) in the presence of 200 nM human Fc-His-FBG and test antibody (100 nM or 1 µM) and supernatants were assayed for IL-8 (FIG. 12A) and TNFa (FIG. 12B). All test antibodies blocked evoked cytokine release. Data indicate mean±s.e. mean of results from 3 separate donors.

FIGS. 13A-13O. Immunostaining of endogenous tenascin-c FBG in fixed frozen sections of knee synovium from a rheumatoid arthritis patient following knee replacement surgery.

Specific staining of the synovium was seen with positive control anti-tenascin-antibody (FIG. 13A), and B12 anti-FBG formatted as mouse IgG2a (FIG. 13C). Lower levels of non-specific staining were observed with non-immune iso-type control antibodies (FIG. 13B, FIG. 13D).

Figure 14A:
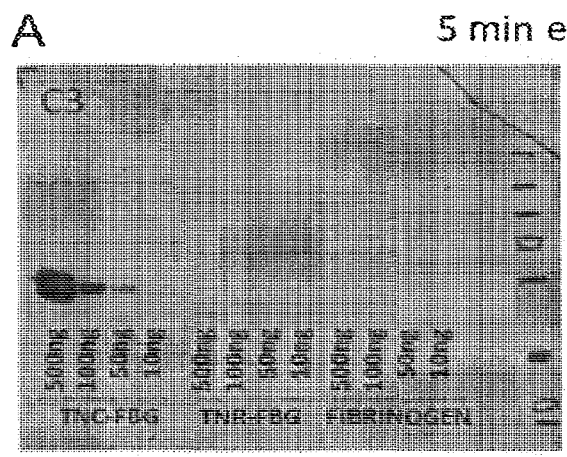

FIGS. 14A-14O. Antibodies C3 (165_13_C3) and B12 show good specificity for TNC-FBG when used for western blot analysis.

Figure 14C:
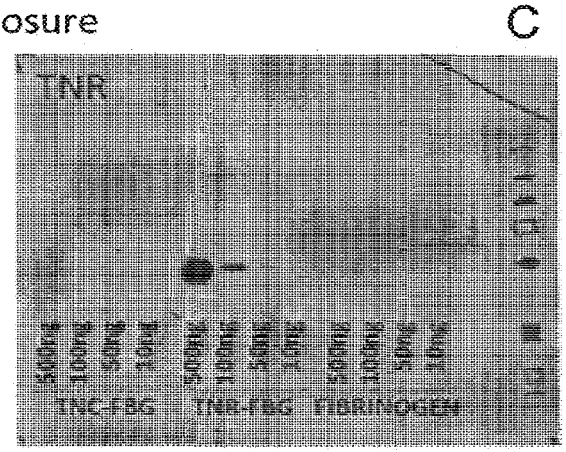
Figure 14B:
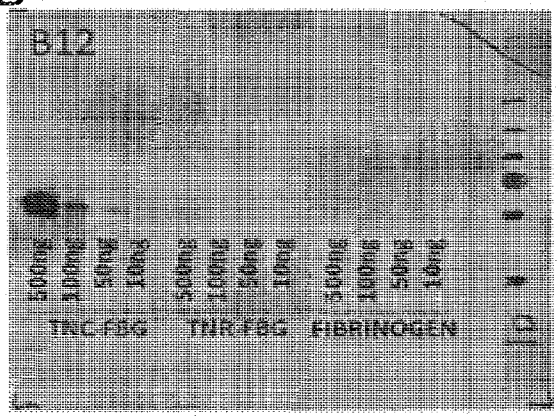
Figure 14D:
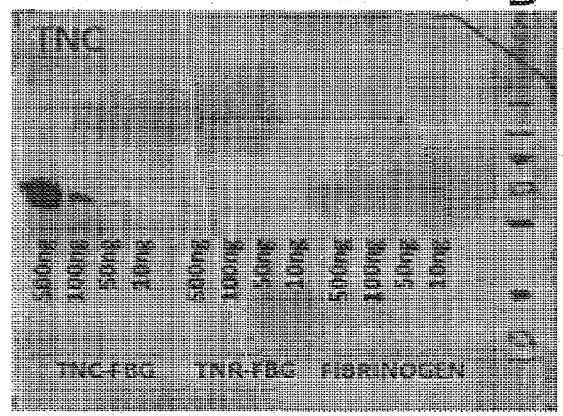

Recombinant TNC-FBG (Nascient), TNR-FBG or FIBRINOGEN (Kennedy Institute of Rheumatology (KIR)) detected with the following antibodies FIG. 14A) 165_13_C3 IgG4 MAb at 1:20,000 (0.25 ug/ml), overnight at 4° C. FIG. 14B) B12 IgG4 MAb at 1:20,000 (0.25 ug/ml), overnight at 4° C. FIG. 14C) Anti-Tenascin-R antibody (Santa Cruz Biotechnology, sc-9875) at 1:2,000 (0.1 ug/ml)

overnight at 4° C. FIG. 14D) Anti-TNC-FBG polyclonal antibody (Midwood group) at 1:500, overnight at 4° C.

Figure 15A:
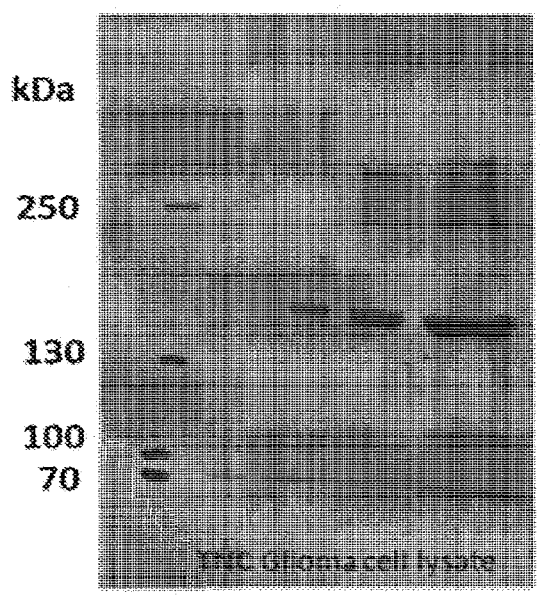
Figure 15B:
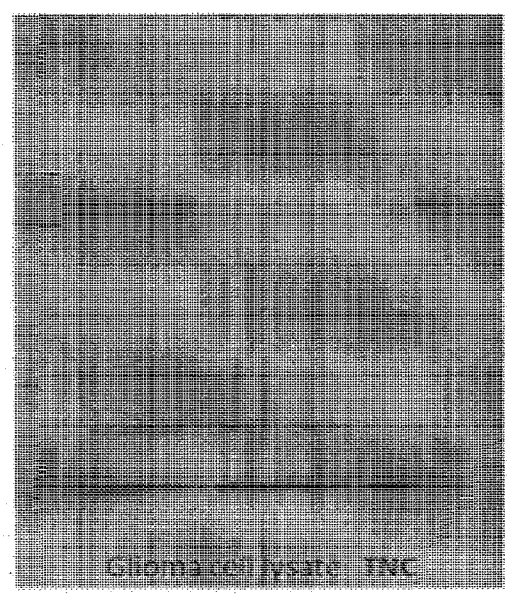

FIGS. 15A-15B. Western blot analysis of glioma cell lysate using monoclonal antibody B12 and corresponding isotype control.

Glioma cell lysate (KIR) and tenascin-C(Nascient) detected with FIG. 15A. B12 IgG4 Mab at 1:20,000, overnight at 4° C.; FIG. 15B. IgG4 isotype control (Eureka therapeutics) at 1:4,000, overnight at 4° C.

Figure 16A:
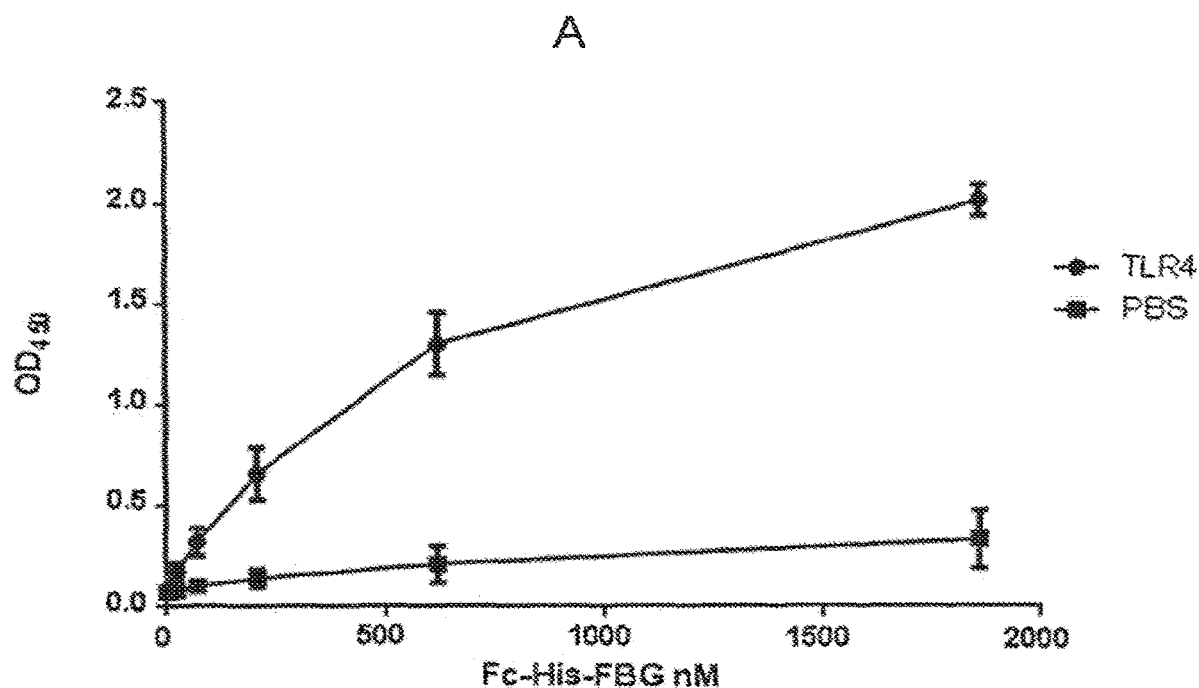

FIG. 16A. Fc-His-FBG binds to TLR4 in vitro in a dose dependent manner. Recombinant human TLR4 (R&D systems) in PBS (or PBS alone) was bound to a 96-well plate, after blocking the indicated concentrations of Human Fc-His-FBG. was added and detection was carried out by incubation of an anti-human IgG1 MAb (AbD Serotec, clone 2C11) at 1 ug/ml, an anti-mouse HRP conjugated secondary antibody (AbD Serotec, STAR13B) at 1 ug/ml, and TMB substrate. n=4 mean and SEM shown.

Figure 16B:
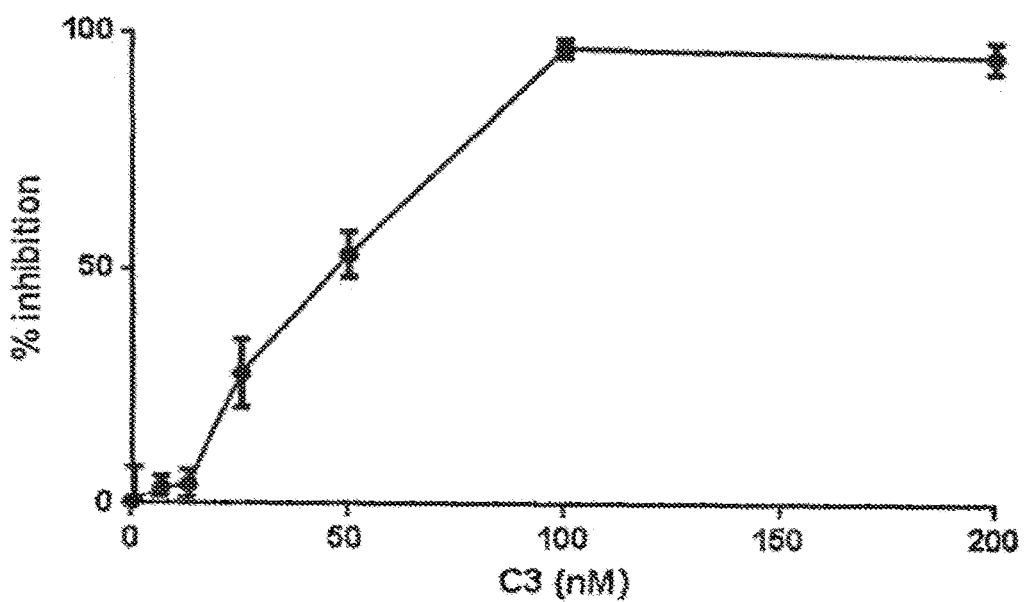

FIG. 16B. Monoclonal Ab C3 (165_13_C3) disrupts the binding FBG and TLR4 in vitro. Recombinant human TLR4 in PBS (or PBS alone) was bound to a 96-well plate, after blocking recombinant human Fc-His-TNC-FBG (100 nM) which had been pre-incubated with C3 Mab or isotype control antibody was added. Detection was carried out by successive incubation of antibody directed against the Fc portion of the protein, an anti-mouse HRP conjugated secondary antibody and TMB substrate. The percentage inhibition in the C3 pre-incubated samples was calculated compared to the isotype control samples (IC50=44.5 nM). n=4

Figure 17A:
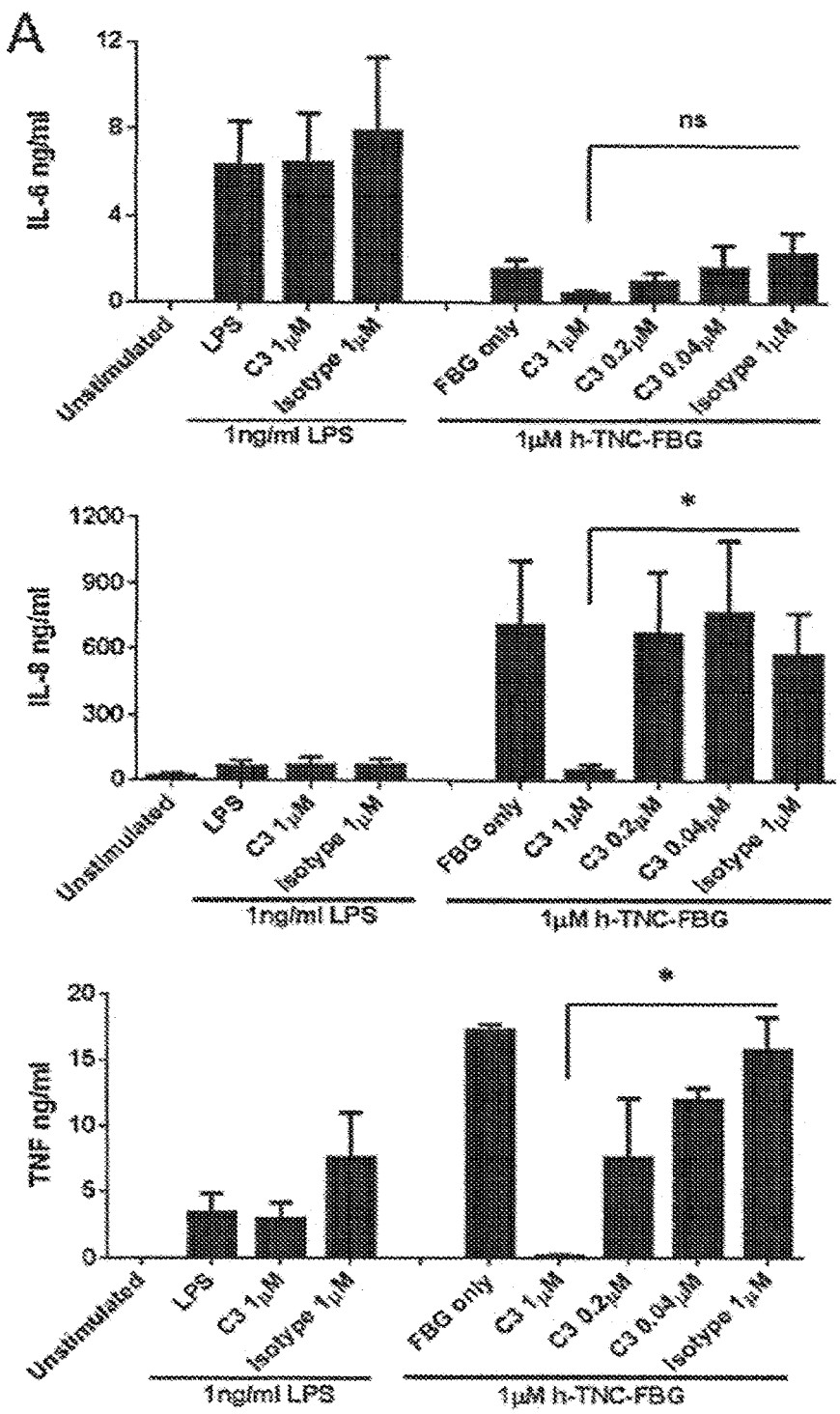
Figure 17B:
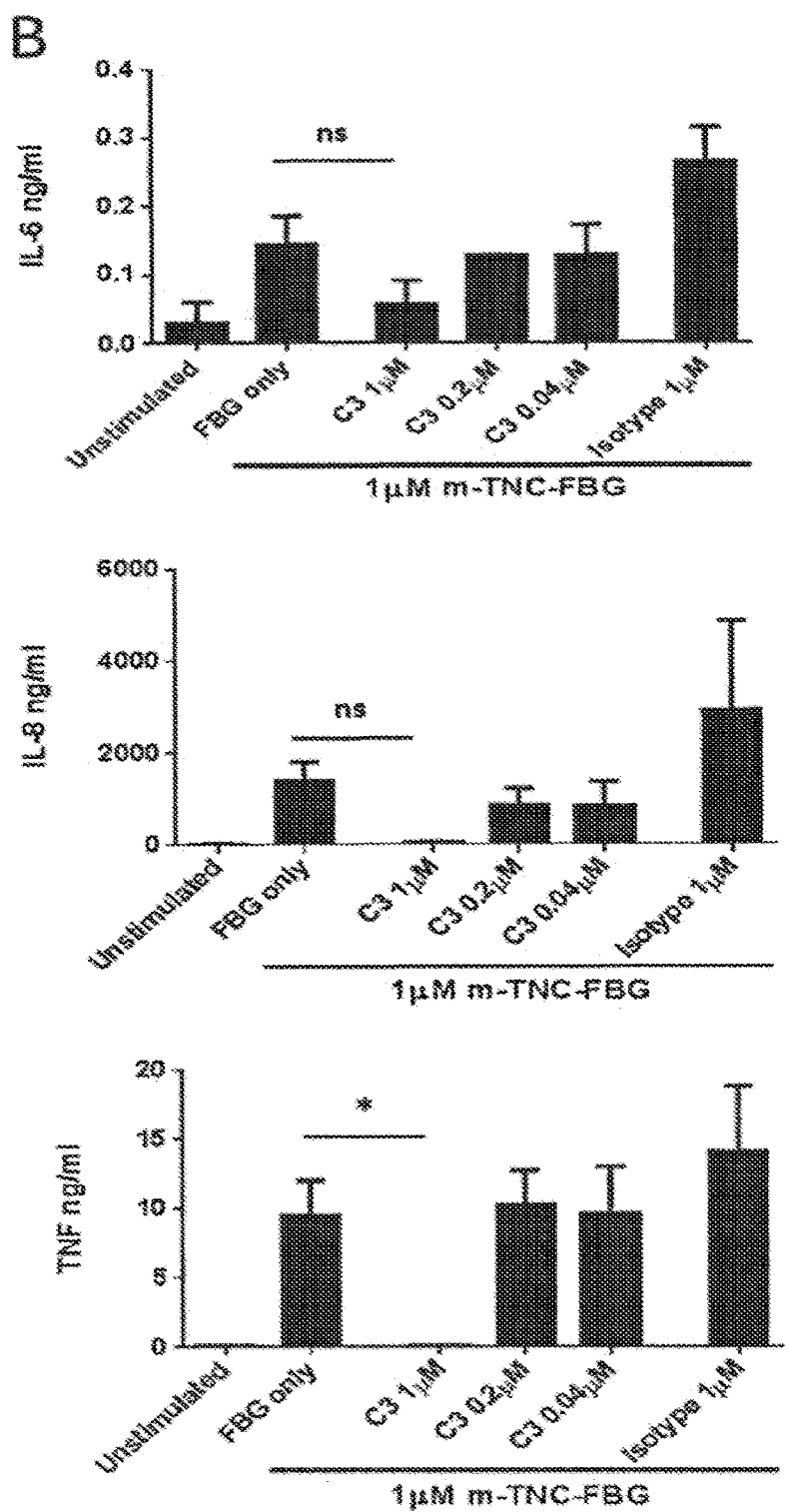
Figure 17C:
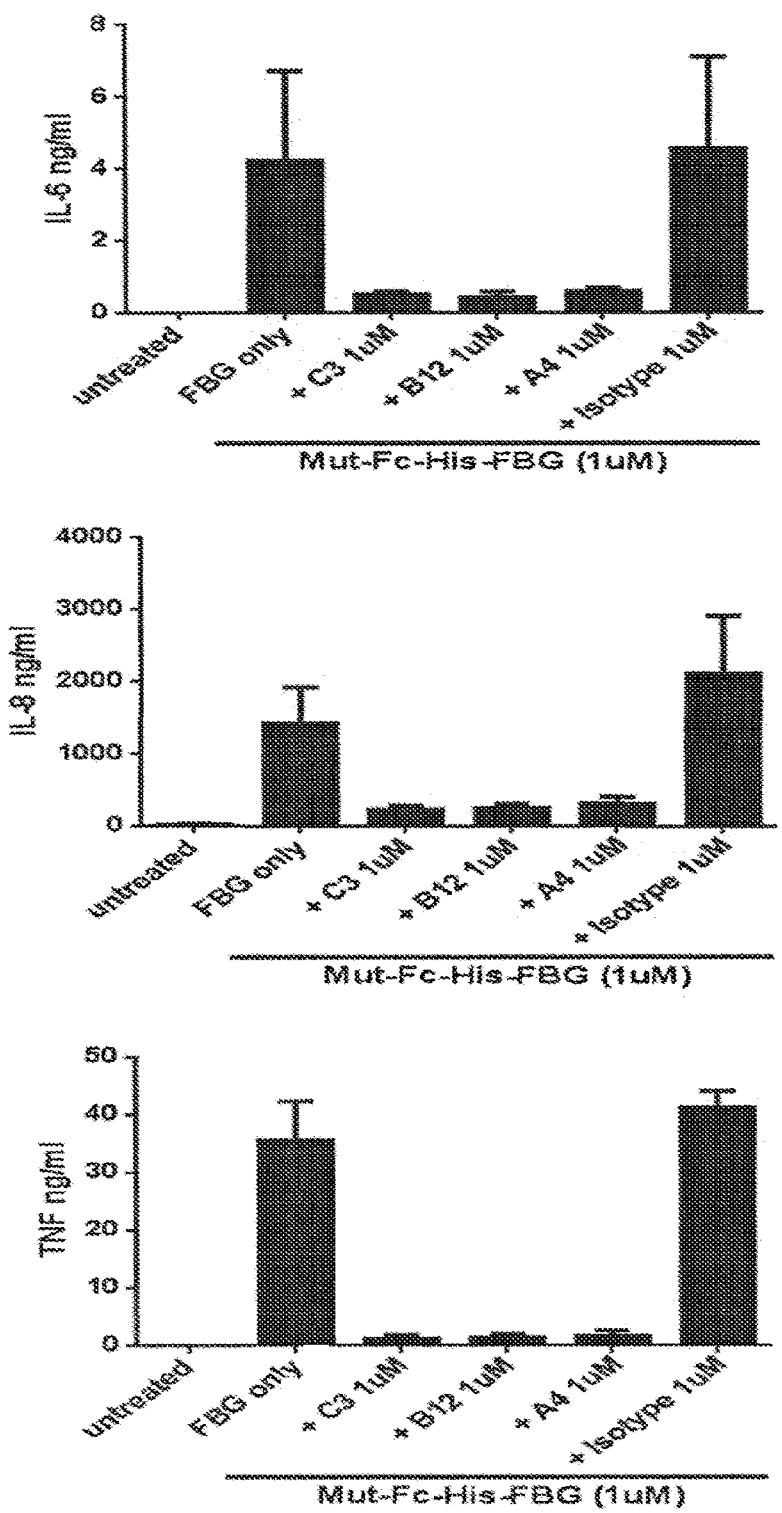

FIGS. 17A-17C. Monoclonal antibody C3 (165_13_C3) reduces the production of pro-inflammatory cytokines by primary human macrophages stimulated with human or mouse TNC-FBG, but not LPS.

(FIG. 17A) Recombinant Human tenascin-C FBG (1 uM) or LPS (Enzo) (1 ng/ml) was pre-incubated for 30 min at RT with MAb C3 (1, 0.2, and 0.04 uM) or isotype control MAb (1 uM) before being added in triplicate to Human M2 macrophage cultures. After 24 h supernatants were taken and subjected to IL-8, IL-6 and TNF cytokine ELISA (BD Biosciences). n=3; (FIG. 17B) Recombinant Murine tenascin-C FBG (1 uM) was pre-incubated for 30 min at RT with MAb C3 (1, 0.2 and 0.04 uM) or isotype control MAb (1 uM) before being added in triplicate to Human M2 macrophage cultures. After 24 h supernatants were taken and subjected to cytokine ELISA. n=3 or over, mean and SEM shown; (FIG. 17C) A protein where the Fc portion is mutated to be inactive (Fc-Mut-His-FBG) was used. Other promising anti-TNC-FBG antibodies, B12 and A4 were also tested in this system. Fc-Mut-His-FBG (1 uM) and C3, 160_01_A4 or B12 (1 uM) were pre-incubated for 30 min at RT before being added to human M2 macrophage cultures. After 24 h supernatants were taken and subjected to cytokine ELISA. n=3, mean and SEM shown.

Figure 18A:
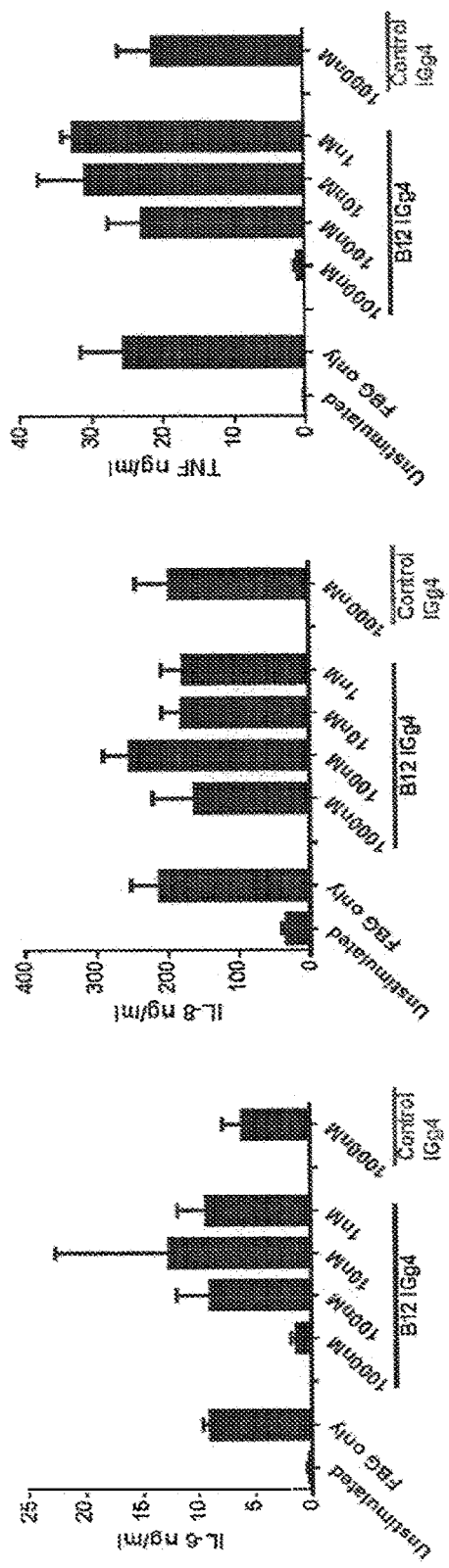

FIG. 18A. Monoclonal antibody B12 reduces the production of pro-inflammatory cytokines by primary human macrophages stimulated with human TNC-FBG.

Recombinant Human tenascin-C FBG (1 uM) was pre-incubated with MAb B12 (1, 0.1, 0.01 or 0.001 uM) or isotype control MAb (1 uM) before being added in triplicate to Human M2 macrophage cultures. After 24 h supernatants were taken and subjected to cytokine ELISA.

Figure 18B:
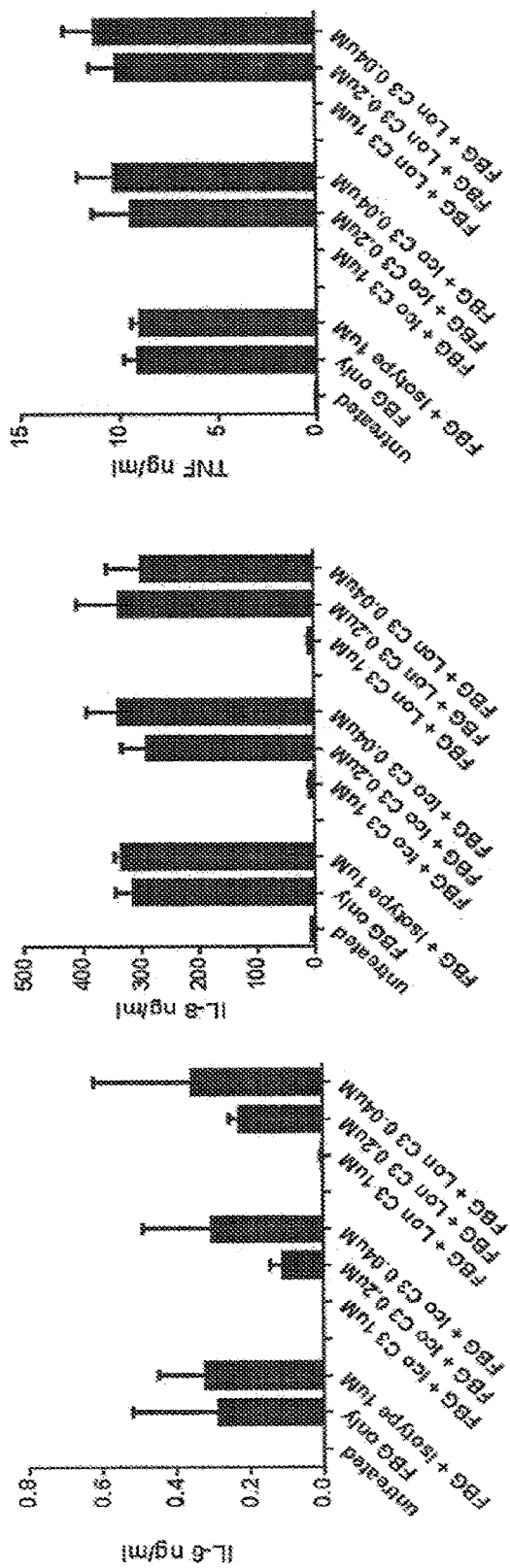

FIG. 18B. Monoclonal antibody C3 (165_13_C3) produced at laboratory and larger scale show the same level of efficacy in blockade of FBG-induced cytokine synthesis by primary human macrophages.

The potency of the antibody produced at larger scale was compared to that produced by at laboratory scale. Recombinant Human tenascin-C FBG (1 uM) was pre-incubated for 30 min at RT with MAb C3 (1, 0.2 and 0.04 uM) or isotype control MAb (1 uM) before being added in triplicate to Human M2 macrophage cultures. After 24 h supernatants were taken and subjected to cytokine ELISA. n=1, Ico=laboratory scale, Lon=larger scale.

Figure 19:
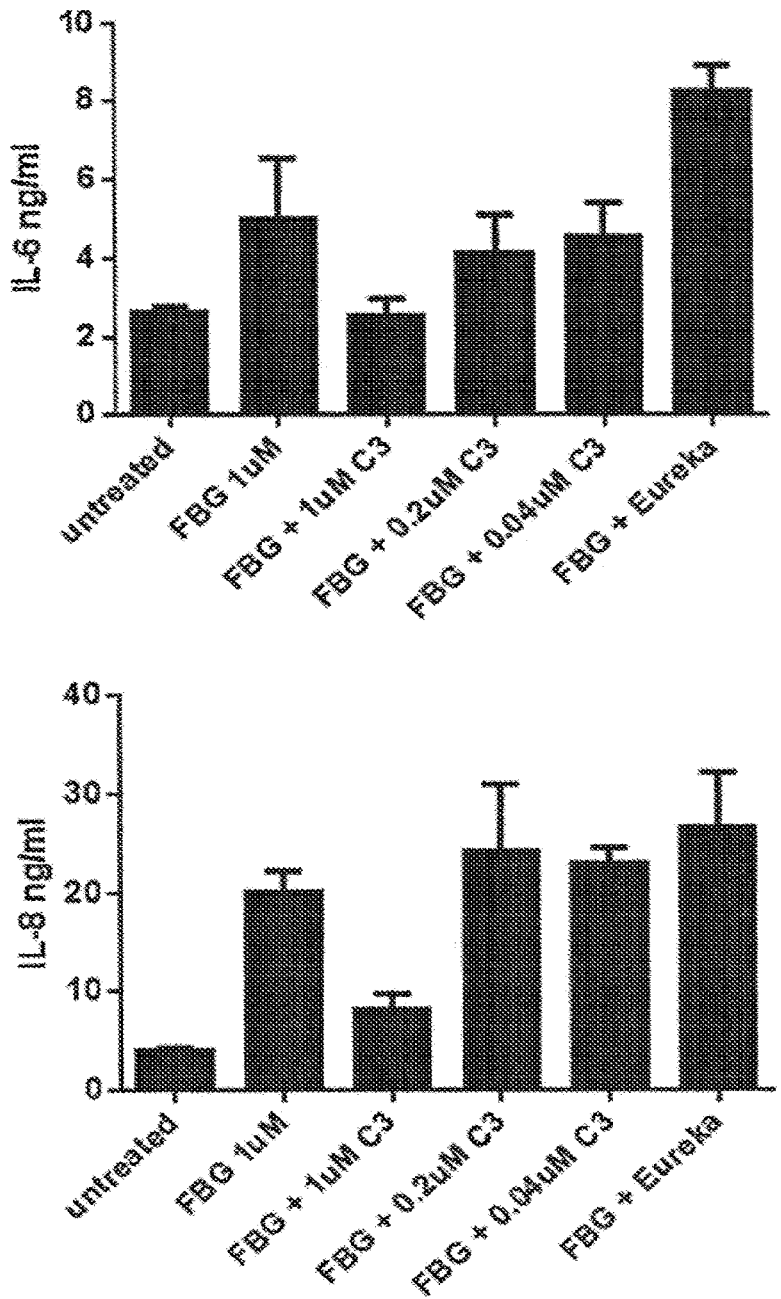

FIG. 19. Monoclonal antibody C3 (165_13_C3) reduces the production of pro-inflammatory cytokines by RA synovial fibroblasts stimulated with human TNC-FBG.

Recombinant Human tenascin-C FBG (1 uM) was pre-incubated for 30 min at RT with MAb C3 or isotype control MAb before being added in triplicate to Human synovial fibroblast cultures from RA patients. After 24 h supernatants were taken and subjected to cytokine ELISA. n=1, mean and SEM shown FIG. 20. Levels of Tenascin-C in rat CIA model.

TNC levels in synovial fluid from a rat model of collagen induced arthritis. The amount of TNC measured is shown plotted against the corresponding clinical score for each paw.

Figure 21:
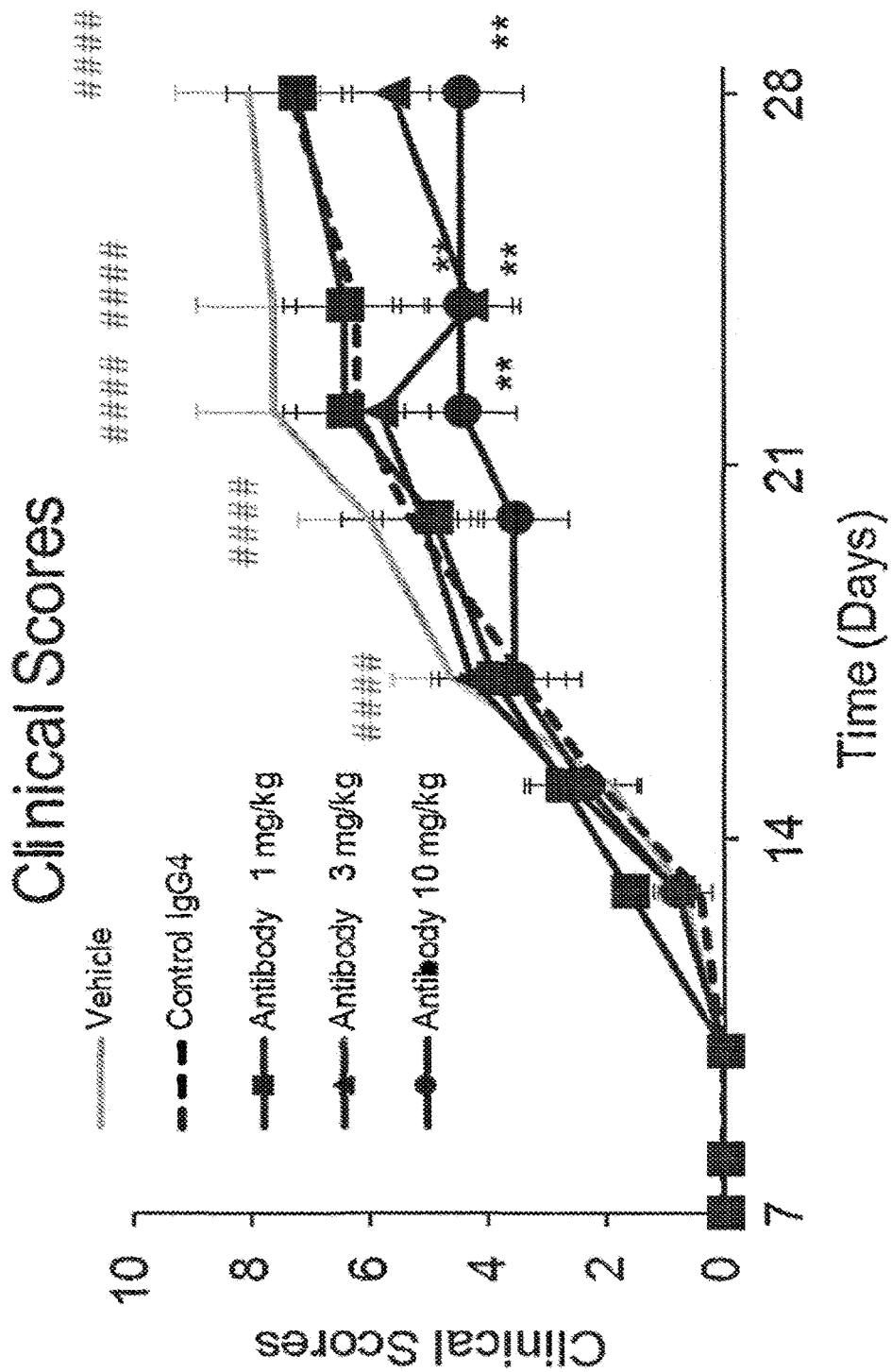

FIG. 21. Clinical scores from evaluation of C3 (165_13_C3) antibody in a rat model of collagen-induced arthritis.

Vehicle versus 1 mg/kg, 3 mg/kg and 10 mg/kg C3 antibody. Data are presented as Mean±SEM. Statistical significances: #### p<0.0001 when compared to Day 7, ** p<0.01 when compared to the vehicle-treated group.

Figure 22:
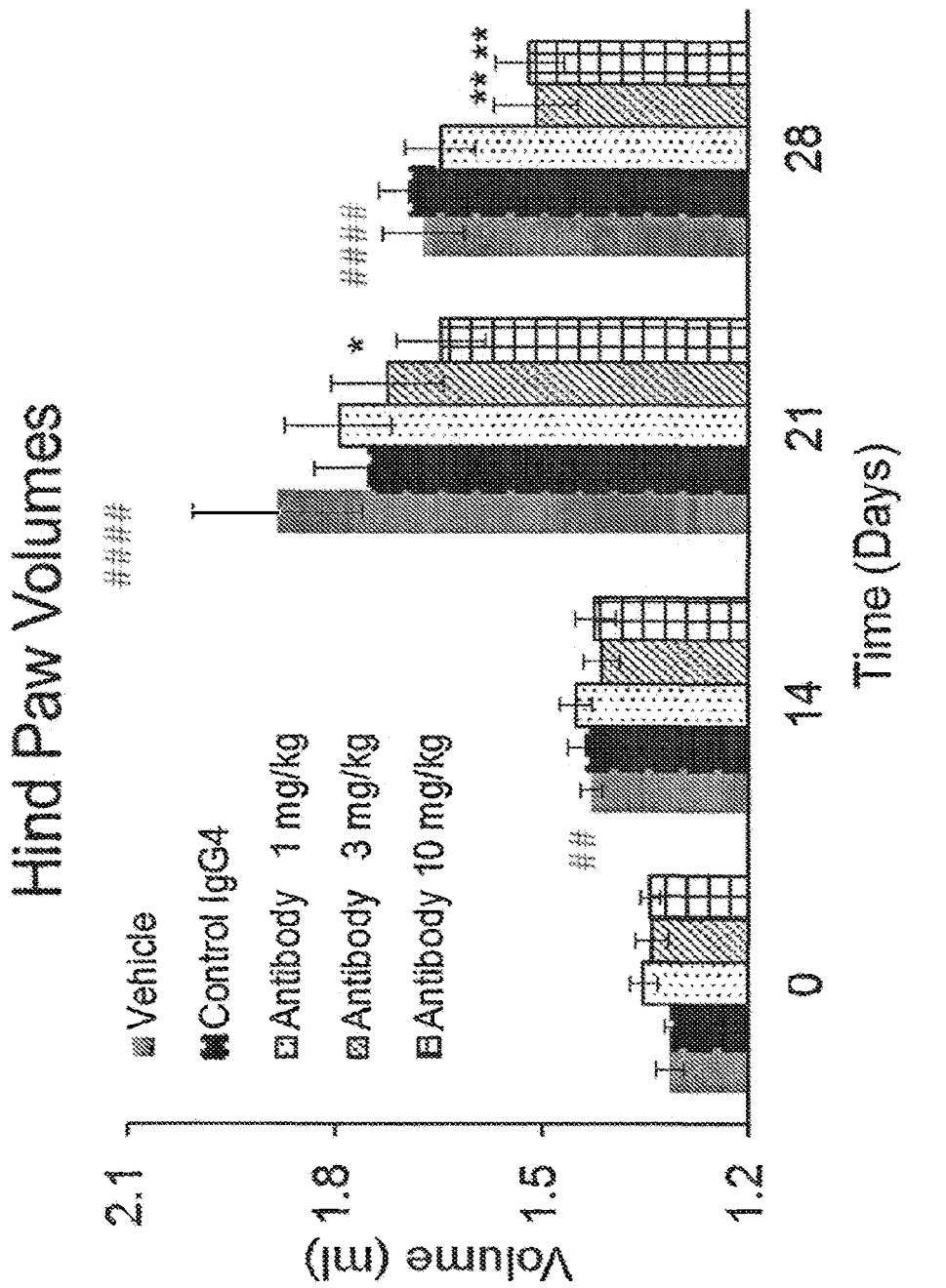

FIG. 22: Hind paw volumes from evaluation of C3 (165_13_C3) antibody in a rat model of collagen-induced arthritis.

Vehicle versus 1 mg/kg, 3 mg/kg and 10 mg/kg C3 antibody. Data are presented as Mean±SEM. Statistical significances: ## p<0.01 and #### p<0.0001 when compared to Day 0, * p<0.05 and ** p<0.01 when compared to the vehicle-treated group.

FIG. 23. Primers used for antigen cloning: human FGB-X forward primer minus 2561 (SEQ ID NO: 149), human FBG-X forward primer plus 2565 (SEQ ID NO: 150), mouse FBG-X forward primer minus 2561 (SEQ ID NO: 151), mouse FBG-X forward primer plus 2566 (SEQ ID NO: 152), human X-FBG forward primer minus 2567C (SEQ ID NO: 153), human X-FBG forward primer plus 2567 (SEQ ID NO: 154), mouse X-FBG forward primer minus 2569C (SEQ ID NO: 155), mouse X-FBG forward primer primer plus 2568C (SEQ ID NO: 156), BamHI-His6-HindIII forward primer 2574 (SEQ ID NO: 157), human His-FBG forward primer plus 2580 (SEQ ID NO: 158), mouse His-FBG forward primer plus 2580 (SEQ ID NO: 159), human FBG-X reverse primer minus 2562 (SEQ ID NO: 160), human FBG-X reverse primer plus 2562 (SEQ ID NO: 161), mouse FBG-X reverse primer minus 2562 (SEQ ID NO: 162), mouse FBG-X reverse primer plus 2562 (SEQ ID NO: 163), human X-FBG reverse primer minus 2570 (SEQ ID NO: 164), human X-FBG reverse primer plus 2570 (SEQ ID NO: 165), mouse X-FBG reverse primer minus 2571 (SEQ ID NO: 166), mouse X-FBG reverse primer plus 2571 (SEQ ID NO: 167), BamHI-His6-HindIII reverse primer 2575 (SEQ ID NO: 168), human His-FBG reverse primer plus 2570 (SEQ ID NO: 169), mouse His-FBG reverse primer plus 2571 (SEQ ID NO: 170). This table details the primers used to generate expression constructs for use in antigen cloning.

EXAMPLE 1—GENERATION OF PURIFIED TENASCIN-C FBG AS ANTIGEN AND ASSAY REAGENTS

Purified soluble proteins containing the FBG domain of tenascin-C (TNC FBG) were generated for use as antigens in antibody selections and as reagents in subsequent screening and characterisation assays. To enable selection strategies for isolation of antibodies that bind tenascin-C of multiple mammalian species, a range of DNA expression constructs were synthesised, which incorporated the TNC FBG domain of either human [SEQ ID NO: 92], mouse [SEQ ID NO: 93], rat [SEQ ID NO: 94] or dog [SEQ ID NO: 95]. A human tenascin-R FBG [SEQ ID NO: 96] construct was also prepared for identification of antibodies that displayed unwanted binding to this homologue. Constructs were produced as 6His-tagged proteins with either a rat CD4 or human IgG1 Fc tag coupled to either a C- or N-terminal FBG domain as described below.

Protein Expression Constructs

All synthetic DNA constructs for antigen expression were synthesised and sequence confirmed by Genscript (Piscataway, USA). FBG domains were cloned into the mammalian expression vectors pBIOCAM4 or BIOCAMS, which fuse the expressed domains with either a rat Cd4 (domains 3 and 4) tag (Chapple et al, 2006) or a human IgG1 Fc tag (Falk et al, 2012) respectively. The vectors were modified from the pCMV/myc/ER plasmid (Invitrogen) (Falk et al, 2012), which contains an endoplasmic reticulum (ER) signal sequence derived from the mouse VH chain, for secretion of expressed proteins. For all constructs which resulted in an N-terminal FBG (e.g. FBG-Fc-His or FBG-rCd4-His) the digested PCR products were ligated with NcoI/NotI cut pBIOCAM4 or pBIOCAM5 vectors. For all constructs which resulted in a C-terminal FBG (e.g. Fc-His-FBG or rCd4-His-FBG), digested PCR products were ligated with BamHI/HindIII cut pBIOCAM4 or pBIOCAM5 vectors. The primers used to amplify the FBG domains are listed in FIG. 25. All constructs were sequence confirmed. To facilitate ELISA screening, an insert encoding a His-tag (primers 2574 and 2575) was cloned between the BamHI and HindIII sites (replacing the His-FLAG tag) for the expression plasmid with a FBG-X (N-terminal FBG) fusion. Full length tenascin C was cloned directly from the Genscript pUC57 plasmid by digestion with BstXI and BamHI and cloned into the BstXI/BamHI cut expression vector pFBG-Fc-His6. To create His-FBG constructs, primers were designed to PCR from an rCd4-His-FBG expression plasmid and the PCR product, encoding His-FBG, was digested with XhoI and HindIII and cloned into the XhoI/HindIII digested pBIOCAM5.

Protein Expression and Cell Culture

Transfection quality plasmid DNA was prepared using the Machery Nagel Nucleobond Xtra Midi kit (740410.50, Fisher Scientific, UK). HEK293F suspension cells and Freestyle media, for antigen and antibody expression, and RPMI media were from Life Technologies (Paisley, UK). Transfection of HEK293F cells was carried out as described previously (Chapple et al, 2006).

Protein Purification and QC

Protein affinity purification employed either Ni-NTA agarose or immobilised recombinant protein A resin.

For purification of His-tagged proteins, culture supernatants were mixed with Ni-NTA agarose (1018240, Qiagen, Crawley, UK) for 1 h and the resin transferred to Proteus 1-step midi spin columns (Generon, UK) for centrifugation (200×g, 2 min). Unbound proteins were washed out with phosphate buffered saline (PBS) supplemented with 20 mM imidazole (pH 8). Bound proteins were eluted in fractions through addition of 300 mM imidazole in PBS (pH 8) and column centrifugation (200×g, 2 min). Pooled fractions containing eluted protein were placed in Gebaflex Midi dialysis tubes (Generon D010; molecular weight cut-off 3.5 kDa) and dialysed against PBS.

Fc-tagged proteins and antibodies expressed as human IgG4 were purified using protein A sepharose (PC-A25, Generon, Maidenhead, UK). Culture supernatants were clarified by centrifugation (2500×g, 15 min) and mixed with protein A sepharose overnight at 4° C. before transfer of the resin to Proteus 1-step midi spin columns (Generon, UK). Columns were centrifuged (200×g, 2 min) and washed with PBS to remove unbound protein. Fc-tagged or IgG4 proteins were eluted in fractions from the protein A with 0.2 M glycine (pH 2.8) into Tris-HCl (pH 8) by centrifugation (200×g, 2 min). Eluted fractions were pooled and dialysed against PBS in Gebaflex Maxi dialysis tubes (Generon D045; molecular weight cut-off 8 kDa).

Proteins were analysed for purity and concentration by SDS-PAGE (4-12% gel) and spectrophotometry (OD280 using theoretical extinction coefficient). Where purified proteins were used in cell-based assays the endotoxin content was first determined by limulus amoebocyte lysate chromogenic endotoxin assay (Pierce). Proteins were not used if endotoxin levels exceeded 1 endotoxin unit per milligram (i.e. 1 EU/mg).

EXAMPLE 2—ISOLATION OF PRIMARY ANTI-FBG ANTIBODIES

Antibody Phage Display

Antibodies against tenascin-C FBG domain were isolated using the Iontas Ltd proprietary human antibody phage display library, which was constructed using DNA isolated from 43 human lymphocyte donors. Selections, phage rescues and subcloning into pSANG10 (Martin et al, 2006) were all performed as described previously (Schofield et al, 2007) using techniques that are well known in the art.

Two rounds of panning selections were performed on immobilised TNC FBG fused to human IgG1 Fc or rCd4 at either the N terminus of the fusion partner (e.g. FBG-Fc, FBG-rCd4) or at the C terminus (Fc-FBG, rCd4-FBG). Phage antibody libraries containing either kappa (κ) or lambda (λ) variable light chains ($V_L$) were panned separately to facilitate later sub-cloning to Fab expression vectors containing either constant light ($C_L$) kappa (κ) or lambda (λ) chains.

Polyclonal phage populations were prepared from the selected populations and were tested in ELISA (polyclonal phage ELISA) using ELISA plates coated with TNC FBG antigen or appropriate fusion partner (Fc or rCd4). After incubation with phage, plates were washed, and bound phage detected using peroxidase-conjugated anti-M13 antibodies. FIG. 3 shows enrichment of antigen-specific binders between rounds 1 and 2 of selection and a greater proportion of FBG binders compared to anti-Fc or -rCd4 phage in the round 2 output populations, indicating that the selections were successful.

Confirmation of scFv Binding to Antigen and Cross-Reactivity Assay by ELISA

Round 2 selection outputs were expressed as individual scFv clones to confirm antigen recognition in ELISA binding assays. Output populations were sub-cloned into the bacterial expression vector pSANG10 (Martin et al, 2006), transformed into E. coli BL21 (DE3), and individual transformants were induced in 96-well plates as described previously (Schofield et al, 2007). *E. coli* supernatants were collected and assayed for binding of scFv to TNC FBG using DELFIA-based ELISA, using europium-labelled anti-FLAG detection antibodies. Results for initial ELISAs are summarised in Table 1.

TABLE 1

Monoclonal scFv ELISA. Values indicate number of clones binding to the relevant immobilised selection antigen.

| Selection (ID) | No. screened | Tag binders | FBG Binders ELISA Signal (Fluorescence Units; FU) | | |
|---|---|---|---|---|---|
| | | | ≥1,000 | ≥10,000 | ≥100,000 |
| λ FBG-rCd4 (145) | 95 | 0 | 0 | 0 | 0 |
| λ FBG-Fc (146) | 95 | 3 | 0 | 0 | 0 |
| λ rCd4-FBG (147) | 95 | 0 | 14 | 4 | 0 |
| λ Fc-FBG (148) | 95 | 1 | 13 | 5 | 1 |
| κ FBG-rCd4 (150) | 95 | 0 | 20 | 8 | 1 |
| κ FBG-Fc (151) | 95 | 0 | 2 | 1 | 0 |
| κ rCd4-FBG (152) | 95 | 8 | 12 | 4 | 0 |
| κ Fc-FBG (153) | 95 | 8 | 10 | 2 | 0 |
| λ + κ FBG-rCd4, Fc | 95 | 0 | 6 | 3 | 1 |
| λ + κ rCD4-FBG, Fc | 95 | 0 | 2 | 1 | 0 |
| Total | | | 79 | 28 | 3 |

The most successful selections with the A library were based on panning against the antigens rCd4-FBG and Fc-FBG (selections 147 and 148). For the K library, the most successful selections were obtained with the antigens FBG-rCd4 (150), rCd4-FBG (152) and Fc-FBG (153). The 79 positive clones from this ELISA screen were selected for further analysis.

Cross-reactivity ELISA showed that $^{67}/_{79}$ (85%) of anti-human FBG scFv were cross-reactive to mouse TNC FBG. DNA sequence analysis of the anti-FBG scFv indicated excellent sequence diversity. For example, selections 147 and 148 from the $V_L$ λ library contained 92% unique variable heavy ($V_H$) complementarity determining region 3 (CDR3) sequences, and selections 150, 152 and 153 from the $V_L$ κ library contained 67%, 91% and 100% unique variable $V_H$ CDR3 sequences, respectively.

A further 1425 clones isolated from the most effective selections were screened by ELISA and this resulted in the identification of an additional 401 scFv with FBG-binding specificity (Table 2). These clones, together with the 79 scFv identified in initial ELISAs were chosen for further evaluation.

TABLE 2

Focused monoclonal scFv ELISA of the most effective selection outputs.

| Selection (ID) | No. screened | Hits (≥5,000 FU) | Tag binders | FBG binders |
|---|---|---|---|---|
| λ rCd4-FBG (147) | 285 | 66 | 0 | 66 |
| λ Fc-FBG (148) | 285 | 60 | 0 | 60 |
| κ FBG-rCd4 (150) | 285 | 86 | 0 | 86 |
| κ rCd4-FBG (152) | 285 | 144 | 2 | 142 |
| κ Fc-FBG (153) | 285 | 94 | 47 | 47 |
| Total | 1425 | 450 | 49 | 401 |

The 1425 clones were further tested in a specificity ELISA in which each scFv was tested for binding to human Tenascin R FBG and also to human, mouse, rat and dog TNC FBG. Clones were ranked according to the ELISA signal obtained for binding to Tenascin C divided by the signal for Tenascin R FBG binding. The top 250 clones with a ratio above 50 were taken for subcloning and further analysis.

EXAMPLE 3—SCREENING OF PRIMARY ANTI-FBG ANTIBODIES IN A FUNCTIONAL ASSAY

Anti-FBG scFv were reformatted either as bivalent scFv-Fc or as monomeric Fabs for evaluation of their activity as inhibitors of FBG-evoked signalling in a whole cell assay system.

The top 50 anti-FBG scFv, ranked by primary ELISA signal, for each of the selections 147, 148, 150, 152 and 153 were sub-cloned into the mammalian expression plasmid pBIOCAM5 (Falk et al, 2012) as individual selection populations and expressed by transient transfection in HEK293F cells (Chapple et al, 2006). For Fab expression, pooled A or K scFv variable heavy ($V_H$) and variable light ($V_L$) inserts were cloned into a dual promoter Fab expression vector (pFab-dual-κ or pFab-dual-λ, depending on the light chain germ-line) using a proprietary Iontas Ltd protocol. Culture supernatants were screened for activity in the THP-1 cell assay and selected scFV-Fc and Fab hits were affinity purified for re-assaying and confirmation of inhibitory activity.

THP1-Blue™ Reporter Cell Assay

Tenascin-C has been shown to elicit the generation of cytokines in inflammatory cells and fibroblasts by interaction of the FBG domain with cellular TLR4 (Midwood et al, 2009). The receptor signalling cascade leading to generation of inflammatory cytokines such as TNFa, IL-8 and IL-6 involves activation of the transcription factor NF-κB. This process can be studied in 'reporter' cell lines modified to respond to NF-κB activation with generation of an easily measured protein signal. The THP1-Blue™ reporter cell line (InvivoGen; Toulouse, France) is derived from the human THP-1 monocyte cell line and stably expresses an NF-κB-inducible secreted alkaline phosphatase (SEAP) reporter construct. These cells also constitutively express cell surface TLR4, which enables the signalling activity of TNC FBG fusion proteins to be readily measured using colorimetric or fluorimetric quantitation of SEAP in culture supernatants using medium- to high-throughput assay methods.

Activity at low FBG concentrations is critical to the success of any screening assay; if the concentrations of FBG required to produce a robust increase in the reporter protein are too high then the expression levels and concentrations of scFv, Fc-ScFv or Fab constructs required to fully inhibit any such signal would be unacceptable for a screen. Fc-FBG produces a robust SEAP signal at low nM levels in this cell assay (CD4-FBG did not produce a response in this concentration range).

THP1-Blue™ cells were cultured and passaged in supplemented RPMI media according to supplier's protocols (http://www.invivogen.com/PDF/THP1_Blue_NF_kB_TDS.pdf), except that cells were grown in ultra-low attachment T75 flasks. For assays, THP1-Blue™ cells were added to 96-well tissue culture plates (100,000 cells/well) containing Fc-FBG (3 or 10 nM) in RPMI medium in a total volume of 170 μl. Culture supernatants containing expressed scFv-Fc or Fab, or affinity purified antibody in PBS, was added in a volume of 30 μl and cells were incubated for 18 h at 37° C. Supernatants were harvested and assayed for either SEAP using the Attophos AP fluorimetric quantitation system (S1000; Promega) or IL-8 content using the DuoSet ELISA development system (DY208; R&D Systems, UK) according to the supplier's instructions. Data were plotted and curves fitted using Prism software (GraphPad).

Screening of anti-FBG antibodies as HEK293F culture supernatants highlighted putative inhibitors of Fc-His-FBG evoked signalling in THP1-Blue™ cells of which 9 were confirmed when re-assayed as purified scFv-Fc (FIG. 4A) or Fab (FIG. 4B). Fc-His-FBG is key to having the potency assays work. Monomeric FBG does not elicit any cytokine response in THP-1Blue and human cells.

EXAMPLE 4—FUNCTIONAL CHARACTERISATION OF PRIMARY ANTI-FBG ANTIBODIES

ELISA Cross-Reactivity Assays

The panel of 9 human FBG signalling inhibitors identified in the THP1-Blue™ functional assay was evaluated by ELISA for cross-reactivity to rat, mouse, and dog FBG. Binding to the human tenascin-R FBG homologue was also determined. Assay wells were coated with human, rat, mouse, and dog TNC FBG-rCD4, or human TNR FBG-rCd4 fusion proteins and binding of Fabs was detected using anti-kappa or anti-lambda mAb followed by Europium-conjugated anti-mouse mAb. ELISA results revealed that 4 Fabs displayed good cross-reactivity to other mammalian homologues of human TNC FBG, with lower apparent binding to human TNR FBG (FIG. 5). These were:
   Fab 2A5 (VH SEQ ID NO: 4; VL SEQ ID NO: 8),
   Fab B12 (VH SEQ ID NO: 12; VL SEQ ID NO: 15),
   Fab D8 (VH SEQ ID NO: 19; VL SEQ ID NO: 21), and
   Fab F3 (VH SEQ ID NO: 25; VL SEQ ID NO: 29).

Fabs that showed poor species cross-reactivity to TNC-FBG were not considered further.

Determination of Binding Affinity by Surface Plasmon Resonance

The affinity and association and dissociation kinetics of selected Fabs for binding to the human, rat and mouse TNC FBG, and human TNR FBG were measured by surface plasmon resonance (SPR) at 25° C. Experiments were performed using a BIAcore T100 instrument with CM5 sensor chip according to the protocol provided with the Human Fab Capture Kit (GE, 28-9583-25). Varying concentrations of rCd4-FBG were injected into a flow-cell with immobilised Fab and a reference flow-cell. After reference signal subtraction, the data was fitted to a global 1:1 fit using theT100 BIAevaluation software (FIGS. 6A-6D).

The calculated kinetic constants are shown in Table 3. The rank order of affinity of Fabs for human TNC FBG was B12 (110 pM)>D8 (8.49 nM)>2A5 (11.4 nM)>F3 (27.4 nM). All Fabs displayed low nanomolar affinity for rodent TNC FBG, and affinities for human TNR FBG were typically greater than 60-fold lower than human TNR FBG.

Inhibitory Potency Assays

The potency of purified Fabs for neutralisation of huFc-His-FBG activity was determined in the THP1-Blue™ assay, using measures of TLR4-mediated secreted alkaline phosphatase and IL-8 cytokine production. Assays were conducted as described in Example 2, except that purified Fabs were added to assay wells at a range of concentrations (0.3-100 nM) to enable calculation of $IC_{50}$ values using Prism software (GraphPad).

TABLE 3

Anti-FBG Fab binding kinetic data determined by surface plasmon resonance (SPR) spectroscopy. $K_D$, equilibrium dissociation constant; $K_a$, association constant; $K_d$, dissociation constant

| Fab | FBG | $K_D$ (nM) | $K_a$ $(M^{-1}s^{-1}) \times 10^5$ | $K_d$ $(s^{-1}) \times 10^{-4}$ | Steady State |
|---|---|---|---|---|---|
| 2A5 | Hu TNC | 11.4 | 4.96 | 56.3 | N/A |
|  | Mu TNC | 78.6 | 4.41 | 346.5 | N/A |
|  | Hu TNR | 757 | 2.49 | 1888.4 | 706 |
| B12 | Hu TNC | 0.111 | 26.62 | 3.0 | N/A |
|  | Mu TNC | 13 | 52.15 | 675.5 | 18.7 |
|  | Rat TNC | 7.9 | 94.59 | 747.9 | N/A |
|  | Hu TNR | 33.9 | 13.96 | 472.5 | 36.1 |
| D8 | Hu TNC | 8.49 | 15.41 | 130.9 | N/A |
|  | Mu TNC | 48.4 | 14.78 | 716.1 | 41.2 |
|  | Hu TNR | 1026 | 5.55 | 5696.0 | 913 |
| F3 | Hu TNC | 27.4 | 1.26 | 34.6 | N/A |
|  | Mu TNC | 70.6 | 0.91 | 64.2 | N/A |
|  | Hu TNR | Off rate too rapid to determine | | | 1808 |

All antibodies displayed concentration-related inhibition of Fc-His-HuFBG-evoked to alkaline phosphatase (FIG. 7) and IL-8 production (FIG. 8). The rank order of potency ($IC_{50}$) for inhibition of alkaline phosphatase inhibition by anti-FBG Fabs was B12 (1.7 nM)>D8 (7.2 nM)>F3 (8.4 nM)>2A5 (20.6 nM), and the potency ($IC_{50}$) ranking was similar for inhibition of IL-8 release: B12 (6.9 nM)>F3 (13.8 nM)>D8 (14.9 nM)>2A5 (28.5 nM).

EXAMPLE 5—GENERATION AND ISOLATION OF OPTIMISED ANTIBODIES TO HUTNC FBG DOMAIN

Affinity Maturation by Targeted CDR Mutagenesis

Anti-FBG antibodies 2A5, B12, and F3 were selected for affinity maturation. Targeted CDR mutagenesis was carried out by randomising VH and VL CDR3 residues in blocks of 6 amino acids using Kunkel mutagenesis (Fellouse and Sidhu, 2007; Kunkel et al., 1987; Sidhu and Weiss, 2004). Due to the longer VH CDR3s (10-16 residues) for the given clones randomisation was done in three overlapping blocks and the VL CDR3s (9 residues) were randomised in two overlapping blocks (FIG. 9A). Randomisations were carried out using NNS (N=A/G/C/T and S=G/C) degenerate primers that could encode any of the 20 amino acids (and only a single amber stop codon) at a given position from 32 codon combinations. Oligonucleotides used in the mutagenesis are provided in FIG. 9B. Thus, 15 libraries (3 libraries per VH and 2 libraries per VL for 3 antibodies) were created initially and all libraries except for F3 VL 3.1 and F3 VL 3.2 were large enough (Table 4) to cover the theoretical diversity arising from randomising 6 residues with an NNS primer ($32^6=1.1\times10^9$). The CDR3 libraries were combined during the rescue process and this resulted in a combined mutant VH library and a combined mutant VL library for each of the parental antibody clones, giving 6 libraries in total.

TABLE 4

Estimated sizes of the CDR3 randomised libraries

| Library | Sub library | Size | Combined size |
|---|---|---|---|
| 2A5 VH | 2A5 VH 3.1 | $2.0 \times 10^9$ | $7.2 \times 10^9$ |
|  | 2A5 VH 3.2 | $2.6 \times 10^9$ |  |
|  | 2A5 VH 3.3 | $2.6 \times 10^9$ |  |

TABLE 4-continued

Estimated sizes of the CDR3 randomised libraries

| Library | Sub library | Size | Combined size |
|---|---|---|---|
| 2A5 VL | 2A5 VL 3.1 | $4.0 \times 10^9$ | $6.5 \times 10^9$ |
| | 2A5 VL 3.2 | $2.5 \times 10^9$ | |
| B12 VH | B12 VH 3.1 | $1.8 \times 10^9$ | $6.1 \times 10^9$ |
| | B12 VH 3.2 | $1.6 \times 10^9$ | |
| | B12 VH 3.3 | $1.7 \times 10^9$ | |
| B12 VL | B12 VL 3.1 | $2.6 \times 10^9$ | $7.7 \times 10^9$ |
| | B12 VL 3.2 | $5.1 \times 10^9$ | |
| F3 VH | F3 VH 3.1 | $6.0 \times 10^9$ | $1.6 \times 10^9$ |
| | F3 VH 3.2 | $4.6 \times 10^9$ | |
| | F3 VH 3.3 | $6.3 \times 10^9$ | |
| F3 VL | F3 VL 3.1 | $2.1 \times 10^9$ | $5.7 \times 10^9$ |
| | F3 VL 3.2 | $3.6 \times 10^9$ | |

High Stringency Phage Display Selections

Phage-antibody selections on streptavidin Dynabeads were performed as described previously (Dyson et al, 2011). Multiple rounds of solution-phase selections were carried out on biotinylated rCd4-His-FBG to enrich for affinity improved clones. The optimum antigen concentrations for each round were determined empirically by selecting against a range of antigen concentrations and comparing the output numbers with a no-antigen control. The stringency of selection was increased by reducing the amount of antigen used in each round. No further rounds of selection were carried out after the selection window (the fold difference between phage titres from selection outputs and no antigen control) dropped below 10. Hence, three rounds of selection (FIG. 10A) were carried out on biotinylated human rCd4-His-FBG for all libraries except B12 which was subjected to a fourth round of selection due to the large selection windows observed at round 3. All libraries were subjected to deselection against streptavidin beads and tenascin-R (100 nM for rounds 1 to 3 and 1 nM for round 4) at each round of selection to avoid unwanted cross reactivity to streptavidin or tenascin-R. In addition, a hybrid selection strategy in which the human and mouse antigens were alternated between rounds of selection (FIG. 10B) was performed for the B12 randomised libraries only. The reason for performing this extra selection on the B12 libraries was the large difference in affinity observed for the B12 parental antibody binding to human and mouse rCd4-his-FBG. This difference was not as pronounced for the 2A5 (6.9-fold) or F3 (2.6-fold) parental antibodies. Furthermore, an additional round of selection was carried out to select for antibody clones with superior off-rates. In off-rate selections, phage were allowed to bind to the biotinylated antigen (1 nM in this case), and a large excess of non-biotinylated antigen (500 nM) was subsequently added to the reaction and incubated for 20 h or 40 h. The non-biotinylated antigen serves as a competitor and captures the phage antibodies that dissociate from the biotinylated antigen, i.e. only the antibodies with longer off-rates will be recovered at the end of the selection (Hawkins et al., 1992; Zahnd et al., 2010). The output phage titres for each round of selection together with calculated selection windows are shown in Tables 5a-c.

The selected populations were sub-cloned into the bacterial expression vector pSANG10 (Martin et al, 2006), transformed into *E. coli* BL21(DE3), and individual transformants picked (46 per selection) for ELISA and HTRF analyses in order to identify clones with improved binding to mouse FBG and human FBG respectively.

TABLE 5a

Selection output titres. Round 1 selections. Phage output titres were determined as described previously (Schofield et al, 2007)

| CDR3 randomised libraries | 10 nM Selection | 1 nM Selection | 0 nM Selection | Selection window for 10 nM selection | Selection window for 1 nM selection |
|---|---|---|---|---|---|
| 2A5 VH | $7 \times 10^7$ | $2.9 \times 10^7$ | $1 \times 10^5$ | 700 | 290 |
| 2A5 VL | $3 \times 10^7$ | $1.7 \times 10^7$ | $5 \times 10^4$ | 600 | 340 |
| B12 VH | $6 \times 10^7$ | $2.6 \times 10^7$ | $1 \times 10^5$ | 600 | 260 |
| B12 VL | $6 \times 10^7$ | $5 \times 10^7$ | $2 \times 10^5$ | 300 | 250 |
| F3 VH | $>1 \times 10^8$ | $8 \times 10^7$ | $2 \times 10^4$ | 5000 | 4000 |
| F3 VL | $5 \times 10^7$ | $1.2 \times 10^7$ | $9 \times 10^4$ | 555 | 133 |

TABLE 5b

Selection output titres. Round 2 selections. Phage output titres were determined as described previously (Schofield et al, 2007)

| CDR3 randomised libraries | 200 pM Selection | 50 pM Selection | 0 nM Selection | Selection window for 200 pM selection | Selection window for 50 pM selection |
|---|---|---|---|---|---|
| 2A5 VH | $7 \times 10^7$ | $3.8 \times 10^7$ | $5 \times 10^4$ | 1400 | 760 |
| 2A5 VL | $1.4 \times 10^7$ | $6 \times 10^6$ | $1 \times 10^4$ | 1400 | 600 |
| B12 VH | $1 \times 10^8$ | $6.75 \times 10^7$ | $2 \times 10^4$ | 5000 | 3375 |
| B12 VL | $1.2 \times 10^8$ | $8.1 \times 10^7$ | $4 \times 10^4$ | 3000 | 2025 |
| F3 VH | $1.1 \times 10^8$ | $9.5 \times 10^7$ | $4 \times 10^4$ | 2750 | 2375 |
| F3 VL | $7 \times 10^7$ | $1.2 \times 10^7$ | $1.2 \times 10^5$ | 583 | 100 |
| B12 VH on mu TNC FBG | $7 \times 10^6$ | | $2 \times 10^4$ | 350 | |
| B12 VL on mu TNC FBG | $7.5 \times 10^6$ | | $4 \times 10^4$ | 187 | |

TABLE 5c

Selection output titres. Round 3 selections. Phage output titres were determined as described previously (Schofield et al, 2007)

| CDR3 randomised libraries | 5 pM Selection | 1 pM Selection | 0 nM Selection | Selection window for 5 pM selection | Selection window for 1 pM selection |
|---|---|---|---|---|---|
| 2A5 VH | $6 \times 10^6$ | $1 \times 10^6$ | $<1 \times 10^5$ | 60 | 10 |
| 2A5 VL | $1.4 \times 10^6$ | $<1 \times 10^5$ | $2 \times 10^5$ | 7 | $<1$ |
| B12 VH | $1.5 \times 10^7$ | $4 \times 10^6$ | $<1 \times 10^5$ | $>150$ | $>40$ |
| B12 VL | $2.7 \times 10^7$ | $3.5 \times 10^6$ | $<1 \times 10^5$ | $>270$ | $>35$ |
| F3 VH | $3.5 \times 10^6$ | $4 \times 10^5$ | $<1 \times 10^5$ | $>35$ | $>4$ |
| F3 VL | $6 \times 10^6$ | $<1 \times 10^5$ | $2 \times 10^5$ | 3 | $<1$ |

| Hybrid selections on B12 libraries (Hu-mu-hu) | 20 pM Selection | 5 pM Selection | 0 pM Selection | Selection window for 20 pM selection | Selection window for 5 pM selection |
|---|---|---|---|---|---|
| B12 VH | $1 \times 10^8$ | $7.7 \times 10^6$ | $<1 \times 10^5$ | $>1000$ | $>77$ |
| B12 VL | $1.3 \times 10^8$ | $1.8 \times 10^7$ | $<1 \times 10^5$ | $>1300$ | $>78$ |

ELISA Screen

An anti-FLAG capture ELISA was performed to screen for clones that had an improved affinity for mouse FBG binding compared with the parental antibodies.

E. coli BL21 (DE3) clones harbouring scFv pSANG10 expression plasmids were induced in 96-well plates with auto-induction media as described previously (Schofield et al, 2007). E. coli supernatants were harvested for ELISA assays. ELISA used the DELFIA (dissociation enhanced lanthanide fluorescent immunoassay) system with Europium-labelled anti-FLAG antibody (Sigma, Aldrich, UK). Black immunosorb plates (Nunc) were coated overnight with anti-FLAG M2 antibody (Sigma, F3165, 5 µg/ml in PBS, 50 µl per well), in wells blocked by the addition of 2% milk powder, PBS (PBS-M, 300 µl per well). Plates were washed three times with PBS-T (PBS, 0.1% Tween-20) and three times with PBS followed by the addition of a 1:2 dilution of 96-well auto-induction culture supernatants containing expressed scFv in PBS-M (50 µl per well). The plates were incubated for 1 h, washed as above and biotinylated mouse or human rCd4-His-FBG (5 µg/ml in PBS-M, 50 µl) added to each well. Plates were incubated for a further 1 h, washed and Strepavidin-Eu added (Perkin Elmer, 1 µg/ml, PBS-M, 50 µl), incubated for 30 min, washed and DELFIA enhancement solution added (50 µl) and plates read on a Perkin Elmer Fusion plate reader (excitation=320 nm, emission 620 nm). The format of the assay is shown in FIG. 11.

In this assay differences in scFv expression level are normalised because the expression levels of scFv in auto-induction cultures saturate the anti-FLAG coated wells. Therefore, the signals obtained in the assay reflect the amount of biotinylated rCd4-His-FBG bound after washing, which will be a function of the off-rate of that clone for mouse or human FBG. ELISA screening of the selection output from the 2A5 and B12 sub-libraries revealed clones with significantly improved binding to mouse TNC FBG.

HTRF Screen

An HTRF-based competition assay was developed to screen for antibody variants with improved binding to human TNC FBG.

All samples and reagents were prepared in assay buffer (50 mM $NaPO_4$, 0.1% BSA, 0.4 M KF, pH 7.0) at 4× the stated concentration. 5 µl of each reagent was subsequently added to low volume 384-well assay plates (Greiner, 784075) to give a final reaction volume of 20 µl. IgG antibodies were labelled using the d2 labelling kit (CisBio, 62D2DPEA) as directed by the manufacturer. Streptavidin europium cryptate (CisBio, 610SAKLA, Lot#25C) was used at a final concentration of 1.8 ng active moiety (SA) per 20 µl reaction as recommended by the manufacturer. Biotinylated rCd4-His-FBG was prepared using EZ-link Sulfo-NHS-LC-Biotin reagent (Thermo Scientific, 21327) the extent of biotinylation was quantified using biotinylation fluorescence quantitation kit (Thermo Scientific, 46610). Where appropriate, supernatants containing scFv (prepared as described above for ELISA assays) were added to the 384-well assay plate at a final dilution of 1/20 (i.e. 1/5 dilution in assay buffer followed by addition of 5 µl diluted sample to the 20 µl FRET assay). The concentrations of d2-labelled 2A5 IgG and B12 IgG used for screening were 15 nM and 1.25 nM respectively. Unless otherwise stated, biotinylated rCd4-His-FBG (biotin:protein ratio=1.8:1) was present at either 2.2 nM (in assays using the 2A5 IgG antibody) or 1 nM (in experiments using B12 IgG). Samples were incubated for approximately 1 h at room temperature and the FRET signal was determined using a BMG Pherastar instrument: excitation=320 nm; emission=620 nm and 665 nm; integration start time=60 µs; integration time=500 µs; 100 flashes per well. For competition assays containing culture supernatant, biotinylated rCd4-His-FBG antigen was pre-incubated with streptavidin europium cryptate for 45 min prior to addition of reagents to the assay plate. All FRET signals are presented as $\Delta R$, where $R=(E665/E620\times104)$ and $\Delta R=(Rsample-Rbackground$ fluorescence).

Culture supernatants containing unlabelled scFv clones from affinity selected mutant libraries were tested for inhibition of the interaction between FBG and the fluorophore-labelled parental IgG antibody. When used to screen the 2A5 variants, this approach yielded a high proportion of clones with improved inhibition relative to the parent (92% of VH CDR3 variants and 79% of VL CDR3 variants). In order to distinguish between the clones that fully inhibited the FRET signal, 2A5 variants were subsequently screened for their ability to compete with B12 IgG. This was a more stringent screen given that the affinity of B12 for human FBG is approximately 100-fold stronger than that of 2A5 (dissociation constants for these interactions, determined by surface plasmon resonance at 25° C. were 0.11 nM and 15 nM, respectively). The relative ranking of clones exhibiting FRET signals within the useful range in both assays was broadly unchanged, indicating that they were competing for similar epitopes. Hence, all 2A5 and B12 scFv variants from affinity maturation selections were screened for their ability to inhibit the binding of B12 IgG molecules to human TNC FBG. The parental clones, expressed as scFvs in parallel with the affinity matured clones, were used as benchmarks (Table 6).

ScFv were sequenced and a panel of clones with unique VH or VL CDR3 sequences was selected for further study in human IgG4 format, based on their binding to mouse and human TNC FBG in the ELISA and HTRF assays, respectively. The chosen variants of antibody 2A5 displayed ≥10-fold improvement in binding to the mouse FBG and an inhibition of ≥90% (VH CDR3 variants) or ≥83% (VL CDR3 variants) in the HTRF assay.

TABLE 6

HTRF screen for clones with improved affinity for human rCD4-FBG.

| CDR3 Selection Library type | Total clones tested | % inhibition of FRET signal | | | | | | % inhibition by parent scFv | |
|---|---|---|---|---|---|---|---|---|---|
| | | 0-25% | 25-50% | 51-75% | 76-85% | 86-90% | 91-95% | ≥96% | 2A5 | B12 |
| 2A5 VH   1 pM | 46 | 3 | 4 | 4 | 15 | 13 | 7 | 0 | 29 | 90 |
| 2A5 VH Off-rate | 46 | 3 | 0 | 11 | 11 | 17 | 3 | 1 | 29 | 90 |
| 2A5 VL   5 pM | 46 | 3 | 2 | 7 | 19 | 14 | 1 | 0 | 21 | 83 |
| 2A5 VL Off-rate | 46 | 10 | 11 | 10 | 5 | 10 | 0 | 0 | 21 | 83 |
| B12 VH 100 fM | 46 | 6 | 2 | 3 | 8 | 5 | 6 | 16 | 19 | 86 |
| B12 VH Hybrid 5 pM | 46 | 3 | 3 | 5 | 5 | 3 | 9 | 18 | 19 | 86 |

Variants of antibody B12 showed ≥4-fold improvement for mouse FBG binding, and ≥91% inhibition of HTRF signal. In total, 31 clones fitting these criteria with unique CDR3 sequences were identified (Table 7).

TABLE 7

Heavy or light chain CDR3 sequences of clones identified with improved binding to mouse and human TNC FBG and chosen for conversion to human IgG format for further study.

| Library | Clone name | CDR sequence | |
|---|---|---|---|
| B12 VH | 165_13_B1 | VMSSMEDAFDI | SEQ ID NO: 30 |
| | 165_13_B6 | GQKGEGDTFDI | SEQ ID NO: 32 |
| | 165_13_D1 | GTRGEGDTFDI | SEQ ID NO: 34 |
| | 165_13_C3 | SYQSDEDAFDI | SEQ ID NO: 36 |
| | 165_13_D4 | GTVGEGDTFDI | SEQ ID NO: 38 |
| | 165_13_A4 | DKYPVLDTFDI | SEQ ID NO: 40 |
| | 165_13_B3 | ALARGHDTFDI | SEQ ID NO: 42 |
| | 165_13_E1 | DISAVMDVPQT | SEQ ID NO: 44 |
| | 180_11_F5 | VMRTGLDTFDI | SEQ ID NO: 46 |
| 2A5 VH | 160_01_E3 | QRYVWEALTY | SEQ ID NO: 48 |
| | 160_01_D6 | AQADPHLFTY | SEQ ID NO: 50 |
| | 160_01_H4 | GRFVWEALTY | SEQ ID NO: 52 |
| | 160_01_A4 | AQKETLGNAI | SEQ ID NO: 54 |
| | 160_01_F1 | AQSPWSGMTY | SEQ ID NO: 56 |
| | 160_01_G2 | YTLDNMALTY | SEQ ID NO: 58 |
| | 161_01_F6 (160_01_F6) | AQKENIANRH | SEQ ID NO: 60 |
| | 161_01_A12 | AQPTALANTY | SEQ ID NO: 62 |
| | 161_01_C09 | AQLPYLAQTY | SEQ ID NO: 64 |
| | 161_01_H10 | AQPVWAPGTY | SEQ ID NO: 66 |
| | 161_01_C11 | AQKEWLPDVT | SEQ ID NO: 68 |
| | 162_02_D3 | AQIHPLGLTY | SEQ ID NO: 70 |
| 2A5 VL | 162_02_C6 | QNQYAGPWT | SEQ ID NO: 72 |
| | 162_02_H5 | QNQYTGPVVT | SEQ ID NO: 74 |
| | 162_02_F3 | QNQYRGPVVT | SEQ ID NO: 76 |
| | 162_02_C1 | LHHYRAPVVT | SEQ ID NO: 78 |
| | 162_02_C2 | MHHYRAPVVT | SEQ ID NO: 80 |
| | 162_02_F4 | MHHYRSPVVT | SEQ ID NO: 82 |
| | 162_02_C3 | MQHYDGPWT | SEQ ID NO: 84 |
| | 162_02_E11 | LHHYRSPTWT | SEQ ID NO: 86 |
| | 162_02_E11 | LHHYRSPVVT | SEQ ID NO: 135 |
| | 163_02_A12 | LHHYREPVVT | SEQ ID NO: 88 |
| | 163_02_D11 | LHHYKSPVVT | SEQ ID NO: 90 |

These are heavy or light chain sequences of antibody clones that bind to human and mouse TNC FBG and thus have potential utility in the methods, uses, compositions and compounds of the present invention. For example, antibodies that bind TNF FBG having these CDR3 sequences may be useful in identifying, inhibiting the function of, detecting and purifying TNC or TNC FBG.

Conversion to IgG4 Format and Determination of Binding Kinetics

The 31 scFv of interest were sub-cloned into a human IgG4 expression vector for generation of antibodies as human IgG4 with a hinge-stabilising mutation (S241P; Angal et al, 1993). IgG4 antibodies were transiently expressed in HEK-293F cells and culture supernatants were screened using surface plasmon resonance spectroscopy for ranking of their off-rates for binding to human and mouse TNC FBG, and human TNR FBG. Briefly, surface plasmon resonance (SPR) experiments were performed using a BIAcore T100 instrument and followed the protocol according to the Human antibody capture kit protocol (GE, BR-1008-39). For off-rate screening, 10,000 response units (RU) of anti-human Fc IgG (GE, BR-1008-39) was immobilised on flow-cells (FC1 and FC2) of a Series 5 CM5 dextran sensor chip (BR-1005-30) using EDC/NHS cross-linking chemistry according to the amine coupling kit protocol (GE, BR-1000-50). Culture supernatants containing expressed IgG4 were diluted 1:2 with 2×PBS-T and injected into FC2 (flowrate 5 µl/min, 60 s contact time) to enable antibody capture at 25° C. Antibody capture levels ranged from 308 to 1975 RU depending on the expression level of the antibody in the supernatant. A fixed concentration of antigen (15 nM of human and mouse TNC rCd4-His-FBG and 100 nM of human TNR rCd4-His-FBG) was injected with a flow-path via FC 1 (reference flow cell) and FC 2 (antibody capture flow cell), with a flow rate of 30 µl/min, and the association and dissociation phases measured over 1 and 5 min time periods, respectively. Regeneration of the binding surface employed 3M MgCl$_2$ with 30 s contact time. Off rates were determined by reference cell subtraction and fitting the sensogram experimental data assuming a 1:1 interaction using BIAevaluation software (GE, BR-1005-97). Results of the off-rate screen are summarised in Table 8.

TABLE 8

Surface plasmon resonance screen for ranking of human IgG4 anti-FBG off-rates

| | kd (s$^{-1}$ × 10$^{-4}$) for rCD4-His-FBG | | |
|---|---|---|---|
| Clone name | Human TNC FBG | Mouse TNC FBG | Human TNR FBG |
| 165_13_B1 | 0.015 | 0.017 | 390 |
| 165_13_B6 | 0.056 | 0.069 | 37 |
| 165_13_D1 | 0.0014 | 0.039 | 43 |
| 165_13_C3 | 0.00095 | 0.033 | 120 |
| 165_13_D4 | 0.0062 | 0.037 | 40 |
| 165_13_A4 | 8.72 | 79.7 | nd |
| 165_13_B3 | 0.014 | 300 | nd |
| 165_13_E1 | 0.014 | 577 | nd |
| 180_11_F5 | 0.26 | 10000 | nd |
| 160_01_E3 | 0 | 558.8 | nd |
| 160_01_D6 | 0.105 | 558.8 | nd |
| 160_01_H4 | 0.16 | 170.8 | nd |
| 160_01_A4 | 0.067 | 0.059 | 110 |
| 160_01_F1 | 0.04 | 1540000 | nd |
| 160_01_G2 | 0.125 | 0.139 | 10 |
| 161_01_F6 (160_01_F6) | 0.028 | 17.1 | 25 |
| 161_01_A12 | 0.013 | 0.043 | 42 |

TABLE 8-continued

Surface plasmon resonance screen for ranking of human IgG4 anti-FBG off-rates

| | kd (s$^{-1}$ × 10$^{-4}$) for rCD4-His-FBG | | |
|---|---|---|---|
| Clone name | Human TNC FBG | Mouse TNC FBG | Human TNR FBG |
| 161_01_C09 | 0.00117 | 0.0023 | 2.9 |
| 161_01_H10 | 0.25 | 0.019 | 91 |
| 161_01_C11 | 0.0022 | nd | nd |
| 162_02_D3 | 0.0039 | 0.0106 | 64 |
| 162_02_C6 | 0.053 | 2.4 | 280 |
| 162_02_H5 | 0.00043 | 1.67 | 820 |
| 162_02_F3 | 0.00083 | 3.3 | 880 |
| 162_02_C1 | 0.00093 | 16 | 27000000 |
| 162_02_C2 | 0.115 | 17 | 535000 |
| 162_02_F4 | 0.0059 | 10 | 151000 |
| 162_02_C3 | 0.0149 | 20 | 6350 |
| 162_02_E11 | 0.011 | 12 | 10110000 |
| 163_02_A12 | 0.0032 | 9.4 | 288000 |
| 163_02_D11 | 0.0032 | 9.8 | 22090000 |
| 2A5 parent | 91 | 590000 | 2720 |
| B12 parent | 1.5 | 300 | 1001 |

Clones were ranked according to low off-rate for human and mouse TNC rCd4-His-FBG, and high-off rate for human TNR rCd4-His-FBG. The 3 highest-ranking antibodies from each library were prioritised for more detailed kinetic analysis as purified IgG4. These clones are shown in Tables 9, 10 and 11.

TABLE 9

Heavy chain CDR3 amino acid sequences of B12 mutants with improved FBG binding off-rate characteristics

| Clone | VH CDR3 | |
|---|---|---|
| B12 parent | DISAVPDTFDI | SEQ ID NO: 11 |
| 165_13_B1 | VMSSMEDAFDI | SEQ ID NO: 30 |
| 165_13_D1 | GTRGEGDTFDI | SEQ ID NO: 34 |
| 165_13_C3 | SYQSDEDAFDI | SEQ ID NO: 36 |

TABLE 10

Heavy chain CDR3 amino acid sequences of 2A5 mutants with improved FBG binding off-rate characteristics

| Clone | VH CDR3 | |
|---|---|---|
| 2A5 parent | AQKETYALTY | SEQ ID NO: 3 |
| 160_01_A4 | AQKETLGNAI | SEQ ID NO: 54 |
| 161_01_H10 | AQPVWAPGTY | SEQ ID NO: 66 |
| 162_02_D3 | AQIHPLGLTY | SEQ ID NO: 70 |

TABLE 11

Light chain CDR3 amino acid sequences of 2A5 mutants with improved FBG binding off-rate characteristics.

| Clone | VL CDR3 | | |
|---|---|---|---|
| 2A5 parent | QQSYSTPWT | SEQ ID NO: | 7 |
| 162_02_F3 | QNQYRGPWT | SEQ ID NO: | 76 |
| 163_02_A12 | LHHYREPWT | SEQ ID NO: | 88 |
| 163_02_D11 | LHHYKSPWT | SEQ ID NO: | 90 |

Detailed kinetic parameters were evaluated for the 9 prioritised IgG4 antibodies. Binding characteristics were determined for interaction with human, rat and dog TNC rCD4-His-FBG, and human TNR rCD4-His-FBG. Kinetic assays followed essentially the same protocols as for the off-rate determinations described above, with some modifications as follows. To improve the accuracy of kinetic parameter determination, anti-human Fc IgG was immobilised at lower levels (2229 RU), resulting in a corresponding reduction in the amount of anti-FBG IgG4 captured. Purified anti-FBG IgG4 was diluted to a concentration of 3.5 nM in PBS, pH 7.4, 0.05% Tween-20 and injected into FC2 at a flow rate of 10 µl/min, 60 s contact time. This typically resulted in an average of 80 RU of antibody captured (range: 55 RU to 90 RU). Antigens were prepared by doubling dilution in PBS, pH 7.4, 0.05% Tween-20 (highest concentration 100 nM except mouse rCD4-His-FBG which was 7 nM). Assays were performed at 37° C. (30 µl/min, 120 s contact time; mouse rCD4-His-FBGFBG 10 µl/min, 60 s contact time), with both the flow cell and injection chamber equilibrated to this temperature. As before, kinetic parameters were determined by reference cell subtraction and fitting the sensogram experimental data assuming a 1:1 interaction using BIAevaluation software (GE, BR-1005-97).

All nine antibodies displayed improved binding to mouse TNC FBG domain compared to the non-affinity matured parent clones, and antibodies 165_13_B1, 165_13_C3, and 160_01_A4 exhibited sub-nanomolar $K_D$ values for binding to human TNC FBG, with >70-fold lower affinity to the human TNR FBG analogue (Table 12).

TABLE 12

Anti-FBG IgG4 binding kinetic data determined by surface plasmon resonance at 37° C.

| Antibody | | rCD4-His-FBG | | $K_D$ | $K_a$ | $K_d$ |
|---|---|---|---|---|---|---|
| IgG4 | Parent | Species | Tenascin | (nM) | $(M^{-1}s^{-1}) \times 10^4$ | $(s^{-1}) \times 10^4$ |
| 2A5 | 2A5 | Human | TNC | 23.8 | 13.6 | 323 |
| | | Mouse | TNC | 123 | 8.68 | 106.5 |
| B12 | B12 | Human | TNC | 0.24 | 47.1 | 11.2 |
| | | Mouse | TNC | 4.5 | 30 | 13.8 |
| 165_13_B1 | B12 | Human | TNC | 0.26 | 72.7 | 18.8 |
| | | Mouse | TNC | 0.96 | 73.3 | 7.06 |
| | | Rat | TNC | 2.20 | 31.1 | 68.4 |
| | | Dog | TNC | 2.85 | 65.5 | 187 |
| | | Human | TNR | 94.4 | 12.2 | 1149 |
| 165_13_C3 | B12 | Human | TNC | 0.072 | 116 | 8.3 |
| | | Mouse | TNC | 0.46 | 97.2 | 4.45 |
| | | Rat | TNC | 1.22 | 38.9 | 47.3 |
| | | Dog | TNC | 1.80 | 59.7 | 108 |
| | | Human | TNR | 35.8 | 12.0 | 431 |
| 160_01_A4 | 2A5 | Human | TNC | 0.21 | 23.5 | 5.0 |
| | | Mouse | TNC | 1.23 | 11.8 | 1.46 |
| | | Rat | TNC | 1.49 | 12.7 | 18.9 |
| | | Dog | TNC | 0.094 | 19.0 | 1.8 |
| | | Human | TNR | 15.2 | 2.6 | 39.9 |

EXAMPLE 6—INHIBITION OF TNC FBG-EVOKED CYTOKINE PRODUCTION IN PRIMARY HUMAN PBMCS

The functional FBG neutralising activity of purified IgG4 antibodies 165_13_B1, 165_13_C3, and 160_01_A4 was confirmed in an in vitro assay of FBG-evoked cytokine release in primary human PBMCs.

Peripheral blood mononuclear cell (PBMC) populations were isolated from three healthy human single donor buffy coat preparations by density gradient centrifugation. Assays were carried out in 96-well plates in a final volume of 200 µl, and the endotoxin content of all reagents and test antibodies was confirmed to be within acceptable limits before use, determined using a limulus amoebocyte lysate (LAL) endotoxin quantitation kit (Pierce).

Freshly isolated PBMC samples ($2 \times 10^5$ cells/well) were cultured in the presence of test antibodies (100 nM and 1 µM), control isotype antibody (Sigma 14639; 100 nM and 1 µM), dexamethasone (1 µM) or PBS control for 1 h prior to submaximal stimulation with either bacterial lipopolysaccharide (LPS; *E. coli* 026:B6; 100 ng/mL) or human Fc-His-FBG (200 nM). Control wells, in which LPS or Fc-His-FBG were replaced with an equal volume of PBS, contained test antibodies or dexamethasone. After incubation (24 h, 37° C.), culture supernatants were collected and stored at −80° C. Samples were thawed to room temperature before assay of supernatants for cytokine content. A 25 µl aliquot of each supernatant was diluted with an equal volume of RPMI medium (Life Technologies) and resulting samples were assayed in duplicate for IL-8 and TNFα by Luminex analysis.

Incubation of PBMCs with 100 ng/mL LPS for 24 h resulted in IL-8 and TNFa production, which was not inhibited by exposure to either control IgG4 antibody or the anti-FBG antibodies. In contrast, IL-8 and TNFa release evoked by Fc-His-FBG was completely blocked by all test antibodies, but not control IgG4, confirming the potent and specific FBG-neutralising activity of the 3 affinity-matured antibodies 165_13_131, 165_13_C3, and 160_01_A4 (FIGS. 12A, 12B).

EXAMPLE 7—ANTI-FBG IGG4 BINDING TO CITRULLINATED FBG

The binding affinity of antibody B12 to citrullinated FBG was determined by surface plasmon resonance (SPR). B12 was expressed as a human IgG4 with the hinge-stabilising S241P mutation using the QMCF expression technology (Icosagen, Estonia) and purified by protein A affinity chromatography (MabSelect Sure; GE Healthcare).

Citrullination of Human TNC FBG

Purified human His-FBG was citrullinated using either peptidylarginine deiminase 2 (PAD2; MQ-16.201-2.5, Modiquest, NL) or peptidylarginine deiminase 4 (PAD4; MQ-16.203-2.5, Modiquest, NL) according to the supplier's instructions. Briefly, His-FBG was diluted to 1 mg/ml in the supplied deimination buffer (0.1 M Tris-HCl pH 7.5, 10 mM $CaCl_2$, 5 mM dithiothreitol) and 250 µl mixed with 125 mU of either PAD2 or PAD4 enzyme followed by incubation at 37° C. for 2 h. Citrullination was confirmed by amino acid analysis of the enzymatically-treated samples. Aliquots of His-FBG in deimination buffer were incubated for 2 h at 37° C. in the absence of added PAD enzyme, for use as non-citrullinated control protein. Citrullinated and unmodified His-FBG proteins were used in SPR experiments as described below.

Surface Plasmon Resonance

SPR experiments were performed on a BIAcore 3000 instrument. Anti-human IgG (GE Healthcare) was covalently coupled to the surface of a CM5 sensor chip using amino coupling chemistry. The amount of the coupled anti-human IgG expressed in RU units varied between 6500-7000 (6.5-7.0 $ng/mm^2$). B12-hIgG4 (1-13 nM) was attached to the immobilised anti-human IgG in HBS-EP buffer (10 mM Hepes, 0.15 M NaCl, 2.5 mM EDTA and 0.005% Tween-20) at 25° C. Binding of the His-FBG variants to the immobilised B12-hIgG4 was also measured in HBS-EP buffer at 25° C. The flow rate was 5 µl/min in the immobilization experiments and 20 µl/min for kinetic analyses. The sensor chip surface was regenerated using 3 M $MgCl_2$. Data were analysed using BIAevaluation program 4.1 (GE Healthcare).

Analysis of B12-IgG4 binding to citrullinated His-FBG revealed that the kinetic parameters were essentially unchanged when compared to values obtained for binding to unmodified His-FBG (Table 13). These results indicate that anti-FBG antibodies of the B12 lineage would be expected to bind both citrullinated and non-citrullinated forms of TNC FBG in therapeutic or diagnostic applications.

TABLE 13

Kinetic parameters for interaction of B12-hIgG4 with the His-FBG variants. Each kinetic parameter represents the mean ± s.d. of 3 independent determinations.

| Analyte | $K_D$ (M) | $K_{on}$ ($M^{-1}s^{-1}$) | $K_{off}$ ($s^{-1}$) |
|---|---|---|---|
| His-FBG | (1.7 ± 0.3) × $10^{-10}$ | (4.1 ± 0.6) × $10^6$ | (6.8 ± 0.9) × $10^{-4}$ |
| His-FBG + PAD2 | (3.2 ± 0.3) × $10^{-10}$ | (3.0 ± 0.4) × $10^6$ | (9.6 ± 0.8) × $10^{-4}$ |
| His-FBG + PAD4 | (3.2 ± 0.7) × $10^{-10}$ | (2.6 ± 0.6) × $10^6$ | (7.8 ± 0.4) × $10^{-4}$ |

EXAMPLE 8—DETECTION OF TNC FBG IN HUMAN RA TISSUE USING IMMUNOHISTOCHEMISTRY

Immunohistochemistry studies were performed to determine whether anti-FBG antibodies effectively recognise endogenous forms of the human TNC FBG protein in human tissue. Tenascin-C is expressed at sites of chronic inflammation and its localisation within the inflamed synovium of joints from individuals with rheumatoid arthritis has previously been demonstrated by immunohistochemistry using commercially available antibodies (Goh et al, 2010; Salter D M, 1993).

The B12 antibody was expressed as mouse IgG2a format using the QMCF expression technology (Icosagen, Estonia) and purified by Protein G affinity chromatography followed by Superdex 200 gel filtration. Control mouse IgG1 anti-tenascin-C antibody (Clone 4F10TT; Takara Clontech), which recognises an EGF domain of full-length human tenascin-C was used as a positive control comparator. Mouse IgG1 (Dako X0931) or IgG2a (Dako X0943) against an irrelevant bacterial antigen were used as control primary antibodies to determine the level of non-specific background staining with these isotypes. Frozen sections of human knee joint synovium from donors with confirmed RA diagnosis (Asterand, UK) were equilibrated to room temperature, fixed (10 min) in 1:1 v/v acetone/methanol, and transferred to wash buffer. Immunostaining was performed using a Dako Autostainer with Envision Flex reagents (Dako K8010) according to manufacturer's protocols. Briefly, fixed tissue slides were placed onto the automated stainer and blocked (peroxidase block, 5 min; protein block, 10 min, Dako X0909) before 30 min application of primary antibody (B12 or Clone 4F10TT; 1, 2, or 4 µg/ml). In some controls, slides were not exposed to primary antibody. After washing, HRP-labelled goat anti-mouse secondary antibody was applied (20 min) and slides were washed again, followed by 10 min application of DAB+ Chromogen. Slides were washed, counterstained with haematoxylin and coverslipped for microscopic visualisation of staining.

In cryosections of RA synovium that were fixed using acetone/methanol, the anti-TNC FBG B12 mouse IgG2a showed a very similar pattern of staining to that obtained with the positive control antibody Clone 4F10TT. Specific immunostaining was observed in the synovium, fibrous capsule, vasculature and within the interstitium. There was no staining within lymphoid aggregates (FIGS. 13A, 13C). Some non-specific immunostaining was present in non-immune control treated tissues (FIGS. 13B, 13D). These results confirm and extend previous reports of tenascin-C expression within RA synovium, demonstrating that B12 is an effective agent for binding endogenous tenascin-C at sites of inflammation and further indicating that FBG is an accessible target in RA.

EXAMPLE 9—ANTIBODY SEQUENCES

Antibody 2A5
VH CDR1:

(SEQ ID NO: 1)
ELSMH

VH CDR2:

(SEQ ID NO: 2)
GFDPEDGETIYAQKFQG

VH CDR3:

(SEQ ID NO: 3)
AQKETYALTY

VH amino acid sequence:

(SEQ ID NO: 4)
EVRLVQSGAEVKKPGASVKVSCKVSGYTLT ELSMH WVRQAPGKGLEWMG

GFDPEDGETIYAQKFQG RVTMTEDTSTDTAYMELSSLRSEDTAVYYCAT

AQKETYALTY WGQGTLVTVSS

-continued

VL CDR1:
RASQYIQGFLN (SEQ ID NO: 5)

VL CDR2:
AASTLQD (SEQ ID NO: 6)

VL CDR3:
QQSYSTPWT (SEQ ID NO: 7)

VL amino acid sequence:
(SEQ ID NO: 8)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWTF
GQGTKVEIKR; or (SEQ ID NO: 124)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWTF
GQGTKVEIK Antibody B12
VH CDR1:
DYAMH (SEQ ID NO: 9)

VH CDR2:
GISGSGGSTYYADSVKG (SEQ ID NO: 10)

VH CDR3:
DISAVPDTFDI (SEQ ID NO: 11)

VH amino acid sequence:
(SEQ ID NO: 12)
QVQLVESGGGLVQPGRSLRLSCAASGFTFDDYAMHWVRQAPGKGLEWVS
GISGSGGSTYYADSVKGRFTISRDNAKNSLYLQMNSLRAEDTALYYCAK
DISAVPDTFDIWGQGTMVTVSS

VL CDR1:
RASQYIQGFLN (SEQ ID NO: 5)

VL CDR2:
DASNLET (SEQ ID NO: 13)

VL CDR3:
QQSYSTPQT (SEQ ID NO: 14)

VL amino acid sequence:
(SEQ ID NO: 15)
DIQMTQSPASLPTPVGDRVTITCRASQYIQGFLNWYQQKPGKAPKLLIY
DASNLETGVPSRFSGSGSGTDFTLTISSLQPEDFATYYCQQSYSTPQTF
GQGTKVDIKR; or (SEQ ID NO: 125)
DIQMTQSPASLPTPVGDRVTITCRASQYIQGFLNWYQQKPGKAPKLLIY
DASNLETGVPSRFSGSGSGTDFTLTISSLQPEDFATYYCQQSYSTPQTF
GQGTKVDIK Antibody D8
VH CDR1:
SYGIS (SEQ ID NO: 16)

VH CDR2:
WISAYNGNTNYAQKLQG (SEQ ID NO: 17)

VH CDR3:
NQDSSSDY (SEQ ID NO: 18)

VH amino acid sequence:
(SEQ ID NO: 19)
EVQLVQSGAEVKKPGASVKVSCKASGYTFTSYGISWVRQAPGQGLEWMG
WISAYNGNTNYAQKLQGRVTMTTDTSTSTAYMELRSLRSDDTAVYYCAR
NQDSSSDYWGQGTLVTVSS

VL CDR1:
RASQYIQGFLN (SEQ ID NO: 5)

VL CDR2:
DASNLET (SEQ ID NO: 13)

VL CDR3:
QQSYSTLQT (SEQ ID NO: 20)

VL amino acid sequence:
(SEQ ID NO: 21)
DIQMTQSPASLPTSVGDRVTITCRASQYIQGFLNWYQQKPGKAPKLLIY
DASNLETGVPSRFSGSGSGTDFTLTISSLQPEDFATYYCQQSYSTLQTF
GQGTKVDIKR; or (SEQ ID NO: 126)
DIQMTQSPASLPTSVGDRVTITCRASQYIQGFLNWYQQKPGKAPILLIY
DASNLETGVPSRFSGSGSGTDFTLTISSLQPEDFATYYCQQSYSTLQTF
GQGTKVDIK Antibody F3
VH CDR1:
SYGMH (SEQ ID NO: 22)

VH CDR2:
VISYDGSNKYYADSVKG (SEQ ID NO: 23)

VH CDR3:
EGYDQLFSAESNAFDI (SEQ ID NO: 24)

VH amino acid sequence:
(SEQ ID NO: 25)
EVQLLESGGGLVQPGGSLRLSCAASGFTFSSYGMHWVRQAPGKGLEWVA
VISYDGSNKYYADSVKGRFTISRGNSKNTLYLQMNSLKAEDTAVYYCAR
EGYDQLFSAESNAFDIWGQGTLVTVSS

VL CDR1:
TRSSGSIASYFVQ (SEQ ID NO: 26)

VL CDR2:
EDNQRPS (SEQ ID NO: 27)

-continued

VL CDR3:
(SEQ ID NO: 28)
QSYDSSNWV

VL amino acid sequence:
(SEQ ID NO: 29)
NFMLAQPHSVSESPGKTVTISC TRSSGSIASYFVQ WFQQRPGSAPTAVI
Y EDNQRPS GVPDRFSGSIDSSSNSASLTISGLKTEDEADYYC QSYDSSN
WV FGGGTKVTVLGQP; or (SEQ ID NO: 127)
NFMLAQPHSVSESPGKTVTISC TRSSGSIASYFVQ WFQQRPGSAPTAVI
Y EDNQRPS GVPDRFSGSIDSSSNSASLTISGLKTEDEADYYC QSYDSSN
WV FGGGTKVTVL Antibody 165_13_B1 (derived from B12)
VH CDR1:
(SEQ ID NO: 9)
DYAMH

VH CDR2:
(SEQ ID NO: 10)
GISGSGGSTYYADSVKG

VH CDR3:
(SEQ ID NO: 30)
VMSSMEDAFDI

VH amino acid sequence:
(SEQ ID NO: 31)
QVQLVESGGGLVQPGRSLRLSCAASGFTFD DYAMH WVRQAPGKGLEWVS
GISGSGGSTYYADSVKG RFTISRDNAKNSLYLQMNSLRAEDTALYYCAK
VMSSMEDAFDI WGQGTMVTVSS

VL CDR1:
(SEQ ID NO: 5)
RASQYIQGFLN

VL CDR2:
(SEQ ID NO: 13)
DASNLET

VL CDR3:
(SEQ ID NO: 14)
QQSYSTPQT

VL amino acid sequence:
(SEQ ID NO: 15)
DIQMTQSPASLPTPVGDRVTITC RASQYIQGFLN WYQQKPGKAPKLLIY
DASNLET GVPSRFSGSGSGTDFTLTISSLQPEDFATYYC QQSYSTPQT F
GQGTKVDIKR; or (SEQ ID NO: 125)
DIQMTQSPASLPTPVGDRVTITC RASQYIQGFLN WYQQKPGKAPKLLIY
DASNLET GVPSRFSGSGSGTDFTLTISSLQPEDFATYYC QQSYSTPQT F
GQGTKVDIK Antibody 165_13_B6 (derived from B12)
VH CDR1:
(SEQ ID NO: 9)
DYAMH

VH CDR2:
(SEQ ID NO: 10)
GISGSGGSTYYADSVKG

VH CDR3:
(SEQ ID NO: 32)
GQKGEGDTFDI

VH amino acid sequence:
(SEQ ID NO: 33)
QVQLVESGGGLVQPGRSLRLSCAASGFTFD DYAMH WVRQAPGKGLEWVS
GISGSGGSTYYADSVKG RFTISRDNAKNSLYLQMNSLRAEDTALYYCAK
GQKGEGDTFDI WGQGTMVTVSS

VL CDR1:
(SEQ ID NO: 5)
RASQYIQGFLN

VL CDR2:
(SEQ ID NO: 13)
DASNLET

VL CDR3:
(SEQ ID NO: 14)
QQSYSTPQT

VL amino acid sequence:
(SEQ ID NO: 15)
DIQMTQSPASLPTPVGDRVTITC RASQYIQGFLN WYQQKPGKAPKLLIY
DASNLET GVPSRFSGSGSGTDFTLTISSLQPEDFATYYC QQSYSTPQT F
GQGTKVDIKR; or (SEQ ID NO: 125)
DIQMTQSPASLPTPVGDRVTITC RASQYIQGFLN WYQQKPGKAPKLLIY
DASNLET GVPSRFSGSGSGTDFTLTISSLQPEDFATYYC QQSYSTPQT F
GQGTKVDIK Antibody 165_13_D1 (derived from B12)
VH CDR1:
(SEQ ID NO: 9)
DYAMH

VH CDR2:
(SEQ ID NO: 10)
GISGSGGSTYYADSVKG

VH CDR3:
(SEQ ID NO: 34)
GTRGEGDTFDI

VH amino acid sequence:
(SEQ ID NO: 35)
QVQLVESGGGLVQPGRSLRLSCAASGFTFD DYAMH WVRQAPGKGLEWVS
GISGSGGSTYYADSVKG RFTISRDNAKNSLYLQMNSLRAEDTALYYCAK
GTRGEGDTFDI WGQGTMVTVSS

VL CDR1:
(SEQ ID NO: 5)
RASQYIQGFLN

VL CDR2:
(SEQ ID NO: 13)
DASNLET

VL CDR3:
(SEQ ID NO: 14)
QQSYSTPQT

VL amino acid sequence:

(SEQ ID NO: 15)
DIQMTQSPASLPTPVGDRVTITCRASQYIQGFLNWYQQKPGKAPKLLIYDASNLETGVPSRFSGSGSGTDFTLTISSLPEDFATYYCQQSYSTPQTFGQGTKVDIKR; or (SEQ ID NO: 125)
DIQMTQSPASLPTPVGDRVTITCRASQYIQGFLNWYQQKPGKAPKLLIYDASNLETGVPSRFSGSGSGTDFTLTISSLPEDFATYYCQQSYSTPQTFGQGTKVDIK

Antibody 165_13_C3 (derived from B12)
VH CDR1:

(SEQ ID NO: 9)
DYAMH

VH CDR2:

(SEQ ID NO: 10)
GISGSGGSTYYADSVKG

VH CDR3:

(SEQ ID NO: 36)
SYQSDEDAFDI

VH amino acid sequence:

(SEQ ID NO: 37)
QVQLVESGGGLVQPGRSLRLSCAASGFTFDDYAMHWVRQAPGKGLEWVSGISGSGGSTYYADSVKGRFTISRDNAKNSLYLQMNSLRAEDTALYYCAKSYQSDEDAFDIWGQGTMVTVSS

VL CDR1:

(SEQ ID NO: 5)
RASQYIQGFLN

VL CDR2:

(SEQ ID NO: 13)
DASNLET

VL CDR3:

(SEQ ID NO: 14)
QQSYSTPQT

VL amino acid sequence:

(SEQ ID NO: 15)
DIQMTQSPASLPTPVGDRVTITCRASQYIQGFLNWYQQKPGKAPKLLIYDASNLETGVPSRFSGSGSGTDFTLTISSLPEDFATYYCQQSYSTPQTFGQGTKVDIKR; or (SEQ ID NO: 125)
DIQMTQSPASLPTPVGDRVTITCRASQYIQGFLNWYQQKPGKAPKLLIYDASNLETGVPSRFSGSGSGTDFTLTISSLPEDFATYYCQQSYSTPQTFGQGTKVDIK

Antibody 165_13_D4 (derived from B12)
VH CDR1:

(SEQ ID NO: 9)
DYAMH

VH CDR2:

(SEQ ID NO: 10)
GISGSGGSTYYADSVKG

VH CDR3:

(SEQ ID NO: 38)
GTVGEGDTFDI

VH amino acid sequence:

(SEQ ID NO: 39)
QVQLVESGGGLVQPGRSLRLSCAASGFTFDDYAMHWVRQAPGKGLEWVSGISGSGGSTYYADSVKGRFTISRDNAKNSLYLQMNSLRAEDTALYYCAKGTVGEGDTFDIWGQGTMVTVSS

VL CDR1:

(SEQ ID NO: 5)
RASQYIQGFLN

VL CDR2:

(SEQ ID NO: 13)
DASNLET

VL CDR3:

(SEQ ID NO: 14)
QQSYSTPQT

VL amino acid sequence:

(SEQ ID NO: 15)
DIQMTQSPASLPTPVGDRVTITCRASQYIQGFLNWYQQKPGKAPKLLIYDASNLETGVPSRFSGSGSGTDFTLTISSLPEDFATYYCQQSYSTPQTFGQGTKVDIKR; or (SEQ ID NO: 125)
DIQMTQSPASLPTPVGDRVTITCRASQYIQGFLNWYQQKPGKAPKLLIYDASNLETGVPSRFSGSGSGTDFTLTISSLPEDFATYYCQQSYSTPQTFGQGTKVDIK

Antibody 165_13_A4 (derived from B12)
VH CDR1:

(SEQ ID NO: 9)
DYAMH

VH CDR2:

(SEQ ID NO: 10)
GISGSGGSTYYADSVKG

VH CDR3:

(SEQ ID NO: 40)
DKYPVLDTFDI

VH amino acid sequence:

(SEQ ID NO: 41)
QVQLVESGGGLVQPGRSLRLSCAASGFTFDDYAMHWVRQAPGKGLEWVSGISGSGGSTYYADSVKGRFTISRDNAKNSLYLQMNSLRAEDTALYYCAKDKYPVLDTFDIWGQGTMVTVSS

VL CDR1:

(SEQ ID NO: 5)
RASQYIQGFLN

VL CDR2:

(SEQ ID NO: 13)
DASNLET

VL CDR3:

(SEQ ID NO: 14)
QQSYSTPQT

VL amino acid sequence:

(SEQ ID NO: 15)
DIQMTQSPASLPTPVGDRVTITCRASQYIQGFLNWYQQKPGKAPKLLIYDASNLETGVPSRFSGSGSGTDFTLTISSLPEDFATYYCQQSYSTPQTFGQGTKVDIKR; or

```
DIQMTQSPASLPTPVGDRVTITCRASQYIQGFLNWYQQKPGKAPKLLIY
                                        (SEQ ID NO: 125)
DASNLETGVPSRFSGSGSGTDFTLTISSLQPEDFATYYCQQSYSTPQTF
GQGTKVDIK
```

Antibody 165_13_B3 (derived from B12)
VH CDR1:
                                        (SEQ ID NO: 9)
DYAMH VH CDR2:
                                        (SEQ ID NO: 10)
GISGSGGSTYYADSVKG

VH CDR3:
                                        (SEQ ID NO: 42)
ALARGHDTFDI

VH amino acid sequence:
                                        (SEQ ID NO: 43)
QVQLVESGGGLVQPGRSLRLSCAASGFTFDDYAMHWVRQAPGKGLEWVS
GISGSGGSTYYADSVKGRFTISRDNAKNSLYLQMNSLRAEDTALYYCAK
ALARGHDTFDIWGQGTMVTVSS

VL CDR1:
                                        (SEQ ID NO: 5)
RASQYIQGFLN

VL CDR2:
                                        (SEQ ID NO: 13)
DASNLET

VL CDR3:
                                        (SEQ ID NO: 14)
QQSYSTPQT

VL amino acid sequence:
                                        (SEQ ID NO: 15)
DIQMTQSPASLPTPVGDRVTITCRASQYIQGFLNWYQQKPGKAPKLLIY
DASNLETGVPSRFSGSGSGTDFTLTISSLQPEDFATYYCQQSYSTPQTF
GQGTKVDIKR; or (SEQ ID NO: 125)
DIQMTQSPASLPTPVGDRVTITCRASQYIQGFLNWYQQKPGKAPKLLIY
DASNLETGVPSRFSGSGSGTDFTLTISSLQPEDFATYYCQQSYSTPQTF
GQGTKVDIK Antibody 165_13_E1 (derived from B12)
VH CDR1:
                                        (SEQ ID NO: 9)
DYAMH VH CDR2:
                                        (SEQ ID NO: 10)
GISGSGGSTYYADSVKG

VH CDR3:
                                        (SEQ ID NO: 44)
DISAVMDVPQT

VH amino acid sequence:
                                        (SEQ ID NO: 45)
QVQLVESGGGLVQPGRSLRLSCAASGFTFDDYAMHWVRQAPGKGLEWVS
GISGSGGSTYYADSVKGRFTISRDNAKNSLYLQMNSLRAEDTALYYCAK
DISAVMDVPQTWGQGTMVTVSS

VL CDR1:
                                        (SEQ ID NO: 5)
RASQYIQGFLN

VL CDR2:
                                        (SEQ ID NO: 13)
DASNLET

VL CDR3:
                                        (SEQ ID NO: 14)
QQSYSTPQT

VL amino acid sequence:
                                        (SEQ ID NO: 15)
DIQMTQSPASLPTPVGDRVTITCRASQYIQGFLNWYQQKPGKAPKLLIY
DASNLETGVPSRFSGSGSGTDFTLTISSLQPEDFATYYCQQSYSTPQTF
GQGTKVDIKR; or (SEQ ID NO: 125)
DIQMTQSPASLPTPVGDRVTITCRASQYIQGFLNWYQQKPGKAPKLLIY
DASNLETGVPSRFSGSGSGTDFTLTISSLQPEDFATYYCQQSYSTPQTF
GQGTKVDIK Antibody 180_11_F5 (derived from B12)
VH CDR1:
                                        (SEQ ID NO: 9)
DYAMH VH CDR2:
                                        (SEQ ID NO: 10)
GISGSGGSTYYADSVKG

VH CDR3:
                                        (SEQ ID NO: 46)
VMRTGLDTFDI

VH amino acid sequence:
                                        (SEQ ID NO: 47)
QVQLVESGGGLVQPGRSLRLSCAASGFTFDDYAMHWVRQAPGKGLEWVS
GISGSGGSTYYADSVKGRFTISRDNAKNSLYLQMNSLRAEDTALYYCAK
VMRTGLDTFDIWGQGTMVTVSS

VL CDR1:
                                        (SEQ ID NO: 5)
RASQYIQGFLN

VL CDR2:
                                        (SEQ ID NO: 13)
DASNLET

VL CDR3:
                                        (SEQ ID NO: 14)
QQSYSTPQT

VL amino acid sequence:
                                        (SEQ ID NO: 15)
DIQMTQSPASLPTPVGDRVTITCRASQYIQGFLNWYQQKPGKAPKLLIY
DASNLETGVPSRFSGSGSGTDFTLTISSLQPEDFATYYCQQSYSTPQTF
GQGTKVDIKR; or (SEQ ID NO: 125)
DIQMTQSPASLPTPVGDRVTITCRASQYIQGFLNWYQQKPGKAPKLLIY
DASNLETGVPSRFSGSGSGTDFTLTISSLQPEDFATYYCQQSYSTPQTF
GQGTKVDIK Antibody 160_01_E3 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 48)
QRYVWEALTY

VH amino acid sequence:
(SEQ ID NO: 49)
EVRLVQSGAEVKKPGASVKVSCKVSGYTLT ELSMH WVRQAPGKGLEWMG QRYVWEALTY WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITC RASQYIQGFLN WYQQKPGKAPRLLIY AASTLQD GVPSRFSGSGYGTDFTLTISSLQPEDFATYYC QQSYSTPWT FGQGTKVEIKR; or
(SEQ ID NO: 124)
DIQMTQSPASLPTSVGDRVTITC RASQYIQGFLN WYQQKPGKAPRLLIY AASTLQD GVPSRFSGSGYGTDFTLTISSLQPEDFATYYC QQSYSTPWT FGQGTKVEIK Antibody 160_01_D6 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 50)
AQADPHLFTY

VH amino acid sequence:
(SEQ ID NO: 51)
EVRLVQSGAEVKKPGASVKVSCKVSGYTLT ELSMH WVRQAPGKGLEWMG GFDPEDGETIYAQKFQG RVTMTEDTSTDTAYMELSSLRSEDTAVYYCAT AQADPHLFTY WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITC RASQYIQGFLN WYQQKPGKAPRLLIY AASTLQD GVPSRFSGSGYGTDFTLTISSLQPEDFATYYC QQSYSTPWT FGQGTKVEIKR; or
(SEQ ID NO: 124)
DIQMTQSPASLPTSVGDRVTITC RASQYIQGFLN WYQQKPGKAPRLLIY AASTLQD GVPSRFSGSGYGTDFTLTISSLQPEDFATYYC QQSYSTPWT FGQGTKVEIK Antibody 160_01_H4 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 52)
GRFVWEALTY

VH amino acid sequence:
(SEQ ID NO: 53)
EVRLVQSGAEVKKPGASVKVSCKVSGYTLT ELSMH WVRQAPGKGLEWMG GFDPEDGETIYAQKFQG RVTMTEDTSTDTAYMELSSLRSEDTAVYYCAT GRFVWEALTY WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITC RASQYIQGFLN WYQQKPGKAPRLLIY AASTLQD GVPSRFSGSGYGTDFTLTISSLQPEDFATYYC QQSYSTPWT FGQGTKVEIKR; or
(SEQ ID NO: 124)
DIQMTQSPASLPTSVGDRVTITC RASQYIQGFLN WYQQKPGKAPRLLIY AASTLQD GVPSRFSGSGYGTDFTLTISSLQPEDFATYYCQQSYSTPWT FGQGTKVEIK Antibody 160_01_A4 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 54)
AQKETLGNAI

-continued

VH amino acid sequence:
(SEQ ID NO: 55)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQKETLGNAIWGQGTIVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIKR; or (SEQ ID NO: 124)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIK Antibody 160_01_F1 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 56)
AQSPWSGMTY

VH amino acid sequence:
(SEQ ID NO: 57)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQSPWSGMTYWGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
GQGTKVEIKR; or (SEQ ID NO: 124)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIK Antibody 160_01_G2 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 58)
YTLDNMALTY

VH amino acid sequence:
(SEQ ID NO: 59)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
YTLDNMALTYWGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIKR; or (SEQ ID NO: 124)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIK Antibody 161_01_F6, also known as 160_01_F6
(derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 60)
AQKENIANRH

VH amino acid sequence:
(SEQ ID NO: 61)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQKENIANRHWGQGTLVTVSS -continued

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIKR; or (SEQ ID NO: 124)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIK Antibody 161_01_A12 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 62)
AQPTALANTY

VH amino acid sequence:
(SEQ ID NO: 63)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQPTALANTYWGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIKR; or (SEQ ID NO: 124)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT Antibody 161_01_C09 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 64)
AQLPYLAQTY

VH amino acid sequence:
(SEQ ID NO: 65)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQLPYLAQTYWGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIKR; or (SEQ ID NO: 124)
DIQMTQSPASLPTSVGDRVTITCRASQYIQGFLNWYQQKPGKAPRLLIY
AASTLQDGVPSRFSGSGYGTDFTLTISSLQPEDFATYYCQQSYSTPWT
FGQGTKVEIK Antibody 161_01_H10 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 66)
AQPVWAPGTY

VH amino acid sequence:
(SEQ ID NO: 67)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQPVWAPGTYWGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

-continued

VL amino acid sequence:
(SEQ ID NO: 8)
DIQMTQSPASLPTSVGDRVTITC RASQYIQGFLN WYQQKPGKAPRLLIY
AASTLQD GVPSRFSGSGYGTDFTLTISSLQPEDFATYYC QQSYSTPWT
FGQGTKVEIKR; or (SEQ ID NO: 124)
DIQMTQSPASLPTSVGDRVTITC RASQYIQGFLN WYQQKPGKAPRLLIY
AASTLQD GVPSRFSGSGYGTDFTLTISSLQPEDFATYYC QQSYSTPWT
FGQGTKVEIK Antibody 161_01_C11 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 68)
AQKEWLPDVT

VH amino acid sequence:
(SEQ ID NO: 69)
EVRLVQSGAEVKKPGASVKVSCKVSGYTLT ELSMH WVRQAPGKGLEWMG
GFDPEDGETIYAQKFQG RVTMTEDTSTDTAYMELSSLRSEDTAVYYCAT
AQKEWLPDVT WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITC RASQYIQGFLN WYQQKPGKAPRLLIY
AASTLQD GVPSRFSGSGYGTDFTLTISSLQPEDFATYYC QQSYSTPWT
FGQGTKVEIKR; or (SEQ ID NO: 124)
DIQMTQSPASLPTSVGDRVTITC RASQYIQGFLN WYQQKPGKAPRLLIY
AASTLQD GVPSRFSGSGYGTDFTLTISSLQPEDFATYYC QQSYSTPWT
FGQGTKVEIK Antibody 162_02_D3 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 70)
AQIHPLGLTY

VH amino acid sequence:
(SEQ ID NO: 71)
EVRLVQSGAEVKKPGASVKVSCKVSGYTLT ELSMH WVRQAPGKGLEWMG
GFDPEDGETIYAQKFQG RVTMTEDTSTDTAYMELSSLRSEDTAVYYCAT
AQLPYLAQTY WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 7)
QQSYSTPWT

VL amino acid sequence:
(SEQ ID NO: 8)
DIQMTQSPASLPTSVGDRVTITC RASQYIQGFLN WYQQKPGKAPRLLIY
AASTLQD GVPSRFSGSGYGTDFTLTISSLQPEDFATYYC QQSYSTPWT
FGQGTKVEIKR; or (SEQ ID NO: 124)
DIQMTQSPASLPTSVGDRVTITC RASQYIQGFLN WYQQKPGKAPRLLIY
AASTLQD GVPSRFSGSGYGTDFTLTISSLQPEDFATYYC QQSYSTPWT
FGQGTKVEIK Antibody 162_02_C6 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 3)
AQKETYALTY

VH amino acid sequence:
(SEQ ID NO: 4)
EVRLVQSGAEVKKPGASVKVSCKVSGYTLT ELSMH WVRQAPGKGLEWMG
GFDPEDGETIYAQKFQG RVTMTEDTSTDTAYMELSSLRSEDTAVYYCAT
AQKETYALTY WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 72)
QNQYAGPWT

VL amino acid sequence:
(SEQ ID NO: 73)
DIQMTQSPASLPTSVGDRVTITC RASQYIQGFLN WYQQKPGKAPRLLIY
AASTLQD GVPSRFSGSGYGTDFTLTISSLQPEDFATYYC QNQYAGPWT
FGQGTKVEIKR; or

```
                                                  (SEQ ID NO: 128)
DIQMTQSPASLPTSVGDRVTITCRASQYIQGFLNWYQQKPGKAPRLLIY
AASTLQDGVPSRFSGSGYGTDFTLTISSLQPEDFATYYCQNYAGPWT
FGQGTKVEIK

Antibody 162_02_H5 (derived from 2A5)
VH CDR1:
                                                  (SEQ ID NO: 1)
ELSMH VH CDR2:
                                                  (SEQ ID NO: 2)
GFDPEDGETIYAQKFQG VH CDR3:
                                                  (SEQ ID NO: 3)
AQKETYALTY VH amino acid sequence:
                                                  (SEQ ID NO: 4)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQKETYALTYWGQGTLVTVSS VL CDR1:
                                                  (SEQ ID NO: 5)
RASQYIQGFLN VL CDR2:
                                                  (SEQ ID NO: 6)
AASTLQD VL CDR3:
                                                  (SEQ ID NO: 74)
QNQYTGPWT VL amino acid sequence:
                                                  (SEQ ID NO: 75)
DIQMTQSPASLPTSVGDRVTITCRASQYIQGFLNWYQQKPGKAPRLLIY
AASTLQDGVPSRFSGSGYGTDFTLTISSLQPEDFATYYCQNQYTGPWT
FGQGTKVEIKR; or (SEQ ID NO: 129)
DIQMTQSPASLPTSVGDRVTITCRASQYIQGFLNWYQQKPGKAPRLLIY
AASTLQDGVPSRFSGSGYGTDFTLTISSLQPEDFATYYCQNQYTGPWT
FGQGTKVEIK Antibody 162_02_F3 (derived from 2A5)
VH CDR1:
                                                  (SEQ ID NO: 1)
ELSMH VH CDR2:
                                                  (SEQ ID NO: 2)
GFDPEDGETIYAQKFQG VH CDR3:
                                                  (SEQ ID NO: 3)
AQKETYALTY VH amino acid sequence:
                                                  (SEQ ID NO: 4)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQKETYALTYWGQGTLVTVSS VL CDR1:
                                                  (SEQ ID NO: 5)
RASQYIQGFLN VL CDR2:
                                                  (SEQ ID NO: 6)
AASTLQD VL CDR3:
                                                  (SEQ ID NO: 76)
QNQYRGPWT VL amino acid sequence:
                                                  (SEQ ID NO: 77)
DIQMTQSPASLPTSVGDRVTITCRASQYIQGFLNWYQQKPGKAPRLLIY
AASTLQDGVPSRFSGSGYGTDFTLTISSLQPEDFATYYCQNQYRGPWT
FGQGTKVEIKR; or
                                                  (SEQ ID NO: 130)
DIQMTQSPASLPTSVGDRVTITCRASQYIQGFLNWYQQKPGKAPRLLIY
AASTLQDGVPSRFSGSGYGTDFTLTISSLQPEDFATYYCQNQYRGPWT
FGQGTKVEIK Antibody 162_02_C1 (derived from 2A5)
VH CDR1:
                                                  (SEQ ID NO: 1)
ELSMH VH CDR2:
                                                  (SEQ ID NO: 2)
GFDPEDGETIYAQKFQG VH CDR3:
                                                  (SEQ ID NO: 3)
AQKETYALTY VH amino acid sequence:
                                                  (SEQ ID NO: 4)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQKETYALTYWGQGTLVTVSS VL CDR1:
                                                  (SEQ ID NO: 5)
RASQYIQGFLN VL CDR2:
                                                  (SEQ ID NO: 6)
AASTLQD VL CDR3:
                                                  (SEQ ID NO: 78)
LHHYRAPWT VL amino acid sequence:
                                                  (SEQ ID NO: 79)
DIQMTQSPASLPTSVGDRVTITCRASQYIQGFLNWYQQKPGKAPRLLIY
AASTLQDGVPSRFSGSGYGTDFTLTISSLQPEDFATYYCLHHYRAPWT
FGQGTKVEIKR; or (SEQ ID NO: 131)
DIQMTQSPASLPTSVGDRVTITCRASQYIQGFLNWYQQKPGKAPRLLIY
AASTLQDGVPSRFSGSGYGTDFTLTISSLQPEDFATYYCLHHYRAPWT
FGQGTKVEIK
```

Antibody 162_02_C2 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 3)
AQKETYALTY

VH amino acid sequence:
(SEQ ID NO: 4)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQKETYALTYWGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 80)
MHHYRAPWT

VL amino acid sequence:
(SEQ ID NO: 81)
DIQMTQSPASLPTSVGDRVTITCRASQYIQGFLNWYQQKPGKAPRLLIY
AASTLQDGVPSRFSGSGYGTDFTLTISSLQPEDFATYYCMHHYRAPWT
FGQGTKVEIKR; or (SEQ ID NO: 132)
DIQMTQSPASLPTSVGDRVTITCRASQYIQGFLNWYQQKPGKAPRLLIY
AASTLQDGVPSRFSGSGYGTDFTLTISSLQPEDFATYYCMHHYRAPWT
FGQGTKVEIK Antibody 162_02_F4 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 3)
AQKETYALTY

VH amino acid sequence:
(SEQ ID NO: 4)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQKETYALTYWGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 82)
MHHYRSPWT

VL amino acid sequence:
(SEQ ID NO: 83)
DIQMTQSPASLPTSVGDRVTITCRASQYIQGFLNWYQQKPGKAPRLLIY
AASTLQDGVPSRFSGSGYGTDFTLTISSLQPEDFATYYCMHHYRSPWT
FGQGTKVEIKR; or (SEQ ID NO: 133)
DIQMTQSPASLPTSVGDRVTITCRASQYIQGFLNWYQQKPGKAPRLLIY
AASTLQDGVPSRFSGSGYGTDFTLTISSLQPEDFATYYCMHHYRSPWT Antibody 162_02_C3 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 3)
AQKETYALTY

VH amino acid sequence:
(SEQ ID NO: 4)
EVRLVQSGAEVKKPGASVKVSCKVSGYTLTELSMHWVRQAPGKGLEWMG
GFDPEDGETIYAQKFQGRVTMTEDTSTDTAYMELSSLRSEDTAVYYCAT
AQKETYALTYWGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 84)
MQHYDGPWT

VL amino acid sequence:
(SEQ ID NO: 85)
DIQMTQSPASLPTSVGDRVTITCRASQYIQGFLNWYQQKPGKAPRLLIY
AASTLQDGVPSRFSGSGYGTDFTLTISSLQPEDFATYYCMQHYDGPWT
FGQGTKVEIKR; or (SEQ ID NO: 134)
DIQMTQSPASLPTSVGDRVTITCRASQYIQGFLNWYQQKPGKAPRLLIY
AASTLQDGVPSRFSGSGYGTDFTLTISSLQPEDFATYYCMQHYDGPWT
FGQGTKVEIK Antibody 162_02_E11 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 3)
AQKETYALTY

VH amino acid sequence:
(SEQ ID NO: 4)
EVRLVQSGAEVKKPGASVKVSCKVSGYTLT ELSMH WRQAPGKGLEWMG GFDPEDGETIYAQKFQG RVTMTEDTSTDTAYMELSSLRSEDTAVYYCAT AQKETYALTY WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 86)
LHHYRSPTWT ; or (SEQ ID NO: 135)
LHHYRSPWT

VL amino acid sequence:
(SEQ ID NO: 87)
DIQMTQSPASLPTSVGDRVTITC RASQYIQGFLN WYQQKPGKAPRLLIY AASTLQD GVPSRFSGSGYGTDFTLTISSLQPEDFATYYC LHHYRSPTWT FGQGTKVEIKR; or (SEQ ID NO: 136)
DIQMTQSPASLPTSVGDRVTITC RASQYIQGFLN WYQQKPGKAPRLLIY AASTLQD GVPSRFSGSGYGTDFTLTISSLQPEDFATYYC LHHYRSPWT FGQGTKVEIK Antibody 163_02_A12 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 3)
AQKETYALTY

VH amino acid sequence:
(SEQ ID NO: 4)
EVRLVQSGAEVKKPGASVKVSCKVSGYTLT ELSMH WRQAPGKGLEWMG GFDPEDGETIYAQKFQG RVTMTEDTSTDTAYMELSSLRSEDTAVYYCAT AQKETYALTY WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 88)
LHHYREPWT

VL amino acid sequence:
(SEQ ID NO: 89)
DIQMTQSPASLPTSVGDRVTITC RASQYIQGFLN WYQQKPGKAPRLLIY AASTLQD GVPSRFSGSGYGTDFTLTISSLQPEDFATYYC LHHYREPWT FGQGTKVEIKR; or (SEQ ID NO: 137)
DIQMTQSPASLPTSVGDRVTITC RASQYIQGFLN WYQQKPGKAPRLLIY AASTLQD GVPSRFSGSGYGTDFTLTISSLQPEDFATYYC LHHYREPWT FGQGTKVEIK Antibody 163_02_D11 (derived from 2A5)
VH CDR1:
(SEQ ID NO: 1)
ELSMH

VH CDR2:
(SEQ ID NO: 2)
GFDPEDGETIYAQKFQG

VH CDR3:
(SEQ ID NO: 3)
AQKETYALTY

VH amino acid sequence:
(SEQ ID NO: 4)
EVRLVQSGAEVKKPGASVKVSCKVSGYTLT ELSMH WRQAPGKGLEWMG GFDPEDGETIYAQKFQG RVTMTEDTSTDTAYMELSSLRSEDTAVYYCAT AQKETYALTY WGQGTLVTVSS

VL CDR1:
(SEQ ID NO: 5)
RASQYIQGFLN

VL CDR2:
(SEQ ID NO: 6)
AASTLQD

VL CDR3:
(SEQ ID NO: 90)
LHHYKSPWT

VL amino acid sequence:
(SEQ ID NO: 91)
DIQMTQSPASLPTSVGDRVTITC RASQYIQGFLN WYQQKPGKAPRLLIY AASTLQD GVPSRFSGSGYGTDFTLTISSLQPEDFATYYC LHHYKSPWT FGQGTKVEIKR; or (SEQ ID NO: 138)
DIQMTQSPASLPTSVGDRVTITC RASQYIQGFLN WYQQKPGKAPRLLIY AASTLQD GVPSRFSGSGYGTDFTLTISSLQPEDFATYYC LHHYKSPWT FGQGTKVEIK IgG4 165_13_C3 (constant region with hinge modification as described in Angal 1993) Reference: Angel 51, King DJ, Bodmer MW, Turner A, Lawson AD, Roberts G, Pedley B, Adair JR. Mol Immunol. 1993 Jan; 30(1):105-8.
QVQLVESGGGLVQPGRSLRLSCAASGFTFDDYAMHWVRQAPGKGLEWVS
GISGSGGSTYYADSVKGRFTISRDNAKNSLYLQMNSLRAEDTALYYCAK
SYQSDEDAFDIWGQGTMVTVSSASTKGPSVFPLAPCSRSTSESTAALGC
LVKDYFPEPVTVSWNSGALTSGVHTFPAVLQSSGLYSLSSVVTVPSSSL
GTKTYTCNVDHKPSNTKVDKRVESKYGPPCPPCPAPEFLGGPSVFLFPP
KPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQP
REPQVYTLPPSQEEMTKNQVSLTCLVKGFPSDIAVEWESNGQPENNYKT
TPPVLDSDGSFFLYSRLTVDKSRWQEGNVFSCSVMHEALHNHYTQKSLS
LSLGK

EXAMPLE 10—PROTEIN SEQUENCES

Amino acid sequence of human tenascin-C FBG domain
[SEQ ID NO: 92]
IGLLYPFPKDCSQAMLNGDTTSGLYTIYLNGDKAEALEVFCDMTSDGGGW
IVFLRRKNGRENFYQNWKAYAAGFGDRREEFWLGLDNLNKITAQGQYELR
VDLRDHGETAFAVYDKFSVGDAKTRYKLKVEGYSGTAGDSMAYHNGRSFS
TFDKDTDSAITNCALSYKGAFWYRNCHRVNLMGRYGDNNHSQGVNWFHWK
GHEHSIQFAEMKLRPSNFRNLEGRRKRA Amino acid sequence of mouse tenascin-C FBG domain
[SEQ ID NO: 93]
IGLLYPFPRDCSQAMLNGDTTSGLYTIYINGDKTQALEVYCDMTSDGGGW
IVFLRRKNGREDFYRNWKAYAAGFGDRREEFWLGLDNLSKITAQGQYELR
VDLQDHGESAYAVYDRFSVGDAKSRYKLKVEGYSGTAGDSMNYHNGRSFS
TYDKDTDSAITNCALSYKGAFWYKNCHRVNLMGRYGDNNHSQGVNWFHWK
GHEYSIQFAEMKLRPSNFRNLEGRRKRA Amino acid sequence of rat tenascin-C FBG domain
[SEQ ID NO: 94]
IGLLYPFPRDCSQAMLNGDTTSGLYTIYINGDKTQALEVYCDMTSDGGGW
IVFLRRKNGREDFYRNWKAYATGFGDRREEFWLGLDNLSKITAQGQYELR
VDLQDHGESAYAVYDRFSVGDAKSRYKLKVEGYSGTAGDSMNYHNGRSFS
TYDKDTDSAITNCALSYKGAFWYKNCHRVNLMGRYGDNNHSQGVNWFHWK
GHEYSIQFAEMKLRPSNFRNLEGRRKRA Amino acid sequence of dog tenascin-C FBG domain
[SEQ ID NO: 95]
IGLLYPFPRDCSQAMLNGDTTSGLYTIYLNGDKAQALEVYCDMTSDGGGW
IVFLRRKNGREDFYRNWKAYAAGFGDRREEFWLGLDNLHKITAQGQYELR
VDLRDHGKTAYAVYDRFSVGDAKTRYKLKVEGYSGTAGDSMAYHNGRSFS
TFDKDTDSAITNCALSYKGAFWYKNCHRVNLMGRYGDNNHSQGVNWFHWK
GHEYSIQFAEMKLRPSNFRNLEGRRKRA Amino acid sequence of human tenascin-R FBG domain
[SEQ ID NO: 96]
FPHPQDCAQHLMNGDTLSGVYPIFLNGELSQKLQVYCDMTTDGGGWIVFQ
RRQNGQTDFFRKWADYRVGFGNVEDEFWLGLDNIHRITSQGRYELRVDMR
DGQEAAFASYDRFSVEDSRNLYKLRIGSYNGTAGDSLSYHQGRPFSTEDR
DNDVAVTNCAMSYKGAVWVYKNCHRTNLNGKYGESRHSQGINWYHWKGHE
FSIPFVEMKMRPYNHRLMAGRKRQSLQF

EXAMPLE 11—GERMLINED SEQUENCES

Closest germline matches were determined using IMGT/DomainGapAlign: Ehrenmann F., Kaas Q. and Lefranc M. P. Nucleic Acids Res., 38, D301-307 (2010)

Changes from non-germlined sequences are shown by an underline of the amino acid. The CDRs are shown by the boxed sequences.

Antibody 2A5
Framework Germlined: VH amino acid sequence:
(SEQ ID NO: 112)
QVQLVQSGAEVKKPGASVKVSCKVSGYTLTELSMHWVRQAPGKGLEWMG

GFDPEDGETIYAQKFQGRVTMTEDTSTDTAYMELSSLRSEDTAVYYCAT

AQKETYALTYWGQGTLVTVSS

Framework Germlined: VL amino acid sequence:
(SEQ ID NO: 113)
DIQMTQSPSSLSASVGDRVTITCRASQYIQGFLNWYQQKPGKAPKLLIY

AASSLQSGVPSRFSGSGSGTDFTLTISSLQPEDFATYYCQQSYSTPWTF

GQGTKVEIKR; or (SEQ ID NO: 139)
DIQMTQSPSSLSASVGDRVTITCRASQYIQGFLNWYQQKPGKAPKLLIY

AASSLQSGVPSRFSGSGSGTDFTLTISSLQPEDFATYYCQQSYSTPWTF

GQGTKVEIK

CDRs changed as a result of the germlined sequence:
(SEQ ID NO: 114)
VL CDR2: AASSLQS Antibody B12
Framework Germlined: VH amino acid sequence:
(SEQ ID NO: 115)
EVQLVESGGGLVQPGRSLRLSCAASGFTFDDYAMHWVRQAPGKGLEWVS

GISGSGGSTYYADSVKYRFTISRDNAKNSLYLQMNSLRAEDTALYYCAK

DISAVPDTFDIWGQGTMVTVSS

CDRs changed as a result of the germlined sequence:
(SEQ ID NO: 116)
VH CDR2: GISGSGGSTYYADSVKY Framework Germlined: VL amino acid sequence:
(SEQ ID NO: 117)
DIQMTQSPSSLSASVGDRVTITCRASQYIQGFLNWYQQKPGKAPKLLIY

DASSLQSGVPSRFSGSGSGTDFTLTISSLQPEDFATYYCQQSYSTPQTFG

QGTKVDIKR; or (SEQ ID NO: 140)
DIQMTQSPSSLSASVGDRVTITCRASQYIQGFLNWYQQKPGKAPKLLIY

DASSLQSGVPSRFSGSGSGTDFTLTISSLQPEDFATYYCQQSYSTPQTFG

QGTKVDIK

CDRs changed as a result of the germlined sequence:
(SEQ ID NO: 118)
VL CDR2: DASSLQS Antibody D8
Framework Germlined: VH amino acid sequence:
(SEQ ID NO: 119)
QVQLVQSGAEVKKPGASVKVSCKASGYTFTSYGISWVRQAPGQGLEWCW

ISAYNGNTNYAQKLQGRVTMTTDTSTSTAYMELRSLRSDDTAVYYCARN

QDSSSDYWGQGTLVTVSS

-continued

Framework Germlined: VL amino acid sequence:
(SEQ ID NO: 120)
DIQMTQSPSSLSASVGDRVTITCRASQYIQGFLNWYQQKPGKAPKLLIY

DASSLQSGVPSRFSGSGSGTDFTLTISSLQPEDFATYYCQQSYSTLQTF

GQGTKVEIKR; or (SEQ ID NO: 141)
DIQMTQSPSSLSASVGDRVTITCRASQYIQGFLNWYQQKPGKAPKLLIY

DASSLQSGVPSRFSGSGSGTDFTLTISSLQPEDFATYYCQQSYSTLQTF

GQGTKVEIK

CDRs changed as a result of the germlined
sequence:
(SEQ ID NO: 121)
VL CDR2: DASSLQS Antibody F3
Framework germlined: VH amino acid sequence:
(SEQ ID NO: 122)
QVQLVESGGGVVQPGRSLRLSCAASGFTFSSYGMHWVRQAPGKGLEWVA

VISYDGSNKYYADSVKGRFTISRDNSKNTLYLQMNSLRAEDTAVYYCAR

EGYDQLFSAESNAFDIWGQGTLVTVSS

Framework germlined: VL amino acid sequence:
(SEQ ID NO: 123)
NFMLTQPHSVSESPGKTVTISCTRSSGSIASYFVQWYQQRPGSSPTTVI

YEDNQRPSGVPDRFSGSIDSSSNSASLTISGLKTEDEADYYCQSYDSSN

WVFGGGTKLTVLGQP; or (SEQ ID NO: 142)
NFMLTQPHSVSESPGKTVTISCTRSSGSIASYFVQWYQQRPGSSPTTVI

YEDNQRPSGVPDRFSGSIDSSSNSASLTISGLKTEDEADYYCQSYDSSN

WVFGGGTKLTVL

EXAMPLE 12—USE OF ANTIBODIES IN WESTERN BLOTTING

In order to confirm that the monoclonal antibodies IgG4 C3 (165_13_C3 as referred to above) and IgG4 B12 could be successfully used for western blotting, first specificity was tested using purified proteins (FIGS. 14A-14D). Next, glioma cell lysate was used to determine the ability of B12 to detect full length TNC in a biologically relevant mixture of other proteins (FIGS. 15A-15B).

As shown by the data in FIGS. 14A-14D, recombinant CD4-TNC-FBG (Nascient), CD4-TNR-FBG or FIBRINOGEN (KIR) were run on four 10% SDS-PAGE gels under reducing conditions before blotting to nitrocellulose membranes and detection with the following antibodies A) C3 IgG4 MAb (Nascient) at 1:20,000 (0.25 ug/ml), overnight at 4° C. B) B12 IgG4 MAb (Nascient) at 1:20,000 (0.25 ug/ml), overnight at 4° C. C) Anti-Tenascin-R antibody (Santa Cruz Biotechnology, sc-9875) at 1:2,000 (0.1 ug/ml) overnight at 4° C. D) Anti-TNC-FBG polyclonal antibody (Midwood group) at 1:500, overnight at 4° C. The secondary antibody used for C3 and B12 antibodies was Abcam (ab6858) at 1:20,000 for 1 h at RT. For TNR antibody the secondary was HRP conjugated anti-goat (Sigma-Aldrich, SAB3700259) at 1:10,000 for 1 h at RT. For the polyclonal TNC antibody the secondary used was HRP conjugated anti-Rabbit (DAKO, P0217) at 1:5,000 for 1 h at RT. Exposure to film was 5 min for all blots shown.

In this experiment both C3 and B12 showed specificity for TNC-FBG with very little cross-reactivity with either TNR-FBG or Fibrinogen, indicating their suitability for western blotting applications as they show good specificity for TNC-FBG.

As shown by the data in FIGS. 15A-15B, glioma cell lysate (KIR) and tenascin-C (Nascient) were run on a 5% SDS-PAGE gel under reducing conditions before blotting to membranes and detection with A. B12 IgG4 Mab (Nascient) at 1:20,000, overnight at 4° C.; B. IgG4 isotype control (Eureka therapeutics) at 1:4,000, overnight at 4° C. The secondary antibody used was Abcam (ab6858) at 1:10,000 for 1 h at RT. Blots were developed with ECL Western Blotting Detection Reagent (GE Healthcare, Amersham). Blots were exposed to film for 1 minute.

These results indicate that B12 can detect full length TNC as well as breakdown products and/or splice variants of TNC, and shows low cross-reactivity to other proteins present in the cell lysate.

EXAMPLE 13—ACTIVITY OF THE C3 ANTIBODY IN VITRO

In order to confirm that the monoclonal antibody C3 (165_13_C3) acts by disrupting the binding of TNC-FBG to its receptor TLR4, first an in vitro binding assay was developed for TLR4 and Fc-His-FBG then the effect of pre-incubation of Fc-His-FBG with C3 was determined.

Recombinant human TLR4 (R&D systems) (1 ug/ml (14.6 nM)) in PBS (or PBS alone) was bound to a 96-well plate. After blocking (10% BSA) the indicated concentrations of Human Fc-His-FBG was added and detection was carried out by incubation of an anti-human IgG1 MAb (AbD Serotec, clone 2C11) at 1 ug/ml, an anti-mouse HRP conjugated secondary antibody (AbD Serotec, STAR13B) at 1 ug/ml, and TMB substrate. The results are shown in FIG. 16A, n=4 mean and SEM shown. This experiment shows that Fc-His-FBG binds TLR4 in vitro in a dose dependent manner.

As shown in FIG. 16B, monoclonal Ab C3 disrupts the binding FBG and TLR4 in vitro. Recombinant human TLR4 in PBS (or PBS alone) was bound to a 96-well plate, after blocking recombinant human Fc-His-TNC-FBG (100 nM) which had been pre-incubated to with C3 Mab or isotype control antibody was added. Detection was carried out by successive incubation of antibody directed against the Fc portion of the protein, an anti-mouse HRP conjugated secondary antibody and TMB substrate. The percentage inhibition in the C3 pre-incubated samples was calculated compared to the isotype control samples (IC50=44.5 nM). n=4.

EXAMPLE 14—ANTI-INFLAMMATORY EFFECT OF ANTIBODIES B12, A4 AND C3

It was confirmed that the anti-TNC-FBG antibodies B12, A4 (160_01_A4) and C3 (165_13_C3) have an anti-inflammatory effect in a biological system. To do this, human monocytes were isolated from peripheral blood (London blood bank) by Ficoll gradient and counter-flow centrifugation. The monocytes were then differentiated with 100 ng/ml M-CSF (Peprotec) for 5 days to produce M2 macrophages.

As shown by the results in FIG. 17A, recombinant human Fc-TNC FBG (1 uM) or LPS (Enzo) (1 ng/ml) was pre-incubated for 30 min at RT with MAb C3 (1, 0.2, and 0.04 uM) or isotype control (Eureka) MAb (1 uM) before being added in triplicate to Human M2 macrophage cultures. After 24 h supernatants were taken and subjected to IL-8, IL-6 and TNF cytokine ELISA (BD Biosciences), n=3. These results show that at 1 uM C3 greatly reduces the pro-inflammatory cytokine release by human M2 macrophages stimulated with TNC-FBG, this reduction is statistically significant for both IL-8 and TNF. As expected C3 has no effect on LPS-induced cytokine release.

FIG. 17B shows results from the experiment where recombinant murine Fc-TNC FBG (1 uM) was pre-incubated for 30 min at RT with MAb C3 (1, 0.2 and 0.04 uM) or isotype control MAb (Eureka) (1 uM) before being added in triplicate to Human M2 macrophage cultures. After 24 h supernatants were taken and subjected to cytokine ELISA. n=3 or over, mean and SEM shown. Again C3 at 1 uM greatly reduced the murine Fc-TNC-FBG-induced cytokine release by macrophages, indicating good cross-species reactivity of the antibody.

To confirm that the FBG-induced cytokine release was induced by the FBG rather than the Fc portion of the protein, a protein where the Fc portion is mutated to be inactive (Fc-Mut-FBG) was used, Anti-TNC-FBG antibodies, B12, C3 (165_13_C3) and A4 (160_01_A4) were also tested for activity against this molecule. Fc-Mut-FBG (1 uM) and C3, A4 or B12 (1 uM) were pre-incubated for 30 min at RT before being added to human M2 macrophage cultures. After 24 h supernatants were taken and subjected to cytokine ELISA. n=3, mean and SEM shown. Results are shown in FIG. 17C. This experiment confirms that Fc-His-FBG-induced cytokine synthesis is not due to the Fc portion signalling through Fc-receptors. Further, it shows that pre-incubation of the related antibodies B12 and A4, as well as C3 greatly reduce FBG-induced cytokine release by human M2 macrophages.

FIG. 18A shows that Monoclonal antibody B12 reduces the production of pro-inflammatory cytokines by primary human macrophages stimulated with human TNC-FBG. In that experiment, recombinant Human tenascin-C FBG (1 uM) was pre-incubated for 30 min at RT with MAb B12 (1, 0.1, 0.01 or 0.001 uM) or isotype control MAb (1 uM) before being added in triplicate to Human M2 macrophage cultures. After 24 h supernatants were taken and subjected to cytokine ELISA, n=1. Here again we see that the B12 antibody pre-incubation reduces FBG-induced cytokine release, in this donor IL-8 gives a minimal response.

FIG. 18B shows that monoclonal antibody C3 produced at laboratory or larger scale show the same level of efficacy in blockade of FBG-induced cytokine synthesis by primary human macrophages.

To take the C3 antibody into animal studies, IgG4 B12 165-13-C3 product was cloned, expressed and purified at a leading contract manufacturing organisation using a commercial GS-CHO expression. cDNAs for the heavy and light chain variable regions were optimised for CHO expression and synthesised (with commercial signal sequences) by Life Technologies prior to cloning into the expression vectors. CHO cells were transfected as pools and the highest expressing pool was taken forward into large-scale shake flask production (22 L—11×2 L in 5 L shake flasks.). Proprietary feeds were administered on day 4 and 8 prior to harvesting the culture on day 12. Material was centrifuged prior to depth filtration and filter sterilisation. Approximately a 5.5 fold concentration of material was performed using tangential flow filtration (30 kDa molecular weight cut off) and the resulting concentrate was filter sterilised again prior to MabSelect SuRe purification. The product was eluted and product was neutralised and then concentrated/diafiltered to approximately 11 mg/mL in 20 mM NaOAc, pH 5.5, 150 mM NaCl. Reduced and non-reduced SDS-PAGE analysis together with size exclusion-HPLC showed material that was highly pure and greater than 98% monomer. Endotoxin was less than 0.1 Eu per mg.

In this experiment the potency of the larger scale antibody batch was compared to the current smaller scale batch. Recombinant Human tenascin-C FBG (1 uM) was pre-incubated for 30 min at RT with MAb C3 (1, 0.2 and 0.04 uM) or isotype control MAb (1 uM) before being added in triplicate to Human M2 macrophage cultures. After 24 h supernatants were taken and subjected to cytokine ELISA. n=1, Ico=laboratory scale Lon=larger scale material. This experiment shows that both batches of antibodies show equal potency in the reduction of FBG-induced cytokine synthesis, i.e. the results are consistent irrespective of production.

EXAMPLE 15—MONOCLONAL ANTIBODY C3 (165_13_C3) REDUCES THE PRODUCTION OF PRO-INFLAMMATORY CYTOKINES BY RA SYNOVIAL FIBROBLASTS STIMULATED WITH HUMAN TNC-FBG

It has been reported that synovial fibroblasts could be an important source of pro-inflammatory cytokine release in RA (R Bucala et al. (1991) Constitutive Production of Mitogenic and Inflammatory Cytokines by Rheumatoid Synovial Fibroblasts. J. Exp. Med. 173:569-574), it was therefore tested whether the C3 antibody also showed similar effects on FBG-induced cytokine release as in the macrophages.

Human RA fibroblasts were grown out of donor RA synovial tissue by digestion of the tissue in RPMI (Lonza) containing 0.5 mg/ml Liberase (Roche) and 0.2 mg/ml DNase (Roche) and incubation at 37° C. for 1-1.5 h. The resulting tissue was pipetted through a 200 μm nylon mesh; the material that did not pass through the mesh was put into a petri-dish containing RPMI with 10% FBS (Life technologies) and 1% pen/strep (Life technologies) and incubated at 37° C. for 5 days. After 5 days synovial fibroblasts grow out of the tissue and the remaining tissue was removed from the RA synovial fibroblast (RASF) culture which was subsequently maintained in DMEM (Lonza) containing 10% FBS and 1% pen/strep. For this experiment RASF were plated out at $1 \times 10^4$ cells/well. Recombinant Human TNC-FBG (1 uM) was pre-incubated for 30 min at RT with MAb C3 (1, 0.2 and 0.04 uM) or isotype control MAb (1 uM) before being added in triplicate to the synovial fibroblast cultures. After 24 h supernatants were taken and subjected to cytokine ELISA. n=1, mean and SEM shown (see FIG. 19).

These results indicate that C3 acts to reduce FBG induced pro-inflammatory cytokine release (both IL-8 and IL-6) in RA synovial fibroblasts, showing that this is a potential mechanism in multiple cell types found in the inflamed RA joint.

EXAMPLE 16—LEVELS OF TENASCIN-C IN RAT MODEL

Expression of tenascin-C in both mouse and rat CIA (collagen-induced arthritis) models was confirmed and disease activity shown to correlate with clinical score.

Figure 20:
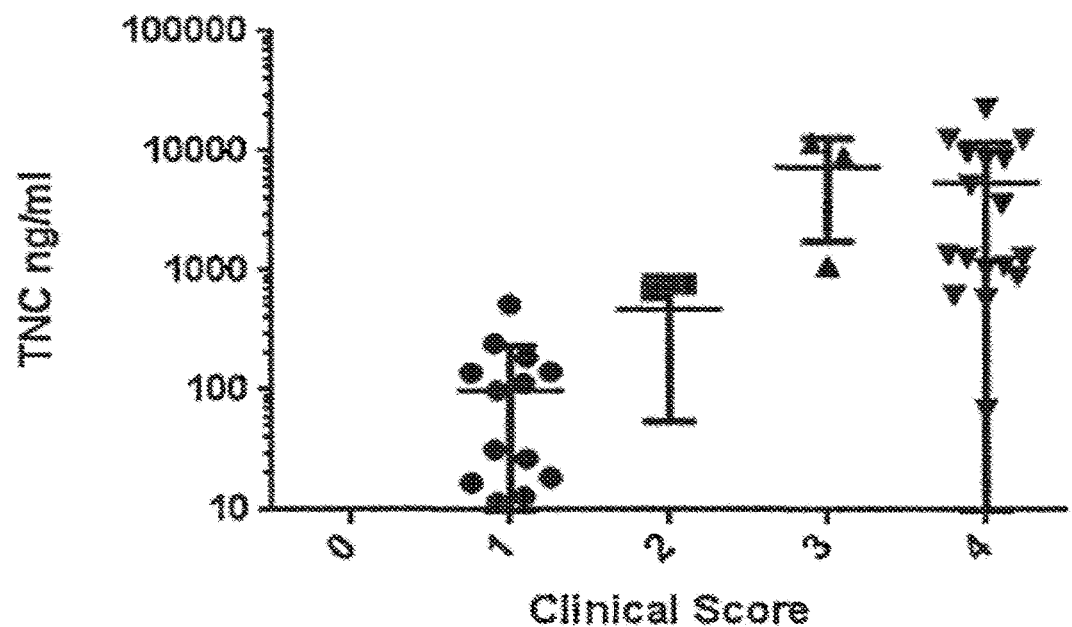

FIG. 20 shows the results of an experiment measuring the levels of tenascin-C in synovial fluid wash-out from the paws of rats at the conclusion of two separate CIA studies (KWS). Tenascin-C levels were measured by ELISA (IBL, large (FN III-B) kit). The measured TNC level was then correlated with the clinical score associated with that paw designated by KWS. This experiment shows that the higher the clinical score for the paw, the higher the level of TNC seen in the synovial fluid from that paw. This indicates that the rat CIA model is a good model for testing of the C3 antibody.

EXAMPLE 17—EVALUATION OF C3 ANTIBODY IN A RAT MODEL OF COLLAGEN-INDUCED ARTHRITIS

IgG4 C3 (165_13_C3) was tested for therapeutic activity in the standard rat collagen induced arthritis model. Adult male Lewis rats were randomly allocated to experimental groups and allowed to acclimatise for one week. On Day 0, animals were administered with 500 μl of a 1 mg/ml emulsion of type II bovine collagen in incomplete Freund's adjuvant (CII/IFA) by intra-dermal injection in the lower back. On Day 7, animals received a second injection of CII/IFA. Injections were performed under gas (isoflurane) anaesthesia. Treatments were administered according to the Administration Schedule shown below in Table 14.

TABLE 14

Administration Schedule

| Group | Treatment | Dose | Route | Regimen | Disease Induction |
|---|---|---|---|---|---|
| 1 | Vehicle (0.9% NaCl) | n/a | IV | Twice weekly*, Day 0-End | Day 0, Day 7: CII/IFA, ID |
| 2 | Control IgG4 [1] | 10 mg/kg | IV | | |
| 3 | IgG4 165_13_C3 | 1 mg/kg | IV | | |
| 4 | IgG4 165_13_C3 | 3 mg/kg | IV | | |
| 5 | IgG4 165_13_C3 | 10 mg/kg | IV | | |

[1] Fully human IgG4 isotype control, preclinical grade, (ET904, Eureka Therapeutics),
n/a: not applicable,
IV: intra-venous injections,
ID: intra-dermal injections,
CII/IFA: Type II collagen and Incomplete Freund's Adjuvant emulsion,
*Day 0, Day 3, Day 7, Day 10, Day 14, Day 17, Day 21 and Day 24

From Day 7 until the end of the experiment, animals were scored three times per week for clinical signs of arthritis by an experimenter blind to the treatments. On Day 0, Day 14, Day 21 and Day 28, paw volumes were measured using a plethysmometer by an experimenter blind to the treatments.

Results

Non-Specific Clinical Observations

From Day 0 until the end of the experiment, animals were checked daily for non-specific clinical signs to include abnormal posture (hunched), abnormal coat condition (pilo-erection) and abnormal activity levels (reduced or increased activity). One animal in Group 6 (ID #6.9, antibody 10 mg/kg-treated) did not recover from the isoflurane anaesthesia on Day 21. Animals did not show any non-specific clinical signs such as abnormal posture, abnormal coat condition and abnormal activity levels. One animal in Group 1 (ID #1.10, vehicle-treated) was culled on Day 22, prior to the end of the experiment, due to the severity of the clinical signs of arthritis.

Clinical Scores

From Day 7 until the end of the experiment, animals were scored three times per week for clinical signs of arthritis to include front and hind limb swelling. The experimenter was blind to the treatments. Each limb was scored on a five-point scale: (0) absence of swelling, (1) slight swelling and/or erythema, (2) mild swelling, (3) moderate swelling and (4) severe swelling and/or joint rigidity. A clinical score was calculated for each animal by adding the score of each limb. Data provided in FIG. 21 were graphed (Mean±SEM for each experimental group) and analysed by two-way ANOVA followed by Dunnett's post-test for multiple comparisons between experimental groups. The last recorded score for the vehicle-treated animal #1.10 was used after Day 22. Data recorded from animal #6.9 were excluded from the analysis. Clinical scores in the vehicle-treated group significantly increased from Day 17 until the end of the experiment on Day 28 when compared to the clinical scores measured on Day 7 ($p<0.0001$). Control IgG4 and IgG4 C3 1 mg/mL dose groups did not induce any significant difference when compared to the vehicle-treated group between Day 7 and the end of the experiment on Day 28. IgG4 C3 administered at 3 mg/kg, induced a significant reduction of the clinical scores when compared to the vehicle-treated group on Day 24 ($p<0.01$). IgG4 C3 administered at 10 mg/kg, induced a significant reduction of the clinical scores when compared to the vehicle-treated group from Day 22 until the end of the experiment on Day 28 ($p<0.01$).

Paw Volumes

On Day 0, Day 14, Day 21 and Day 28, hind paw volumes were measured using a plethysmometer (water-displacement device). Measurements were performed under gas (isoflurane) anaesthesia. The experimenter was blind to the treatment. Right and left hind paw volumes from each animal on each experimental day were averaged. FIG. 22 shows graphed data (Mean±SEM for each experimental group). Data were analysed by two-way ANOVA followed by Dunnett's post-test for multiple comparisons between experimental groups. The last recorded value for the vehicle-treated animal #1.10 was used on Day 28. Data recorded from animal #6.9 were excluded from the analysis.

Paw volumes measured in the vehicle-treated group increased significantly from Day 14 until the end of the experiment on Day 28 when compared to the paw volumes measured on Day 0 ($p<0.01$ on Day 14, $p<0.0001$ on Day 21 and Day 28). The control IgG4 and 1 mg/kg IgG4 C3 dose groups did not induced any difference in hind paw volumes when compared to the vehicle-treated group between Day 0 and Day 28. IgG4 C3 administered at 3 mg/kg induced a significant decrease of the hind paw volumes when compared to the vehicle-treated group on Day 28 ($p<0.01$). IgG4 C3 administered at 10 mg/kg induced a significant decrease of the hind paw volumes when compared to the vehicle-treated group on Day 21 ($p<0.05$) and Day 28 ($p<0.01$).

CONCLUSIONS

The test antibody, IgG4 C3 (165_13_C3), when administered at 3 mg/kg or 10 mg/kg, significantly reduced the severity of the clinical signs.

REFERENCES

1. Smolen, J. S. & Maini, R. N. Interleukin-6: a new therapeutic target. *Arthritis Res Ther* 8 Suppl 2, S5 (2006).
2. Williams, R. O., Paleolog, E. & Feldmann, M. Cytokine inhibitors in rheumatoid arthritis and other autoimmune diseases. *Curr Opin Pharmacol* 7, 412-417 (2007).
3. Brentano, F., Kyburz, D., Schorr, O., Gay, R. & Gay, S. The role of Toll-like receptor signalling in the pathogenesis of arthritis. *Cell Immunol* 233, 90-96 (2005).

4. O'Neill, L. A. Primer: Toll-like receptor signaling pathways-what do rheumatologists need to know? *Nat Clin Pract Rheumatol* (2008).
5. Matzinger, P. The danger model: a renewed sense of self. *Science* 296, 301-305 (2002).
6. Bianchi, M. E. DAMPs, PAMPs and alarmins: all we need to know about danger. *J Leukoc Biol* 81, 1-5 (2007).
7. Gordon, S. Pattern recognition receptors: doubling up for the innate immune response. *Cell* 111, 927-930 (2002).
8. Medzhitov, R. & Janeway, C. A., Jr. Decoding the patterns of self and nonself by the innate immune system. *Science* 296, 298-300 (2002).
9. Radstake, T. R., et al. Expression of toll-like receptors 2 and 4 in rheumatoid synovial tissue and regulation by proinflammatory cytokines interleukin-12 and interleukin-18 via interferon-gamma. *Arthritis Rheum* 50, 3856-3865 (2004).
10. Roelofs, M. F., et al. The expression of toll-like receptors 3 and 7 in rheumatoid arthritis synovium is increased and costimulation of toll-like receptors 3, 4, and ⅞ results in synergistic cytokine production by dendritic cells. *Arthritis Rheum* 52, 2313-2322 (2005).
11. Sacre, S. M., et al. The Toll-like receptor adaptor proteins MyD88 and Mal/TIRAP contribute to the inflammatory and destructive processes in a human model of rheumatoid arthritis. *Am J Pathol* 170, 518-525 (2007).
12. Choe, J. Y., Crain, B., Wu, S. R. & Corr, M. Interleukin 1 receptor dependence of serum transferred arthritis can be circumvented by toll-like receptor 4 signaling. *J Exp Med* 197, 537-542 (2003).
13. Lee, E. K., Kang, S. M., Paik, D. J., Kim, J. M. & Youn, J. Essential roles of Toll-like receptor-4 signaling in arthritis induced by type II collagen antibody and LPS. *Int Immunol* 17, 325-333 (2005).
14. Abdollahi-Roodsaz, S., et al. Inhibition of Toll-like receptor 4 breaks the inflammatory loop in autoimmune destructive arthritis. *Arthritis Rheum* 56, 2957-2967 (2007).
15. Vanags, D., et al. Therapeutic efficacy and safety of chaperonin 10 in patients with rheumatoid arthritis: a double-blind randomised trial. *Lancet* 368, 855-863 (2006).
16. Chiquet-Ehrismann, R. & Chiquet, M. Tenascins: regulation and putative functions during pathological stress. *J Pathol* 200, 488-499 (2003).
17. Cutolo, M., Picasso, M., Ponassi, M., Sun, M. Z. & Balza, E. Tenascin and fibronectin distribution in human normal and pathological synovium. *J Rheumatol* 19, 1439-1447 (1992).
18. McCachren, S. S. & Lightner, V. A. Expression of human tenascin in synovitis and its regulation by interleukin-1. *Arthritis Rheum* 35, 1185-1196 (1992).
19. Salter, D. M. Tenascin is increased in cartilage and synovium from arthritic knees. *Br J Rheumatol* 32, 780-786 (1993).
20. Chevalier, X., Groult, N., Larget-Piet, B., Zardi, L. & Hornebeck, W. Tenascin distribution in articular cartilage from normal subjects and from patients with osteoarthritis and rheumatoid arthritis. *Arthritis Rheum* 37, 1013-1022 (1994).
21. Hasegawa, M., et al. Expression of large tenascin-C splice variants in synovial fluid of patients with rheumatoid arthritis. *J Orthop Res* 25, 563-568 (2007).
22. Orend, G. Potential oncogenic action of tenascin-C in tumorigenesis. *Int J Biochem Cell Biol* 37, 1066-1083 (2005).
23. Brackertz, D., Mitchell, G. F. & Mackay, I. R. Antigen-induced arthritis in mice. I. Induction of arthritis in various strains of mice. *Arthritis Rheum* 20, 841-850 (1977).
24. Brennan, F. M., Chantry, D., Jackson, A., Maini, R. & Feldmann, M. Inhibitory effect of TNF alpha antibodies on synovial cell interleukin-1 production in rheumatoid arthritis. *Lancet* 2, 244-247 (1989).
25. Smiley, S. T., King, J. A. & Hancock, W. W. Fibrinogen stimulates macrophage chemokine secretion through toll-like receptor 4. *J Immunol* 167, 2887-2894 (2001).
26. Fitzgerald, K. A., Rowe, D. C. & Golenbock, D. T. Endotoxin recognition and signal transduction by the TLR4/MD2-complex. *Microbes Infect* 6, 1361-1367 (2004).
27. Jiang, Z., et al. CD14 is required for MyD88-independent LPS signaling. *Nat Immunol* 6, 565-570 (2005).
28. Coats, S. R., Do, C. T., Karimi-Naser, L. M., Braham, P. H. & Darveau, R. P. Antagonistic lipopolysaccharides block *E. coli* lipopolysaccharide function at human TLR4 via interaction with the human MD-2 lipopolysaccharide binding site. *Cell Microbiol* 9, 1191-1202 (2007).
29. Siri, A., et al. Human tenascin: primary structure, pre-mRNA splicing patterns and localization of the epitopes recognized by two monoclonal antibodies. *Nucleic Acids Res* 19, 525-531 (1991).
30. Gondokaryono, S. P., et al. The extra domain A of fibronectin stimulates murine mast cells via toll-like receptor 4. *J Leukoc Biol* 82, 657-665 (2007).
31. Taylor, K. R., et al. Recognition of hyaluronan released in sterile injury involves a unique receptor complex dependent on Toll-like receptor 4, CD44, and MD-2. *J Biol Chem* 282, 18265-18275 (2007).
32. Kim, H. M., et al. Crystal structure of the TLR4-MD-2 complex with bound endotoxin antagonist Eritoran. *Cell* 130, 906-917 (2007).
33. Schaefer, L., et al. The matrix component biglycan is proinflammatory and signals through Toll-like receptors 4 and 2 in macrophages. *J Clin Invest* 115, 2223-2233 (2005).
34. Foell, D., Wittkowski, H. & Roth, J. Mechanisms of disease: a 'DAMP' view of inflammatory arthritis. *Nat Clin Pract Rheumatol* 3, 382-390 (2007).
35. Taniguchi, N., et al. High mobility group box chromosomal protein 1 plays a role in the pathogenesis of rheumatoid arthritis as a novel cytokine. *Arthritis Rheum* 48, 971-981 (2003).
36. Pullerits, R., et al. High mobility group box chromosomal protein 1, a DNA binding cytokine, induces arthritis. *Arthritis Rheum* 48, 1693-1700 (2003).
37. Kokkola, R., et al. Successful treatment of collagen-induced arthritis in mice and rats by targeting extracellular high mobility group box chromosomal protein 1 activity. *Arthritis Rheum* 48, 2052-2058 (2003).
38. Gutowski, N. J., Newcombe, J. & Cuzner, M. L. Tenascin-R and C in multiple sclerosis lesions: relevance to extracellular matrix remodelling. *Neuropathol Appl Neurobiol* 25, 207-214 (1999).
39. Amin, K., et al. Inflammation and structural changes in the airways of patients with primary Sjogren's syndrome. *Respir Med* 95, 904-910 (2001).
40. Loots, M. A., et al. Differences in cellular infiltrate and extracellular matrix of chronic diabetic and venous ulcers versus acute wounds. *J Invest Dermatol* 111, 850-857 (1998).
41. Lange, K., et al. Endothelin receptor type B counteracts tenascin-C-induced endothelin receptor type A-dependent focal adhesion and actin stress fiber disorganization. *Cancer Res* 67, 6163-6173 (2007).

42. Saga, Y., Yagi, T., Ikawa, Y., Sakakura, T. & Aizawa, S. Mice develop normally without tenascin. *Genes Dev* 6, 1821-1831 (1992).

43. Hoshino, K., et al. Cutting edge: Toll-like receptor 4 (TLR4)-deficient mice are hyporesponsive to lipopolysaccharide: evidence for TLR4 as the Lps gene product. *J Immunol* 162, 3749-3752 (1999).

44. Takeuchi, O., et al. Differential roles of TLR2 and TLR4 in recognition of gram-negative and gram-positive bacterial cell wall components. *Immunity* 11, 443-451 (1999).

45. Keystone, E. C., Schorlemmer, H. U., Pope, C. & Allison, A. C. Zymosan-induced arthritis: a model of chronic proliferative arthritis following activation of the alternative pathway of complement. *Arthritis Rheum* 20, 1396-1401 (1977).

46. van Lent, P. L., et al. Fcgamma receptors directly mediate cartilage, but not bone, destruction in murine antigen-induced arthritis: uncoupling of cartilage damage from bone erosion and joint inflammation. *Arthritis Rheum* 54, 3868-3877 (2006).

47. Foxwell, B., et al. Efficient adenoviral infection with IkappaB alpha reveals that macrophage tumor necrosis factor alpha production in rheumatoid arthritis is NF-kappaB dependent. *Proc Natl Acad Sci USA* 95, 8211-8215 (1998).

48. Kurt-Jones, E. A., et al. Use of murine embryonic fibroblasts to define Toll-like receptor activation and specificity. *J Endotoxin Res* 10, 419-424 (2004).

49. Todaro, G. J. & Green, H. Quantitative studies of the growth of mouse embryo cells in culture and their development into established lines. *J Cell Biol* 17, 299-313 (1963).

50. Butler, D. M., Malfait, A. M., Maini, R. N., Brennan, F. M. & Feldmann, M. Anti-IL-12 and anti-TNF antibodies synergistically suppress the progression of murine collagen-induced arthritis. *Eur J Immunol* 29, 2205-2212 (1999).

51. Ho, S. N., Hunt, H. D., Horton, R. M., Pullen, J. K. & Pease, L. R. Site-directed to mutagenesis by overlap extension using the polymerase chain reaction. *Gene* 77, 51-59 (1989).

52. Clark, R. A., Erickson, H. P. & Springer, T. A. Tenascin supports lymphocyte rolling. *J Cell Biol* 137, 755-765 (1997).

53. El-Karef, A., et al. Deficiency of tenascin-C attenuates liver fibrosis in immune-mediated chronic hepatitis in mice. *J Pathol* 211, 86-94 (2007).

54. Loike, J. D., Cao, L., Budhu, S., Hoffman, S. & Silverstein, S. C. Blockade of alpha 5 beta 1 integrins reverses the inhibitory effect of tenascin on chemotaxis of human monocytes and polymorphonuclear leukocytes through three-dimensional gels of extracellular matrix proteins. *J Immunol* 166, 7534-7542 (2001).

55. Talts, J. F., Wirl, G., Dictor, M., Muller, W. J. & Fassler, R. tenascin-C modulates tumor stroma and monocyte/macrophage recruitment but not tumor growth or metastasis in a mouse strain with spontaneous mammary cancer. *J Cell Sci* 112 (Pt 12), 1855-1864 (1999).

56. Jones (2000) *Matrix Biol.,* 19, 581-96

57. Harandl (2009) *Expert Review of Vaccines,* 8, 293-298

58. McIntyre (2006) *BMC Biotechnol.* 6: 1

59. Paddison (2002) *Genes Dev.* 16 (8): 948-58

60. Andreakos (2004) *Blood,* 103, 2229-37

61. Goh, F. G., Piccinini, A. M., Krausgruber, T., Udalova, I. A. & Midwood, K. S. Transcriptional regulation of the endogenous danger signal tenascin-C: a novel autocrine loop in inflammation. *J Immunol* 184, 2655-2662 (2010).

62. Midwood, K. et al. Tenascin-C is an endogenous activator of Toll-like receptor 4 that is essential for maintaining inflammation in arthritic joint disease. *Nat Med* 15, 774-780 (2009).

63. LaFleur, D. W. et al. Aortic smooth muscle cells interact with tenascin-C through its fibrinogen-like domain. *J Biol Chem* 272, 32798-32803 (1997).

64. Taylor, P. C. & Feldmann, M. Anti-TNF biologic agents: still the therapy of choice for rheumatoid arthritis. *Nat Rev Rheumatol* 5, 578-582 (2009).

65. Yokoyama, K., Erickson, H. P., Ikeda, Y. & Takada, Y. Identification of amino acid sequences in fibrinogen gamma-chain and tenascin C C-terminal domains critical for binding to integrin alpha vbeta 3. *J Biol Chem* 275, 16891-16898 (2000).

66. Angal S, et al (1993) A single amino acid substitution abolishes the heterogeneity of chimeric mouse/human (IgG4) antibody. Mol. Immunology 30(1): 105-108.

67. Chapple S D, et al (2006) Multiplexed expression and screening for recombinant protein production in mammalian cells. BMC Biotechnol. 6:49.

68. Dyson M R, et al (2011) Mapping protein interactions by combining antibody affinity maturation and mass spectrometry. Anal Biochem. 417(1): 25-35.

69. Falk R, et al (2012) Generation of anti-Notch antibodies and their application in blocking Notch signalling in neural stem cells. Methods 58(1): 69-78.

70. Fellouse F A, and Sidhu, S S (2007) Making antibodies in bacteria. Making and Using Antibodies (G. C. Howard & M. R. Kaser, Eds.), pp 157-180, CRC Press, Boca Raton, Fla.

71. Hawkins R E, Russell S J, and Winter, G (1992) Selection of phage antibodies by binding affinity. Mimicking affinity maturation. J. Mol. Biol. 226: 889-896.

72. Kunkel T A, Roberts J D, and Zakour R A (1987) Rapid and efficient site-specific mutagenesis without phenotypic selection. Meth. Enzymol. 154: 367-382.

73. Martin C D, et al (2006) A simple vector system to improve performance and utilisation of recombinant antibodies. BMC Biotechnol. 6:46.

74. Schofield D J, et al (2007) Application of phage display to high throughput antibody generation and characterization. Genome Biol. 8(11): R254.

75. Sidhu S S, and Weiss G A (2004) Constructing phage display libraries by oligonucleotide-directed mutagenesis. Phage Display: a Practical Approach.

76. Zahnd C, Sarkar C A, and Plückthun A (2010) Computational analysis of off-rate selection experiments to optimize affinity maturation by directed evolution. Protein Eng. Des. Sel. 23: 175-184.

77. Ehrenmann F., Kaas Q. and Lefranc M. P. Nucleic Acids Res., 38, D301-307 (2010).

78. Page et al. (2012). Arthritis Research & Therapy 14: R260

Embodiments of the invention will now be described in the following numbered paragraphs:

1. An antibody or antigen-binding fragment, derivative or variant thereof which is capable of binding to the FBG domain of tenascin-C, wherein the antibody or antigen-binding fragment, derivative or variant thereof comprises: one or more sequences selected from SEQ ID NOs: 1-8, 48-91 and 112-114; and/or one or more sequences selected from SEQ ID NOs: 5, 9-15, 30-47 and 115-118; and/or one or more sequences selected from SEQ ID NOs: 5, 13, 16-21 and 119-121; and/or one or more sequences selected from SEQ ID NOs: 22-29 and 122-123.

2. The antibody or antigen-binding fragment, derivative or variant thereof of paragraph 1 wherein the antibody or antigen-binding fragment, derivative or variant thereof comprises: one or more CDR sequences selected from SEQ ID NOs: 1-3, 5-7, 48, 50, 52, 54, 56, 58, 60, 62, 64, 66, 68, 70, 72, 74, 76, 78, 80, 82, 84, 86, 88, 90 and 114; and/or one or more CDR sequences selected from SEQ ID NOs: 9-11, 5, 13-14, 30, 32, 34, 36, 38, 40, 42, 44, 46, 116 and 118; and/or one or more CDR sequences selected from SEQ ID NOs 16-18, 5, 13, 20 and 121; and/or one or more CDR sequences selected from SEQ ID NOs 22-24 and 26-28.

3. The antibody or antigen-binding fragment, derivative or variant thereof of paragraph 1 or 2 wherein the antibody or antigen-binding fragment, derivative or variant thereof comprises: one or more CDR3 sequences selected from SEQ ID NOs: 3, 7, 48, 50, 52, 54, 56, 58, 60, 62, 64, 66, 68, 70, 72, 74, 76, 78, 80, 82, 84, 86, 88 and 90; and/or one or more CDR3 sequences selected from SEQ ID NOs: 11, 14, 30, 32, 34, 36, 38, 40, 42, 44 and 46; and/or one or more CDR3 sequences selected from SEQ ID NOs 18 and 20; and/or one or more CDR3 sequences selected from SEQ ID NOs 24 and 28.

4. An antibody or antigen-binding fragment, derivative or variant thereof as paragraphed in paragraph 3 wherein the antibody or antigen-binding fragment, derivative or variant thereof comprises: one or more CDR3 sequences selected from SEQ ID NOs: 3, 54, 66 and 70; and/or one or more CDR3 sequences selected from SEQ ID NOs: 7, 76, 88 and 90; and/or one or more CDR3 sequences selected from SEQ ID NOs: 11, 30, 34 and 36.

5. An antibody or antigen-binding fragment, derivative or variant thereof as paragraphed in paragraph 1 wherein the antibody or antigen-binding fragment, derivative or variant thereof comprises: a VH CDR3 sequence selected from SEQ ID NOs: 3, 48, 50, 52, 54, 56, 58, 60, 62, 64, 66, 68 and 70; a VH CDR3 sequence selected from SEQ ID NOs: 3, 54, 66 and 70; or a VH CDR3 sequence selected from SEQ ID NOs: 3 and 54.

6. An antibody or antigen-binding fragment, derivative or variant thereof as paragraphed in paragraph 1 or 5 wherein the antibody or antigen-binding fragment, derivative or variant thereof comprises: a VL CDR3 sequence selected from SEQ ID NOs: 7, 72, 74, 76, 78, 80, 82, 84, 86, 88 and 90; a VL CDR3 sequence selected from SEQ ID NOs: 7, 76, 88 and 90; or a VL CDR3 sequence of SEQ ID NO 7.

7. An antibody or antigen-binding fragment, derivative or variant thereof as paragraphed in paragraph 1 wherein the antibody or antigen-binding fragment, derivative or variant thereof comprises a VH sequence comprising the sequence of SEQ ID NO: 4 or 112, and wherein the VH sequence comprises a CDR3 sequence which is replaced with: a VH CDR3 sequence selected from SEQ ID NOs: 48, 50, 52, 54, 56, 58, 60, 62, 64, 66, 68 and 70; a VH CDR3 sequence selected from SEQ ID NOs: 54, 66 and 70; or a VH CDR3 sequence of SEQ ID NO: 54.

8. An antibody or antigen-binding fragment, derivative or variant thereof as paragraphed in paragraph 1 or 7 wherein the antibody or antigen-binding fragment, derivative or variant thereof comprises a VL sequence comprising the sequence of SEQ ID NO: 8 or 113, and wherein the VL sequence comprises a CDR3 sequence which is replaced with: a VL CDR3 sequence selected from SEQ ID NOs: 72, 74, 76, 78, 80, 82, 84, 86, 88 and 90; or a VL CDR3 sequence selected from SEQ ID NOs: 76, 88 and 90.

9. An antibody or antigen-binding fragment, derivative or variant thereof as paragraphed in paragraph 1 wherein the antibody or antigen-binding fragment, derivative or variant thereof comprises: a VH CDR3 sequence selected from SEQ ID NOs: 11, 30, 32, 34, 36, 38, 40, 42, 44 and 46; a VH CDR3 sequence selected from SEQ ID NOs: 11, 30, 34 and 36; or a VH CDR3 sequence selected from SEQ ID NOs 11, 30 and 36.

10. An antibody or antigen-binding fragment, derivative or variant thereof as paragraphed in paragraph 1 wherein the antibody or antigen-binding fragment, derivative or variant thereof comprises a VL sequence comprising the sequence of SEQ ID NO: 15 or 117.

11. An antibody or antigen-binding fragment, derivative or variant thereof as paragraphed in paragraph 1 or 10 wherein the antibody or antigen-binding fragment, derivative or variant thereof comprises a VH sequence comprising the sequence of SEQ ID NO: 12 or 115, and wherein the VH sequence comprises a CDR3 sequence which is replaced with: a VH CDR3 sequence selected from SEQ ID NOs: 30, 32, 34, 36, 38, 40, 42, 44 and 46; a VH CDR3 sequence selected from SEQ ID NOs: 30, 34 and 36; or a VH CDR3 sequence selected from SEQ ID NOs 30 and 36.

12. The antibody or antigen-binding fragment, derivative or variant thereof of paragraph 1 wherein the antibody or antigen-binding fragment, derivative or variant thereof comprises: a VL CDR3 sequence of SEQ ID NO: 7 and a VH CDR3 sequence selected from SEQ ID NOs: 3 and 48-70; or comprises a VH CDR3 sequence of SEQ ID NO: 3 and a VL CDR3 sequence selected from SEQ ID NOs: 7 and 72-90; or comprises a VL CDR3 sequence of SEQ ID NO: 14 and a VH CDR3 sequence selected from SEQ ID NOs: 11 and 30-46; or comprises a VH CDR3 sequence of SEQ ID NO: 18 and a VL CDR3 sequence of SEQ ID NO: 20; or comprises a VH CDR3 sequence of SEQ ID NO: 24 and a VL CDR3 sequence of SEQ ID NO: 28.

13. The antibody or antigen-binding fragment, derivative or variant thereof of paragraph 1 wherein the antibody or antigen-binding fragment, derivative or variant thereof comprises: at least one CDR sequence selected from SEQ ID NOs: 1-3, and 5-7; or at least one CDR sequence selected from SEQ ID NOs: 1, 2, 48 and 5-7; or at least one CDR sequence selected from SEQ ID NOs: 1, 2, 50 and 5-7; or at least one CDR sequence selected from SEQ ID NOs: 1, 2, 52 and 5-7; or at least one CDR sequence selected from SEQ ID NOs: 1, 2, 54 and 5-7; or at least one CDR sequence selected from SEQ ID NOs: 1, 2, 56 and 5-7; or at least one CDR sequence selected from SEQ ID NOs: 1, 2, 58 and 5-7; or at least one CDR sequence selected from SEQ ID NOs: 1, 2, 60 and 5-7; or at least one CDR sequence selected from SEQ ID NOs: 1, 2, 62 and 5-7; or at least one CDR sequence selected from SEQ ID NOs: 1, 2, 64 and 5-7; or at least one CDR sequence selected from SEQ ID NOs: 1, 2, 66 and 5-7; or at least one CDR sequence selected from SEQ ID NOs: 1, 2, 68 and 5-7; or at least one CDR sequence selected from SEQ ID NOs: 1, 2, 70 and 5-7; or at least one CDR sequence selected from SEQ ID NOs: 1-3, 5, 6 and 72; or at least one CDR sequence selected from SEQ ID NOs: 1-3, 5-6 and 74; or at least one CDR sequence selected from SEQ ID NOs: 1-3, 5, 6 and 76; or at least one CDR sequence selected from SEQ ID NOs: 1-3, 5, 6 and 78; or at least one CDR sequence selected from SEQ ID NOs: 1-3, 5, 6 and 80; or at least one CDR sequence selected from SEQ ID NOs: 1-3, 5, 6 and 82; or at least one CDR sequence selected from SEQ ID NOs: 1-3, 5, 6 and 84; or at least one CDR sequence selected from SEQ ID NOs: 1-3, 5, 6 and 86; or at least one CDR sequence selected from SEQ ID NOs: 1-3, 5, 6 and 88; or at least one CDR sequence selected from SEQ ID NOs: 1-3, 5, 6 and 90; or at least one CDR selected from SEQ ID NOs: 1-3, 5, 7 and 114; or at least one CDR sequence selected from SEQ ID NOs: 9-11 and 5, 13 and 14; or at least one CDR sequence selected from SEQ ID NOs: 9, 10, 30, 5, 13 and 14; or at least one CDR sequence selected from SEQ ID NOs: 9, 10, 32, 5, 13 and 14; or at least one CDR sequence selected from SEQ ID NOs: 9, 10, 34, 5, 13 and 14; or at least one CDR sequence selected from SEQ ID NOs: 9, 10, 36, 5, 13 and 14; or at least one CDR sequence selected from SEQ ID NOs: 9, 10, 38, 5, 13 and 14; or at least one CDR sequence selected from SEQ ID NOs: 9, 10, 40, 5, 13 and 14; or at least one CDR sequence selected from SEQ ID NOs: 9, 10, 42, 5, 13 and 14; or at least one CDR sequence selected from SEQ ID NOs: 9, 10, 44, 5, 13 and 14; or at least one CDR sequence selected from SEQ ID NOs: 9, 10, 46, 5, 13 and 14; or at least one CDR selected from SEQ ID NOs: 9, 11, 116, 5, 14 and 118; or at least one CDR sequence selected from SEQ ID NOs: 16-18 and 5, 13 and 20; or at least one CDR sequence selected from SEQ ID NOs: 16-18 and 5, 121 and 20; or at least one CDR sequence selected from SEQ ID NOs: 22-24 and 26-28.

14. An antibody or antigen-binding fragment, derivative or variant thereof as paragraphed in paragraph 3 wherein the antibody or antigen-binding fragment, derivative or variant thereof comprises: a VH CDR3 sequence selected from SEQ ID NOs: 3 and 54; or a VH CDR3 sequence selected from SEQ ID NOs: 11, 30 and 36.

15. An antibody or antigen-binding fragment, derivative or variant thereof as paragraphed in paragraph 1 wherein the antibody or antigen-binding fragment, derivative or variant thereof comprises VH and/or VL sequences comprising: one or more sequences selected from SEQ ID NOs: 4, 8, 49, 51, 53, 55, 57, 59, 61, 63, 65, 67, 69, 71, 73, 75, 77, 79, 81, 83, 85, 87, 89, 91, 112 and 113; and/or one or more sequences selected from SEQ ID NOs 12, 15, 31, 33, 35, 37, 39, 41, 43, 45, 47, 115 and 117; and/or one or more sequences selected from SEQ ID NOs 19, 21, 119 and 120; and/or one or more sequences selected from SEQ ID NOs 25, 29, 122 and 123.

16. The antibody or antigen-binding fragment, derivative or variant thereof of paragraph 15 wherein the VH sequence is selected from SEQ ID NOs: 4, 49, 51, 53, 55, 57, 59, 61, 63, 65, 67, 69, 71 and 112; and/or selected from SEQ ID NOs 12, 31, 33, 35, 37, 39, 41, 43, 45, 47 and 115; and/or selected from SEQ ID NOs: 19 and 119; and/or selected from: SEQ ID NOs 25 and 122.

17. The antibody or antigen-binding fragment, derivative or variant thereof of paragraphs 15 or 16 wherein the VL sequence is selected from SEQ ID NOs: 8, 73, 75, 77, 79, 81, 83, 85, 87, 89, 91 and 113; and/or is selected from SEQ ID NOs: 15 and 117; and/or is selected from SEQ ID NOs: 21 and 120; and/or is selected from SEQ ID NOs: 29 and 123.

18. The antibody or antigen-binding fragment, derivative or variant thereof of paragraph 1 wherein the antibody or antigen-binding fragment, derivative or variant thereof comprises both a VH and a VL sequence comprising the sequences of a VH and VL sequence pair selected from the sequence pairs: SEQ ID NOs 4 and 8; SEQ ID NOs 49 and 8; SEQ ID NOs 51 and 8; SEQ ID NOs 53 and 8; SEQ ID NOs 55 and 8; SEQ ID NOs 57 and 8; SEQ ID NOs 59 and 8; SEQ ID NOs 61 and 8; SEQ ID NOs 63 and 8; SEQ ID NOs 65 and 8; SEQ ID NOs 67 and 8; SEQ ID NOs 69 and 8; SEQ ID NOs 71 and 8; SEQ ID NOs 112 and 8; SEQ ID NOs 4 and 113; SEQ ID NOs 49 and 113; SEQ ID NOs 51 and 113; SEQ ID NOs 53 and 113; SEQ ID NOs 55 and 113; SEQ ID NOs 57 and 113; SEQ ID NOs 59 and 113; SEQ ID NOs 61 and 113; SEQ ID NOs 63 and 113; SEQ ID NOs 65 and 113; SEQ ID NOs 67 and 113; SEQ ID NOs 69 and 113; SEQ ID NOs 71 and 113; SEQ ID NOs 4 and 73; SEQ ID NOs 4 and 75; SEQ ID NOs 4 and 77; SEQ ID NOs 4 and 79; SEQ ID NOs 4 and 81; SEQ ID NOs 4 and 83; SEQ ID NOs 4 and 85; SEQ ID NOs 4 and 87; SEQ ID NOs 4 and 89; SEQ ID NOs and 4 and 91; SEQ ID NOs 112 and 73; SEQ ID NOs 112 and 75; SEQ ID NOs 112 and 77; SEQ ID NOs 112 and 79; SEQ ID NOs 112 and 81; SEQ ID NOs 112 and 83; SEQ ID NOs 112 and 85; SEQ ID NOs 112 and 87; SEQ ID NOs 112 and 89; SEQ ID NOs and 112 and 91; SEQ ID NOs and 112 and 113; or selected from the sequence pairs: SEQ ID NOs 12 and 15; SEQ ID NOs 31 and 15; SEQ ID NOs 33 and 15; SEQ ID NOs 35 and 15; SEQ ID NOs 37 and 15; SEQ ID NOs 39 and 15; SEQ ID NOs 41 and 15; SEQ ID NOs 43 and 15; SEQ ID NOs 45 and 15; SEQ ID NOs 47 and 15; SEQ ID NOs 115 and 15; SEQ ID NOs 12 and 117; SEQ ID NOs 31 and 117; SEQ ID NOs 33 and 117; SEQ ID NOs 35 and 117; SEQ ID NOs 37 and 117; SEQ ID NOs 39 and 117; SEQ ID NOs 41 and 117; SEQ ID NOs 43 and 117; SEQ ID NOs 45 and 117; SEQ ID NOs 47 and 117; and SEQ ID NOs 115 and 117; or selected from the sequence pairs: SEQ ID NOs 19 and 21; SEQ ID NOs 19 and 120; SEQ ID NOs 119 and 21; and SEQ ID NOs 119 and 120; or selected from the sequence pairs: SEQ ID NOs 25 and 29; SEQ ID NOs 25 and 123; SEQ ID NOs 122 and 29; and SEQ ID NOs 122 and 123.

19. The antibody or antigen-binding fragment, derivative or variant thereof of paragraph 1 comprising a VH sequence comprising a sequence selected from SEQ ID NOs: 4, 49, 51, 53, 55, 57, 59, 61, 63, 65, 67, 69, 71 and 112.

20. The antibody or antigen-binding fragment, derivative or variant thereof of paragraph 1 or 19 comprising a VL sequence comprising a sequence selected from SEQ ID NOs: 8, 73, 75, 77, 79, 81, 83, 85, 87, 89, 91 and 113.

21. The antibody or antigen-binding fragment, derivative or variant thereof of paragraph 1 or 20 comprising a VH sequence comprising the sequence of SEQ ID NO: 4 or 112.

22. The antibody or antigen-binding fragment, derivative or variant thereof of paragraph 1 comprising a VH sequence comprising the sequence of SEQ ID NO: 55.

23. The antibody or antigen-binding fragment, derivative or variant thereof of paragraph 1 comprising a VH sequence comprising a sequence selected from SEQ ID NOs: 12, 31, 33, 35, 37, 39, 41, 43, 45, 47 and 115.

24. The antibody or antigen-binding fragment, derivative or variant thereof of paragraph 1 comprising a VH sequence comprising the sequence of SEQ ID NO: 12 or 115.

25. The antibody or antigen-binding fragment, derivative or variant thereof of paragraph 1 comprising a VH sequence comprising the sequence of SEQ ID NO: 31.

26. The antibody or antigen-binding fragment, derivative or variant thereof of paragraph 1 comprising a VH sequence comprising the sequence of SEQ ID NO: 37.

27. The antibody or antigen-binding fragment, derivative or variant thereof of paragraph 19 or 21-22 additionally comprising a VL sequence comprising the sequence of SEQ ID NO: 8 or 113.

28. The antibody or antigen-binding fragment, derivative or variant thereof of any of paragraphs 23-26 additionally comprising a VL sequence comprising the sequence of SEQ ID NO: 15 or 117.

29. The antibody or antigen-binding fragment, derivative or variant thereof of paragraph 1 comprising: a VH sequence comprising the sequence of SEQ ID NO: 37; and a VL sequence comprising the sequence of SEQ ID NO: 15.

30. An antibody or antigen-binding fragment, derivative or variant thereof according to any of the preceding paragraphs wherein the antibody or antigen-binding fragment, derivative or variant thereof is a polyclonal or a monoclonal antibody or antigen-binding fragment, derivative or variant thereof.

31. An antibody or antigen-binding fragment, derivative or variant thereof according to paragraph 30 wherein the antibody or antigen-binding fragment, derivative or variant thereof is selected from the group consisting of Fv fragments, scFv fragments, Fab, single variable domains and domain antibodies.

32. An antibody or antigen-binding fragment, derivative or variant thereof as paragraphed in any previous paragraph wherein the antibody or antigen-binding fragment, derivative or variant thereof is humanised.

33. An antibody or antigen-binding fragment, derivative or variant thereof as paragraphed in any previous paragraph wherein the antibody or antigen-binding fragment, derivative or variant thereof has specificity for tenascin-C or a domain thereof.

34. An antibody or antigen-binding fragment, derivative or variant thereof as paragraphed in any of paragraph 33 wherein the antibody or antigen-binding fragment, derivative or variant thereof has specificity for the FBG domain of tenascin-C.

35. An antibody or antigen-binding fragment, derivative or variant thereof as paragraphed in any of paragraph 34 wherein the antibody or antigen-binding fragment, derivative or variant thereof neutralises the activity of the FBG domain of tenascin-C.

36. An antibody or antigen-binding fragment, derivative or variant thereof as paragraphed in any previous paragraph wherein said tenascin-C is citrullinated tenascin-C.

37. An antibody or antigen-binding fragment, derivative or variant thereof as paragraphed in paragraph 36 wherein the citrullinated tenascin-C is citrullinated at the FBG domain.

38. An antibody or antigen-binding fragment, derivative or variant thereof as paragraphed in paragraph 37 wherein the citrullinated tenascin-C is citrullinated at only the FBG domain.

39. An antibody or antigen-binding fragment, derivative or variant thereof as paragraphed in any previous paragraph wherein the antibody or antigen-binding fragment, derivative or variant thereof is for modulation of a chronic inflammatory response.

40. The antibody or antigen-binding fragment, derivative or variant thereof as paragraphed in paragraph 39 wherein the antibody or antigen-binding fragment, derivative or variant thereof modulates the biological activity of tenascin-C.

41. An antibody or antigen-binding fragment, derivative or variant thereof as paragraphed in paragraph 40 wherein the agent modulates the biological activity of tenascin-C by altering the transcription, translation and/or binding properties of tenascin-C.

42. An antibody or antigen-binding fragment, derivative or variant thereof as paragraphed in any previous paragraph wherein the antibody or antigen-binding fragment, derivative or variant thereof down-regulates the biological activity of tenascin-C.

43. An antibody or antigen-binding fragment, derivative or variant thereof as paragraphed in any previous paragraph wherein the antibody or antigen-binding fragment, derivative or variant thereof up-regulates the biological activity of tenascin-C.

44. An antibody or antigen-binding fragment, derivative or variant thereof as paragraphed in any previous paragraph wherein the antibody or antigen-binding fragment, derivative or variant thereof is an inhibitor of transcription, translation and/or the binding properties of tenascin-C.

45. An antibody or antigen-binding fragment, derivative or variant thereof as paragraphed in any previous paragraph wherein the antibody or antigen-binding fragment, derivative or variant thereof is a competitive binding inhibitor of tenascin-C.

46. A composition comprising an antibody or antigen-binding fragment, derivative or variant thereof as defined in any of paragraphs 1-45 and a pharmaceutically acceptable carrier, excipient and/or diluent.

47. A composition as paragraphed in paragraph 46 further comprising at least one other agent.

48. A composition as paragraphed in paragraph 47 wherein the at least one other agent is an anti-inflammatory agent, a statin, a biological agent (biologicals), an immunosuppressive agent, a salicylate and/or a microbicidal agent.

49. A composition as paragraphed in paragraph 48 wherein the anti-inflammatory agent is selected from the group consisting non-steroidal anti-inflammatories (NSAIDs), corticosteroids, disease-modifying antirheumatic drugs (DMARDs) or immunosuppressants.

50. An antibody or antigen-binding fragment, derivative or variant thereof or composition as defined in paragraphs 1-49 for use as a medicament.

51. An antibody or antigen-binding fragment, derivative or variant thereof or composition as defined in paragraphs 1-49 for use in the treatment of a chronic inflammatory condition.

52. Use of an antibody or antigen-binding fragment, derivative or variant thereof or composition as defined in paragraphs 1-49 in the manufacture of a medicament for the treatment or diagnosis of a chronic inflammatory condition.

53. A method of treating a chronic inflammatory condition comprising administering to a subject an effective amount of an antibody or antigen-binding fragment, derivative or variant thereof or composition as defined in paragraphs 1-49.

54. An antibody or antigen-binding fragment, derivative or variant thereof or composition as defined in paragraphs 1-49 for use in the diagnosis of a chronic inflammatory condition and/or determination of prognosis of a patient with a chronic inflammatory condition.

55. A method of diagnosing a chronic inflammatory condition and/or determination of prognosis of a patient with a chronic inflammatory condition comprising detecting the presence or absence or amount of the FBG domain of tenascin-C using an antibody or antigen-binding fragment, derivative or variant thereof or composition as defined in paragraphs 1-49.

56. An antibody or antigen-binding fragment, derivative or variant thereof or method as defined in paragraph 54 or 55 wherein an increase in the amount of the FBG domain of tenascin-C detected is indicative of a chronic inflammatory condition determination and/or of prognosis of a patient with a chronic inflammatory condition.

57. The antibody or antigen-binding fragment, derivative or variant thereof or method of paragraph 56 wherein an increase of at least 50% in the amount of FBG domain of tenascin-C detected compared to normal levels is indicative of a chronic inflammatory condition determination and/or prognosis of a patient with a chronic inflammatory condition.

58. An antibody or antigen-binding fragment, derivative or variant thereof or composition as defined in paragraphs 1-49 for use in determining the appropriate treatment for an individual, wherein the amount of the FBG domain of tenascin-C detected indicates the appropriate treatment for the individual.

59. A method of determining the appropriate treatment for an individual comprising detecting the presence or absence or amount of the FBG domain of tenascin-C using an antibody or antigen-binding fragment, derivative or variant thereof or composition as defined in paragraphs 1-49, wherein the amount of the FBG domain of tenascin-C detected indicates the appropriate treatment for the individual.

60. The antibody or antigen-binding fragment, derivative or variant thereof or composition or method of paragraphs 58 or 59 wherein the appropriate treatment comprises the administration of an effective amount of an agent or composition, the agent or composition may be one or more of: an antibody or antigen-binding fragment, derivative or variant thereof or composition as defined in paragraphs 1-49; DMARDS (such as methotrexate); anti-TNF drug; an anti-IL17 therapy; a T-cell co-stimulation modulator (such as Orencia™—abatacept): an interleukin-6 (IL-6) inhibitor (such as Actemra™—tocilizumab); an anti-CD20 antibody (such as Rituxan™—rituxumab; a B cell activating factor (such as anti-BAFF); an inhibitor of janus kinase (JAK) (such as Tofacitinib™); an inhibitor of spleen tyrosine kinase (Syk) (such as Fostamatinib™); antiTNC antibodies or antibodies to citrullinated tenascin-C domains; and/or an agent that modulates the biological activity of citrullinated and/or non-citrullinated tenascin-C.

61. The antibody or antigen-binding fragment, derivative or variant thereof or composition method of paragraphs 58-60 wherein the appropriate treatment targets the FBG domain of tenascin-C.

62. The antibody or antigen-binding fragment, derivative or variant thereof or composition or method of paragraphs 58-61 wherein the appropriate treatment is the administration of an effective amount of an antibody or antigen-binding fragment, derivative or variant thereof, or composition as defined in paragraphs 1-49.

63. The antibody or antigen-binding fragment, derivative or variant thereof or composition or method of paragraphs 58-62 wherein the individual has a chronic inflammatory condition.

64. The antibody or antigen-binding fragment, derivative or variant thereof or composition or method of paragraphs 58-63 wherein an increase in the amount of FBG domain of tenascin-C detected indicates the appropriate treatment.

65. The antibody or antigen-binding fragment, derivative or variant thereof or composition or method of paragraph 64 wherein an increase in the amount of FBG domain of tenascin-C detected indicates that an increased amount of the appropriate treatment is required.

66. The antibody or antigen-binding fragment, derivative or variant thereof or composition or method of paragraphs 64 or 65 wherein the increase in the amount of FBG domain of tenascin-C detected is an increase of at least 50% compared to normal levels of FBG domain of tenascin-C.

67. The antibody or antigen-binding fragment, derivative or variant thereof or composition or method of paragraphs 56-66 wherein the amount of FBG domain of tenascin-C is determined by the use of one or more of: immunoassays; spectrometry; western blot; ELISA; immunoprecipitation; slot or dot blot assay; isoelectric focussing; SDS-PAGE; antibody microarray; immunohistological staining; radio immuno assay (RIA), fluoroimmunoassay; and/or an immunoassay using an avidin-biotin and/or streptoavidin-biotin system.

68. An antibody or antigen-binding fragment, derivative or variant thereof, composition, use or method as paragraphed in paragraphs 51-67 wherein the chronic inflammatory response is associated with a condition characterised by inappropriate inflammation.

69. An antibody or antigen-binding fragment, derivative or variant thereof, composition, use or method as paragraphed in paragraphs 51-67 wherein the chronic inflammatory response is associated with rheumatoid arthritis (RA), autoimmune conditions, inflammatory bowel diseases (including Crohn's disease and ulcerative colitis), non-healing wounds, multiple sclerosis, cancer, atherosclerosis, sjogrens disease, diabetes, lupus erythrematosus (including systemic lupus erythematosus), asthma, fibrotic diseases (including liver cirrhosis), pulmonary fibrosis, UV damage, psoriasis, ankylosing spondylitis and cardiovascular disease.

70. A kit of parts comprising:
(i) an antibody or antigen-binding fragment, derivative or variant thereof or composition as defined in paragraphs 1-49;
(ii) administration means; and
(iii) instructions for their use 71. A kit of parts as paragraphed in paragraph 70 optionally comprising
(iv) at least one other agent.

72. A kit of parts for use in determining the chronic inflammatory condition status of a subject comprising:
(i) an antibody or antigen-binding fragment, derivative or variant thereof or composition as defined in paragraphs 1-49; and
(ii) instructions for use It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the following claims.

The invention claimed is:

1. An anti-fibrinogen-like globe (FBG) domain of tenascin-C antibody or antigen-binding fragment thereof comprising a VH region and a VL region, wherein the VH region comprises SEQ ID NO: 37 and wherein the VL region comprises RASQYIQGFLN (SEQ ID NO: 5) for CDRL1, DASNLET (SEQ ID NO: 13) for CDRL2, and QQSYSTPQT (SEQ ID NO: 14) for CDRL3.

2. A composition comprising an antibody or antigen-binding fragment of claim 1 and a pharmaceutically acceptable carrier, excipient and/or diluent.

3. A method of treating rheumatoid arthritis comprising administering to a subject an effective amount of an antibody or antigen-binding fragment according to claim 1.

* * * * *